(12) United States Patent
Darzins et al.

(10) Patent No.: US 10,246,690 B2
(45) Date of Patent: *Apr. 2, 2019

(54) MUTANT HYDROLASE PROTEINS WITH ENHANCED KINETICS AND FUNCTIONAL EXPRESSION

(71) Applicant: Promega Corporation, Madison, WI (US)

(72) Inventors: Aldis Darzins, Highlands Ranch, CO (US); Lance P. Encell, Fitchburg, WI (US); Rachel Friedman Ohana, Madison, WI (US); Paul Otto, Madison, WI (US); Michael R. Slater, Madison, WI (US); Gediminas Vidugiris, Fitchburg, WI (US); Keith V. Wood, Mt. Horeb, WI (US); Monika G. Wood, Mt. Horeb, WI (US); Kate Qin Zhao, Verona, WI (US); Kris Zimmerman, Madison, WI (US)

(73) Assignee: Promega Corporation, Madison, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 15/877,980

(22) Filed: Jan. 23, 2018

(65) Prior Publication Data

US 2018/0223267 A1   Aug. 9, 2018

Related U.S. Application Data

(60) Continuation of application No. 15/414,291, filed on Jan. 24, 2017, now Pat. No. 9,873,866, which is a continuation of application No. 14/285,327, filed on May 22, 2014, now Pat. No. 9,593,316, which is a continuation of application No. 13/863,924, filed on Apr. 16, 2013, now Pat. No. 8,748,148, which is a division of application No. 11/978,950, filed on Oct. 30, 2007, now Pat. No. 8,420,367.

(60) Provisional application No. 60/855,237, filed on Oct. 30, 2006, provisional application No. 60/930,201, filed on May 15, 2007.

(51) Int. Cl.
| | |
|---|---|
| *C12N 9/14* | (2006.01) |
| *C12N 9/96* | (2006.01) |
| *C12N 11/00* | (2006.01) |
| *C12Q 1/34* | (2006.01) |
| *G01N 33/58* | (2006.01) |

(52) U.S. Cl.
CPC ............... *C12N 9/14* (2013.01); *C12N 9/96* (2013.01); *C12N 11/00* (2013.01); *C12Q 1/34* (2013.01); *G01N 33/581* (2013.01); *C12Y 308/01* (2013.01)

(58) Field of Classification Search
CPC ............. C12N 9/14; C12N 11/00; C12N 9/96
See application file for complete search history.

(56) References Cited

U.S. PATENT DOCUMENTS

| | | |
|---|---|---|
| 3,131,122 A | 4/1964 | Freter |
| 4,574,079 A | 3/1986 | Gavras et al. |
| 4,818,807 A | 4/1989 | Morita et al. |
| 5,071,469 A | 12/1991 | Artz |
| 5,099,020 A | 3/1992 | Grote et al. |
| 5,110,833 A | 5/1992 | Mosbach |
| 5,128,247 A | 7/1992 | Koller |
| 5,372,944 A | 12/1994 | Swanson |
| 5,476,770 A | 12/1995 | Pradelles |
| 5,503,977 A | 4/1996 | Johnsson et al. |
| 5,523,209 A | 6/1996 | Ginsberg et al. |
| 5,576,424 A | 11/1996 | Mao et al. |
| 5,700,908 A | 12/1997 | Ruoslahti et al. |
| 5,700,935 A | 12/1997 | Takenishi et al. |
| 5,786,428 A | 7/1998 | Arnold et al. |
| 5,821,047 A | 10/1998 | Garrard et al. |
| 5,932,421 A | 8/1999 | Ginsberg et al. |
| 5,945,526 A | 8/1999 | Lee et al. |
| 6,255,461 B1 | 7/2001 | Mosbach et al. |
| 6,333,154 B1 | 12/2001 | Ladant et al. |
| 6,416,733 B1 | 7/2002 | Barrett et al. |
| 6,492,560 B2 | 12/2002 | Wilbur et al. |
| 6,537,776 B1 | 3/2003 | Short et al. |
| 6,800,453 B2 | 10/2004 | Labaer et al. |
| 7,238,842 B2 | 7/2007 | Wood et al. |
| 7,425,436 B2 | 9/2008 | Darzins et al. |
| 7,429,472 B2 | 9/2008 | Darzins et al. |
| 8,420,367 B2 | 4/2013 | Darzins et al. |
| 8,748,148 B2 | 6/2014 | Darzins et al. |
| 9,593,316 B2 | 3/2017 | Darzins et al. |
| 9,873,866 B2 | 1/2018 | Darzins et al. |

(Continued)

FOREIGN PATENT DOCUMENTS

| | | |
|---|---|---|
| BE | 616245 | 10/1962 |
| CZ | 259396 | 10/1998 |

(Continued)

OTHER PUBLICATIONS

Witkowski et al., Biochemistry 38:11643-11650, 1999.*
Branden et al., Introduction to Protein Structure, Garland Publishing Inc., New York, p. 247, 1991.*
Tang et al., Phil Trans R Soc B 368:20120318, 1-10, 2013.*
Seffernick et al., J. Bacteriol. 183(8):2405-2410, 2001.*
Sadowski et al., Current Opinion in Structural Biology 19:357-362, 2009.*
Newman et al., "Haloalkane Dehalogenases: Structure of a Rhodococcus Enzyme," Biochemistry, 38, pp. 16105-16114.
Partial Search Report for corresponding PCT Application No. PCT/US2005/027307 (dated Jun. 11, 2006).

(Continued)

*Primary Examiner* — Delia M Ramirez
(74) *Attorney, Agent, or Firm* — Casimir Jones SC; David W. Staple

(57) ABSTRACT

The invention provides a mutant hydrolase protein with enhanced kinetics and functional expression, as well as polynucleotides encoding the mutant proteins and methods of using the polynucleotides and mutant proteins.

6 Claims, 40 Drawing Sheets

Specification includes a Sequence Listing.

(56) References Cited

U.S. PATENT DOCUMENTS

| | | |
|---|---|---|
| 2002/0042055 A1 | 4/2002 | Affholter |
| 2002/0137171 A1 | 9/2002 | Short et al. |
| 2003/0166957 A1 | 9/2003 | Benneteau et al. |
| 2004/0152880 A1 | 8/2004 | Minden |
| 2005/0048580 A1 | 3/2005 | Labaer et al. |
| 2005/0095651 A1 | 5/2005 | Camarero et al. |
| 2006/0024808 A1 | 2/2006 | Darzins et al. |
| 2007/0087400 A1 | 4/2007 | Darzins et al. |
| 2007/0224620 A1 | 9/2007 | Hartzell et al. |
| 2008/0026407 A1 | 1/2008 | Wood et al. |
| 2008/0274488 A1 | 11/2008 | Darzins et al. |
| 2009/0098627 A1 | 4/2009 | Darzins et al. |

FOREIGN PATENT DOCUMENTS

| | | |
|---|---|---|
| EP | 0718300 | 6/1996 |
| JP | 2002-537836 | 4/2004 |
| JP | 2005-501515 | 1/2005 |
| WO | 98/36080 | 8/1998 |
| WO | 01/53303 | 7/2001 |
| WO | 01/60415 | 8/2001 |
| WO | 01/77668 | 10/2001 |
| WO | 02/28841 | 4/2002 |
| WO | 02/057411 | 7/2002 |
| WO | 02/068583 | 9/2002 |
| WO | 02/083937 | 10/2002 |
| WO | 03/040096 | 5/2003 |
| WO | 04/009788 | 1/2004 |
| WO | 04/072232 | 8/2004 |
| WO | 06/093529 | 9/2006 |
| WO | 07/092579 | 8/2007 |
| WO | 08/054821 | 5/2008 |

OTHER PUBLICATIONS

Pavel et al. "Mechanism of Enhanced Conversion of 1,2,3-trichloropropane by mutant haloalkane dehalogenase revealed by molecular modeling," J Computer Aided Molecular Design, 20, pp. 375-383 (2006).
Phillips, "The challenge of gene therapy and DNA delivery," J Pharm Pharmacol, 53, pp. 1169-1174 (2001).
Pieters, et al., "Design and Synthesis of Reagants for phage display screening of dehalogenases," Bioorganic & Medicinal Chem Lett, 9, pp. 161-166 (1999).
Polgar et al., "The catalytic triad of serine peptidases," Cell Mol Life Sci, 62(19-20), pp. 2161-2172 (2005).
Pompeo et al., "The pharmacogenetics of NAT: structural aspects," Pharmacogenomics, 3(1), pp. 19-30 (2002).
Pries et al., "Activation of an Asp-124 -> Asn Mutant of Haloalkane Dehalogenase by Hydrolytic Deamidation of Asparagine," FEBS Lett, 358, pp. 171-174 (1995).
Pries et al., "Histidine 289 is essential for hydrolysis for the alkyl-enzyme intermediate of haloalkane dehalogenase," J Biol Chem, 270, pp. 10405-10411 (1995).
Puig et al., "The Tandem Affinity Purification (TAP) Method: A General Procedure of Protein Complex Function," Methods, 24, pp. 218-229 (2001).
Rohila et al., "Improved Tandem Affinity Purification Tag and Methods for Isolation of Protein Heterocomplexes from Plants," Plant J, 38, pp. 172-181 (2004).
Rouille et al., "Proteolytic processing mechanisms in the biosynthesis of neuroendocrine peptides: the subtilisin-like proprotein convertases," Front Neuroendocrinol, 16(4), pp. 322-361 (1995).
Santra et al., "Luminescent Nanoparticle Probes for Bioimaging," J Nanosci Nanotechnol, 4, pp. 590-599 (2004).
Scholten et al., "Novel Enzymatic hydrolytic degalogenation of a chlorinated aromatic," Science, 253, pp. 182-185 (1991).
Seffernick et al., "Melamine deaminase and atrazine chlorohydrolase: 98 percent identical but functionally different," J Bacteriol, 183(8), pp. 2405-2410 (2001).
Stroffekova et al., "The protein-labeling reagent FLASH-EDT2 binds not only to CCXXCC motifs but also non-specifically to endogenous cysteine-rich proteins," Pflugers Arch, 442, pp. 859-866 (2001).
Stryer, et al. "Biochemistry," Third Edition, pp. 757-758 (1988).
Tou et al., "Kinetic study of the stabilities of chloromethyl ether and bis(chloromethyl) ether in humid air," Analyt. Chem, 46, pp. 1866-1869 (1974).
U.S. Patent Office Action for U.S. Appl. No. 11/509,796 dated Mar. 28, 2008.
U.S. Patent Office Action for U.S. Appl. No. 11/509,796 dated Apr. 11, 2007.
U.S. Patent Office Action for U.S. Appl. No. 11/509,796 dated Sep. 24, 2007.
Yokota et al., "Purification and Properties of Haloalkane Dehalogenase from *Corynebacterium* SP. Strain M15-3," J Bacteriology, 169, pp. 4094-4054.
U.S. Patent Office Action for U.S. Appl. No. 11/509,796 dated Nov. 12, 2008.
U.S. Patent Office Action for U.S. Appl. No. 11/786,792 dated Nov. 2, 2009.
U.S. Patent Office Action for U.S. Appl. No. 12/075,160 dated Nov. 16, 2009.
U.S. Patent Office Action for U.S. Appl. No. 12/284,010 dated Sep. 29, 2009.
U.S. Patent Office Action for U.S. Appl. No. 12/284,010—dated Mar. 23, 2009.
U.S. Patent Office Action for U.S. Appl. No. 10/768,976—Final Office Action (dated Mar. 14, 2006) 9 pgs.
U.S. Patent Office Action for U.S. Appl. No. 10/768,976—Non Final Office Action (dated Aug. 1, 2006).
U.S. Patent Office Action for U.S. Appl. No. 10/768,976—Non Final Office Action (dated Sep. 9, 2005).
U.S. Patent Office Action for U.S. Appl. No. 11/006,031—Advisory Action dated May 7, 2007.
U.S. Patent Office Action for U.S. Appl. No. 11/006,031—Non Final office Action dated Mar. 15, 2006.
U.S. Patent Office Action for U.S. Appl. No. 11/006,031—Final office Action dated Feb. 8, 2007.
U.S. Patent Office Action for U.S. Appl. No. 11/006,031—Non Final Office Action dated Aug. 9, 2006, 13 pgs.
U.S. Patent Office Action for U.S. Appl. No. 11/194,110—Non Final Office Action, dated Mar. 29, 2007.
U.S. Patent Office Action for U.S. Appl. No. 11/704,150 Non Final Office Action dated Sep. 8, 2009.
U.S. Patent Office Action for U.S. Appl. No. 11/786,792 dated Feb. 5, 2009.
U.S. Patent Office Action for U.S. Appl. No. 11/786,792 dated Jul. 10, 2009.
Vincze et al., "Three-Dimensional Trace Element Analysis by Cofocal X-Ray Microfluorescence Imaging," Analytical Chem, 76, pp. 6786-6791 (2004).
Wada et al., "Codon usage tabulated from the GenBank genetic sequence data," Nucleic Acids Res, pp. 2111-2118 (1992).
Wang et al., "Detection of Tumor Marker CA125 in Ovarian Carcinoma Using Quantum Dots," Acta Biochem Biophys , 36(10), pp. 681-686 (2004).
Wayback Machine, http://www.promega-rd.info/bioimage2003/abstracts/lecturer/default.asap (Mar. 17, 2007).
Weissleder et al., "Shedding Light Onto Live Molecular Targets," Nature Med, 9, pp. 123-128 (2003).
Wheeler et al., "Conjugation of haloalkanes by bacterial and mammalian glutathione transferases: mono and vicinal dihaloethanes," Chem Res Toxicol, 14, 1107-1117 (2001).
Winberg et al., "The Catalytic Triad in Short-Chain Dehyrdogenases," Dept of Biochem, Inst. of Med Biol, Univ of Tromso, Abstract, (2002).
Witkowski et al., "Conversion of a beta-ketoacyl synthase to a malonyl decarboxylase by replacement of the active-site cysteine with glutamine," Biochemistry, 38, pp. 11643-11650 (1999).
Wolfgang et al., "Nonhuman primate transgenesis: progress and prospects," Trends in Biotechnol, 20(11), pp. 479-484 (2002).

(56) References Cited

OTHER PUBLICATIONS

Yang, G. et al., "Identification of Active Site Residues Essential to 4-chlorobenzoyl-Coenzyme A Dehalogenase Catalysis by Chemical Modification and Site Directed Mutagenesis," Biochemistry, 35, pp. 10879-10885 (1996).
Yang, M. et al., "Whole-Body Optical Imaging of Green Fluorescent Protein-Expressing Tumors and Metastases," PNAS, 97, pp. 1206-1211 (2000).
"Functional group," Encyclopedia Britannica Article online, http://www.searced.com/eb/article-9035655 (Mar. 19, 2007).
"Valence" Hawley's Condensed Chemical Dictionary (14th Ed) Online, John Wiley and Sons, 2002, http://www.knovel.com/knovel2/Toc.jsp?BookID=704&VerticIID=0 (Mar. 20, 2007).
Adachi et al. "Site-directed mutants, at position 166, of RTEM-1 beta-lactamase that form a stable acyl-enzyme Intermediate with penicillin," J Biol Chem, 266(5), pp. 3186-3191 (1991).
Adamczyk, et al., "Surface Plasmon resonance (SPR) as a tool for antibody conjugate anaylsis," Bioconjug Chem, 10(6), pp. 1032-1037.
Affholter et al., "Recombinant Haloaliphatic Dehalogenases," EMBL Database, Genetic Sequence, Entry Name: EMBL:BD057138 (2002).
Akiyama et al. "N-Hydroxy Amides, Part 8. Synthesis and Fe (III) Holding Properties of di0 and Trihydroxamic Acids Extending from Benezenedi- and Tricarbonyl Units through Oligo(ethyleneoxy) Arms," J Chem Soc Perkin Transactions, 2 Physical Org Chem, 9, pp. 1213-1218 (1989).
Albertson et al., "A Synthesis of DL-proline," J Amer Chem Soc, 71, pp. 2818-2820.
Amat-Guerri et al., "Methacrylate-tethered analogs o the laser dye PM567 synthesis, copolymerization, with methyl methacrylate and photostabilit of the copolymers," Phytochem Photobiol, 77(6), pp. 577-584 (2003.
Anonynmous, "The Second Symposium on Biological Imaging: New Dimensions in In Vivo Imaging," Lecturer Abstracts, obtained from www.promega-rd.info/bioimage2003/abstracts/lecture/default.asp (2003).
Arand et al., "Sequence similarity of mammalian epoxide hydrolases to the bacterial haloalkane dehalogenase and other related proteins," FEBS Lett, 338, pp. 251-256 (1994).
Aravind, "An evolutionary classification of the metallo-beta-lactamase fold proteins," In Silico Biol, 1(2), pp. 69-91 (1999).
Australian Patent Office Action for Application Serial No. 2004211584, First Examiner Report dated Jan. 6, 2009.
Banas et al., "Mechanism of enhanced conversion of 1,2,3-trichloropropane by mutant haloalkane dehalogenase revealed by molecular modeling," J Comp Aided Molec Design, 20(6), pp. 375-383 (2006).
Banks et al., "Understanding Fluorescene Polarization and its Data Analysis—Physical Principles of Fluorescene Polarization," http://www.perkinelmer.com/lifesciences, 12 pgs. (2001).
Barrett et al., "Synthesis and Characterization of an New Polymer Support for a Metallocene Catalyst," Tetrahedron, 58 (19), pp. 3785-3792.
Bier, "Covalys—one tag does it all," Market Portrait, pp. 46-47 (2003).
Bodwell et al., "Synthesis, Structure and AM1 Conformational Study of [3] Paracyclo [3] (1,3) indolophane, a Novel Chiral Cyclophane," Tetrahedron, 55(45): pp. 12939-12956 (1999).
Bosma et al., "Biodegradation of 1,2,3-trichloropropane through directed evolution and heterologous expression of a haloalkane dehalogenase gene," Appl Environ Microbiol, pp. 3582-3587 (2002).
Branden et al., Introduction to Protein Structure, Garland Publishing Inc, New York, pp. 247 (1991).
Broom et al., "Two approaches to drug discovery in SOD1-mediated ALS," J Biomol Screen, 11(7), pp. 729-735 (2006).
Cameron, "Recent advances in transgenic technology," Mol Biotechnol, 7, pp. 253-265 (1997).
Campbell et al., "A Monomeric Red Fluorescent Protein," PNAS, 99(12), pp. 7877-7882 (2002).

Castro et al., "Biodehalogenation, reductive reactivities of microbial and mammalian cytochromes P-450 compared with heme and whole-cell models," J Agric Food Chem, 36,pp. 915-919 (1988).
Chaloupkova , "Modification of activity and specificity of haloalkane dehalogenase from Sphingomonas paucimobilis UT26 by engineering of its entrance tunnel," J Biol Chem, pp. 52622-52628 (2003).
Chan et al., "Microarray-based detection of *Salmonella enteric* serovar typhimurium transposon mutants that cannot survive in macrophages and mice," Infect Immun, 73(9), pp. 5438-5449 (2005).
Chen et al., "Site-specific labeling of proteins with small molecules in live cells," Curr Opin Biotech, 16, pp. 35-40 (2005).
Chen et al., "Relocation of the Catalytic Carboxylate Group in Class A Beta-lactamase: The Structure and Function of the Mutant Enzyme Glu-166-Gln: Asn-170" Protein Engineer, 12(7), pp. 573-579 (1999).
Cheuk, "Synthesis of Optically Active Poly(Phenylacetylenes) Containing Amino Acid Pendent Groups," Polymeric Mater Sci Engineer, 82, pp. 56-57 (2000).
Chinese Application Serial No. 200480008194.4 Response filed to Second Office Action dated May 22, 2009.
Chinese Patent Application No. 200480008194.4—Office Action dated Oct. 9, 2009 with English transl.
Chinese Patent Application No. 20048000819.4 First Office Action dated Dec. 22, 2006.
Cohen et al., "Synthesis of Some Substituted Dibenzodiazenpinones and Pyridobenzodiazepinones," J Heter Chem, 35, pp. 675-686 (1998).
Dahl et al., "The reactivity of affinity labels: a kinetic study of the reaction of alkyl halides with thiolate anions—a model reaction for protein alkylation," Bioorg Chem, 10, pp. 329-341 (2005).
Dodson et al., "Catalytic triads and their relatives," Trends Biochem Sci, 23(9), pp. 347-352 (1998).
Dorwald et al., "Side reactions in organic synthesis," A Guide of Successful Synthesis Design, Wiley: VCH, (2005) 4 pages.
Doubrovin et al., "Reviews—Multimodality in Vivo Molecular—Genetic Imaging," Bioconjugate Chem, 15, pp. 1376-1388 (2004).
European Patent Office Action for Application Serial No. 04707032.1—Commuication dated Jun. 22, 2009.
European Patent Office Action for Application Serial No. 04707032.1—dated Mar. 12, 2007.
European Patent Office Action for Application No. 05857556.4 dated May 7, 2009.
European Patent Office Action for Application No. 07763411.1 dated Dec. 17, 2008.
European Patent Office Action for Application No. 07763411.1 dated Mar. 17, 2009.
European Patent Office Action for Application No. 07867352.2 dated Feb. 1, 2010.
Farinas et al., "Receptor-mediated Targeting of Fluorescent Probes in Living Cells," J Biol Chem, 274, pp. 7603-7606.
Franken et al., "Crystal Structure of haloalkane dehalogenase: an enzyme to detoxify halogenated alkanes," EMBO J, 10(6), pp. 1297-1302 (1991).
Gambhir, "Molecular Imaging of Cancer with Positron Emission Tomography," Nature Reviews, 2, pp. 683-693 (2002).
Gao et al., "Construction of murine phage antibody library and selection of ricin-specific single chanin antibodies," IUBMB Life, 48(5), pp. 513-517 (1999).
Gardlik et al., "Vectors and delivery systems in gene therapy," Med Sci Monit, 11(4), pp. RA110-RA121 (2005).
Gibbons et al., "Chipper: Discovering Transcription Factor Targets from Chromatin Immunoprecipitation Microarrays Using Variance Stabilization," Genome Biology, 6(11), Article R96 (2005).
Gite et al., "Ultrasensitive Fluorescence-Based Detection of Nascent Proteins in Gels," Analytical Biochem, 279, pp. 218-225 (2000).
Zawadzke et al., "Elimination of the hydrolytic water molecule in a class A beta-lactamase mutant: crystal structure and kinetics," Biochemistry, pp. 16475-16485 (1996).
Zeph et al., "Use of biotinylated DNA probe to detect bacteria transduced by bacteriophage P1 in soil," Appl Environ Microbiol, 55(3), pp. 661-665 (1989).
JP Office Action, Application No. 2009-534717, 8 pages.

(56) References Cited

OTHER PUBLICATIONS

Poelarends et al., Degradation of 1,2-dibromoethane by *Mycobacterium* sp. strain GP1. J Bacteriol. Apr. 1999;181(7):2050-8.

Gorbalenya et al., "Cysteine proteases of positive strand RNA viruses and chymotrypsin-like serine proteases. A distinct protein superfamily with a common structural fold," FEBS Lett, 243(2), pp. 103-114 (1989).

Gould et al., "Tandem Affinity Purification and Identification of Protein Complex Components," Methods, 33, pp. 239-244 (2004).

Gray et al., "Rapid Evolution of reversible denaturation and elevated melting temperature in a microbial haloalkane dehalogenase," Adv. Synth. Catayl, pp. 601-617 (2001).

Griffin et al., "Specific covalent labeling of recombinant protein molecules inside live cells," Science, 281, pp. 269-272 (1998).

Grogan, "Emergent-mechanistic diversity of enzyme-catalyzed beta-diketone cleavage," Biochem J, 388(pt. 3) pp. 721-730 (2005).

Gurskaya et al., "GFP-like Chromoproteins as a Source of Far-red Fluorescent Proteins," FEBS Letters, 507, pp. 16-20 (2001).

Hall et al., "Regulation of Gene Expression by a Metabolic Enzyme," Science, 306, pp. 482-484 (2004).

Heck et al., "Aromatic haloethylation with palladium and copper halides," J Amer Chem Soc, 90, pp. 5538-5542 (1968.

Henze et al., "The number of structurally isomeric alcohols of the methanol series," J Amer Chem Soc, 53, pp. 3042-3046 (1931).

Hodneland et al., "Selective Immobilization of Proteins to Self-Assembled Monolayers Presenting Active Site-Directed Capture Ligands," Proc Natl Acad Sci USA, 99(8), pp. 5048-5052 (2002).

Holloway et al., "A Colorimetric Assay for Detecting Haloalkine Dehalogenase Activity," J Microbiol Materials, 32, pp. 31-36 (1998).

Horton et al., "Reactions with reactive alkyl halidies," Meth Enyzmol, 11, pp. 556-565 (1967).

Houdebine, "The methods to generate transgenic animals and to control transgene expression," J Biotechnol, 98, pp. 145-160 (2002).

Huber et al., "SPR-based Interaction Studies with Small Molecular Weight Ligands Using hAGT Fusion Proteins," Anayl Biochem, 333, pp. 280-288 (2004).

Hynkova et al., "Identification of the Catalytic Triad in the Haloalkane Dehalogenase from Sphingomonas paucimobilis UT26" FEBS Letters, 446, pp. 177-181 (1999).

Ichiyama et al., "Novel Catalytic Mechanism of Nucleophilic Subsitution by Asparagine Residue Involving Cyanoalanine Intermediate Revealed by Mass Spectrometric Monitoring of an Enzyme Reaction," J Biol Chem, 275, pp. 40804-40809 (2000).

Indian Patent Office Action for Application No. 3867/DELNP/2005 First Examination Report dated Sep. 28, 2007.

Indian Patent Office Action for Application No. 3867/DELNP/2005 dated Sep. 9, 2008.

Instant Notes—Chemistry for Biologists, 2nd edition, Fisher and Arnolds, Garland Science/Bios Scientific Publishers, pp. 245-256 (2004).

International Preliminary Report on Patentability for PCT Application No. PCT/US2004/002607 dated Jun. 23, 2005.

International Search Report and Written Opinion for Application No. PCT/US2004/002607 dated Nov. 24, 2004.

International Search Report and Written Opinion for Application No. PCT/US2005/027307 dated Jan. 29, 2007.

International Search Report and Written Opinion for Application No. PCT/US2007/003416 dated Sep. 14, 2007.

International Search Report and Written Opinion for Application No. PCT/US2007/023205 dated Nov. 3, 2008.

Japanese Office Action for Application No. 2006-503174 dated Oct. 27, 2009.

Jeong et al., "Kinase assay based on thiophosphorylation and biotinylation," Biotechniques, 27 (6), pp. 1232-1238 (1999).

Jones et al., "Solvolysis mechanisms, SNI-like behavior of methyl chloromethyl ether, sensitivity to solvent ionizing power and alpha-deuterium isotope effect," J Amer Chem Soc, 89, pp. 4863-4867 (1967).

Kappel et al., "Regulating gene expression in transgenic animals," Curr Opin Biotechnol, 3, pp. 548-553 (1992).

Keppler et al., "A general method for the covalent labeling of fusion proteins with small molecules in vivo," Nature Biotechnol, 21, pp. 86-89 (2003).

Krooshof et al., "Repositioning the catalytic triad aspartic acid of haloalkane dehalogenase: effects on stability, kinetics, and structure," Biochemistry, 36, pp. 9571-9580.

Kulakova et al., "The plasmid-located Haloalkane Dehalogenase Gene From Rhodococcus rhodochrous NCIMB 13064," Microbiology, 143, pp. 109-115 (1997).

Kumar et al., "Large-scale mutagenesis of the yeast genome using a Tn7-derived multipurpose transposon," Genome Res, 14(10A), pp. 1975-1986 (2004).

Mullins et al., "Transgenesis in the rat and larger mammals," J Clin Invest, 97 (7), pp. 1557-1560 (1996).

Kurihara et al., "Comprehensive Site-directed Mutagenesis of L-2Halo Acid Dehalogenase to Probe Catalytic Amino Acid Residue," J Biochem, 117, pp. 1317-1322 (1995).

Kwon et al., "Antibody Arrays Prepared by Cutinase-Mediated Immobilization on Self-Assembled Monolayers," Anal Chem, 76, pp. 5713-5720 (2004).

Lautens et al., "An Expedient Route for the Stereoselective Construction of Bridged Polyheterocyclic Ring Systems Using the Tandem "Pincer" Diels-Alder Reaction," J Org Chem, 62, pp. 4418-4427 (1997).

Lewis et al., "Detection and quantification of biotinylated proteins using the storm 840 optical scanner," J Nutri Biochem, 14, pp. 196-202 (2003).

Li et al., "A Modified Mammalian Tandem Affinity Purification Procedure to Prepare Functional Polycystin-2 Channel" FEBS Letters, 576, pp. 231-236 (2004).

Lin et al., "Methods for Labeling Quantum Dots to Biomolecules," J Neurosci Nanotechnol, 4, pp. 641-645 (2004).

Los et al., "Chapter 14—The Halo Tagtm—a novel technology for cell imaging and protein analysis," Methods Molec Biol, 356, pp. 195-208 (2007).

Luo et al., "A Glucose based on Chitsosan-Glucose Oxidase-Gold Nanoparticles Biocomposite Formed by One-Step Endrodeposition," Analytical Biochem, 334, pp. 284-289 (2004).

Manoury et al., "Synthesis of a series of compounds related to betaxolol, a new beta 1-adrenoceptor antagonist with a pharmacological and pharmacokinetic profile optimized for the treatment of chronic cardiovascular diseases," J Med Chem, 30, pp. 1003-1011 (1987).

Mathieu et al., "Monitoring E-Selection-Mediated Adhesion Using Green and Red Fluorescent Proteins," J Immunol Methods, 272, pp. 81-92 (2003).

Michl et al., Electronic Aspects of Organic Photochemistry, John Wiley and Sons, pp. 61-78 (1990).

Miller et al., "Selective chemical labeling of proteins in living cells," Curr Opin Chem Biol, 9, pp. 56-61 (2005).

Miyazaki-Imamura et al., "Improvement of H2O2 stability of manganese peroxidase by combinatorial mutagenesis and high-throughput screening using in vitro expression with protein disulfide isomerase," Protein Eng, 16(6) pp. 423-438 (2003).

Momose et al., "Novel 5-Substituted-1H-Tetrazole Derivatives as Potent Glucose and Lipid Lowering Agents," Chemical & Pharmaceutical Bulletin, Pharmaceutical Society of Japan, 50, pp. 100-111 (2002).

Morzycki et al., "Synthesis of Dimeric Steroids as Components of Lipid Membranes," Tetrahedron, 53(30), pp. 10579-10590 (1997).

Mullins et al., "Transgenesis in nonmurine species," Hypertension, 22(4), pp. 630-633 (1993).

* cited by examiner

DhaA
MSEIGTGFPFDPHYVEVLGERMHYVDVGPRDGTPVLFLHGNPTSSYLWRNIIPHVAPSH
R
DhaA.H272F
------------------------------------------------------------
-
DhaA.D106C
------------------------------------------------------------
-

DhaA
CIAPDLIGMGKSDKPDLDYFFDDHVRYLDAFIEALGLEEVVLVIHDWGSALGFHWAKRN
P
DhaA.H272F
------------------------------------------------------------
-
DhaA.D106C
------------------------------------------C-----------------
-

DhaA
ERVKGIACMEFIRPIPTWDEWPEFARETFQAFRTADVGRELIIDQNAFIEGALPKCVVR
P
DhaA.H272F
------------------------------------------------------------
-
DhaA.D106C
------------------------------------------------------------
-

DhaA
LTEVEMDHYREPFLKPVDREPLWRFPNELPIAGEPANIVALVEAYMNWLHQSPVPKLLF
W
DhaA.H272F
------------------------------------------------------------
-
DhaA.D106C
------------------------------------------------------------
-

DhaA
GTPGVLIPPAEAARLAESLPNCKTVDIGPGLHYLQEDNPDLIGSEIARWLPAL
DhaA.H272F
------------------------------------F---------------
DhaA.D106C
----------------------------------------------------

*FIG. 1B*

| Clone | Codon 175 | | Codon 176 | | Codon 273 | |
|---|---|---|---|---|---|---|
| H272F | AAA | (Lys) | TGC | (Cys) | TAC | (Tyr) |
| D11 | ---- | ---- | TCG | (Ser) | ---- | ---- |
| H5b | ---- | ---- | AGT | (Ser) | ---- | ---- |
| F11B | ---- | ---- | TCT | (Ser) | ---- | ---- |
| G4B | ---- | ---- | AAT | (Asn) | ---- | ---- |
| A7 | ---- | ---- | GGT | (Gly) | ---- | ---- |
| G9C | ---- | ---- | GAT | (Asp) | ---- | ---- |
| E7C | ---- | ---- | ACG | (Thr) | ---- | ---- |
| 3A7 | ---- | ---- | GCT | (Ala) | ---- | ---- |
| C176R | ---- | ---- | AGG | (Arg) | ---- | ---- |
| 2A4 | ATG | (Met) | AAT | (Asn) | ---- | ---- |
| VN | GTG | (Val) | AAT | (Asn) | ---- | ---- |
| ES | GAG | (Glu) | TCG | (Ser) | ---- | ---- |
| DD | GAT | (Asp) | GAT | (Asp) | ---- | ---- |
| 1C6 | GCG | (Ala) | AGT | (Ser) | ---- | ---- |
| 2G7 | GCT | (Ala) | AGT | (Ser) | ---- | ---- |
| H11 | ATG | (Met) | GGG | (Gly) | ---- | ---- |
| 1G6 | TGT | (Cys) | GGT | (Gly) | ---- | ---- |
| 1G5 | CTT | (Leu) | GGT | (Gly) | ---- | ---- |
| 1B4 | TCT | (Ser) | GGG | (Gly) | ---- | ---- |
| K175M | ATG | (Met) | ---- | ---- | ---- | ---- |
| YL | ---- | ---- | ---- | ---- | TTG | (Leu) |
| YM | ---- | ---- | ---- | ---- | ATG | (Met) |
| YC | ---- | ---- | ---- | ---- | TGT | (Cys) |

*FIG. 2A*

| Clone | Codon 175 | Codon 176 |
|---|---|---|
| D106C | AAA (Lys) | TGC (Cys) |
| E2 | --- --- | GGC (Gly) |
| D9 | AGT (Ser) | GGT (Gly) |
| 15-F3 | TGT (Cys) | GGT (Gly) |
| 2-B9 | TGT (Cys) | GGG (Gly) |
| 11-E8 | TTG (Leu) | GGT (Gly) |
| 9-C11 | AGT (Ser) | GGG (Gly) |
| D5 | GAG (Glu) | GGT (Gly) |
| 30H4 | ATG (Met) | GGG (Gly) |
| 7A6 | CCG (Pro) | GGT (Gly) |
| 35- | CCT (Pro) | GGG (Gly) |
| 21-F3 | GCG (Ala) | GGT (Gly) |
| 9-H8 | AAT (Asn) | GGG (Gly) |
| 9-F5 | CAG (Gln) | GGT (Gly) |
| 15-B5 | GTT (Val) | GGG (Gly) |
| 27D10 | ATT (Ile) | GCG (Ala) |
| 4-F2 | AGT (Ser) | GCG (Ala) |
| 33- | TCG (Ser) | GCT (Ala) |
| 2-D7 | GCG (Ala) | GCT (Ala) |
| 14-F1 | GTT (Val) | GCT (Ala) |
| 17-G9 | ATG (Met) | CAG (Gln) |

*FIG. 2B*

V2
atggcagaaatcggtactggctttccattcgaccccattatgtggaagtcctgggcga
gcgcatgcactacgtcgatgttggtccgcgcgatggcacccctgtgctgttcctgcacg
gtaacccgacctcctcctacctgtggcgcaacatcatcccgcatgttgcaccgacccat
cgctgcattgctccagacctgatcggtatgggcaaatccgacaaaccagacctgggtta
tttcttcgacgaccacgtccgctacctggatgccttcatcgaagccctgggtctggaag
aggtcgtcctggtcattcacgactggggctccgctctgggtttccactgggccaagcgc
aatccagagcgcgtcaaaggtattgcatgtatggagttcatccgccctatcccgacctg
ggacgaatggccagaattgcccgcgagaccttccaggccttccgcaccaccgacgtcg
gccgcgagctgatcatcgatcagaacgctttatcgagggtacgctgccgatgggtgtc
gtccgcccgctgactgaagtcgagatggaccattaccgcgagccgttcctgaagcctgt
tgaccgcgagccactgtggcgcttcccaaacgagctgccaatcgccggtgagccagcga
acatcgtcgcgctggtcgaagaatacatgaactggctgcaccagtccctgtcccgaag
ctgctgttctggggcacccaggcgttctgatccaccggcgaagccgctcgcctggc
cgaaagcctgcctaactgcaagactgtggacatcggcccgggtctgaattttctgcaag
aagacaacccggacctgatcggcagcgagatcgcgcgctggctgtcgacgctgcaatat

V3
atggcagaaatcggtactggctttccattcgaccccattatgtggaagtcctgggcga
gcgcatgcactacgtcgatgttggtccgcgcgatggcacccctgtgctgttcctgcacg
gtaacccgacctcctcctacctgtggcgcaacatcatcccgcatgttgcaccgacccat
cgctgcattgctccagacctgatcggtatgggcaaatccgacaaaccagacctgggtta
tttcttcgacgaccacgtccgctacctggatgccttcatcgaagccctgggtctggaag
aggtcgtcctggtcattcacgactggggctccgctctgggtttccactgggccaagcgc
aatccagagcgcgtcaaaggtattgcatgtatggagttcatccgccctatcccgacctg
ggacgaatggccagaattgcccgcgagaccttccaggccttccgcaccaccgacgtcg
gccgcgagctgatcatcgatcagaacgctttatcgagggtacgctgccgatgggtgtc
gtccgcccgctgactgaagtcgagatggaccattaccgcgagccgttcctgaagcctgt
tgaccgcgagccactgtggcgcttcccaaacgagctgccaatcgccggtgagccagcga
acatcgtcgcgctggtcgaagaatacatgaactggctgcaccagtccctgtcccgaag
ctgctgttctggggcacccaggcgttctgatccaccggcgaagccgctcgcctggc
cgaaagcctgcctaactgcaagactgtggacatcggcccgggtctgaatctgctgcaag
aagacaacccggacctgatcggcagcgagatcgcgcgctggctgtcgacgctgcaatat

V4
atggcagaaatcggtactggctttccattcgaccccattatgtggaagtcctgggcga
gcgcatgcactacgtcgatgttggtccgcgcgatggcacccctgtgctgttcctgcacg
gtaacccgacctcctcctacctgtggcgcaacatcatcccgcatgttgcaccgacccat
cgctgcattgctccagacctgatcggtatgggcaaatccgacaaaccagacctgggtta
tttcttcgacgaccacgtccgcttcctggatgccttcatcgaagccctgggtctggaag
aggtcgtcctggtcattcacgactggggctccgctctgggtttccactgggccaagcgc
aatccagagcgcgtcaaaggtattgcatgtatggagttcatccgccctatcccgacctg
ggacgaatggccagaattgcccgcgagaccttccaggccttccgcaccaccgacgtcg
gccgcgagctgatcatcgatcagaacgctttatcgagggtacgctgccgatgggtgtc
gtccgcccgctgactgaagtcgagatggaccattaccgcgagccgttcctgaagcctgt

*FIG. 3A* tgaccgcgagccactgtggcgcttcccaaacgagctgccaatcgccggtgagccagcga
acatcgtcgcgctggtcgaagaatacatggactggctgcaccagtcccctgtcccgaag
ctgctgttctggggcacccaggcgttctgatcccaccggccgaagccgctcgcctggc
cgaaagcctgcctaactgcaagactgtggacatcggcccgggtctgaattttctgcaag
aagacaacccggacctgatcggcagcgagatcgcgcgctggctgcaggagctgcaatat

V5
Atggcagaaatcggtactggctttccattcgaccccattatgtggaagtcctgggcga
gcgcatgcactacgtcgatgttggtccgcgcgatagcacccctgtgctgttcctgcacg
gtaacccgacctcctcctacctgtggcgcaacatcatccgcatgttgcaccgaccat
cgctgcattgctccagacctgatcggtatgggcaaatccgacaaaccagacctgggtta
tttcttcgacgaccacgtccgcttcctggatgccttcatcgaagccctgggtctggaag
aggtcgtcctggtcattcacgactggggctccgctctggttttccactgggccaagcgc
aatccagagcgcgtcaaaggtattgcatgtatggagttcatccgccctatcccgacctg
ggacgaatggccagaatttgcccgcgagaccttccaggccttccgcaccaccgacgtcg
gccgcgagctgatcatcgatcagaacgcttttatcgagggtacgctgccgatgggtgtc
gtccgcccgctgactgaagtcgagatggaccattaccgcgagccgttcctgaagcctgt
tgaccgcgagccactgtggcgcttcccaaacgagctgccaatcgccggtgagccagcga
acatcgtcgcgctggtcgaagaatacatggactggctgcaccagtcccctgtcccgaag
ctgctgttctggggcacccaggcgttctgatcccaccggccgaagccgctcgcctggc
cgaaagcctgcctaactgcaagactgtggacatcggcccgggtctgaatctgctgcaag
aagacaacccggacctgatcggcagcgagatcgcgcgctggctgcaggagctgcaatat

V6
atggcagaaatcggtactggctttccattcgaccccattatgtggaagtcctgggcga
gcgcatgcactacgtcgatgttggtccgcgcgatggcacccctgtgctgttcctgcacg
gtaacccgacctcctcctacgtgtggcgcaacatcatccgcatgttgcaccgaccat
cgctgcattgctccagacctgatcggtatgggcaaatccgacaaaccagacctgggtta
tttcttcgacgaccacgtccgcttcatggatgccttcatcgaagccctgggtctggaag
aggtcgtcctggtcattcacgactggggctccgctctggttttccactgggccaagcgc
aatccagagcgcgtcaaaggtattgcatttatggagttcatccgccctatcccgacctg
ggacgaatggccagaatttgcccgcgagaccttccaggccttccgcaccaccgacgtcg
gccgcaagctgatcatcgatcagaacgtttttatcgagggtacgctgccgatgggtgtc
gtccgcccgctgactgaagtcgagatggaccattaccgcgagccgttcctgaatcctgt
tgaccgcgagccactgtggcgcttcccaaacgagctgccaatcgccggtgagccagcga
acatcgtcgcgctggtcgaagaatacatggactggctgcaccagtcccctgtcccgaag
ctgctgttctggggcacccaggcgttctgatcccaccggccgaagccgctcgcctggc
caaaagcctgcctaactgcaaggctgtggacatcggcccgggtctgaatctgctgcaag
aagacaacccggacctgatcggcagcgagatcgcgcgctggctgtcgacgctgcaatat

*FIG. 3B*

```
                 PvuII                    NcoI
                ───────                  ───────
        NheI            EcoRV            BamHI
       ───────         ───────          ───────
                                   MetGlySerGlu IleGlyThr·
                                   ─────────────────────────
1051  GCTAGCCAG CTGGCGCGGA TATCGCCACC ATGGGATCCG AAATCGGTAC
      CGATCGGTC GACCGCGCCT ATAGCGGTGG TACCCTAGGC TTTAGCCATG

·GlyPhePro PheAspProHis TyrValGlu ValLeuGly GluArgMetHis·
     ──────────────────────────────────────────────────────────
1101  AGGCTTCCCC TTCGACCCCC ATTATGTGGA AGTCCTGGGC GAGCGTATGC
      TCCGAAGGGG AAGCTGGGGG TAATACACCT TCAGGACCCG CTCGCATACG

·HTyrValAsp ValGlyPro ArgAspGlyThr ProValLeu PheLeuHis
     ──────────────────────────────────────────────────────
1151  ACTACGTCGA TGTTGGACCG CGGGATGGCA CGCCTGTGCT GTTCCTGCAC
      TGATGCAGCT ACAACCTGGC GCCCTACCGT GCGGACACGA CAAGGACGTG

GlyAsnProThr SerSerTyr LeuTrpArg AsnIleIlePro HisValAla·
     ──────────────────────────────────────────────────────────
1201  GGTAACCCGA CCTCGTCCTA CCTGTGGCGC AACATCATCC CGCATGTAGC
      CCATTGGGCT GGAGCAGGAT GGACACCGCG TTGTAGTAGG GCGTACATCG

·ProSerHis ArgCysIleAla ProAspLeu IleGlyMet GlyLysSerAsp·
     ──────────────────────────────────────────────────────────
1251  ACCGAGTCAT CGGTGCATTG CTCCAGACCT GATCGGGATG GGAAAATCGG
      TGGCTCAGTA GCCACGTAAC GAGGTCTGGA CTAGCCCTAC CCTTTTAGCC

·ALysProAsp LeuAspTyr PhePheAspAsp HisValArg TyrLeuAsp
     ──────────────────────────────────────────────────────
1301  ACAAACCAGA CCTCGATTAT TTCTTCGACG ACCACGTCCG CTACCTCGAT
      TGTTTGGTCT GGAGCTAATA AAGAAGCTGC TGGTGCAGGC GATGGAGCTA

AlaPheIleGlu AlaLeuGly LeuGluGlu ValValLeuVal IleHisAsp·
     ──────────────────────────────────────────────────────────
1351  GCCTTCATCG AAGCCTTGGG TTTGGAAGAG GTCGTCCTGG TCATCCACGA
      CGGAAGTAGC TTCGGAACCC AAACCTTCTC CAGCAGGACC AGTAGGTGCT

·TrpGlySer AlaLeuGlyPhe HisTrpAla LysArgAsn ProGluArgVal·
     ──────────────────────────────────────────────────────────
1401  CTGGGGCTCA GCTCTCGGAT TCCACTGGGC CAAGCGCAAT CCGGAACGGG
      GACCCCGAGT CGAGAGCCTA AGGTGACCCG GTTCGCGTTA GGCCTTGCCC
```

*FIG. 4A*

```
              ·VLysGlyIle AlaCysMet GluPheIleArg ProIlePro ThrTrpAsp
        ------------------------------------------------------------
  1451  TCAAAGGTAT TGCATGTATG AATTCATCC  GGCCTATCCC GACGTGGGAC
        AGTTTCCATA ACGTACATAC CTTAAGTAGG CCGGATAGGG CTGCACCCTG

GluTrpProGlu PheAlaArg GluThrPhe GlnAlaPheArg ThrAlaAsp·
        ------------------------------------------------------------
  1501  GAATGGCCAG AATTCGCCCG TGAGACCTTC CAGGCCTTCC GGACCGCCGA
        CTTACCGGTC TTAAGCGGGC ACTCTGGAAG GTCCGGAAGG CCTGGCGGCT

·ValGlyArg GluLeuIleIle AspGlnAsn AlaPheIle GluGlyAlaLeu·
        ------------------------------------------------------------
  1551  CGTCGGCCGA GAGTTGATCA TCGATCAGAA CGCTTTCATC GAGGGTGCGC
        GCAGCCGGCT CTCAACTAGT AGCTAGTCTT GCGAAAGTAG CTCCCACGCG

·LProMetGly ValValArg ProLeuThrGlu ValGluMet AspHisTyr
        ------------------------------------------------------------
  1601  TCCCGATGGG GGTCGTCCGT CCGCTTACGG AGGTCGAGAT GGACCACTAT
        AGGGCTACCC CCAGCAGGCA GGCGAATGCC TCCAGCTCTA CCTGGTGATA

ArgGluProPhe LeuLysPro ValAspArg GluProLeuTrp ArgPhePro·
        ------------------------------------------------------------
  1651  CGCGAGCCCT TCCTCAAGCC TGTTGACCGA GAGCCACTGT GGCGATTCCC
        GCGCTCGGGA AGGAGTTCGG ACAACTGGCT CTCGGTGACA CCGCTAAGGG

·AsnGluLeu ProIleAlaGly GluProAla AsnIleVal AlaLeuValGlu·
        ------------------------------------------------------------
  1701  CAACGAGCTG CCCATCGCCG GTGAGCCCGC GAACATCGTC GCGCTCGTCG
        GTTGCTCGAC GGGTAGCGGC CACTCGGGCG CTTGTAGCAG CGCGAGCAGC

·GAlaTyrMet AsnTrpLeu HisGlnSerPro ValProLys LeuLeuPhe
        ------------------------------------------------------------
  1751  AGGCATACAT GAACTGGCTG CACCAGTCAC CTGTCCCGAA GTTGTTGTTC
        TCCGTATGTA CTTGACCGAC GTGGTCAGTG GACAGGGCTT CAACAACAAG

TrpGlyThrPro GlyValLeu IleProPro AlaGluAlaAla ArgLeuAla·
        ------------------------------------------------------------
  1801  TGGGGCACAC CCGGCGTACT GATCCCCCCG GCCGAAGCCG CGAGACTTGC
        ACCCCGTGTG GGCCGCATGA CTAGGGGGGC CGGCTTCGGC GCTCTGAACG

·GluSerLeu ProAsnCysLys ThrValAsp IleGlyPro GlyLeuPheLeu·
        ------------------------------------------------------------
  1851  CGAAAGCCTC CCCAACTGCA AGACAGTGGA CATCGGCCCG GGATTGTTCT
        GCTTTCGGAG GGGTTGACGT TCTGTCACCT GTAGCCGGGC CCTAACAAGA
```

*FIG. 4B*

```
                ·LLeuGlnGlu AspAsnPro AspLeuIleGly SerGluIle AlaArgTrp
                ------------------------------------------------------
           1901 TGCTCCAGGA AGACAACCCG GACCTTATCG GCAGTGAGAT CGCGCGCTGG
                ACGAGGTCCT TCTGTTGGGC CTGGAATAGC CGTCACTCTA GCGCGCGACC

NgoMIV
                           ------
                           NaeI            PacI            NotI
                           ------          ----------      ----------
                LeuProGlyLeu AlaGly** *
                ------------------------
           1951 CTCCCCGGGC TGGCCGGCTA ATAGTTAATT AAGTAGGCGG CCGC
                GAGGGGCCCG ACCGGCCGAT TATCAATTAA TTCATCCGCC GGCG
```

*FIG. 4C*

H54Y
L161M
A224D
Q165R
V55I
G176A
T264S
M175R
F131L
F144L
Q165K
R288H
G96A
P12S
P180Q
A116G
Y295C (linker)
K263R
R30H
D82G
K124I
E183K
Q294E
D280Y
L221M
P233L
I218V
P134H
A56S
F131I
G7D
E121K
T182S
V197A
Q231K

*FIG. 5*

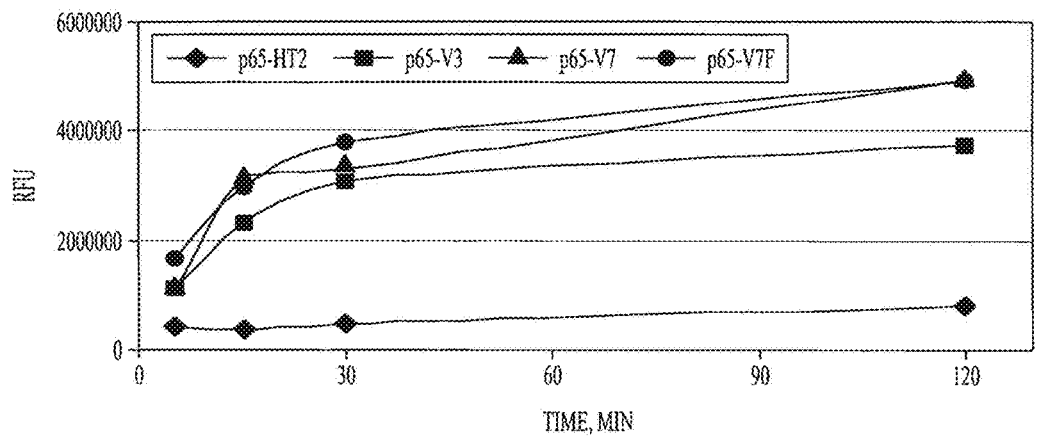
*FIG. 10A*
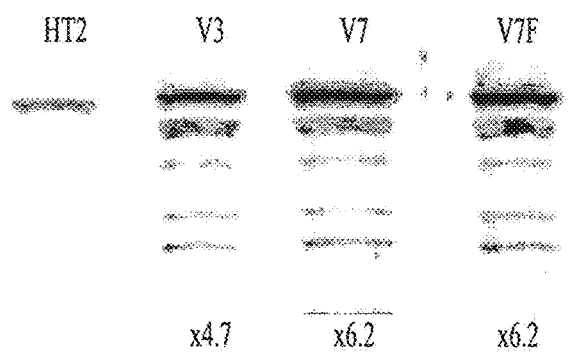
*FIG. 10B*
| | E. COLI | HeLa CELLS | RR TNT | WHEAT GERM TNT |
|---|---|---|---|---|
| V7 N | 38-140 | | 3-170 | 2-20 |
| V7 C | UP TO 130 | 6.2 | UP TO 140 | |
*FIG. 11*

| | FOLD IMPROVEMENT |
|---|---|
| V3 | 45 |
| V6 | 60 |
| V7 | 77 |

| CLONE | $k_{TMR-LIGAND}$ (FOLD IMPROVED) | $k_{FAM-LIGAND}$ (FOLD IMPROVED) |
|---|---|---|
| HT | $3.0 \times 10^6$ (1.0) | $1.5 \times 10^4$ (1.0) |
| V3 | $4.0 \times 10^6$ (1.3) | $2.9 \times 10^4$ (2.0) |
| V6 | $1.0 \times 10^7$ (3.3) | $6.2 \times 10^5$ (41) |
| V7 | $1.2 \times 10^7$ (4.0) | $1.1 \times 10^6$ (73) |
| V7Phe | $2.0 \times 10^7$ (6.7) | $3.3 \times 10^6$ (220) | n=mutant DhaA on N-terminus
c=mutant DhaA on C-terminus

HT2(c)
Tccgaaatcggtacaggcttcccctttcgaccccattatgtggaagtcctgggcgagcgtatgcactacgt
cgatgttggaccgcgggatggcacgcctgtgctgttcctgcacggtaacccgacctcgtcctacctgtggc
gcaacatcatcccgcatgtagcaccgagtcatcggtgcattgctccagacctgatcgggatgggaaaatcg
gacaaaccagacctcgattatttcttcgacgaccacgtccgctacctcgatgccttcatcgaagccttggg
tttggaagaggtcgtcctggtcatccacgactggggctcagctctcggattccactgggccaagcgcaatc
cggaacgggtcaaaggtattgcatgtatggaattcatccggcctatcccgacgtgggacgaatggccagaa
ttcgcccgtgagaccttccaggccttccggaccgccgacgtcggcgagagttcgatcatcgatcagaacgc
tttcatcgagggtgcgctcccgatggggrgtcgtccgtccgcttacgggtcgagatggaccactatcgcg
agcccttcctcaagcctgttgaccgagagccactgtggcgattcccaacgagctgccatcgccggtgag
cccgcgaacatcgtcgcgctcgtcgaggcatacatgaactggctgcaccagtccctgtcccgaagttgtt
gttctggggcacacccggcgtactgatccccggccgaagccgcgagacttgccgaaagcctccccaact
gcaagacagtggacatcggcccgggattgttcttgctccaggaagacaacccggaccttatcggcagtgag
atcgcgcgctggctcccggcactc (SEQ ID NO:17)

Seigtgfpfdphyvevlgermhyvdvgprdgtpvlflhgnptssylwrniiphvapshrciapdligmgks
dkpdldyffddhvryldafiealgleevvlvihdwgsalgfhwakrnpervkgiacmefirpiptwdewpe
faretfqafrtadvgreliidqnafiegalpmgvvrpltevemdhyrepflkpvdreplwrfpnelpiage
panivalveaymnwlhqspvpkllfwgtpgvlippaeaarlaeslpncktvdigpglfllqednpdligse
iarwlpal (SEQ ID NO:18)

V2n
Atggcagaaatcggtactggctttccattcgaccccattatgtggaagtcctgggcgagcgcatgcacta
cgtcgatgttggtccgcgcgatggcacccctgtgctgttcctgcacggtaacccgacctcctcctacctgt
ggcgcaacatcatcccgcatgttgcaccgacccatcgctgcattgctccagacctgatcggtatgggcaaa
tccgacaaaccagacctgggttatttcttcgacgaccacgtccgctacctggatgccttcatcgaagccct
gggtctggaagaggtcgtcctggtcattcacgactggggctcggctctgggttttccactgggccaagcgca
atccagagcgcgtcaaaggtattgcatgtatggagttcatccgccctatcccgacctgggacgaatggcca
gaatttgcccgcgagaccttccaggcctccgcaccacgacgtcggccgcgagctgatcatcgatcagaa
cgcttttatcgagggtacgctgccgatgggtgtcgtccgcccgctgactgaagtcgagatggaccattacc
gcgagccgttcctgaagcctgttgaccgcgagccactgtggcgcttcccaaacgagctgccaatcgccggt
gagccagcgaacatcgtcgcgctggtcgaagaatacatgaactggctgcaccagtccctgtcccgaagct
gctgttctggggcacccaggcgttctgatcccaccggccgaagccgctcgcctggccgaaagcctgccta
actgcaagactgtggacatcggccggggtctgaattttctgcaagaagacaacccggacctgatcggcagc
gagatcgcgcgctggctgtcgacgctgcaatat (SEQ ID NO:32)

Maeigtgfpfdphyvevlgermhyvdvgprdgtpvlflhgnptssylwrniiphvapthrciapdligmgk
sdkpdlgyffddhvryldafiealgleevvlvihdwgsalgfhwakrnpervkgiacmefirpiptwdewp
efaretfqafrttdvgreliidqnafiegtlpmgvvrpltevemdhyrepflkpvdreplwrfpnelpiag
epanivalveeymnwlhqspvpkllfwgtpgvlippaeaarlaeslpncktvdigpglnflqednpdligs
eiarwlstlqy (SEQ ID NO:22)

V3n
Atggcagaaatcggtactggctttccattcgaccccattatgtggaagtcctggcgagcgcatgcacta
cgtcgatgttggtccgcgcgatggcacccctgtgctgttcctgcacggtaacccgacctcctcctacctgt
ggcgcaacatcatcccgcatgttgcaccgacccatcgctgcattgctccagacctgatcggtatgggcaaa
tccgacaaaccagacctgggttatttcttcgacgaccacgtccgctacctggatgccttcatcgaagccct
gggtctggaagaggtcgtcctggtcattcacgactggggctcggctctgggttttccactgggccaagcgca
atccagagcgcgtcaaaggtattgcatgtatggagttcatccgccctatcccgacctgggacgaatggcca
gaatttgcccgcgagaccttccaggcctccgcaccacgacgtcggccgcgagctgatcatcgatcagaa

FIG. 19A cgcttttatcgagggtacgctgccgatgggtgtcgtccgcccgctgactgaagtcgagatggaccattacc
gcgagccgttcctgaagcctgttgaccgcgagccactgtggcgcttcccaaacgagctgccaatcgccggt
gagccagcgaacatcgtcgcgctggtcgaagaatacatgaactggctgcaccagtcccctgtcccgaagct
gctgttctggggcaccccaggcgttctgatcccaccggccgaagccgctcgcctggccgaaagcctgccta
actgcaagactgtggacatcggcccgggtctgaatctgctgcaagaagacaacccggacctgatcggcagc
gagatcgcgcgctggctgtcgacgctgcaatat (SEQ ID NO:33)

Maeigtgfpfdphyvevlgermhyvdvgprdgtpvlflhgnptssylwrniiphvapthrciapdligmgk
sdkpdlgyffddhvryldafiealgleevvlvihdwgsalgfhwakrnpervkgiacmefirpiptwdewp
efaretfqafrttdvgreliidqnafiegtlpmgvvrpltevemdhyrepflkpvdreplwrfpnelpiag
epanivalveeymnwlhqspvpkllfwgtpgvlippaeaarlaeslpncktvdigpglnllqednpdligs
eiarwlstlqy (SEQ ID NO:23)

V4n
Atggcagaaatcggtactggctttccattcgaccccattatgtggaagtcctgggcgagcgcatgcacta
cgtcgatgttggtccgcgcgatggcacccctgtgctgttcctgcacggtaacccgacctcctcctacctgt
ggcgcaacatcatcccgcatgttgcaccgacccatcgctgcattgctccagacctgatcggtatgggcaaa
tccgacaaaccagacctgggttatttcttcgacgaccacgtccgcttcctggatgccttcatcgaagccct
gggtctggaagaggtcgtcctggtcattcacgactggggctccgctctgggtttccactggccaagcgca
atccagagcgcgtcaaaggtattgcatgtatggagttcatccgccctatcccgacctgggacgaatggcca
gaatttgcccgcgagaccttccaggccttccgcaccaccgacgtcggccgcgagctgatcatcgatcagaa
cgcttttatcgagggtacgctgccgatgggtgtcgtccgcccgctgactgaagtcgagatggaccattacc
gcgagccgttcctgaagcctgttgaccgcgagccactgtggcgcttcccaaacgagctgccaatcgccggt
gagccagcgaacatcgtcgcgctggtcgaagaatacatggactggctgcaccagtcccctgtcccgaagct
gctgttctggggcaccccaggcgttctgatcccaccggccgaagccgctcgcctggccgaaagcctgccta
actgcaagactgtggacatcggcccgggtctgaattttctgcaagaagacaacccggacctgatcggcagc
gagatcgcgcgctggctgcaggagctgcaatat (SEQ ID NO:34)

Maeigtgfpfdphyvevlgermhyvdvgprdgtpvlflhgnptssylwrniiphvapthrciapdligmgk
sdkpdlgyffddhvrfldafiealgleevvlvihdwgsalgfhwakrnpervkgiacmefirpiptwdewp
efaretfqafrttdvgreliidqnafiegtlpmgvvrpltevemdhyrepflkpvdreplwrfpnelpiag
epanivalveeymdwlhqspvpkllfwgtpgvlippaeaarlaeslpncktvdigpglnflqednpdligs
eiarwlqelqy (SEQ ID NO:24)

V5n
Atggcagaaatcggtactggctttccattcgaccccattatgtggaagtcctgggcgagcgcatgcacta
cgtcgatgttggtccgcgcgatagcacccctgtgctgttcctgcacggtaacccgacctcctcctacctgt
ggcgcaacatcatcccgcatgttgcaccgacccatcgctgcattgctccagacctgatcggtatgggcaaa
tccgacaaaccagacctgggttatttcttcgacgaccacgtccgcttcctggatgccttcatcgaagccct
gggtctggaagaggtcgtcctggtcattcacgactggggctccgctctgggtttccactggccaagcgca
atccagagcgcgtcaaaggtattgcatgtatggagttcatccgccctatcccgacctgggacgaatggcca
gaatttgcccgcgagaccttccaggccttccgcaccaccgacgtcggccgcgagctgatcatcgatcagaa
cgcttttatcgagggtacgctgccgatgggtgtcgtccgcccgctgactgaagtcgagatggaccattacc
gcgagccgttcctgaagcctgttgaccgcgagccactgtggcgcttcccaaacgagctgccaatcgccggt
gagccagcgaacatcgtcgcgctggtcgaagaatacatggactggctgcaccagtcccctgtcccgaagct
gctgttctggggcaccccaggcgttctgatcccaccggccgaagccgctcgcctggccgaaagcctgccta
actgcaagactgtggacatcggcccgggtctgaatctgctgcaagaagacaacccggacctgatcggcagc
gagatcgcgcgctggctgcaggagctgcaatat (SEQ ID NO:35)

FIG. 19B

Maeigtgfpfdphyvevlgermhyvdvgprdstpvlflhgnptssylwrniiphvapthrciapdligmgk
sdkpdlgyffddhvrfldafiealgleevvlvihdwgsalgfhwakrnpervkgiacmefirpiptwdewp
efaretfqafrttdvgreliidqnafiegtlpmgvvrpltevemdhyrepflkpvdreplwrfpnelpiag
epanivalveeymdwlhqspvpkllfwgtpgvlippaeaarlaeslpncktvdigpglnllqednpdligs
eiarwlqelqy  (SEQ ID NO:25)

V6n
Atggcagaaatcggtactggctttccattcgaccccattatgtggaagtcctgggcgagcgcatgcacta
cgtcgatgttggtccgcgcgatggcacccctgtgctgttcctgcacggtaacccgacctcctcctacgtgt
ggcgcaacatcatcccgcatgttgcaccgacccatcgctgcattgctccagacctgatcggtatgggcaaa
tccgacaaaccagacctgggttatttcttcgacgaccacgtccgcttcatggatgccttcatcgaagccct
gggtctggaagaggtcgtcctggtcattcacgactggggctccgctctggtttccactgggccaagcgca
atccagagcgcgtcaaaggtattgcatttatggagttcatccgccctatcccgacctgggacgaatggcca
gaatttgcccgcgagaccttccaggccttccgcaccaccgacgtcggccgcaagctgatcatcgatcagaa
cgtttttatcgagggtacgctgccgatgggtgtcgtccgcccgctgactgaagtcgagatggaccattacc
gcgagccgttcctgaatcctgttgaccgcgagccactgtggcgcttcccaaacgagctgccaatcgccggt
gagccagcgaacatcgtcgcgctggtcgaagaatacatggactggctgcaccagtccctgtcccgaagct
gctgttctggggcacccaggcgttctgatcccaccggccgaagccgctcgcctggccaaaagcctgccta
actgcaaggctgtggacatcggcccgggtctgaatctgctgcaagaagacaacccggacctgatcggcagc
gagatcgcgcgctggctgtcgacgctgcaatat  (SEQ ID NO:36)

Maeigtgfpfdphyvevlgermhyvdvgprdgtpvlflhgnptssyvwrniiphvapthrciapdligmgk
sdkpdlgyffddhvrfmdafiealgleevvlvihdwgsalgfhwakrnpervkgiafmefirpiptwdewp
efaretfqafrttdvgrkliidqnvfiegtlpmgvvrpltevemdhyrepflnpvdreplwrfpnelpiag
epanivalveeymdwlhqspvpkllfwgtpgvlippaeaarlakslpnckavdigpglnllqednpdligs
eiarwlstlqy  (SEQ ID NO:26)

V7n
Atggcagaaatcggtactggctttccattcgaccccattatgtggaagtcctgggcgagcgcatgcacta
cgtcgatgttggtccgcgcgatggcacccctgtgctgttcctgcacggtaacccgacctcctcctacgtgt
ggcgcaacatcatcccgcatgttgcaccgacccatcgctgcattgctccagacctgatcggtatgggcaaa
tccgacaaaccagacctgggttatttcttcgacgaccacgtccgcttcatggatgccttcatcgaagccct
gggtctggaagaggtcgtcctggtcattcacgactggggctccgctctggtttccactgggccaagcgca
atccagagcgcgtcaaaggtattgcatttatggagttcatccgccctatcccgacctgggacgaatggcca
gaatttgcccgcgagaccttccaggccttccgcaccaccgacgtcggccgcaagctgatcatcgatcagaa
cgtttttatcgagggtacgctgccgatgggtgtcgtccgcccgctgactgaagtcgagatggaccattacc
gcgagccgttcctgaatcctgttgaccgcgagccactgtggcgcttcccaaacgagctgccaatcgccggt
gagccagcgaacatcgtcgcgctggtcgaagaatacatggactggctgcaccagtccctgtcccgaagct
gctgttctggggcacccaggcgttctgatcccaccggccgaagccgctcgcctggccaaaagcctgccta
actgcaaggctgtggacatcggcccgggtctgaatctgctgcaagaagacaacccggacctgatcggcagc
gagatcgcgcgctggctgtcgacgctcgagatttccggc  (SEQ ID NO:37)

Maeigtgfpfdphyvevlgermhyvdvgprdgtpvlflhgnptssyvwrniiphvapthrciapdligmgk
sdkpdlgyffddhvrfmdafiealgleevvlvihdwgsalgfhwakrnpervkgiafmefirpiptwdewp
efaretfqafrttdvgrkliidqnvfiegtlpmgvvrpltevemdhyrepflnpvdreplwrfpnelpiag
epanivalveeymdwlhqspvpkllfwgtpgvlippaeaarlakslpnckavdigpglnllqednpdligs
eiarwlstleisg  (SEQ ID NO:27)

*FIG. 19C*

```
Tccgaaatcggtactggctttccattcgaccccattatgtggaagtcctgggcgagcgcatgcactacgt
cgatgttggtccgcgcgatggcacccctgtgctgttcctgcacggtaacccgacctcctcctacctgtggc
gcaacatcatcccgcatgttgcaccgacccatcgctgcattgctccagacctgatcggtatgggcaaatcc
gacaaaccagacctgggttatttcttcgacgaccacgtccgctacctggatgccttcatcgaagccctggg
tctggaagaggtcgtcctggtcattcacgactggggctccgctctggtttccactgggccaagcgcaatc
cagagcgcgtcaaaggtattgcatgtatggagttcatccgccctatcccgacctgggacgaatggccagaa
tttgcccgcgagaccttccaggccttccgcaccaccgacgtcggccgcgagctgatcatcgatcagaacgc
ttttatcgagggtacgctgccgatgggtgtcgtccgccgctgactgaagtcgagatggaccattaccgcg
agccgttcctgaagcctgttgaccgcgagccactgtggcgcttcccaaacgagctgccaatcgccggtgag
ccagcgaacatcgtcgcgctggtcgaagaatacatgaactggctgcaccagtccctgtcccgaagctgct
gttctggggcacccaggcgttctgatcccaccggccgaagccgctcgcctggccgaaagcctgcctaact
gcaagactgtggacatcggcccgggtctgaatttctgcaagaagacaacccggacctgatcggcagcgag
atcgcgcgctggctgtcgacgctgcaatat  (SEQ ID NO:52)
```

Seigtgfpfdphyvevlgermhyvdvgprdgtpvlflhgnptssylwrniiphvapthrciapdligmgks
dkpdlgyffddhvryldafiealgleevvlvihdwgsalgfhwakrnpervkgiacmefirpiptwdewpe
faretfqafrttdvgrelliidqnafiegtlpmgvvrpltevemdhyrepflkpvdreplwrfpnelpiage
panivalveeymnwlhqspvpkllfwgtpgvlippaeaarlaeslpncktvdigpglnflqednpdligse
iarwlstlqy  (SEQ ID NO:42)

V3c
```
Tccgaaatcggtactggctttccattcgaccccattatgtggaagtcctgggcgagcgcatgcactacgt
cgatgttggtccgcgcgatggcacccctgtgctgttcctgcacggtaacccgacctcctcctacctgtggc
gcaacatcatcccgcatgttgcaccgacccatcgctgcattgctccagacctgatcggtatgggcaaatcc
gacaaaccagacctgggttatttcttcgacgaccacgtccgctacctggatgccttcatcgaagccctggg
tctggaagaggtcgtcctggtcattcacgactggggctccgctctggtttccactgggccaagcgcaatc
cagagcgcgtcaaaggtattgcatgtatggagttcatccgccctatcccgacctgggacgaatggccagaa
tttgcccgcgagaccttccaggccttccgcaccaccgacgtcggccgcgagctgatcatcgatcagaacgc
ttttatcgagggtacgctgccgatgggtgtcgtccgccgctgactgaagtcgagatggaccattaccgcg
agccgttcctgaagcctgttgaccgcgagccactgtggcgcttcccaaacgagctgccaatcgccggtgag
ccagcgaacatcgtcgcgctggtcgaagaatacatgaactggctgcaccagtccctgtcccgaagctgct
gttctggggcacccaggcgttctgatcccaccggccgaagccgctcgcctggccgaaagcctgcctaact
gcaagactgtggacatcggcccgggtctgaatctgctgcaagaagacaacccggacctgatcggcagcgag
atcgcgcgctggctgtcgacgctgcaatat  (SEQ ID NO:53)
```

Seigtgfpfdphyvevlgermhyvdvgprdgtpvlflhgnptssylwrniiphvapthrciapdligmgks
dkpdlgyffddhvryldafiealgleevvlvihdwgsalgfhwakrnpervkgiacmefirpiptwdewpe
faretfqafrttdvgrelliidqnafiegtlpmgvvrpltevemdhyrepflkpvdreplwrfpnelpiage
panivalveeymnwlhqspvpkllfwgtpgvlippaeaarlaeslpncktvdigpglnllqednpdligse
iarwlstlqy  (SEQ ID NO:43)

V4c
```
Tccgaaatcggtactggctttccattcgaccccattatgtggaagtcctgggcgagcgcatgcactacgt
cgatgttggtccgcgcgatggcacccctgtgctgttcctgcacggtaacccgacctcctcctacctgtggc
gcaacatcatcccgcatgttgcaccgacccatcgctgcattgctccagacctgatcggtatgggcaaatcc
gacaaaccagacctgggttatttcttcgacgaccacgtccgcttcctggatgccttcatcgaagccctggg
tctggaagaggtcgtcctggtcattcacgactggggctccgctctggtttccactgggccaagcgcaatc
cagagcgcgtcaaaggtattgcatgtatggagttcatccgccctatcccgacctgggacgaatggccagaa
tttgcccgcgagaccttccaggccttccgcaccaccgacgtcggccgcgagctgatcatcgatcagaacgc
ttttatcgagggtacgctgccgatgggtgtcgtccgccgctgactgaagtcgagatggaccattaccgcg
agccgttcctgaagcctgttgaccgcgagccactgtggcgcttcccaaacgagctgccaatcgccggtgag
```

FIG. 19D ccagcgaacatcgtcgcgctggtcgaagaatacatggactggctgcaccagtccctgtcccgaagctgct
gttctggggcacccaggcgttctgatcccaccggccgaagccgctcgcctggccgaaagcctgcctaact
gcaagactgtggacatcggcccgggtctgaattttctgcaagaagacaacccggacctgatcggcagcgag
atcgcgcgctggctgcaggagctgcaatat (SEQ ID NO:54)

Seigtgfpfdphyvevlgermhyvdvgprdgtpvlflhgnptssylwrniiphvapthrciapdligmgks
dkpdlgyffddhvrfldafiealgleevvlvihdwgsalgfhwakrnpervkgiacmefirpiptwdewpe
faretfqafrttdvgreliidqnafiegtlpmgvvrpltevemdhyrepflkpvdreplwrfpnelpiage
panivalveeymdwlhqspvpkllfwgtpgvlippaeaarlaeslpncktvdigpglnflqednpdligse
iarwlqelqy (SEQ ID NO:44)

V5c
Tccgaaatcggtactggctttccattcgaccccattatgtggaagtcctgggcgagcgcatgcactacgt
cgatgttggtccgcgcgatagcacccctgtgctgttcctgcacggtaacccgacctcctcctacctgtggc
gcaacatcatcccgcatgttgcaccgacccatcgctgcattgctcagacctgatcggtatgggcaaatcc
gacaaaccagacctgggttatttcttcgacgaccacgtccgcttcctggatgccttcatcgaagccctggg
tctggaagaggtcgtcctggtcattcacgactggggctccgctctgggtttccactgggccaagcgcaatc
cagagcgcgtcaaaggtattgcatgtatggagttcatcgccctatcccgacctgggacgaatggccagaa
tttgcccgcgagaccttccaggccttccgcaccaccgacgtcggccgcgagctgatcatcgatcagaacgc
ttttatcgagggtacgctgccgatgggtgtcgtccgcccgctgactgaagtcgagatggaccattaccgcg
agccgttcctgaagcctgttgaccgcgagccactgtggcgcttcccaaacgagctgccaatcgccggtgag
ccagcgaacatcgtcgcgctggtcgaagaatacatggactggctgcaccagtccctgtcccgaagctgct
gttctggggcacccaggcgttctgatcccaccggccgaagccgctcgcctggccgaaagcctgcctaact
gcaagactgtggacatcggcccgggtctgaatctgctgcaagaagacaacccggacctgatcggcagcgag
atcgcgcgctggctgcaggagctgcaatat (SEQ ID NO:55)

Seigtgfpfdphyvevlgermhyvdvgprdstpvlflhgnptssylwrniiphvapthrciapdligmgks
dkpdlgyffddhvrfldafiealgleevvlvihdwgsalgfhwakrnpervkgiacmefirpiptwdewpe
faretfqafrttdvgreliidqnafiegtlpmgvvrpltevemdhyrepflkpvdreplwrfpnelpiage
panivalveeymdwlhqspvpkllfwgtpgvlippaeaarlaeslpncktvdigpglnllqednpdligse
iarwlqelqy (SEQ ID NO:45)

V6c
Tccgaaatcggtactggctttccattcgaccccattatgtggaagtcctgggcgagcgcatgcactacgt
cgatgttggtccgcgcgatggcacccctgtgctgttcctgcacggtaacccgacctcctcctacgtgtggc
gcaacatcatcccgcatgttgcaccgacccatcgctgcattgctcagacctgatcggtatgggcaaatcc
gacaaaccagacctgggttatttcttcgacgaccacgtccgcttcatggatgccttcatcgaagccctggg
tctggaagaggtcgtcctggtcattcacgactggggctccgctctgggtttccactgggccaagcgcaatc
cagagcgcgtcaaaggtattgcatttatggagttcatcgccctatcccgacctgggacgaatggccagaa
tttgcccgcgagaccttccaggccttccgcaccaccgacgtcggccgcaagctgatcatcgatcagaacgt
ttttatcgagggtacgctgccgatgggtgtcgtccgcccgctgactgaagtcgagatggaccattaccgcg
agccgttcctgaatcctgttgaccgcgagccactgtggcgcttcccaaacgagctgccaatcgccggtgag
ccagcgaacatcgtcgcgctggtcgaagaatacatggactggctgcaccagtccctgtcccgaagctgct
gttctggggcacccaggcgttctgatcccaccggccgaagccgctcgcctggccaaaagcctgcctaact
gcaaggctgtggacatcggcccgggtctgaatctgctgcaagaagacaacccggacctgatcggcagcgag
atcgcgcgctggctgtcgacgctgcaatat (SEQ ID NO:56)

Seigtgfpfdphyvevlgermhyvdvgprdgtpvlflhgnptssyvwrniiphvapthrciapdligmgks
dkpdlgyffddhvrfmdafiealgleevvlvihdwgsalgfhwakrnpervkgiafmefirpiptwdewpe
faretfqafrttdvgrkliidqnvfiegtlpmgvvrpltevemdhyrepflnpvdreplwrfpnelpiage

*FIG. 19E* panivalveeymdwlhqspvpkllfwgtpgvlippaeaarlakslpnckavdigpglnllqednpdligse
iarwlstlqy   (SEQ ID NO:46)

V7c
Tccgaaatcggtactggcttcccattcgaccccattatgtggaagtcctgggcgagcgcatgcactacgt
cgatgttggtccgcgcgatggcacccctgtgctgttcctgcacggtaacccgacctcctcctacgtgtggc
gcaacatcatcccgcatgttgcaccgacccatcgctgcattgctccagacctgatcggtatgggcaaatcc
gacaaaccagacctgggttattcttcgacgaccacgtccgcttcatggatgccttcatcgaagccctggg
tctggaagaggtcgtcctggtcattcacgactggggctccgctctgggtttccactgggccaagcgcaatc
cagagcgcgtcaaaggtattgcatttatggagttcatccgccctatcccgacctgggacgaatggccagaa
tttgcccgcgagaccttccaggccttccgcaccaccgacgtcggccgcaagctgatcatcgatcagaacgt
tttatcgagggtacgctgccgatgggtgtcgtccgcccgctgactgaagtcgagatggaccattaccgcg
agccgttcctgaatcctgttgaccgcgagccactgtggcgcttcccaaacgagctgccaatcgccggtgag
ccagcgaacatcgtcgcgctggtcgaagaatacatggactggctgcaccagtcccctgtcccgaagctgct
gttctggggcacccaggcgttctgatcccaccggccgaagccgctcgcctggccaaaagcctgcctaact
gcaaggctgtggacatcggcccgggtctgaatctgctgcaagaagacaacccggacctgatcggcagcgag
atcgcgcgctggctgtctactctggagatttccggt   (SEQ ID NO:57)

Seigtgfpfdphyvevlgermhyvdvgprdgtpvlflhgnptssyvwrniiphvapthrciapdligmgks
dkpdlgyffddhvrfmdafiealgleevvlvihdwgsalgfhwakrnpervkgiafmefirpiptwdewpe
faretfqafrttdvgrklidqnvfiegtlpmgvvrpltevemdhyrepflnpvdreplwrfpnelpiage
panivalveeymdwlhqspvpkllfwgtpgvlippaeaarlakslpnckavdigpglnllqednpdligse
iarwlstleisg (SEQ ID NO:47)

Connector when DhaA is on N-terminus:

GAG CCA ACC ACT GAG GAT CTG TAC TTT CAG AGC GAT AAC GCG ATC GCC
Glu Pro Thr Thr Glu Asp Leu Tyr Phe Gln Ser Asp Asn Ala Ile Ala
(SEQ ID NO:48)

Connector when DhaA is on the C-terminus:

GTT TCT CTC GAG CCA ACC ACT GAG GAT CTG TAC TTT CAG AGC GAT AAC GAT
Val Ser Leu Glu Pro Thr Thr Glu Asp Leu Tyr Phe Gln Ser Asp Asn Asp
(SEQ ID NO:49)

V2 (min/no tail)

X₁X₂eigtgfpfdphyvevlgermhyvdvgprdgtpvlflhgnptssylwrniiphvapthrciapdligmg
ksdkpdlgyffddhvryldafiealgleevvlvihdwgsalgfhwakrnpervkgiacmefirpiptwdew
pefaretfqafrttdvgreliidqnafiegtlpmgvvrpltevemdhyrepflkpvdreplwrfpnelpia
gepanivalveeymnwlhqspvpkllfwgtpgvlippaeaarlaeslpncktvdigpglnflqednpdlig
seiarwlstl wherein X₁ is M or G and X₂ is A or S
(SEQ ID NO:60)

V3 (min/no tail)

FIG. 19F

X₁X₂eigtgfpfdphyvevlgermhyvdvgprdgtpvlflhgnptssylwrniiphvapthrciapdligmg
ksdkpdlgyffddhvryldafiealgleevvlvihdwgsalgfhwakrnpervkgiacmefirpiptwdew
pefaretfqafrttdvgreliidqnafiegtlpmgvvrpltevemdhyrepflkpvdreplwrfpnelpia
gepanivalveeymnwlhqspvpkllfwgtpgvlippaeaarlaeslpncktvdigpglnllqednpdlig
seiarwlstl wherein X₁ is M or G and X₂ is A or S
(SEQ ID NO:61)

V4 (min/no tail)

X₁X₂eigtgfpfdphyvevlgermhyvdvgprdgtpvlflhgnptssylwrniiphvapthrciapdligmg
ksdkpdlgyffddhvrfldafiealgleevvlvihdwgsalgfhwakrnpervkgiacmefirpiptwdew
pefaretfqafrttdvgreliidqnafiegtlpmgvvrpltevemdhyrepflkpvdreplwrfpnelpia
gepanivalveeymdwlhqspvpkllfwgtpgvlippaeaarlaeslpncktvdigpglnflqednpdlig
seiarwlqel wherein X₁ is M or G and X₂ is A or S
(SEQ ID NO:62)

V5 (min/no tail)

X₁X₂eigtgfpfdphyvevlgermhyvdvgprdstpvlflhgnptssylwrniiphvapthrciapdligmg
ksdkpdlgyffddhvrfldafiealgleevvlvihdwgsalgfhwakrnpervkgiacmefirpiptwdew
pefaretfqafrttdvgreliidqnafiegtlpmgvvrpltevemdhyrepflkpvdreplwrfpnelpia
gepanivalveeymdwlhqspvpkllfwgtpgvlippaeaarlaeslpncktvdigpglnllqednpdlig
seiarwlqel wherein X₁ is M or G and X₂ is A or S
(SEQ ID NO:63)

V6 (min/no tail)

X₁X₂eigtgfpfdphyvevlgermhyvdvgprdgtpvlflhgnptssyvwrniiphvapthrciapdligmg
ksdkpdlgyffddhvrfmdafiealgleevvlvihdwgsalgfhwakrnpervkgiafmefirpiptwdew
pefaretfqafrttdvgrkliidqnvfiegtlpmgvvrpltevemdhyrepflnpvdreplwrfpnelpia
gepanivalveeymdwlhqspvpkllfwgtpgvlippaeaarlakslpnckavdigpglnllqednpdlig
seiarwlstl wherein X₁ is M or G and X₂ is A or S
(SEQ ID NO:64)

V7 (min/no tail)

X₁X₂eigtgfpfdphyvevlgermhyvdvgprdgtpvlflhgnptssyvwrniiphvapthrciapdligmg
ksdkpdlgyffddhvrfmdafiealgleevvlvihdwgsalgfhwakrnpervkgiafmefirpiptwdew
pefaretfqafrttdvgrkliidqnvfiegtlpmgvvrpltevemdhyrepflnpvdreplwrfpnelpia
gepanivalveeymdwlhqspvpkllfwgtpgvlippaeaarlakslpnckavdigpglnllqednpdlig
seiarwlstl wherein X₁ is M or G and X₂ is A or S
(SEQ ID NO:65)

V2 (min/tail)

X₁X₂eigtgfpfdphyvevlgermhyvdvgprdgtpvlflhgnptssylwrniiphvapthrciapdligmg
ksdkpdlgyffddhvryldafiealgleevvlvihdwgsalgfhwakrnpervkgiacmefirpiptwdew
pefaretfqafrttdvgreliidqnafiegtlpmgvvrpltevemdhyrepflkpvdreplwrfpnelpia
gepanivalveeymnwlhqspvpkllfwgtpgvlippaeaarlaeslpncktvdigpglnflqednpdlig
seiarwlX₃X₄LX₅X₆X₇X₈

FIG. 19G wherein $X_1$ is M or G, $X_2$ is A or S, $X_3$ is S, Q or P, $X_4$ is T, E or A, $X_5$ is Q or E, $X_6$ is Y or I, $X_7$ is S or absent, and $X_8$ is G or absent
(SEQ ID NO:66)

V3 (min/tail)

$X_1X_2$eigtgfpfdphyvevlgermhyvdvgprdgtpvlflhgnptssylwrniiphvapthrciapdligmg
ksdkpdlgyffddhvryldafiealgleevvlvihdwgsalgfhwakrnpervkgiacmefirpiptwdew
pefaretfqafrttdvgreliidqnafiegtlpmgvvrpltevemdhyrepflkpvdreplwrfpnelpia
gepanivalveeymnwlhqspvpkllfwgtpgvlippaeaarlaeslpncktvdigpglnllqednpdlig
seiarwl$X_3X_4LX_5X_6X_7X_8$
wherein $X_1$ is M or G, $X_2$ is A or S, $X_3$ is S, Q or P, $X_4$ is T, E or A, $X_5$ is Q or E, $X_6$ is Y or I, $X_7$ is S or absent, and $X_8$ is G or absent (SEQ ID NO:67)

V4 (min/tail)

$X_1X_2$eigtgfpfdphyvevlgermhyvdvgprdgtpvlflhgnptssylwrniiphvapthrciapdligmg
ksdkpdlgyffddhvrfldafiealgleevvlvihdwgsalgfhwakrnpervkgiacmefirpiptwdew
pefaretfqafrttdvgreliidqnafiegtlpmgvvrpltevemdhyrepflkpvdreplwrfpnelpia
gepanivalveeymdwlhqspvpkllfwgtpgvlippaeaarlaeslpncktvdigpglnflqednpdlig
seiarwl$X_3X_4LX_5X_6X_7X_8$
wherein $X_1$ is M or G, $X_2$ is A or S, $X_3$ is S, Q or P, $X_4$ is T, E or A, $X_5$ is Q or E, $X_6$ is Y or I, $X_7$ is S or absent, and $X_8$ is G or absent (SEQ ID NO:68)

V5 (min/tail)

$X_1X_2$eigtgfpfdphyvevlgermhyvdvgprdstpvlflhgnptssylwrniiphvapthrciapdligmg
ksdkpdlgyffddhvrfldafiealgleevvlvihdwgsalgfhwakrnpervkgiacmefirpiptwdew
pefaretfqafrttdvgreliidqnafiegtlpmgvvrpltevemdhyrepflkpvdreplwrfpnelpia
gepanivalveeymdwlhqspvpkllfwgtpgvlippaeaarlaeslpncktvdigpglnllqednpdlig
seiarwl$X_3X_4LX_5X_6X_7X_8$
wherein $X_1$ is M or G, $X_2$ is A or S, $X_3$ is S, Q or P, $X_4$ is T, E or A, $X_5$ is Q or E, $X_6$ is Y or I, $X_7$ is S or absent, and $X_8$ is G or absent (SEQ ID NO:69)

V6 (min/tail)

$X_1X_2$eigtgfpfdphyvevlgermhyvdvgprdgtpvlflhgnptssyvwrniiphvapthrciapdligmg
ksdkpdlgyffddhvrfmdafiealgleevvlvihdwgsalgfhwakrnpervkgiafmefirpiptwdew
pefaretfqafrttdvgrklidqnvfiegtlpmgvvrpltevemdhyrepflnpvdreplwrfpnelpia
gepanivalveeymdwlhqspvpkllfwgtpgvlippaeaarlakslpnckavdigpglnllqednpdlig
seiarwl$X_3X_4LX_5X_6X_7X_8$
wherein $X_1$ is M or G, $X_2$ is A or S, $X_3$ is S, Q or P, $X_4$ is T, E or A, $X_5$ is Q or E, $X_6$ is Y or I, $X_7$ is S or absent, and $X_8$ is G or absent (SEQ ID NO:70)

*FIG. 19H*

```
V7 (min/tail)

X₁X₂eigtgfpfdphyvevlgermhyvdvgprdgtpvlflhgnptssyvwrniiphvapthrciapdligmg
ksdkpdlgyffddhvrfmdafiealgleevvlvihdwgsalgfhwakrnpervkgiafmefirpiptwdew
pefaretfqafrttdvgrklidqnvfiegtlpmgvvrpltevemdhyrepflnpvdreplwrfpnelpia
gepanivalveeymdwlhqspvpkllfwgtpgvlippaeaarlakslpnckavdigpglnllqednpdlig
seiarwlX₃X₄LX₅X₆X₇X₈
wherein X₁ is M or G, X₂ is A or S, X₃ is S, Q or P, X₄ is T, E or A, X₅ is
Q or E, X₆ is Y or I, X₇ is S or absent, and X₈ is G or absent (SEQ ID NO:71)
```

*FIG. 19I*

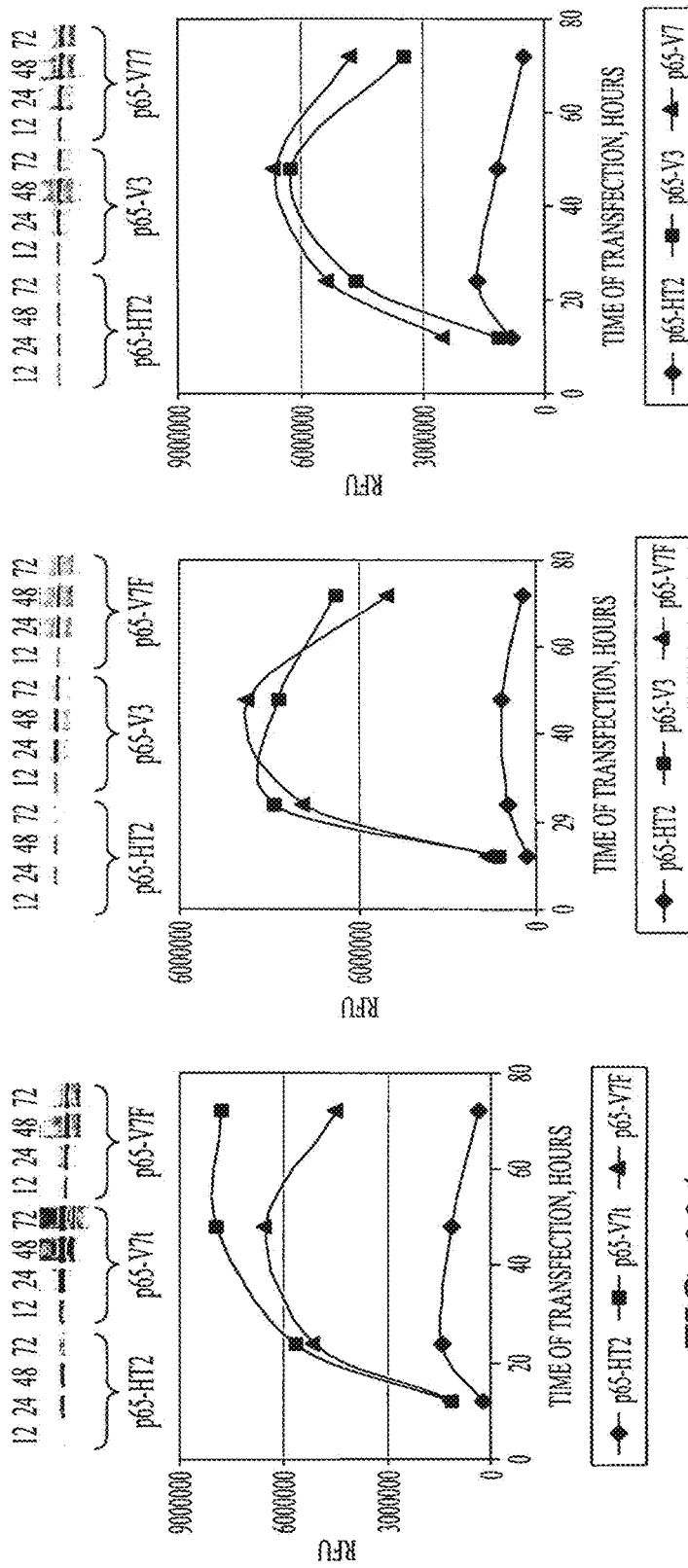

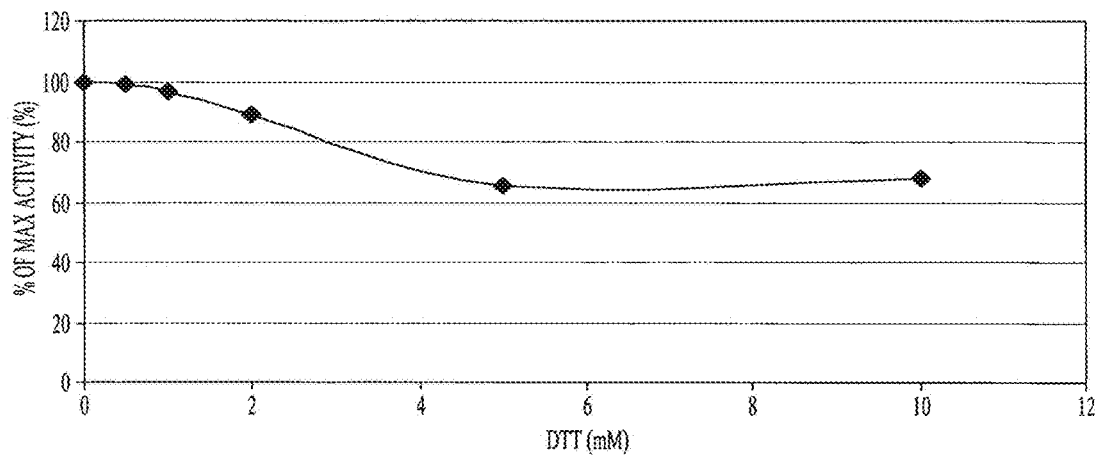
FIG. 24
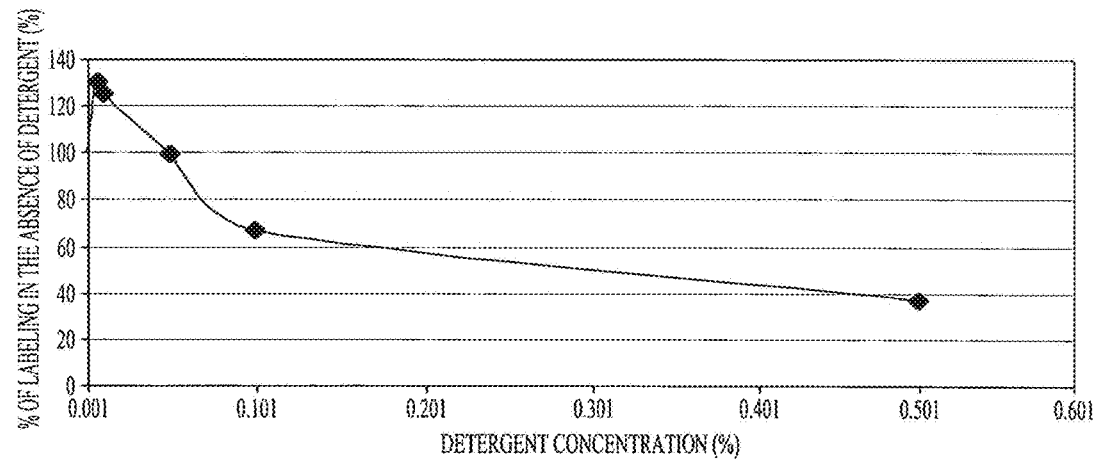
FIG. 25A
| DETERGENT | INCREASED LABELING KINETICS | INHIBITION |
|---|---|---|
| DEGITONIN | ≤ 0.01% | ≥ 0.1% |
| | | |
| | | |
| | | |
| | | |
FIG. 25B

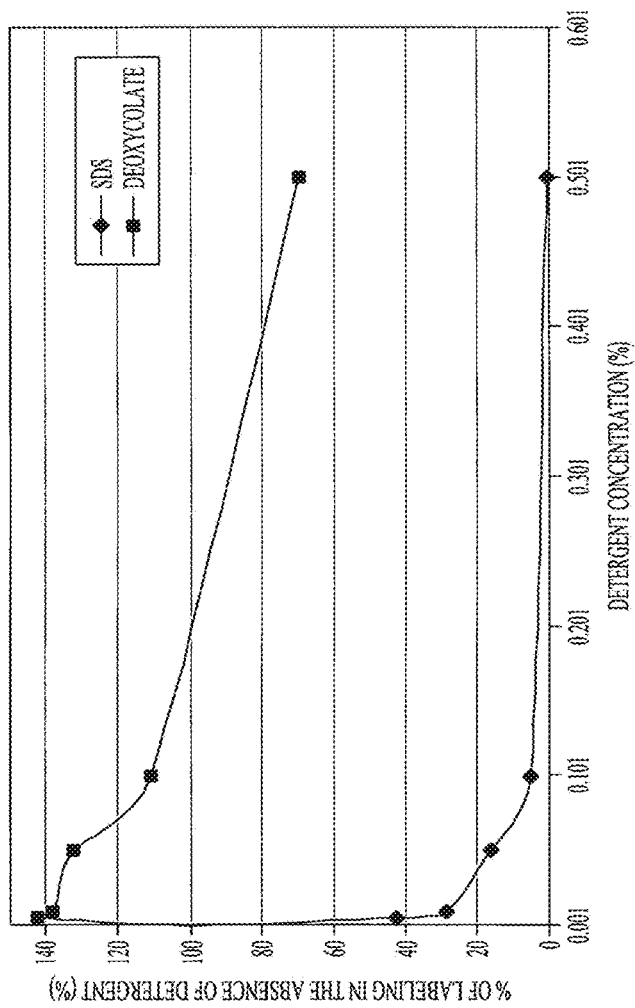

MUTANT HYDROLASE PROTEINS WITH ENHANCED KINETICS AND FUNCTIONAL EXPRESSION

CROSS REFERENCE TO RELATED APPLICATIONS

This application is a continuation of U.S. application Ser. No. 15/414,291, filed Jan. 24, 2017, U.S. application Ser. No. 14/285,327, filed May 22, 2014, now U.S. Pat. No. 9,593,316, which is a continuation of U.S. application Ser. No. 13/863,924, filed Apr. 16, 2013, now U.S. Pat. No. 8,748,148, which is a divisional of U.S. application Ser. No. 11/978,950, filed Oct. 30, 2007, now U.S. Pat. No. 8,420,367, which claims the benefit of the filing date of U.S. application Ser. No. 60/855,237, filed on Oct. 30, 2006, and of U.S. application Ser. No. 60/930,201, filed on May 15, 2007, the disclosures of which are incorporated by reference herein.

BACKGROUND

The specific detection of a molecule is a keystone in understanding the role of that molecule in the cell. Labels, e.g., those that are covalently linked to a molecule of interest, permit the ready detection of that molecule in a complex mixture. The label may be one that is added by chemical synthesis in vitro or attached in vivo, e.g., via recombinant techniques. For instance, the attachment of fluorescent or other labels onto proteins has traditionally been accomplished by in vitro chemical modification after protein purification (Hermanson, 1996). For in vivo attachment of a label, green fluorescent protein (GFP) from the jellyfish Aequorea victoria can be genetically fused with many host proteins to produce fluorescent chimeras in situ (Tsien, 1998; Chalfie et al., 1998). However, while GFP-based indicators are currently employed in a variety of assays, e.g., measuring pH (Kneen et al., 1998; Llopis et al., 1998; Miesenböck et al., 1998), $Ca^{2+}$ (Miyawaki et al., 1997; Rosomer et al., 1997), and membrane potential (Siegel et al., 1997), the fluorescence of intrinsically labeled proteins such as GFP is limited by the properties of protein structure, e.g., a limited range of fluorescent colors and relatively low intrinsic brightness (Cubitt et al., 1995; Ormö et al., 1996).

To address the deficiencies of GFP labeling in situ, Griffen et al. (1998) synthesized a tight-binding pair of molecular components: a small receptor domain composed of as few as six natural amino acids and a small (<700 dalton), synthetic ligand that could be linked to various spectroscopic probes or crosslinks. The receptor domain included four cysteines at the i, i+1, i+4, and i+5 positions of an c helix and the ligand was 4′,5′-bis(1,3,2-dithioarsolan-2-yl)fluorescein (FLASH). Griffen et al. disclose that the ligand had relatively few binding sites in nontransfected mammalian cells, was membrane-permeant and was nonfluorescent until it bound with high affinity and specificity to a tetracysteine domain in a recombinant protein, resulting in cells being fluorescently labeled ("FLASH" labeled) with a nanomolar or lower dissociation constant. However, with respect to background binding in cells, Stroffekova et al. (2001) disclose that FLASH-$EDT_2$ binds non-specifically to endogenous cysteine-rich proteins. Furthermore, labeling proteins by FLASH is limited by the range of fluorophores that may be used.

Receptor-mediated targeting methods use genetically encoded targeting sequences to localize fluorophores to virtually any cellular site, provided that the targeted protein is able to fold properly. For example, Farinas et al. (1999) disclose that cDNA transfection was used to target a single-chain antibody (sFv) to a specified site in a cell. Farinas et al. disclose that conjugates of a hapten (4-ethoxymethylene-2-phenyl-2-oxazolin-5-one, phOx) and a fluorescent probe (e.g., BODIPY Fl, tetramethylrhodamine, and fluorescein) were bound with high affinity (about 5 nM) to the subcellular site for the sFv in living Chinese hamster ovary cells, indicating that the targeted antibody functioned as a high affinity receptor for the cell-permeable hapten-fluorophore conjugates. Nevertheless, functional sFv expression may be relatively poor in reducing environments.

Thus, what is needed is an improved method to label a desired molecule.

SUMMARY OF THE INVENTION

While certain proteins are effective for a variety of in vivo applications, they may be less than optimal for in vitro applications (e.g., pull downs) due to their level of functional expression in E. coli and cell-free expression systems. The present invention provides mutant hydrolase sequences that exhibit improved functional expression in a variety of systems, as determined by improved fluorescence polarization (FP) signal, and enhanced protein production, as measured by active protein (substrate labeling) and total protein. Also described are sequences that result in mutant hydrolase proteins with improved intrinsic binding kinetics.

The invention provides methods, compositions and kits for tethering (linking), e.g., via a covalent or otherwise stable bond, one or more functional groups to a protein of the invention or to a fusion protein (chimera) which includes a protein of the invention. A protein of the invention (mutant hydrolase) is structurally related to a wild-type (native) hydrolase but includes at least one amino acid substitution, e.g., one that results in improved functional expression or improved binding kinetics, and in some embodiments at least two amino acid substitutions, e.g., one that results in stable bond formation with a hydrolase substrate and at least one other that results in improved functional expression, improved binding kinetics, or both, relative to the corresponding wild-type hydrolase. The aforementioned tethering occurs, for instance, in solution or suspension, in a cell, on a solid support or at solution/surface interfaces, by employing a substrate for a hydrolase which includes a reactive group and which has been modified to include one or more functional groups.

In one embodiment, the mutant hydrolase has at least about 80% or more, e.g., at least about 85%, 90%, 95% or 98%, but less than 100%, amino acid sequence identity to a corresponding wild-type hydrolase, i.e., the mutant hydrolase includes a plurality of substitutions. In one embodiment, the mutant hydrolase has at least about 80% or more, e.g., at least about 85%, 90%, 95% or 98%, but less than 100%, amino acid sequence identity to SEQ ID NO: 1, i.e., the mutant hydrolase includes a plurality of substitutions. Those substitutions include those that provide for stable bond formation and improved functional expression and/or binding kinetics, as well as those in regions tolerant to substitution, i.e., regions which do not alter the function(s) of a mutant hydrolase of the invention. Thus, in one embodiment, a mutant hydrolase of the invention includes at least two amino acid substitutions relative to a corresponding wild-type hydrolase, where one amino acid substitution results in the mutant hydrolase forming a bond with the substrate which is more stable than the bond formed between the corresponding wild-type hydrolase and the substrate. The one substitution is at an amino acid residue that in the corresponding wild-type hydrolase is associated with activating a water molecule which cleaves the bond formed between the corresponding wild-type hydrolase and the substrate or at an amino acid residue in the corresponding wild-type hydrolase that forms an ester intermediate with the substrate, or has a substitution at both residues. Another substitution is at a residue which improves functional expression, binding kinetics, or both, of the mutant hydrolase, e.g., relative to a mutant hydrolase with only the substitution that results in stable bond formation with the substrate.

In one embodiment, the mutant hydrolase has one amino acid substitution that results in the mutant hydrolase forming a bond with the substrate which is more stable than the bond formed between the corresponding wild-type hydrolase and the substrate, where the substitution is at an amino acid residue in the corresponding wild-type hydrolase that is associated with activating a water molecule which cleaves the bond formed between the corresponding wild-type hydrolase and the substrate or at an amino acid residue in the corresponding wild-type hydrolase that forms an ester intermediate with the substrate. In one embodiment, the substitution at an amino acid residue that is associated with activating a water molecule which cleaves the bond formed between the corresponding wild-type hydrolase and the substrate, is a substitution at a position corresponding position 272 in SEQ ID NO:1. In one embodiment, the substitution at an amino acid residue that forms an ester intermediate with the substrate is a substitution at a position corresponding to position 106 in SEQ ID NO:1. In one embodiment, the mutant hydrolase has substitution at a position corresponding to position 272 in SEQ ID NO: 1 and at a position corresponding to position 106 in SEQ ID NO:1. A substitution in a mutant hydrolase that provides for improved expression or binding kinetics relative to a corresponding mutant hydrolase with a substitution that provides for stable bond formation relative to a corresponding wild-type hydrolase, includes a substitution at one or more of the following positions: a position corresponding to position 5, 11, 20, 30, 32, 47, 58, 60, 65, 78, 80, 87, 88, 94, 109, 113, 117, 118, 124, 128, 134, 136, 150, 151, 155, 157, 160, 167, 172, 175, 176, 187, 195, 204, 221, 224, 227, 231, 250, 256, 257, 263, 264, 273, 277, 282, 291 or 292 of SEQ ID NO: 1. The mutant hydrolase may thus have a plurality of substitutions including a plurality of substitutions at positions corresponding to positions 5, 11, 20, 30, 32, 47, 58, 60, 65, 78, 80, 87, 88, 94, 109, 113, 117, 118, 124, 128, 134, 136, 150, 151, 155, 157, 160, 167, 172, 187, 195, 204, 221, 224, 227, 231, 250, 256, 257, 263, 264, 277, 282, 291 or 292 of SEQ ID NO: 1, at least one of which confers improved expression or binding kinetics, and may include further substitutions in positions tolerant to substitution. In one embodiment, the mutant hydrolase may have a plurality of substitutions including a plurality of substitutions at positions corresponding to positions 5, 7, 11, 12, 20, 30, 32, 47, 54, 55, 56, 58, 60, 65, 78, 80, 82, 87, 88, 94, 96, 109, 113, 116, 117, 118, 121, 124, 128, 131, 134, 136, 144, 147, 150, 151, 155, 157, 160, 161, 164, 165, 167, 172, 175, 176, 180, 182, 183, 187, 195, 197, 204, 218, 221, 224, 227, 231, 233, 250, 256, 257, 263, 264, 273, 277, 280, 282, 288, 291, 292, and/or 294 of SEQ ID NO: 1. In one embodiment, the mutant hydrolase is a mutant dehalogenase with a plurality of substitutions, e.g., at least 5, 10, 15 but less than 60, e.g., 50 or fewer substitutions, which includes a substitution at a position corresponding to position 106 and/or 272 in SEQ ID NO: 1 that results in the mutant dehalogenase forming a bond with a dehalogenase substrate which is more stable than the bond formed between a corresponding wild-type dehalogenase and the substrate, and a plurality of substitutions, e.g., at least 5, 10, 15 but less than 60 substitutions, which may include a plurality of substitutions corresponding to position 5, 11, 20, 30, 32, 47, 58, 60, 65, 78, 80, 87, 88, 94, 109, 113, 117, 118, 124, 128, 134, 136, 150, 151, 155, 157, 160, 167, 172, 175, 176, 187, 195, 204, 221, 224, 227, 231, 250, 256, 257, 263, 264, 273, 277, 282, 291 or 292 of SEQ ID NO: 1, at least one of which confers improved expression or binding kinetics, e.g., one or more of positions 5, 11, 20, 30, 32, 47, 58, 60, 65, 78, 80, 87, 88, 94, 109, 113, 117, 118, 124, 128, 134, 136, 150, 151, 155, 157, 160, 167, 172, 187, 195, 204, 221, 224, 227, 231, 250, 256, 257, 263, 264, 277, 282, 291 or 292, as well as other positions tolerant to substitution.

In one embodiment, the mutant hydrolase has at least three amino acid substitutions relative to a corresponding wild-type hydrolase. Two amino acid substitutions result in the mutant hydrolase forming a bond with the substrate which is more stable than the bond formed between the corresponding wild-type hydrolase and the substrate, where one substitution is at an amino acid residue in the corresponding wild-type hydrolase that is associated with activating a water molecule which cleaves the bond formed between the corresponding wild-type hydrolase and the substrate, and the other substitution is at an amino acid residue in the corresponding wild-type hydrolase that forms an ester intermediate with the substrate. At least one other substitution is at position corresponding to position 5, 11, 20, 30, 32, 47, 58, 60, 65, 78, 80, 87, 88, 94, 109, 113, 117, 118, 124, 128, 134, 136, 150, 151, 155, 157, 160, 167, 172, 175, 176, 187, 195, 204, 221, 224, 227, 231, 250, 256, 257, 263, 264, 273, 277, 282, 291 or 292 of SEQ ID NO: 1. In one embodiment, the mutant hydrolase is a mutant dehalogenase with a plurality of substitutions, e.g., at least 5, 10, 15 but less than 60, e.g., less than 25 or less than 50 substitutions, which includes a substitution at a position corresponding to position 106 and/or 272 in SEQ ID NO: 1 that results in the mutant dehalogenase forming a bond with a dehalogenase substrate which is more stable than the bond formed between a corresponding wild-type dehalogenase and the substrate. In one embodiment, the mutant hydrolase may have a plurality of substitutions including a plurality of substitutions at positions corresponding to positions 5, 7, 11, 12, 20, 30, 32, 47, 54, 55, 56, 58, 60, 65, 78, 80, 82, 87, 88, 94, 96, 109, 113, 116, 117, 118, 121, 124, 128, 131, 134, 136, 144, 147, 150, 151, 155, 157, 160, 161, 164, 165, 167, 172, 175, 176, 180, 182, 183, 187, 195, 197, 204, 218, 221, 224, 227, 231, 233, 250, 256, 257, 263, 264, 273, 277, 280, 282, 288, 291, 292, and/or 294 of SEQ ID NO: 1. The mutant dehalogenase also includes a plurality of substitutions, e.g., at least 5, 10, 15 but less than 25, e.g., less than 20 substitutions, corresponding to position 5, 11, 20, 30, 32, 47, 58, 60, 65, 78, 80, 87, 88, 94, 109, 113, 117, 118, 124, 128, 134, 136, 150, 151, 155, 157, 160, 167, 172, 175, 176, 187, 195, 204, 221, 224, 227, 231, 250, 256, 257, 263, 264, 273, 277, 282, 291 or 292 of SEQ ID NO: 1, at least one of which confers improved expression or binding kinetics, e.g., one or more of positions 5, 11, 20, 30, 32, 47, 58, 60, 65, 78, 80, 87, 88, 94, 109, 113, 117, 118, 124, 128, 134, 136, 150, 151, 155, 157, 160, 167, 172, 187, 195, 204, 221, 224, 227, 231, 250, 256, 257, 263, 264, 277, 282, 291 or 292 of SEQ ID NO: 1.

The mutant hydrolase of the invention may include one or more amino acid substitutions at the N-terminus, e.g., those resulting from altering the nucleotide sequence to have certain restriction sites, or one or more amino acid substitutions and one or more additional residues ("tails") at the C-terminus, e.g., those resulting from altering the nucleotide sequence to have certain restriction sites or selection to improve expression, relative to a corresponding wild-type hydrolase. For instance, a tail may include up to 70 or 80 amino acid residues, so long as the activity of the mutant hydrolase with the tail is not substantially altered, e.g., a decrease in activity of no more than 10%, 25% or 50%, relative to a corresponding mutant hydrolase without the tail.

The mutant hydrolase may be a fusion protein, e.g., a fusion protein expressed from a recombinant DNA which encodes the mutant hydrolase and at least one protein of interest or a fusion protein formed by chemical synthesis. For instance, the fusion protein may comprise a mutant hydrolase and an enzyme of interest, e.g., luciferase, RNasin or RNase, and/or a channel protein, e.g., ion channel protein, a receptor, a membrane protein, a cytosolic protein, a nuclear protein, a structural protein, a phosphoprotein, a kinase, a signaling protein, a metabolic protein, a mitochondrial protein, a receptor associated protein, a fluorescent protein, an enzyme substrate, a transcription factor, selectable marker protein, nucleic acid binding protein, extracellular matrix protein, secreted protein, receptor ligand, serum protein, a protein with reactive cysteines, a transporter protein and/or a targeting sequence, e.g., a myristylation sequence, a mitochondrial localization sequence, or a nuclear localization sequence, that directs the mutant hydrolase, for example, to a particular location. The protein of interest may be fused to the N-terminus or the C-terminus of the mutant hydrolase. In one embodiment, the fusion protein comprises a protein of interest at the N-terminus, and another protein, e.g., a different protein, at the C-terminus of the mutant hydrolase. For example, the protein of interest may be a fluorescent protein or an antibody.

Optionally, the proteins in the fusion are separated by a connector sequence, e.g., preferably one having at least 2 amino acid residues, such as one having 13 and up to 40 or 50 amino acid residues. The presence of a connector sequence in a fusion protein of the invention does not substantially alter the function of either protein in the fusion relative to the function of each individual protein, likely due to the connector sequence providing flexibility (autonomy) for each protein in the fusion. For instance, for a fusion of a mutant dehalogenase having at least one substitution that results in stable bond formation with the substrate and *Renilla* luciferase, the presence of a connector sequence does not substantially alter the stability of the bond formed between the mutant dehalogenase and a substrate thereof or the activity of the luciferase. Moreover, in one embodiment, the connector sequence does not substantially decrease, and may increase, functional expression or binding kinetics of either or both proteins in the fusion. For any particular combination of proteins in a fusion, a wide variety of connector sequences may be employed. In one embodiment, the connector sequence is a sequence recognized by an enzyme or is photocleavable. In one embodiment, the connector sequence includes a protease recognition site.

Also provided is an isolated nucleic acid molecule (polynucleotide) comprising a nucleic acid sequence encoding a hydrolase, e.g., a mutant hydrolase of the invention. Further provided is an isolated nucleic acid molecule comprising a nucleic acid sequence encoding a fusion protein comprising a mutant hydrolase of the invention and one or more amino acid residues at the N-terminus and/or C-terminus of the mutant hydrolase. In one embodiment, the encoded fusion protein comprises at least two different fusion partners, where one may be a sequence for purification, a sequence intended to alter a property of the remainder of the fusion protein, e.g., a protein destabilization sequence, or a sequence with a distinguishable property. In one embodiment, the isolated nucleic acid molecule comprises a nucleic acid sequence which is optimized for expression in at least one selected host. Optimized sequences include sequences which are codon optimized, i.e., codons which are employed more frequently in one organism relative to another organism, e.g., a distantly related organism, as well as modifications to add or modify Kozak sequences and/or introns, and/or to remove undesirable sequences, for instance, potential transcription factor binding sites. In one embodiment, the polynucleotide includes a nucleic acid sequence encoding a dehalogenase, which nucleic acid sequence is optimized for expression is a selected host cell. In one embodiment, the optimized polynucleotide no longer hybridizes to the corresponding non-optimized sequence, e.g., does not hybridize to the non-optimized sequence under medium or high stringency conditions. In another embodiment, the polynucleotide has less than 90%, e.g., less than 80%, nucleic acid sequence identity to the corresponding non-optimized sequence and optionally encodes a polypeptide having at least 80%, e.g., at least 85%, 90% or more, amino acid sequence identity with the polypeptide encoded by the non-optimized sequence. The optimization of nucleic acid sequences is known to the art, see, for example WO 02/16944. The isolated nucleic acid molecule, e.g., an optimized polynucleotide, of the invention may be introduced to in vitro transcription/translation reactions or to host cells, so as to express the encoded protein.

Constructs, e.g., expression cassettes, and vectors comprising the isolated nucleic acid molecule, e.g., optimized polynucleotide, as well as host cells having the construct, and kits comprising the isolated nucleic acid molecule or one or more constructs or vectors, are also provided. Host cells include prokaryotic cells or eukaryotic cells such as a plant or vertebrate cells, e.g., mammalian cells, including but not limited to a human, non-human primate, canine, feline, bovine, equine, ovine or rodent (e.g., rabbit, rat, ferret or mouse) cell. Preferably, the expression cassette comprises a promoter, e.g., a constitutive or regulatable promoter, operably linked to the nucleic acid molecule. In one embodiment, the expression cassette contains an inducible promoter. In one embodiment, the invention includes a vector comprising a nucleic acid sequence encoding a fusion protein comprising a mutant dehalogenase.

A substrate useful in the invention is one which is specifically bound by a mutant hydrolase, and preferably results in a bond formed with an amino acid, e.g., the reactive residue, of the mutant hydrolase, which bond is more stable than the bond formed between the substrate and the corresponding amino acid of the wild-type hydrolase. While the mutant hydrolase specifically binds substrates which may be specifically bound by the corresponding wild-type hydrolase, in one embodiment, no product or substantially less product, e.g., 2-, 10-, 100-, or 1000-fold less, is formed from the interaction between the mutant hydrolase and the substrate under conditions which result in product formation by a reaction between the corresponding wild-type hydrolase and substrate. In one embodiment, the bond formed between a mutant hydrolase and a substrate of the invention has a half-life (i.e., $t_{1/2}$) that is at least 2-fold, and more preferably at least 4- or even 10-fold, and up to 100-, 1000- or 10,000-fold, greater than the $t_{1/2}$ of the bond formed between a corresponding wild-type hydrolase and the substrate under conditions which result in product formation by the corresponding wild-type hydrolase. Preferably, the bond formed between the mutant hydrolase and the substrate has a $t_{1/2}$ of at least 30 minutes and preferably at least 4 hours, and up to at least 10 hours, and is resistant to disruption by washing, protein denaturants, and/or high temperatures, e.g., the bond is stable to boiling in SDS. In one embodiment, the substrate is a substrate for a dehalogenase, e.g., a haloalkane dehalogenase or a dehalogenase that cleaves carbon-halogen bonds in an aliphatic or aromatic halogenated substrate, such as a substrate for *Rhodococcus, Staphylococcus, Pseudomonas, Burkholderia, Agrobacterium* or *Xanthobacter* dehalogenase, or a substrate for a serine beta-lactamase.

In one embodiment, a substrate of the invention optionally includes a linker which physically separates one or more functional groups from the reactive group in the substrate. For instance, for some mutant hydrolases, i.e., those with deep catalytic pockets, a substrate of the invention can include a linker of sufficient length and structure so that the one or more functional groups of the substrate of the invention do not disturb the 3-D structure of the hydrolase (wild-type or mutant).

The invention also includes compositions and kits comprising a substrate for a hydrolase which includes a linker, a substrate for a hydrolase which includes one or more functional groups and optionally a linker, a linker which includes one or more functional groups, a substrate for a hydrolase which lacks one or more functional groups and optionally includes a linker, a linker, or a mutant hydrolase, or any combination thereof. For example, the invention includes a solid support comprising a substrate of the mutant hydrolase, a solid support comprising a mutant hydrolase of the invention or a fusion thereof, a kit comprising a vector encoding a mutant hydrolase of the invention or a fusion thereof.

The substrates and mutant hydrolases of the invention are useful to isolate, detect, identify, image, display, or localize molecules of interest, label cells, including live cell imaging, or label proteins in vitro and/or in vivo. For instance, a substrate of the mutant hydrolase bound to a solid support or a mutant hydrolase bound to a solid support may be used to generate protein arrays, cell arrays, vesicle/organelle arrays, gene arrays, and/or cell membrane arrays. In one embodiment, the invention provides a method to isolate a molecule of interest. The method includes providing a sample comprising one or more fusion proteins at least one of which comprises a mutant hydrolase of the invention and a protein which is optionally prebound to the molecule of interest, and a solid support having one or more hydrolase substrates. The sample and the solid support are then contacted so as to isolate the molecule of interest.

Further provided is a method of expressing a mutant hydrolase of the invention. The method comprises introducing to a host cell or an in vitro transcription/translation reaction, a recombinant nucleic acid molecule encoding a mutant hydrolase of the invention so as to express the mutant hydrolase. In one embodiment, the mutant hydrolase may be isolated from the cell or reaction. The mutant hydrolase may be expressed transiently or stably, constitutively or under tissue-specific or drug-regulated promoters, and the like. Also provided is an isolated host cell comprising a recombinant nucleic acid molecule encoding a mutant hydrolase of the invention.

In one embodiment, the invention provides a method to detect or determine the presence or amount of a mutant hydrolase. The method includes contacting a mutant hydrolase of the invention with a hydrolase substrate which comprises one or more functional groups. The presence or amount of the functional group is detected or determined, thereby detecting or determining the presence or amount of the mutant hydrolase. In one embodiment, the mutant hydrolase is in or on the surface of a cell. In another embodiment, the mutant hydrolase is in a cell lysate. In yet another embodiment, the mutant hydrolase is the product of an in vitro transcription/translation reaction.

Further provided is a method to isolate a protein or molecule of interest. In one embodiment, the method includes providing a sample comprising one or more fusion proteins at least one of which comprises a mutant hydrolase and a protein of interest and a solid support comprising one or more hydrolase substrates. The mutant hydrolase has at least two amino acid substitutions relative to a corresponding wild-type hydrolase, where one amino acid substitution results in the mutant hydrolase forming a bond with the substrate which is more stable than the bond formed between the corresponding wild-type hydrolase and the substrate and the substitution is at an amino acid residue in the corresponding wild-type hydrolase that is associated with activating a water molecule which cleaves the bond formed between the corresponding wild-type hydrolase and the substrate or at an amino acid residue in the corresponding wild-type hydrolase that forms an ester intermediate with the substrate. In one embodiment, the mutant hydrolase has a substitution at an amino acid that results in the mutant hydrolase forming a bond with the substrate which is more stable than the bond formed between the corresponding wild-type hydrolase and the substrate, which substitution is at an amino acid residue in the corresponding wild-type hydrolase that is associated with activating a water molecule which cleaves the bond formed between the corresponding wild-type hydrolase and the substrate or at an amino acid residue in the corresponding wild-type hydrolase that forms an ester intermediate with the substrate. The mutant hydrolase also includes substitutions at one or more positions corresponding to position 5, 11, 20, 30, 32, 47, 58, 60, 65, 78, 80, 87, 88, 94, 109, 113, 117, 118, 124, 128, 134, 136, 150, 151, 155, 157, 160, 167, 172, 187, 195, 204, 221, 224, 227, 231, 250, 256, 257, 263, 264, 277, 282, 291 or 292 of SEQ ID NO: 1. In one embodiment, the mutant hydrolase may have a plurality of substitutions including a plurality of substitutions at positions corresponding to positions 5, 7, 11, 12, 20, 30, 32, 47, 54, 55, 56, 58, 60, 65, 78, 80, 82, 87, 88, 94, 96, 109, 113, 116, 117, 118, 121, 124, 128, 131, 134, 136, 144, 147, 150, 151, 155, 157, 160, 161, 164, 165, 167, 172, 175, 176, 180, 182, 183, 187, 195, 197, 204, 218, 221, 224, 227, 231, 233, 250, 256, 257, 263, 264, 273, 277, 280, 282, 288, 291, 292, and/or 294 of SEQ ID NO: 1. The sample and the solid support are contacted so as to isolate the protein of interest. In one embodiment, the protein of interest in the sample is bound to a molecule of interest prior to contact with the solid support. In another embodiment, after the sample and solid support are contacted, a mixture suspected of having a molecule that binds to the protein of interest is added.

Also provided are methods of using a mutant hydrolase of the invention and a substrate for a corresponding hydrolase which includes one or more functional groups, e.g., to isolate a molecule or to detect or determine the presence or amount of, location, e.g., intracellular, subcellular or extracellular location, or movement of, certain molecules in cells. For instance, vectors encoding a mutant dehalogenase of which is fused to a protein of interest, is introduced to a cell, cell lysate, in vitro transcription/translation mixture, or supernatant, and a hydrolase substrate labeled with a functional group is added thereto. For instance, a cell is contacted with a vector comprising a promoter, e.g., a regulatable promoter, and a nucleic acid sequence encoding a mutant hydrolase which is fused to a protein which interacts with a molecule of interest. In one embodiment, a transfected cell is cultured under conditions in which the promoter induces transient expression of the fusion, and then an activity associated with the functional group is detected.

The invention thus provides methods to monitor the expression, location and/or movement (trafficking) of proteins in a cell as well as to monitor changes in microenvironments within a sample, e.g., a cell. In another embodiment, the use of two pairs of a mutant hydrolase/substrate permits multiplexing, simultaneous detection, and FRET- or BRET-based assays.

Other applications include detecting or labeling cells. Thus, the use of a mutant hydrolase of the invention and a corresponding substrate of the invention permits the detection of cells, for instance, to detect cell migration in vitro (e.g., angiogenesis/chemotaxis assays, and the like), and live cell imaging followed by immunocytochemistry.

In one embodiment, the invention provides a method to label a cell. The method includes contacting a sample having a cell or lysate thereof comprising a mutant hydrolase with a hydrolase substrate which comprises one or more functional groups. The mutant hydrolase has at least two amino acid substitutions relative to a corresponding wild-type hydrolase, where one amino acid substitution results in the mutant hydrolase forming a bond with the substrate which is more stable than the bond formed between the corresponding wild-type hydrolase and the substrate and the substitution is at an amino acid residue in the corresponding wild-type hydrolase that is associated with activating a water molecule which cleaves a bond formed between the corresponding wild-type hydrolase and the substrate or at an amino acid residue in the corresponding wild-type hydrolase that forms an ester intermediate with the substrate. In one embodiment, the second substitution is at position corresponding to position 5, 11, 20, 30, 32, 47, 58, 60, 65, 78, 80, 87, 88, 94, 109, 113, 117, 118, 124, 128, 134, 136, 150, 151, 155, 157, 160, 167, 172, 187, 195, 204, 221, 224, 227, 231, 250, 256, 257, 263, 264, 277, 282, 291 or 292 of SEQ ID NO: 1. In one embodiment, the mutant hydrolase has a plurality of substitutions, e.g., substitutions in addition to substitutions at, for example, position 106 or 272, at positions corresponding to positions 5, 7, 11, 12, 20, 30, 32, 47, 54, 55, 56, 58, 60, 65, 78, 80, 82, 87, 88, 94, 96, 109, 113, 116, 117, 118, 121, 124, 128, 131, 134, 136, 144, 147, 150, 151, 155, 157, 160, 161, 164, 165, 167, 172, 175, 176, 180, 182, 183, 187, 195, 197, 204, 218, 221, 224, 227, 231, 233, 250, 256, 257, 263, 264, 273, 277, 280, 282, 288, 291, 292, and/or 294 of SEQ ID NO: 1. The presence or amount of the functional group in the sample is detected or determined.

BRIEF DESCRIPTION OF THE FIGURES

FIG. 1B shows the sequence of a *Rhodococcus rhodochrous* dehalogenase (DhaA) protein (Kulakova et al., 1997) (SEQ ID NO: 1). The catalytic triad residues Asp(D), Glu(E) and His(H) are underlined. The residues that make up the cap domain are shown in italics. The DhaA.H272F and DhaA.D106C protein mutants, capable of generating covalent linkages with alkylhalide substrates, contain replacements of the catalytic triad His (H) and Asp (D) residues with Phe (F) and Cys (C), respectively.

FIGS. 2A-B show the sequence of substitutions at positions 175, 176 and 273 for DhaA.H272F (panel A) and the sequence of substitutions at positions 175 and 176 for DhaA.D106C (panel B).

FIGS. 3A-3B provide exemplary sequences of mutant dehalogenases within the scope of the invention (SEQ ID Nos. 12-16). Two additional residues are encoded at the 3' end (Gln-Tyr) as a result of cloning. Mutant dehalogenase encoding nucleic acid molecules with codons for those two additional residues are expressed at levels similar to or higher than those for mutant dehalogenases without those residues.

FIGS. 4A-4C show the nucleotide (SEQ ID NO:20) and amino acid (SEQ ID NO:21) sequence of HT2. The restriction sites listed were incorporated to facilitate generation of functional N- and C-terminal fusions. The C-terminal residues Ala-Gly may be replaced with Val.

FIG. 5 provides additional substitutions which improve functional expression of DhaA mutants with those substitutions in *E. coli*.

FIGS. 10A-10B show a (A) graph and (B) Western depicting in vivo labeling in HeLa cells.

FIG. 11 summarizes the properties of V7 relative to HT2.

FIGS. 19A-19l show nucleotide and amino acid sequences for various DhaA mutants, including those with tails at the C-terminus (N fusions) or substitutions at positions 1 or 2 at the N-terminus (C fusions) (HT2, SEQ ID NO:18 is encoded by SEQ ID NO:17; V2n, SEQ ID NO:22 is encoded by SEQ ID NO:32; V3n, SEQ ID NO:23 is encoded by SEQ ID NO:33; V4n, SEQ ID NO:24 is encoded by SEQ ID NO:34; V5n, SEQ ID NO:25 is encoded by SEQ ID NO:35; V6n, SEQ ID NO:26 is encoded by SEQ ID NO:36; V7n, SEQ ID NO:27 is encoded by SEQ ID NO:37; V2c, SEQ ID NO:42 is encoded by SEQ ID NO:52; V3c, SEQ ID NO:43 is encoded by SEQ ID NO:53; V4c, SEQ ID NO:44 is encoded by SEQ ID NO:54; V5c, SEQ ID NO:45 is encoded by SEQ ID NO:55; V6c, SEQ ID NO:46 is encoded by SEQ ID NO:56; V7n, SEQ ID NO:47 is encoded by SEQ ID NO:57). SEQ ID NOs: 48, 49, 28 and 29 are representative connector sequences. SEQ ID NOs: 60-65 represent residues 1-293 of minimal (no tail) mutant DhaA sequences, and SEQ ID NOs:66-71 represent mutant DhaA sequences with C-terminal substitutions and tails.

FIGS. 20A-20C show replicates (A-C) of detection of p65-mutant DhaA fusion proteins at different times after transfection (cell-to-gel analysis). HeLa cells were transiently transfected with p65-HT2 (green), p65-V3 (pink), p65-V7 (blue/white), p65-V7F (yellow) for different period of times, labeled with TMR ligand (5 µM for 15 minutes), lysed and analyzed on fluorimager Typhoone-9400. Note that V7t is a mutant DhaA having the sequence of V7 with a 63 amino acid tail (eisggggsggggsggggenlyfqaielgtrgss-rvdlqacklirlltkperklswllpplsnn; SEQ ID NO:72).

FIG. 24 shows the effect of DTT on labeling kinetics. Concentrations<1 mM DTT had no impact on labeling kinetics, while concentrations>1 mM DTT inhibited the labeling kinetics.

FIGS. 25A-25B show a (A) graph and (B) table depicting the effect of digitonin on labeling kinetics.

FIGS. 28A-28B show a (A) graph and (B) table depicting the effect of ionic detergents on labeling kinetics.

DETAILED DESCRIPTION OF THE INVENTION

Figure 1A:
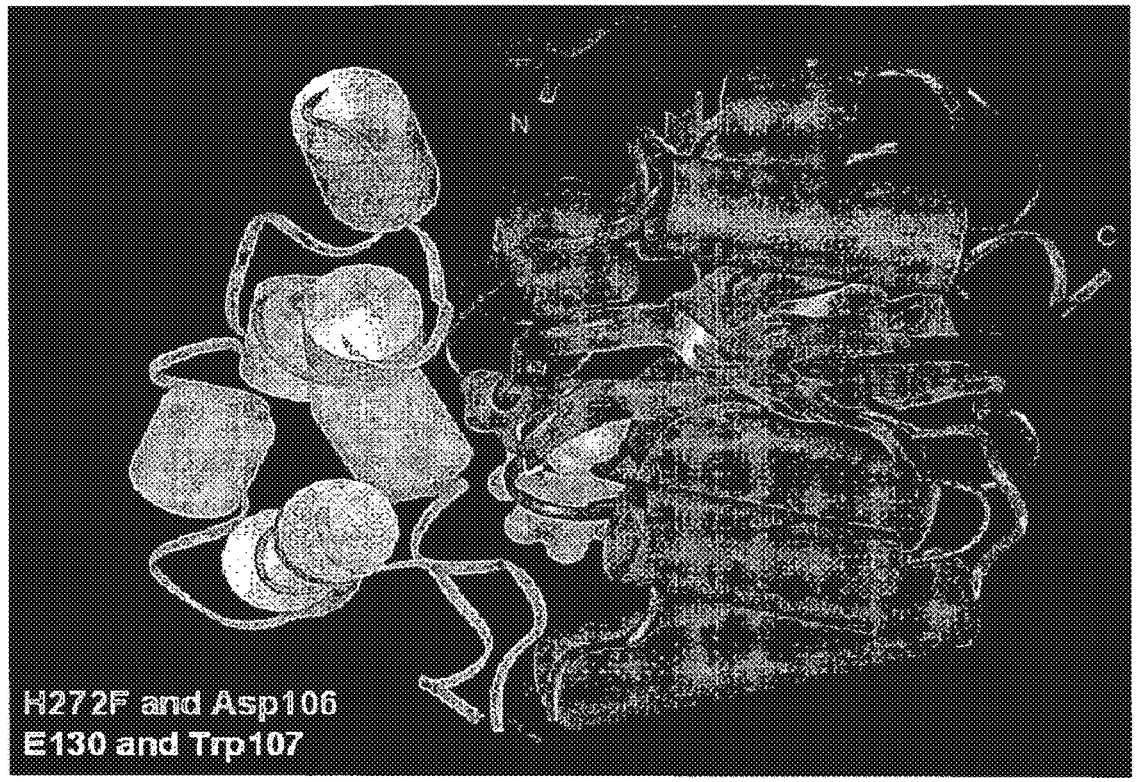
FIG. 1A shows a molecular model of the DhaA.H272F protein. The helical cap domain is shown in light blue. The α/β hydrolase core domain (dark blue) contains the catalytic triad residues. The red shaded residues near the cap and core domain interface represent H272F and the D106 nucleophile. The yellow shaded residues denote the positions of E130 and the halide-chelating residue W107.
Figure 1C:
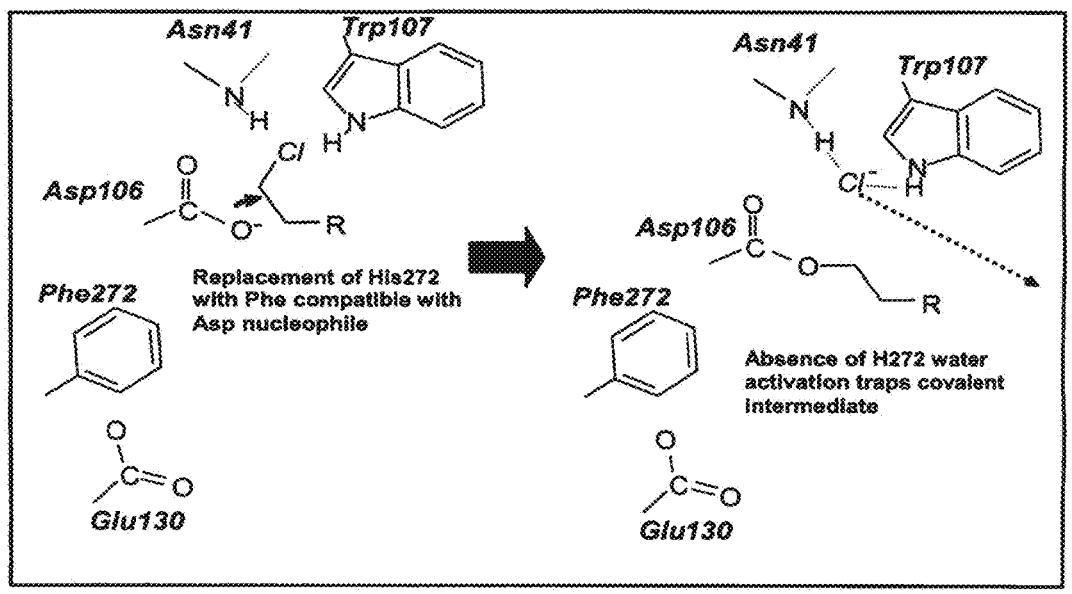
FIG. 1C illustrates the mechanism of covalent intermediate formation by DhaA.H272F with an alkylhalide substrate. Nucleophilic displacement of the halide group by Asp106 is followed by the formation of the covalent ester intermediate. Replacement of His272 with a Phe residue prevents water activation and traps the covalent intermediate.
Figure 1D:
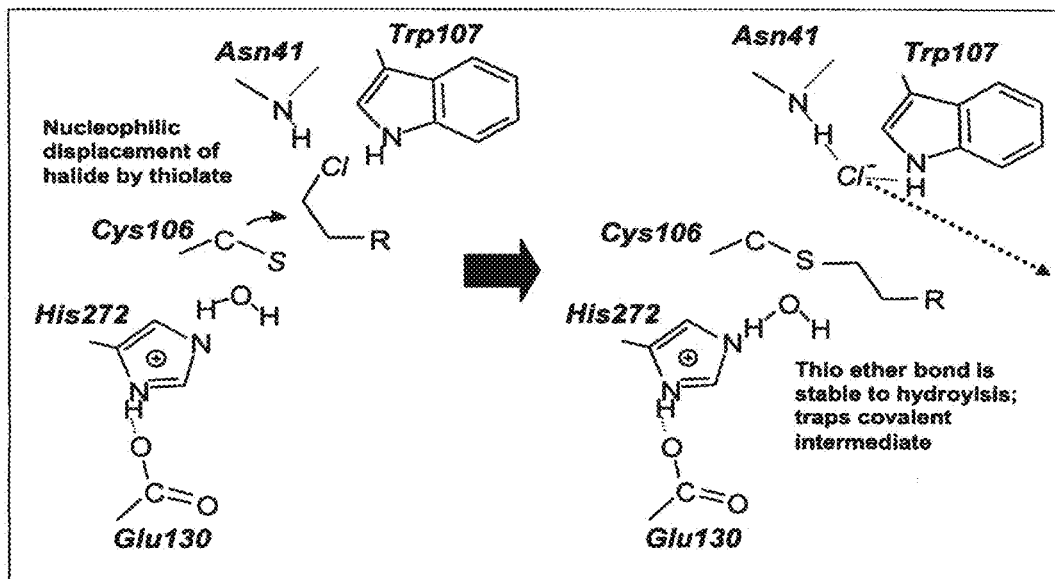
FIG. 1D depicts the mechanism of covalent intermediate formation by DhaA.D106C with an alkylhalide substrate. Nucleophilic displacement of the halide by the Cys106 thiolate generates a thioether intermediate that is stable to hydrolysis.
Figure 1E:
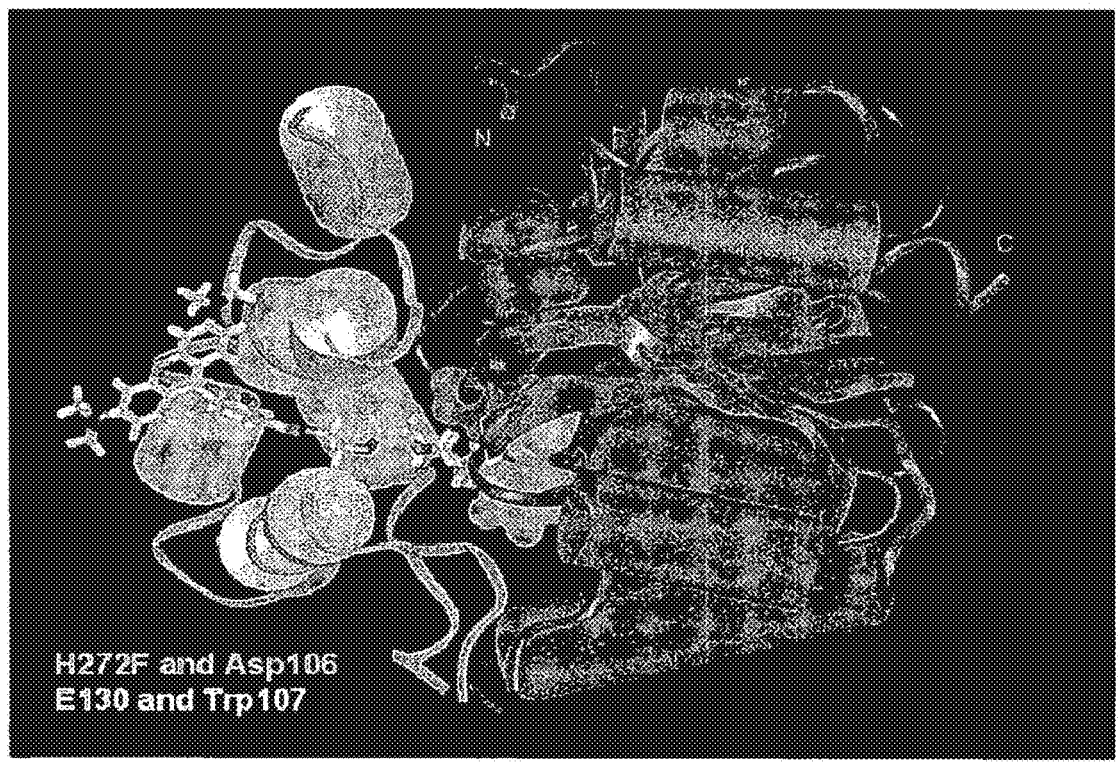
FIG. 1E depicts a structural model of the DhaA.H272F variant with a covalently attached carboxytetramethylrhodamine-$C_{10}H_{21}NO_2$—Cl ligand situated in the active site activity. The red shaded residues near the cap and core domain interface represent H272F and the D106 nucleophile. The yellow shaded residues denote the positions of E130 and the halide-chelating residue W107.
Figure 1F:
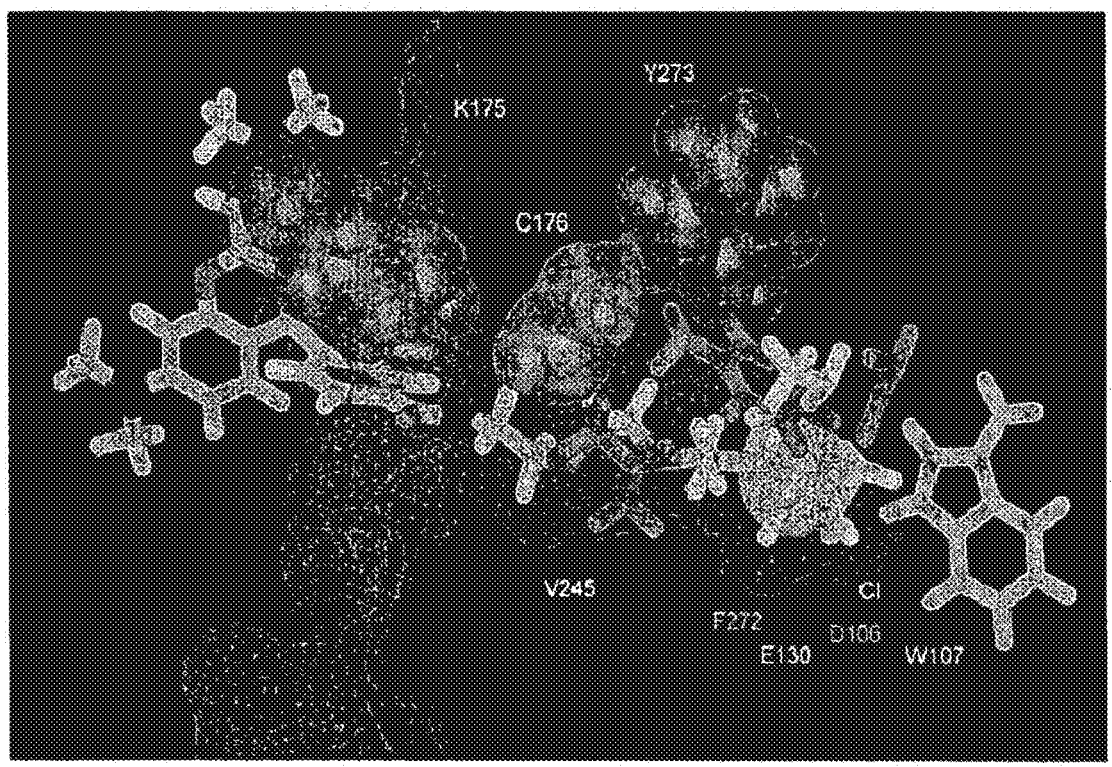
FIG. 1F shows a structural model of the DhaA.H272F substrate binding tunnel.

As used herein, a "substrate" includes a substrate having a reactive group and optionally one or more functional groups. A substrate which includes one or more functional groups is generally referred to herein as a substrate of the invention. A substrate, e.g., a substrate of the invention, may also optionally include a linker, e.g., a cleavable linker, which physically separates one or more functional groups from the reactive group in the substrate, and in one embodiment, the linker is preferably 12 to 30 atoms in length. The linker may not always be present in a substrate of the invention, however, in some embodiments, the physical separation of the reactive group and the functional group may be needed so that the reactive group can interact with the reactive residue in the mutant hydrolase to form a covalent bond. Preferably, when present, the linker does not substantially alter, e.g., impair, the specificity or reactivity of a substrate having the linker with the wild-type or mutant hydrolase relative to the specificity or reactivity of a corresponding substrate which lacks the linker with the wild-type or mutant hydrolase. Further, the presence of the linker preferably does not substantially alter, e.g., impair, one or more properties, e.g., the function, of the functional group. For instance, for some mutant hydrolases, i.e., those with deep catalytic pockets, a substrate of the invention can include a linker of sufficient length and structure so that the one or more functional groups of the substrate of the invention do not disturb the 3-D structure of the hydrolase (wild-type or mutant). A substrate may have two or more distinct functional groups.

As used herein, a "functional group" is a molecule which is detectable or is capable of detection, for instance, a molecule which is measurable by direct or indirect means (e.g., a photoactivatable molecule, digoxigenin, nickel NTA (nitrilotriacetic acid), a chromophore, fluorophore or luminophore), can be bound or attached to a second molecule (e.g., biotin, hapten, or a cross-linking group), or may be a solid support. A functional group may have more than one property such as being capable of detection and of being bound to another molecule.

As used herein a "reactive group" is the minimum number of atoms in a substrate which are specifically recognized by a particular wild-type or mutant hydrolase of the invention. The interaction of a reactive group in a substrate and a wild-type hydrolase results in a product and the regeneration of the wild-type hydrolase.

As used herein, the term "heterologous" nucleic acid sequence or protein refers to a sequence that relative to a reference sequence has a different source, e.g., originates from a foreign species, or, if from the same species, it may be substantially modified from the original form.

The term "fusion polypeptide" as used herein refers to a chimeric protein containing a protein of interest (e.g., luciferase, an affinity tag or a targeting sequence) joined to a different protein, e.g., a mutant hydrolase.

A "nucleophile" is a molecule which donates electrons.

As used herein, a "marker gene" or "reporter gene" is a gene that imparts a distinct phenotype to cells expressing the gene and thus permits cells having the gene to be distinguished from cells that do not have the gene. Such genes may encode either a selectable or screenable marker, depending on whether the marker confers a trait which one can 'select' for by chemical means, i.e., through the use of a selective agent (e.g., a herbicide, antibiotic, or the like), or whether it is simply a "reporter" trait that one can identify through observation or testing, i.e., by 'screening'. Elements of the present disclosure are exemplified in detail through the use of particular marker genes. Of course, many examples of suitable marker genes or reporter genes are known to the art and can be employed in the practice of the invention. Therefore, it will be understood that the following discussion is exemplary rather than exhaustive. In light of the techniques disclosed herein and the general recombinant techniques which are known in the art, the present invention renders possible the alteration of any gene. Exemplary modified reporter proteins are encoded by nucleic acid molecules comprising modified reporter genes including, but are not limited to, modifications of a neo gene, a β-gal gene, a gus gene, a cat gene, a gpt gene, a hyg gene, a hisD gene, a ble gene, a mprt gene, a bar gene, a nitrilase gene, a galactopyranoside gene, a xylosidase gene, a thymidine kinase gene, an arabinosidase gene, a mutant acetolactate synthase gene (ALS) or acetoacid synthase gene (AAS), a methotrexate-resistant dhfr gene, a dalapon dehalogenase gene, a mutated anthranilate synthase gene that confers resistance to 5-methyl tryptophan (WO 97/26366), an R-locus gene, a β-lactamase gene, a xylE gene, an ca-amylase gene, a tyrosinase gene, a luciferase (luc) gene (e.g., a *Renilla reniformis* luciferase gene, a firefly luciferase gene, or a click beetle luciferase (*Pyrophorus* plagiophthalamus) gene, an aequorin gene, a red fluorescent protein gene, or a green fluorescent protein gene. Included within the terms selectable or screenable marker genes are also genes which encode a "secretable marker" whose secretion can be detected as a means of identifying or selecting for transformed cells. Examples include markers which encode a secretable antigen that can be identified by antibody interaction, or even secretable enzymes which can be detected by their catalytic activity. Secretable proteins fall into a number of classes, including small, diffusible proteins detectable, e.g., by ELISA, and proteins that are inserted or trapped in the cell membrane.

A "selectable marker protein" encodes an enzymatic activity that confers to a cell the ability to grow in medium lacking what would otherwise be an essential nutrient (e.g., the TRPl gene in yeast cells) or in a medium with an antibiotic or other drug, i.e., the expression of the gene encoding the selectable marker protein in a cell confers resistance to an antibiotic or drug to that cell relative to a corresponding cell without the gene. When a host cell must express a selectable marker to grow in selective medium, the marker is said to be a positive selectable marker (e.g., antibiotic resistance genes which confer the ability to grow in the presence of the appropriate antibiotic). Selectable markers can also be used to select against host cells containing a particular gene (e.g., the sacB gene which, if expressed, kills the bacterial host cells grown in medium containing 5% sucrose); selectable markers used in this manner are referred to as negative selectable markers or counter-selectable markers. Common selectable marker gene sequences include those for resistance to antibiotics such as ampicillin, tetracycline, kanamycin, puromycin, bleomycin, streptomycin, hygromycin, neomycin, Zeocin™, and the like. Selectable auxotrophic gene sequences include, for example, hisD, which allows growth in histidine free media in the presence of histidinol. Suitable selectable marker genes include a bleomycin-resistance gene, a metallothionein gene, a hygromycin B-phosphotransferase gene, the AURI gene, an adenosine deaminase gene, an aminoglycoside phosphotransferase gene, a dihydrofolate reductase gene, a thymidine kinase gene, a xanthine-guanine phosphoribosyltransferase gene, and the like.

A "nucleic acid", as used herein, is a covalently linked sequence of nucleotides in which the 3' position of the pentose of one nucleotide is joined by a phosphodiester group to the 5' position of the pentose of the next, and in which the nucleotide residues (bases) are linked in specific sequence, i.e., a linear order of nucleotides, and includes analogs thereof, such as those having one or more modified bases, sugars and/or phosphate backbones. A "polynucleotide", as used herein, is a nucleic acid containing a sequence that is greater than about 100 nucleotides in length. An "oligonucleotide" or "primer", as used herein, is a short polynucleotide or a portion of a polynucleotide. The term "oligonucleotide" or "oligo" as used herein is defined as a molecule comprised of 2 or more deoxyribonucleotides or ribonucleotides, preferably more than 3, and usually more than 10, but less than 250, preferably less than 200, deoxyribonucleotides or ribonucleotides. The oligonucleotide may be generated in any manner, including chemical synthesis, DNA replication, amplification, e.g., polymerase chain reaction (PCR), reverse transcription (RT), or a combination thereof. A "primer" is an oligonucleotide which is capable of acting as a point of initiation for nucleic acid synthesis when placed under conditions in which primer extension is initiated. A primer is selected to have on its 3' end a region that is substantially complementary to a specific sequence of the target (template). A primer must be sufficiently complementary to hybridize with a target for primer elongation to occur. A primer sequence need not reflect the exact sequence of the target. For example, a non-complementary nucleotide fragment may be attached to the 5' end of the primer, with the remainder of the primer sequence being substantially complementary to the target. Non-complementary bases or longer sequences can be interspersed into the primer provided that the primer sequence has sufficient complementarity with the sequence of the target to hybridize and thereby form a complex for synthesis of the extension product of the primer. Primers matching or complementary to a gene sequence may be used in amplification reactions, RT-PCR and the like.

Nucleic acid molecules are said to have a "5'-terminus" (5' end) and a "3'-terminus" (3' end) because nucleic acid phosphodiester linkages occur to the 5' carbon and 3' carbon of the pentose ring of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. A terminal nucleotide, as used herein, is the nucleotide at the end position of the 3'- or 5'-terminus.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring.

As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. Typically, promoter and enhancer elements that direct transcription of a linked gene (e.g., open reading frame or coding region) are generally located 5' or upstream of the coding region. However, enhancer elements can exert their effect even when located 3' of the promoter element and the coding region. Transcription termination and polyadenylation signals are located 3' or downstream of the coding region.

The term "codon" as used herein, is a basic genetic coding unit, consisting of a sequence of three nucleotides that specify a particular amino acid to be incorporation into a polypeptide chain, or a start or stop signal. The term "coding region" when used in reference to structural gene refers to the nucleotide sequences that encode the amino acids found in the nascent polypeptide as a result of translation of a mRNA molecule. Typically, the coding region is bounded on the 5' side by the nucleotide triplet "ATG" which encodes the initiator methionine and on the 3' side by a stop codon (e.g., TAA, TAG, TGA). In some cases the coding region is also known to initiate by a nucleotide triplet "TTG".

As used herein, the terms "isolated" refer to in vitro preparation, isolation and/or purification of a nucleic acid molecule, a polypeptide, peptide or protein, so that it is not associated with in vivo substances. Thus, the term "isolated" when used in relation to a nucleic acid, as in "isolated oligonucleotide" or "isolated polynucleotide" refers to a nucleic acid sequence that is identified and separated from at least one contaminant with which it is ordinarily associated in its source. An isolated nucleic acid is present in a form or setting that is different from that in which it is found in nature. In contrast, non-isolated nucleic acids (e.g., DNA and RNA) are found in the state they exist in nature. For example, a given DNA sequence (e.g., a gene) is found on the host cell chromosome in proximity to neighboring genes; RNA sequences (e.g., a specific mRNA sequence encoding a specific protein), are found in the cell as a mixture with numerous other mRNAs that encode a multitude of proteins. Hence, with respect to an "isolated nucleic acid molecule", which includes a polynucleotide of genomic, cDNA, or synthetic origin or some combination thereof, the "isolated nucleic acid molecule" (1) is not associated with all or a portion of a polynucleotide in which the "isolated nucleic acid molecule" is found in nature, (2) is operably linked to a polynucleotide which it is not linked to in nature, or (3) does not occur in nature as part of a larger sequence. The isolated nucleic acid molecule may be present in single-stranded or double-stranded form. When a nucleic acid molecule is to be utilized to express a protein, the nucleic acid contains at a minimum, the sense or coding strand (i.e., the nucleic acid may be single-stranded), but may contain both the sense and anti-sense strands (i.e., the nucleic acid may be double-stranded).

The term "isolated" when used in relation to a polypeptide, as in "isolated protein" or "isolated polypeptide" refers to a polypeptide that is identified and separated from at least one contaminant with which it is ordinarily associated in its source. Thus, an isolated polypeptide (1) is not associated with proteins found in nature, (2) is free of other proteins from the same source, e.g., free of human proteins, (3) is expressed by a cell from a different species, or (4) does not occur in nature. Thus, an isolated polypeptide is present in a form or setting that is different from that in which it is found in nature. In contrast, non-isolated polypeptides (e.g., proteins and enzymes) are found in the state they exist in nature. The terms "isolated polypeptide", "isolated peptide" or "isolated protein" include a polypeptide, peptide or protein encoded by cDNA or recombinant RNA including one of synthetic origin, or some combination thereof.

The term "wild-type" as used herein, refers to a gene or gene product that has the characteristics of that gene or gene product isolated from a naturally occurring source. A wild-type gene is that which is most frequently observed in a population and is thus arbitrarily designated the "wild-type" form of the gene. In contrast, the term "mutant" refers to a gene or gene product that displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "gene" refers to a DNA sequence that comprises coding sequences and optionally control sequences necessary for the production of a polypeptide from the DNA sequence.

Nucleic acids are known to contain different types of mutations. A "point" mutation refers to an alteration in the sequence of a nucleotide at a single base position from the wild-type sequence. Mutations may also refer to insertion or deletion of one or more bases, so that the nucleic acid sequence differs from a reference, e.g., a wild-type, sequence.

The term "recombinant DNA molecule" means a hybrid DNA sequence comprising at least two nucleotide sequences not normally found together in nature. The term "vector" is used in reference to nucleic acid molecules into which fragments of DNA may be inserted or cloned and can be used to transfer DNA segment(s) into a cell and capable of replication in a cell. Vectors may be derived from plasmids, bacteriophages, viruses, cosmids, and the like.

The terms "recombinant vector", "expression vector" or "construct" as used herein refer to DNA or RNA sequences containing a desired coding sequence and appropriate DNA or RNA sequences necessary for the expression of the operably linked coding sequence in a particular host organism. Prokaryotic expression vectors include a promoter, a ribosome binding site, an origin of replication for autonomous replication in a host cell and possibly other sequences, e.g. an optional operator sequence, optional restriction enzyme sites. A promoter is defined as a DNA sequence that directs RNA polymerase to bind to DNA and to initiate RNA synthesis. Eukaryotic expression vectors include a promoter, optionally a polyadenylation signal and optionally an enhancer sequence.

A polynucleotide having a nucleotide sequence "encoding a peptide, protein or polypeptide" means a nucleic acid sequence comprising the coding region of a gene, or a fragment thereof which encodes a gene product having substantially the same activity as the corresponding full-length peptide, protein or polypeptide. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. In further embodiments, the coding region may contain a combination of both endogenous and exogenous control elements.

The term "transcription regulatory element" or "transcription regulatory sequence" refers to a genetic element or sequence that controls some aspect of the expression of nucleic acid sequence(s). For example, a promoter is a regulatory element that facilitates the initiation of transcription of an operably linked coding region. Other regulatory elements include, but are not limited to, transcription factor binding sites, splicing signals, polyadenylation signals, termination signals and enhancer elements, and include elements which increase or decrease transcription of linked sequences, e.g., in the presence of trans-acting elements.

Transcriptional control signals in eukaryotes comprise "promoter" and "enhancer" elements. Promoters and enhancers consist of short arrays of DNA sequences that interact specifically with cellular proteins involved in transcription. Promoter and enhancer elements have been isolated from a variety of eukaryotic sources including genes in yeast, insect and mammalian cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types. For example, the SV40 early gene enhancer is very active in a wide variety of cell types from many mammalian species and has been widely used for the expression of proteins in mammalian cells. Two other examples of promoter/enhancer elements active in a broad range of mammalian cell types are those from the human elongation factor 1 gene and the long terminal repeats of the Rous sarcoma virus; and the human cytomegalovirus.

The term "promoter/enhancer" denotes a segment of DNA containing sequences capable of providing both promoter and enhancer functions (i.e., the functions provided by a promoter element and an enhancer element as described above). For example, the long terminal repeats of retroviruses contain both promoter and enhancer functions. The enhancer/promoter may be "endogenous" or "exogenous" or "heterologous." An "endogenous" enhancer/promoter is one that is naturally linked with a given gene in the genome. An "exogenous" or "heterologous" enhancer/promoter is one that is placed in juxtaposition to a gene by means of genetic manipulation (i.e., molecular biological techniques) such that transcription of the gene is directed by the linked enhancer/promoter.

The presence of "splicing signals" on an expression vector often results in higher levels of expression of the recombinant transcript in eukaryotic host cells. Splicing signals mediate the removal of introns from the primary RNA transcript and consist of a splice donor and acceptor site. A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly(A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly(A) signal. The SV40 poly(A) signal is contained on a 237 bp BamH I/Bcl I restriction fragment and directs both termination and polyadenylation.

Eukaryotic expression vectors may also contain "viral replicons" or "viral origins of replication." Viral replicons are viral DNA sequences which allow for the extrachromosomal replication of a vector in a host cell expressing the appropriate replication factors. Vectors containing either the SV40 or polyoma virus origin of replication replicate to high copy number (up to $10^4$ copies/cell) in cells that express the appropriate viral T antigen. In contrast, vectors containing the replicons from bovine papillomavirus or Epstein-Barr virus replicate extrachromosomally at low copy number (about 100 copies/cell).

The term "in vitro" refers to an artificial environment and to processes or reactions that occur within an artificial environment. In vitro environments include, but are not limited to, test tubes and cell lysates. The term "in situ" refers to cell culture. The term "in vivo" refers to the natural environment (e.g., an animal or a cell) and to processes or reaction that occur within a natural environment.

The term "expression system" refers to any assay or system for determining (e.g., detecting) the expression of a gene of interest. Those skilled in the field of molecular biology will understand that any of a wide variety of expression systems may be used. A wide range of suitable mammalian cells are available from a wide range of sources (e.g., the American Type Culture Collection, Rockland, Md.). The method of transformation or transfection and the choice of expression vehicle will depend on the host system selected. Transformation and transfection methods are known to the art. Expression systems include in vitro gene expression assays where a gene of interest (e.g., a reporter gene) is linked to a regulatory sequence and the expression of the gene is monitored following treatment with an agent that inhibits or induces expression of the gene. Detection of gene expression can be through any suitable means including, but not limited to, detection of expressed mRNA or protein (e.g., a detectable product of a reporter gene) or through a detectable change in the phenotype of a cell expressing the gene of interest. Expression systems may also comprise assays where a cleavage event or other nucleic acid or cellular change is detected.

As used herein, the terms "hybridize" and "hybridization" refer to the annealing of a complementary sequence to the target nucleic acid, i.e., the ability of two polymers of nucleic acid (polynucleotides) containing complementary sequences to anneal through base pairing. The terms "annealed" and "hybridized" are used interchangeably throughout, and are intended to encompass any specific and reproducible interaction between a complementary sequence and a target nucleic acid, including binding of regions having only partial complementarity. Certain bases not commonly found in natural nucleic acids may be included in the nucleic acids of the present invention and include, for example, inosine and 7-deazaguanine. Those skilled in the art of nucleic acid technology can determine duplex stability empirically considering a number of variables including, for example, the length of the complementary sequence, base composition and sequence of the oligonucleotide, ionic strength and incidence of mismatched base pairs. The stability of a nucleic acid duplex is measured by the melting temperature, or "$T_m$". The $T_m$ of a particular nucleic acid duplex under specified conditions is the temperature at which on average half of the base pairs have disassociated.

The term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "medium" or "low" stringency are often required when it is desired that nucleic acids which are not completely complementary to one another be hybridized or annealed together. The art knows well that numerous equivalent conditions can be employed to comprise medium or low stringency conditions. The choice of hybridization conditions is generally evident to one skilled in the art and is usually guided by the purpose of the hybridization, the type of hybridization (DNA-DNA or DNA-RNA), and the level of desired relatedness between the sequences (e.g., Sambrook et al., 1989; Nucleic Acid Hybridization, A Practical Approach, IRL Press, Washington D.C., 1985, for a general discussion of the methods).

The stability of nucleic acid duplexes is known to decrease with an increased number of mismatched bases, and further to be decreased to a greater or lesser degree depending on the relative positions of mismatches in the hybrid duplexes. Thus, the stringency of hybridization can be used to maximize or minimize stability of such duplexes. Hybridization stringency can be altered by: adjusting the temperature of hybridization; adjusting the percentage of helix destabilizing agents, such as formamide, in the hybridization mix; and adjusting the temperature and/or salt concentration of the wash solutions. For filter hybridizations, the final stringency of hybridizations often is determined by the salt concentration and/or temperature used for the post-hybridization washes.

"High stringency conditions" when used in reference to nucleic acid hybridization include conditions equivalent to binding or hybridization at 42EC in a solution consisting of 5×SSPE (43.8 g/l NaCl, 6.9 g/l NaH$_2$PO$_4$ H2O and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1× SSPE, 1.0% SDS at 42EC when a probe of about 500 nucleotides in length is employed.

"Medium stringency conditions" when used in reference to nucleic acid hybridization include conditions equivalent to binding or hybridization at 42EC in a solution consisting of 5×SSPE (43.8 g/l NaCl, 6.9 g/l NaH$_2$PO$_4$ H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42EC when a probe of about 500 nucleotides in length is employed.

"Low stringency conditions" include conditions equivalent to binding or hybridization at 42EC in a solution consisting of 5×SSPE (43.8 g/l NaCl, 6.9 g/l NaH$_2$PO$_4$ H$_2$O and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 g/ml denatured salmon sperm DNA followed by washing in a solution comprising 5×SSPE, 0.1% SDS at 42EC when a probe of about 500 nucleotides in length is employed.

By "peptide", "protein" and "polypeptide" is meant any chain of amino acids, regardless of length or post-translational modification (e.g., glycosylation or phosphorylation). Unless otherwise specified, the terms are interchangeable. The nucleic acid molecules of the invention encode a variant (mutant) of a naturally-occurring (wild-type) protein. Preferably, such a mutant protein has an amino acid sequence that is at least 80%, e.g., at least 85%, 90%, and 95% or 99%, identical to the amino acid sequence of a corresponding wild-type protein. The term "homology" refers to a degree of complementarity. There may be partial homology or complete homology (i.e., identity). Homology is often measured using sequence analysis software (e.g., Sequence Analysis Software Package of Accelryn, Inc., San Diego). Such software matches similar sequences by assigning degrees of homology to various substitutions, deletions, insertions, and other modifications. In one embodiment, the mutant protein has a plurality of conservative substitutions relative to the corresponding wild-type protein. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

Polypeptide molecules are said to have an "amino terminus" (N-terminus) and a "carboxy terminus" (C-terminus) because peptide linkages occur between the backbone amino group of a first amino acid residue and the backbone carboxyl group of a second amino acid residue. The terms "N-terminal" and "C-terminal" in reference to polypeptide sequences refer to regions of polypeptides including portions of the N-terminal and C-terminal regions of the polypeptide, respectively. A sequence that includes a portion of the N-terminal region of polypeptide includes amino acids predominantly from the N-terminal half of the polypeptide chain, but is not limited to such sequences. For example, an N-terminal sequence may include an interior portion of the polypeptide sequence including bases from both the N-terminal and C-terminal halves of the polypeptide. The same applies to C-terminal regions. N-terminal and C-terminal regions may, but need not, include the amino acid defining the ultimate N-terminus and C-terminus of the polypeptide, respectively.

The term "recombinant protein" or "recombinant polypeptide" as used herein refers to a protein molecule expressed from a recombinant DNA molecule. In contrast, the term "native protein" is used herein to indicate a protein isolated from a naturally occurring (i.e., a nonrecombinant) source. Molecular biological techniques may be used to produce a recombinant form of a protein with identical properties as compared to the native form of the protein.

As used herein, the term "antibody" refers to a protein having one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad of immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies may exist as intact immunoglobulins, or as modifications in a variety of forms including, for example, FabFc$_2$, Fab, Fv, Fd, (FabN)$_2$, an Fv fragment containing only the light and heavy chain variable regions, a Fab or (Fab)N$_2$ fragment containing the variable regions and parts of the constant regions, a single-chain antibody, e.g., scFv, CDR-grafted antibodies and the like. The heavy and light chain of a Fv may be derived from the same antibody or different antibodies thereby producing a chimeric Fv region. The antibody may be of animal (especially mouse or rat) or human origin or may be chimeric or humanized. As used herein the term "antibody" includes these various forms.

The terms "cell," "cell line," "host cell," as used herein, are used interchangeably, and all such designations include progeny or potential progeny of these designations. By "transformed cell" is meant a cell into which (or into an ancestor of which) has been introduced a nucleic acid molecule of the invention. Optionally, a nucleic acid molecule of the invention may be introduced into a suitable cell line so as to create a stably transfected cell line capable of producing the protein or polypeptide encoded by the nucleic acid molecule. Vectors, cells, and methods for constructing such cell lines are well known in the art. The words "transformants" or "transformed cells" include the primary transformed cells derived from the originally transformed cell without regard to the number of transfers. All progeny may not be precisely identical in DNA content, due to deliberate or inadvertent mutations. Nonetheless, mutant progeny that have the same functionality as screened for in the originally transformed cell are included in the definition of transformants.

The term "purified" or "to purify" means the result of any process that removes some of a contaminant from the component of interest, such as a protein or nucleic acid. The percent of a purified component is thereby increased in the sample.

The term "operably linked" as used herein refer to the linkage of nucleic acid sequences in such a manner that a nucleic acid molecule capable of directing the transcription of a given gene and/or the synthesis of a desired protein molecule is produced. The term also refers to the linkage of sequences encoding amino acids in such a manner that a functional (e.g., enzymatically active, capable of binding to a binding partner, capable of inhibiting, etc.) protein or polypeptide, or a precursor thereof, e.g., the pre- or preproform of the protein or polypeptide, is produced.

All amino acid residues identified herein are in the natural L-configuration. In keeping with standard polypeptide nomenclature, abbreviations for amino acid residues are as shown in the following Table of Correspondence.

| TABLE OF CORRESPONDENCE | | |
|---|---|---|
| 1-Letter | 3-Letter | AMINO ACID |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

As used herein, the term "poly-histidine tract" or (His tag) refers to a molecule comprising two to ten histidine residues, e.g., a poly-histidine tract of five to ten residues. A poly-histidine tract allows the affinity purification of a covalently linked molecule on an immobilized metal, e.g., nickel, zinc, cobalt or copper, chelate column or through an interaction with another molecule (e.g., an antibody reactive with the His tag).

A "protein destabilization sequence" or "protein destabilization domain" includes one or more amino acid residues, which, when present at the N-terminus or C-terminus of a protein, reduces or decreases the half-life of the linked protein of by at least 80%, preferably at least 90%, more preferably at least 95% or more, e.g., 99%, relative to a corresponding protein which lacks the protein destabilization sequence or domain. A protein destabilization sequence includes, but is not limited to, a PEST sequence, for example, a PEST sequence from cyclin, e.g., mitotic cyclins, uracil permease or ODC, a sequence from the C-terminal region of a short-lived protein such as ODC, early response proteins such as cytokines, lymphokines, protooncogenes, e.g., c-myc or c-fos, MyoD, HMG CoA reductase, S-adenosyl methionine decarboxylase, CL sequences, a cyclin destruction box, N-degron, or a protein or a fragment thereof which is ubiquitinated in vivo.

As used herein, "pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a "substantially pure" composition will comprise more than about 80 percent of all macromolecular species present in the composition, more preferably more than about 85%, about 90%, about 95%, and about 99%. Most preferably, the object species is purified to essential homogeneity (contaminant species cannot be detected in the composition by conventional detection methods) wherein the composition consists essentially of a single macromolecular species.

Mutant Hydrolases

Mutant hydrolases within the scope of the invention include but are not limited to those prepared via recombinant techniques, e.g., site-directed mutagenesis or recursive mutagenesis, and comprise one or more amino acid substitutions. In one embodiment, at least one of the substitutions renders the mutant hydrolase capable of forming a stable, e.g., covalent, bond with a substrate for a corresponding nonmutant (wild-type) hydrolase, including a wild-type substrate modified to contain one or more functional groups, which bond is more stable than the bond formed between a corresponding wild-type hydrolase and the substrate. In one embodiment, at least one of the substitutions in the mutant hydrolase results in improved functional expression or binding kinetics, or both. Hydrolases within the scope of the invention include, but are not limited to, those disclosed at, for example, expasy.ch/enzyme/enzyme-byclass.html, and including peptidases, esterases (e.g., cholesterol esterase), glycosidases (e.g., glucosamylase), phosphatases (e.g., alkaline phosphatase) and the like. For instance, hydrolases include, but are not limited to, enzymes acting on ester bonds such as carboxylic ester hydrolases, thiolester hydrolases, phosphoric monoester hydrolases, phosphoric diester hydrolases, triphosphoric monoester hydrolases, sulfuric ester hydrolases, diphosphoric monoester hydrolases, phosphoric triester hydrolases, exodeoxyribonucleases producing 5'-phosphomonoesters, exoribonucleases producing 5'-phosphomonoesters, exoribonucleases producing 3'-phosphomonoesters, exonucleases active with either ribo- or deoxyribonucleic acid, exonucleases active with either ribo- or deoxyribonucleic acid, endodeoxyribonucleases producing 5'-phosphomonoesters, endodeoxyribonucleases producing other than 5'-phosphomonoesters, site-specific endodeoxyribonucleases specific for altered bases, endoribonucleases producing 5'-phosphomonoesters, endoribonucleases producing other than 5'-phosphomonoesters, endoribonucleases active with either ribo- or deoxyribonucleic, endoribonucleases active with either ribo- or deoxyribonucleic glycosylases; glycosidases, e.g., enzymes hydrolyzing O- and S-glycosyl, and hydrolyzing N-glycosyl compounds; acting on ether bonds such as trialkylsulfonium hydrolases or ether hydrolases; enzymes acting on peptide bonds (peptide hydrolases) such as aminopeptidases, dipeptidases, dipeptidyl-peptidases and tripeptidyl-peptidases, peptidyl-dipeptidases, serine-type carboxypeptidases, metallocarboxypeptidases, cysteine-type carboxypeptidases, omega peptidases, serine endopeptidases, cysteine endopeptidases, aspartic endopeptidases, metalloendopeptidases, threonine endopeptidases, and endopeptidases of unknown catalytic mechanism; enzymes acting on carbon-nitrogen bonds, other than peptide bonds, such as those in linear amides, in cyclic amides, in linear amidines, in cyclic amidines, in nitriles, or other compounds; enzymes acting on acid anhydrides such as those in phosphorous-containing anhydrides and in sulfonyl-containing anhydrides; enzymes acting on acid anhydrides (catalyzing transmembrane movement); enzymes acting on acid anhydrides or involved in cellular and subcellular movement; enzymes acting on carbon-carbon bonds (e.g., in ketonic substances); enzymes acting on halide bonds (e.g., in C-halide compounds), enzymes acting on phosphorus-nitrogen bonds; enzymes acting on sulfur-nitrogen bonds; enzymes acting on carbon-phosphorus bonds; and enzymes acting on sulfur-sulfur bonds. Exemplary hydrolases acting on halide bonds include, but are not limited to, alkylhalidase, 2-haloacid dehalogenase, haloacetate dehalogenase, thyroxine deiodinase, haloalkane dehalogenase, 4-chlorobenzoate dehalogenase, 4-chlorobenzoyl-CoA dehalogenase, and atrazine chlorohydrolase. Exemplary hydrolases that act on carbon-nitrogen bonds in cyclic amides include, but are not limited to, barbiturase, dihydropyrimidinase, dihydroorotase, carboxymethylhydantoinase, allantoinase, p3-lactamase, imidazolonepropionase, 5-oxoprolinase (ATP-hydrolysing), creatininase, L-lysine-lactamase, 6-aminohexanoate-cyclic-dimer hydrolase, 2,5-dioxopiperazine hydrolase, N-methylhydantoinase (ATP-hydrolysing), cyanuric acid amidohydrolase, maleimide hydrolase. "Beta-lactamase" as used herein includes Class A, Class C and Class D beta-lactamases as well as D-ala carboxypeptidase/transpeptidase, esterase EstB, penicillin binding protein 2x, penicillin binding protein 5, and D-amino peptidase. Preferably, the beta-lactamase is a serine beta-lactamase, e.g., one having a catalytic serine residue at a position corresponding to residue 70 in the serine beta-lactamase of *S. aureus* PC1, and a glutamic acid residue at a position corresponding to residue 166 in the serine beta-lactamase of *S. aureus* PC1, optionally having a lysine residue at a position corresponding to residue 73, and also optionally having a lysine residue at a position corresponding to residue 234, in the beta-lactamase of *S. aureus* PC1.

In one embodiment, the mutant hydrolase of the invention comprises at least one amino acid substitution in a residue which, in the wild-type hydrolase, is associated with activating a water molecule, e.g., a residue in a catalytic triad or an auxiliary residue, wherein the activated water molecule cleaves the bond formed between a catalytic residue in the wild-type hydrolase and a substrate of the hydrolase. As used herein, an "auxiliary residue" is a residue which alters the activity of another residue, e.g., it enhances the activity of a residue that activates a water molecule. Residues which activate water within the scope of the invention include but are not limited to those involved in acid-base catalysis, for instance, histidine, aspartic acid and glutamic acid. In another embodiment, the mutant hydrolase of the invention comprises at least one amino acid substitution in a residue which, in the wild-type hydrolase, forms an ester intermediate by nucleophilic attack of a substrate for the hydrolase.

In yet another embodiment, the mutant hydrolase of the invention comprises at least two amino acid substitutions that are associated with stable bond formation with a substrate, one substitution in a residue which, in the wild-type hydrolase, is associated with activating a water molecule or in a residue which, in the wild-type hydrolase, forms an ester intermediate by nucleophilic attack of a substrate for the hydrolase, and another substitution in a residue which, in the wild-type hydrolase, is at or near a binding site(s) for a hydrolase substrate, e.g., at least one atom of the residue is within 3, or within 5, Å of a hydrolase substrate bound to a wild-type hydrolase but is not in a residue that, in the corresponding wild-type hydrolase, is associated with activating a water molecule or which forms ester intermediate with a substrate. In one embodiment, the second substitution may be at a residue which, in the wild-type hydrolase lines the site(s) for substrate entry into the active site cavity and has at least one atom within 3 or 5 Å of a hydrolase substrate bound to the wild-type hydrolase, such as a residue in a tunnel for the substrate that is not a residue in the corresponding wild-type hydrolase which is associated with activating a water molecule or which forms an ester intermediate with a substrate. The additional substitution(s) preferably increase the rate of stable covalent bond formation of those mutants to a substrate of a corresponding wild-type hydrolase.

In one embodiment, at least one substitution is in a residue corresponding to residue 272 in DhaA from *Rhodococcus rhodochrous*. A "corresponding residue" is a residue which has the same activity (function) in one wild-type protein relative to a reference wild-type protein and optionally is in the same relative position when the primary sequences of the two proteins are aligned. For example, a residue which forms part of a catalytic triad and activates a water molecule in one enzyme may be residue 272 in that enzyme, which residue 272 corresponds to residue 73 in another enzyme, wherein residue 73 forms part of a catalytic triad and activates a water molecule. Thus, in one embodiment, a mutant dehalogenase of the invention has a residue other than histidine, e.g., a phenylalanine residue, at a position corresponding to residue 272 in DhaA from *Rhodococcus rhodochrous*. In another embodiment of the invention, a mutant hydrolase is a mutant dehalogenase comprising at least one amino acid substitution in a residue corresponding to residue 106 in DhaA from *Rhodococcus rhodochrous*, e.g., a substitution to a residue other than aspartate. For example, a mutant dehalogenase of the invention has a cysteine or a glutamate residue at a position corresponding to residue 106 in DhaA from *Rhodococcus rhodochrous*. In a further embodiment, the mutant hydrolase is a mutant dehalogenase comprising at least two amino acid substitutions, one in a residue corresponding to residue 106 and one in a residue corresponding to residue 272 in DhaA from *Rhodococcus rhodochrous*. In one embodiment, the mutant hydrolase is a mutant dehalogenase comprising at least two amino acid substitutions, one in a residue corresponding to residue 272 in DhaA from *Rhodococcus rhodochrous* and another in a residue corresponding to residue 175, 176, 245 and/or 273 in DhaA from *Rhodococcus rhodochrous*. In yet a further embodiment, the mutant hydrolase is a mutant serine beta-lactamase comprising at least one amino acid substitution in a residue corresponding to residue 166 or residue 170 in a serine beta-lactamase of *Staphylococcus aureus* PC1.

In one embodiment, one substitution is at a residue in the wild-type hydrolase that activates the water molecule, e.g., a histidine residue, and is at a position corresponding to amino acid residue 272 of a *Rhodococcus rhodochrous* dehalogenase, e.g., the substituted amino acid at the position corresponding to amino acid residue 272 is alanine, glutamine, asparagine, phenylalanine or glycine. In another embodiment, one substitution is at a residue in the wild-type hydrolase which forms an ester intermediate with the substrate, e.g., an aspartate residue, and at a position corresponding to amino acid residue 106 of a *Rhodococcus rhodochrous* dehalogenase. In one embodiment, the substituted amino acid at the position corresponding to amino acid 106 is cysteine. In one embodiment, the second substitution is at an amino acid residue corresponding to a position 175, 176 or 273 of *Rhodococcus rhodochrous* dehalogenase, e.g., the substituted amino acid at the position corresponding to amino acid residue 175 is methionine, valine, glutamate, aspartate, alanine, leucine, serine or cysteine, the substituted amino acid at the position corresponding to amino acid residue 176 is serine, glycine, asparagine, aspartate, threonine, alanine or arginine, and/or the substituted amino acid at the position corresponding to amino acid residue 273 is phenylalanine, leucine, methionine or cysteine. In yet another embodiment, the mutant hydrolase further comprises a third and optionally a fourth substitution at an amino acid residue in the wild-type hydrolase that is within the active site cavity and within 3 or 5 Å of a hydrolase substrate bound to the wild-type hydrolase, e.g., the third substitution is at a position corresponding to amino acid residue 273 of a *Rhodococcus rhodochrous* dehalogenase, and the fourth substitution is at a position corresponding to amino acid residue 175 or 176 of a *Rhodococcus rhodochrous* dehalogenase.

For example, wild-type dehalogenase DhaA cleaves carbon-halogen bonds in halogenated hydrocarbons (HaloC$_3$-HaloC$_{10}$). The catalytic center of DhaA is a classic catalytic triad including a nucleophile, an acid and a histidine residue. The amino acids in the triad are located deep inside DhaA (about 10 Å long and about 20 Å$^2$ in cross section). The halogen atom in a halogenated substrate for DhaA, for instance, the chlorine atom of a Cl-alkane substrate, is positioned in close proximity to the catalytic center of DhaA. DhaA binds the substrate, likely forms an ES complex, and an ester intermediate is formed by nucleophilic attack of the substrate by Asp106 (the numbering is based on the protein sequence of DhaA) of DhaA. His272 of DhaA then activates water and the activated water hydrolyzes the intermediate, releasing product from the catalytic center. Thus, in one embodiment of the invention, a mutant hydrolase is a mutant dehalogenase comprising at least one amino acid substitution in a residue which, in the wild-type dehalogenase, is associated with activating a water molecule, e.g., a residue in a catalytic triad or an auxiliary residue, wherein the activated water molecule cleaves the bond formed between a catalytic residue in the wild-type dehalogenase and a substrate of the dehalogenase.

In one embodiment, the mutant hydrolase is a haloalkane dehalogenase, e.g., such as those found in Gram-negative (Keuning et al., 1985) and Gram-positive haloalkane-utilizing bacteria (Keuning et al., 1985; Yokota et al., 1987; Scholtz et al., 1987; Sallis et al., 1990). Haloalkane dehalogenases, including Dh1A from *Xanthobacter autotrophicus* GJ10 (Janssen et al., 1988, 1989), DhaA from *Rhodococcus rhodochrous*, and LinB from *Spingomonas paucimobilis* UT26 (Nagata et al., 1997) are enzymes which catalyze hydrolytic dehalogenation of corresponding hydrocarbons. Halogenated aliphatic hydrocarbons subject to conversion include C$_2$-C$_{10}$ saturated aliphatic hydrocarbons which have one or more halogen groups attached, wherein at least two of the halogens are on adjacent carbon atoms. Such aliphatic hydrocarbons include volatile chlorinated aliphatic (VCA) hydrocarbons. VCA's include, for example, aliphatic hydrocarbons such as dichloroethane, 1,2-dichloropropane, 1,2-dichlorobutane and 1,2,3-trichloropropane. The term "halogenated hydrocarbon" as used herein means a halogenated aliphatic hydrocarbon. As used herein the term "halogen" includes chlorine, bromine, iodine, fluorine, astatine and the like. A preferred halogen is chlorine.

In one embodiment, the mutant hydrolase is a thermostable hydrolase such as a thermostable dehalogenase comprising at least one substitution at a position corresponding to amino acid residue 117 and/or 175 of a *Rhodococcus rhodochrous* dehalogenase, which substitution is correlated with enhanced thermostability. In one embodiment, the thermostable hydrolase is capable of binding a hydrolase substrate at low temperatures, e.g., from 0° C. to about 25° C. In one embodiment, a thermostable hydrolase is a thermostable mutant hydrolase, i.e., one having one or more substitutions in addition to the substitution at a position corresponding to amino acid residue 117 and/or 175 of a *Rhodococcus rhodochrous* dehalogenase. In one embodiment, a thermostable mutant dehalogenase has a substitution which results in removal of a charged residue, e.g., lysine. In one embodiment, a thermostable mutant dehalogenase has a serine or methionine at a position corresponding to residue 117 and/or 175 in DhaA from *Rhodococcus rhodochrous*.

In one embodiment, the mutant hydrolase of the invention comprises at least two amino acid substitutions, at least one of which is associated with stable bond formation, e.g., a residue in the wild-type hydrolase that activates the water molecule, e.g., a histidine residue, and is at a position corresponding to amino acid residue 272 of a *Rhodococcus rhodochrous* dehalogenase, e.g., the substituted amino acid is alanine, asparagine, glycine or phenylalanine, and at least one other is associated with improved functional expression or binding kinetics, or both, e.g., at a position corresponding to position 5, 11, 20, 30, 32, 47, 58, 60, 65, 78, 80, 87, 88, 94, 109, 113, 117, 118, 124, 128, 134, 136, 150, 151, 155, 157, 160, 167, 172, 187, 195, 204, 221, 224, 227, 231, 250, 256, 257, 263, 264, 277, 282, 291 or 292 of SEQ ID NO: 1. In one embodiment, the mutant hydrolase has substitutions at positions corresponding to positions 175, 176, 272, and 273, as well as at least one other substitution at a position corresponding to position 5, 11, 20, 30, 32, 47, 58, 60, 65, 78, 80, 87, 88, 94, 109, 113, 117, 118, 124, 128, 134, 136, 150, 151, 155, 157, 160, 167, 172, 187, 195, 204, 221, 224, 227, 231, 250, 256, 257, 263, 264, 277, 282, 291 or 292 of SEQ ID NO: 1. In one embodiment, the mutant hydrolase may have a plurality of substitutions including a plurality of substitutions at positions corresponding to positions 5, 7, 11, 12, 20, 30, 32, 47, 54, 55, 56, 58, 60, 65, 78, 80, 82, 87, 88, 94, 96, 109, 113, 116, 117, 118, 121, 124, 128, 131, 134, 136, 144, 147, 150, 151, 155, 157, 160, 161, 164, 165, 167, 172, 175, 176, 180, 182, 183, 187, 195, 197, 204, 218, 221, 224, 227, 231, 233, 250, 256, 257, 263, 264, 273, 277, 280, 282, 288, 291, 292, and/or 294 of SEQ ID NO: 1.

In one embodiment, the mutant hydrolase has substitutions at positions corresponding to positions 106, 175, and 176, as well as at least one other substitution at a position corresponding to position 5, 11, 20, 30, 32, 47, 58, 60, 65, 78, 80, 87, 88, 94, 109, 113, 117, 118, 124, 128, 134, 136, 150, 151, 155, 157, 160, 167, 172, 187, 195, 204, 221, 224, 227, 231, 250, 256, 257, 263, 264, 277, 282, 291 or 292 of SEQ ID NO: 1. In one embodiment, the mutant hydrolase has substitutions at positions corresponding to positions 106, 175, 176, 272, and 273, as well as at least one other substitution at a position corresponding to position 5, 11, 20, 30, 32, 47, 58, 60, 65, 78, 80, 87, 88, 94, 109, 113, 117, 118, 124, 128, 134, 136, 150, 151, 155, 157, 160, 167, 172, 187, 195, 204, 221, 224, 227, 231, 250, 256, 257, 263, 264, 277, 282, 291 or 292 of SEQ ID NO: 1. In one embodiment, the mutant hydrolase may have a plurality of substitutions including a plurality of substitutions at positions corresponding to positions 5, 7, 11, 12, 20, 30, 32, 47, 54, 55, 56, 58, 60, 65, 78, 80, 82, 87, 88, 94, 96, 109, 113, 116, 117, 118, 121, 124, 128, 131, 134, 136, 144, 147, 150, 151, 155, 157, 160, 161, 164, 165, 167, 172, 175, 176, 180, 182, 183, 187, 195, 197, 204, 218, 221, 224, 227, 231, 233, 250, 256, 257, 263, 264, 273, 277, 280, 282, 288, 291, 292, and/or 294 of SEQ ID NO: 1.

A mutant hydrolase may include other substitution(s), e.g., those which are introduced to facilitate cloning of the corresponding gene or a portion thereof, and/or additional residue(s) at or near the N- and/or C-terminus, e.g., those which are introduced to facilitate cloning of the corresponding gene or a portion thereof but which do not necessarily have an activity, e.g., are not separately detectable.

Fusion Partners

A polynucleotide of the invention which encodes a mutant hydrolase may be employed with other nucleic acid sequences, e.g., a native sequence such as a cDNA or one which has been manipulated in vitro, e.g., to prepare N-terminal, C-terminal, or N- and C-terminal fusion proteins. Many examples of suitable fusion partners are known to the art and can be employed in the practice of the invention.

For instance, the invention also provides a fusion protein comprising a mutant hydrolase and amino acid sequences for a protein or peptide of interest, e.g., sequences for a marker protein, e.g., a selectable marker protein, affinity tag, e.g., a polyhistidine sequence, an enzyme of interest, e.g., luciferase, RNasin, RNase, and/or GFP, a nucleic acid binding protein, an extracellular matrix protein, a secreted protein, an antibody or a portion thereof such as Fc, a bioluminescent protein, a receptor ligand, a regulatory protein, a serum protein, an immunogenic protein, a fluorescent protein, a protein with reactive cysteines, a receptor protein, e.g., NMDA receptor, a channel protein, e.g., an ion channel protein such as a sodium-, potassium- or a calcium-sensitive channel protein including a HERG channel protein, a membrane protein, a cytosolic protein, a nuclear protein, a structural protein, a phosphoprotein, a kinase, a signaling protein, a metabolic protein, a mitochondrial protein, a receptor associated protein, a fluorescent protein, an enzyme substrate, e.g., a protease substrate, a transcription factor, a protein destabilization sequence, or a transporter protein, e.g., EAAT1-4 glutamate transporter, as well as targeting signals, e.g., a plastid targeting signal, such as a mitochondrial localization sequence, a nuclear localization signal or a myristilation sequence, that directs the mutant hydrolase to a particular location.

In one embodiment, the fusion protein may comprise a protein of interest at the N-terminus and, optionally, a different protein of interest at the C-terminus of the mutant hydrolase.

In one embodiment, a fusion protein includes a mutant hydrolase and a protein that is associated with a membrane or a portion thereof, e.g., targeting proteins such as those for endoplasmic reticulum targeting, cell membrane bound proteins, e.g., an integrin protein or a domain thereof such as the cytoplasmic, transmembrane and/or extracellular stalk domain of an integrin protein, and/or a protein that links the mutant hydrolase to the cell surface, e.g., a glycosylphosphoinositol signal sequence.

Fusion partners may include those having an enzymatic activity. For example, a functional protein sequence may encode a kinase catalytic domain (Hanks and Hunter, 1995), producing a fusion protein that can enzymatically add phosphate moieties to particular amino acids, or may encode a Src Homology 2 (SH2) domain (Sadowski et al., 1986; Mayer and Baltimore, 1993), producing a fusion protein that specifically binds to phosphorylated tyrosines.

The fusion may also include an affinity domain, including peptide sequences that can interact with a binding partner, e.g., such as one immobilized on a solid support, useful for identification or purification. DNA sequences encoding multiple consecutive single amino acids, such as histidine, when fused to the expressed protein, may be used for one-step purification of the recombinant protein by high affinity binding to a resin column, such as nickel sepharose. Exemplary affinity domains include His5 (HHHHH) (SEQ ID NO:3), HisX6 (HHHHHH) (SEQ ID NO:4), C-myc (EQKLISEEDL) (SEQ ID NO:5), Flag (DYKDDDDK) (SEQ ID NO:6), StrepTag (WSHPQFEK) (SEQ ID NO:7), hemagluttinin, e.g., HA Tag (YPYDVPDYA) (SEQ ID NO:8), GST, thioredoxin, cellulose binding domain, RYIRS (SEQ ID NO:9), Phe-His-His-Thr (SEQ ID NO: 10), chitin binding domain, S-peptide, T7 peptide, SH2 domain, C-end RNA tag, WEAAAREACCRECCARA (SEQ ID NO: 11), metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, S100 proteins, parvalbumin, calbindin $D_{9K}$, calbindin $D_{28K}$, and calretinin, inteins, biotin, streptavidin, MyoD, Id, leucine zipper sequences, and maltose binding protein.

Exemplary heterologous sequences include but are not limited to sequences such as those in FRB and FKBP, the regulatory subunit of protein kinase (PKa-R) and the catalytic subunit of protein kinase (PKa-C), a src homology region (SH2) and a sequence capable of being phosphorylated, e.g., a tyrosine containing sequence, an isoform of 14-3-3, e.g., 14-3-3t (see Mils et al., 2000), and a sequence capable of being phosphorylated, a protein having a WW region (a sequence in a protein which binds proline rich molecules (see Ilsley et al., 2002; and Einbond et al., 1996) and a heterologous sequence capable of being phosphorylated, e.g., a serine and/or a threonine containing sequence, as well as sequences in dihydrofolate reductase (DHFR) and gyrase B (GyrB).

Optimized Hydrolase Sequences, and Vectors and Host Cells Encoding the Hydrolase Also provided is an isolated nucleic acid molecule (polynucleotide) comprising a nucleic acid sequence encoding a hydrolase or a fusion thereof. In one embodiment, the isolated nucleic acid molecule comprises a nucleic acid sequence which is optimized for expression in at least one selected host. Optimized sequences include sequences which are codon optimized, i.e., codons which are employed more frequently in one organism relative to another organism, e.g., a distantly related organism, as well as modifications to add or modify Kozak sequences and/or introns, and/or to remove undesirable sequences, for instance, potential transcription factor binding sites. In one embodiment, the polynucleotide includes a nucleic acid sequence encoding a mutant dehalogenase, which nucleic acid sequence is optimized for expression is a selected host cell. In one embodiment, the optimized polynucleotide no longer hybridizes to the corresponding non-optimized sequence, e.g., does not hybridize to the non-optimized sequence under medium or high stringency conditions. In another embodiment, the polynucleotide has less than 90%, e.g., less than 80%, nucleic acid sequence identity to the corresponding non-optimized sequence and optionally encodes a polypeptide having at least 80%, e.g., at least 85%, 90% or more, amino acid sequence identity with the polypeptide encoded by the non-optimized sequence. Constructs, e.g., expression cassettes, and vectors comprising the isolated nucleic acid molecule, as well as kits comprising the isolated nucleic acid molecule, construct or vector are also provided.

A nucleic acid molecule comprising a nucleic acid sequence encoding a fusion with a hydrolase is optionally optimized for expression in a particular host cell and also optionally operably linked to transcription regulatory sequences, e.g., one or more enhancers, a promoter, a transcription termination sequence or a combination thereof, to form an expression cassette.

In one embodiment, a nucleic acid sequence encoding a hydrolase or a fusion thereof is optimized by replacing codons in a wild-type or mutant hydrolase sequence with codons which are preferentially employed in a particular (selected) cell. Preferred codons have a relatively high codon usage frequency in a selected cell, and preferably their introduction results in the introduction of relatively few transcription factor binding sites for transcription factors present in the selected host cell, and relatively few other undesirable structural attributes. Thus, the optimized nucleic acid product has an improved level of expression due to improved codon usage frequency, and a reduced risk of inappropriate transcriptional behavior due to a reduced number of undesirable transcription regulatory sequences.

An isolated and optimized nucleic acid molecule of the invention may have a codon composition that differs from that of the corresponding wild-type nucleic acid sequence at more than 30%, 35%, 40% or more than 45%, e.g., 50%, 55%, 60% or more of the codons. Preferred codons for use in the invention are those which are employed more frequently than at least one other codon for the same amino acid in a particular organism and, more preferably, are also not low-usage codons in that organism and are not low-usage codons in the organism used to clone or screen for the expression of the nucleic acid molecule. Moreover, preferred codons for certain amino acids (i.e., those amino acids that have three or more codons), may include two or more codons that are employed more frequently than the other (non-preferred) codon(s). The presence of codons in the nucleic acid molecule that are employed more frequently in one organism than in another organism results in a nucleic acid molecule which, when introduced into the cells of the organism that employs those codons more frequently, is expressed in those cells at a level that is greater than the expression of the wild-type or parent nucleic acid sequence in those cells.

In one embodiment of the invention, the codons that are different are those employed more frequently in a mammal, while in another embodiment the codons that are different are those employed more frequently in a plant. Preferred codons for different organisms are known to the art, e.g., see kazusa.or.jp./codon/. A particular type of mammal, e.g., a human, may have a different set of preferred codons than another type of mammal. Likewise, a particular type of plant may have a different set of preferred codons than another type of plant. In one embodiment of the invention, the majority of the codons that differ are ones that are preferred codons in a desired host cell. Preferred codons for organisms including mammals (e.g., humans) and plants are known to the art (e.g., Wada et al., 1990; Ausubel et al., 1997). For example, preferred human codons include, but are not limited to, CGC (Arg), CUG (Leu), UCU (Ser), AGC (Ser), ACC (Thr), CCA (Pro), CCT (Pro), GCC (Ala), GGC (Gly), GUG (Val), AUC (Ile), AUU (Ile), AAG (Lys), AAC (Asn), CAG (Gln), CAC (His), GAG (Glu), GAC (Asp), UAC (Tyr), UGC (Cys) and TTC (Phe) (Wada et al., 1990). Thus, in one embodiment, synthetic nucleic acid molecules of the invention have a codon composition which differs from a wild-type nucleic acid sequence by having an increased number of the preferred human codons, e.g., CGC, CUG, UCU, AGC, ACC, CCA, CCU, GCC, GGC, GUG, AUC, AUU, AAG, AAC, CAG, CAC, GAG, GAC, UAC, UGC, UUC, or any combination thereof. For example, the nucleic acid molecule of the invention may have an increased number of CUG or UUG leucine-encoding codons, GUG or GUC valine-encoding codons, GGC or GGU glycine-encoding codons, AUC or AUU isoleucine-encoding codons, CCA or CCU proline-encoding codons, CGC or CGU arginine-encoding codons, AGC or TCU serine-encoding codons, ACC or ACU threonine-encoding codon, GCC or GCU alanine-encoding codons, or any combination thereof, relative to the wild-type nucleic acid sequence. In another embodiment, preferred *C. elegans* codons include, but are not limited to, UUC (Phe), UUU (Phe), CUU (Leu), UUG (Leu), AUU (Ile), GUU (Val), GUG (Val), UCA (Ser), UCU (Ser), CCA (Pro), ACA (Thr), ACU (Thr), GCU (Ala), GCA (Ala), UAU (Tyr), CAU (His), CAA (Gln), AAU (Asn), AAA (Lys), GAU (Asp), GAA (Glu), UGU (Cys), AGA (Arg), CGA (Arg), CGU (Arg), GGA (Gly), or any combination thereof. In yet another embodiment, preferred Drosophilia codons include, but are not limited to, UUC (Phe), CUG (Leu), CUC (Leu), AUC (Ile), AUU (Ile), GUG (Val), GUC (Val), AGC (Ser), UCC (Ser), CCC (Pro), CCG (Pro), ACC (Thr), ACG (Thr), GCC (Ala), GCU (Ala), UAC (Tyr), CAC (His), CAG (Gln), AAC (Asn), AAG (Lys), GAU (Asp), GAG (Glu), UGC (Cys), CGC (Arg), GGC (Gly), GGA (gly), or any combination thereof. Preferred yeast codons include but are not limited to UUU (Phe), UUG (Leu), UUA (Leu), CCU (Leu), AUU (Ile), GUU (Val), UCU (Ser), UCA (Ser), CCA (Pro), CCU (Pro), ACU (Thr), ACA (Thr), GCU (Ala), GCA (Ala), UAU (Tyr), UAC (Tyr), CAU (His), CAA (Gln), AAU (Asn), AAC (Asn), AAA (Lys), AAG (Lys), GAU (Asp), GAA (Glu), GAG (Glu), UGU (Cys), CGU (Trp), AGA (Arg), CGU (Arg), GGU (Gly), GGA (Gly), or any combination thereof. Similarly, nucleic acid molecules having an increased number of codons that are employed more frequently in plants, have a codon composition which differs from a wild-type or parent nucleic acid sequence by having an increased number of the plant codons including, but not limited to, CGC (Arg), CUU (Leu), UCU (Ser), UCC (Ser), ACC (Thr), CCA (Pro), CCU (Pro), GCU (Ser), GGA (Gly), GUG (Val), AUC (Ile), AUU (Ile), AAG (Lys), AAC (Asn), CAA (Gln), CAC (His), GAG (Glu), GAC (Asp), UAC (Tyr), UGC (Cys), UUC (Phe), or any combination thereof (Murray et al., 1989). Preferred codons may differ for different types of plants (Wada et al., 1990).

In one embodiment, an optimized nucleic acid sequence encoding a hydrolase or fusion thereof has less than 100%, e.g., less than 90% or less than 80%, nucleic acid sequence identity relative to a non-optimized nucleic acid sequence encoding a corresponding hydrolase or fusion thereof. For instance, an optimized nucleic acid sequence encoding DhaA has less than about 80% nucleic acid sequence identity relative to non-optimized (wild-type) nucleic acid sequence encoding a corresponding DhaA, and the DhaA encoded by the optimized nucleic acid sequence optionally has at least 85% amino acid sequence identity to a corresponding wild-type DhaA. In one embodiment, the activity of a DhaA encoded by the optimized nucleic acid sequence is at least 10%, e.g., 50% or more, of the activity of a DhaA encoded by the non-optimized sequence, e.g., a mutant DhaA encoded by the optimized nucleic acid sequence binds a substrate with substantially the same efficiency, i.e., at least 50%, 80%, 100% or more, as the mutant DhaA encoded by the non-optimized nucleic acid sequence binds the same substrate.

An exemplary optimized DhaA gene for a mutant DhaA has the following codon optimized sequence (eliminates rare codons for E. coli and a variety of mammalian species) and encodes D78G, K175M, C176G, H272N, and Y273F substitutions:
atggcagaaatcggtactggctttccattcgaccccattatgtggaagtcctgggc-
gagcgcatgcactacgtcgatgttggtccgcgcgatggcaccctgtgctgttcct-
gcacggtaaccccgacctcctcctacctgtggcgcaacatcatcccgcatgttgcac-
cgagccatcgctgcattgctccagacc
tgatcggtatgggcaaatccgacaaaccagacc tgggttatttcttcgacgac-
cacgtccgctacctggatgccttcatcgaagccctgggtctggaagaggtcgtc-
ctggtcattcacgactggggctccgctctgggtttccactgggccaagcgcaatc-
cagagcgcgtcaaaggtattgcatgtatggagttcatccgccctatcccgacctg-
ggacgaatggccagaatttgcccgcgagaccttccaggccttccgcaccgc-
cgacgtcggcc gcgagctgatcatcgatcagaacgctttatcgagggtgcgct-
gccgatgggtgtcgtccgcccgctgactgaagtcgagatggaccattaccgc-
gagcgcttcctgaagcctgttgaccgcgagccactgtggcgcttcccaaacga-
gctgccaatcgccggtgagccagcgaacatcgtcgcgctggtcgaagca tacat-
gaactggctgcaccagtccccgtcccgaagctgctgttctggggcaccccag-
gcgttctgatcccaccggccgaagccgctcgcctggccgaaagcctgcctaact-
gcaagactgtggacatcggcccgggtctgaattttctgcaagaagacaaccggacctgatcggcagcgagatcgcgcgctggc tgccggcgctg (SEQ ID NO:30) which encodes maeigtgfpfdphyvevlgermhyvdvg-prdgtpvlflhgnptssylwrniiphvapshrciapdligmgksdkpdlgyffd-dhvryldafiealgleevvlvihdwgsalgfhwakrnpervkgiacme-firpiptwdewpefaretfqafrtadvgreliidqnafiegalpmgvvrpltev-emdhyrepflkp vdreplwrfpnelpiagepanivalveaymnwlhqspvp-kllfwgtpgvlippaeaarlaeslpncktvdigpglnflqednpdligseiarwl-pal (SEQ ID NO:73).

The nucleic acid molecule or expression cassette may be introduced to a vector, e.g., a plasmid or viral vector, which optionally includes a selectable marker gene, and the vector introduced to a cell of interest, for example, a prokaryotic cell such as E. coli, Streptomyces spp., Bacillus spp., Staphylococcus spp. and the like, as well as eukaryotic cells including a plant (dicot or monocot), fungus, yeast, e.g., Pichia, Saccharomyces or Schizosaccharomyces, or mammalian cell. Preferred mammalian cells include bovine, caprine, ovine, canine, feline, non-human primate, e.g., simian, and human cells. Preferred mammalian cell lines include, but are not limited to, CHO, COS, 293, Hela, CV-1, SH-SY5Y (human neuroblastoma cells), HEK293, and NIH3T3 cells.

The expression of the encoded mutant hydrolase may be controlled by any promoter capable of expression in prokaryotic cells or eukaryotic cells. Preferred prokaryotic promoters include, but are not limited to, SP6, T7, T5, tac, bla, trp, gal, lac or maltose promoters. Preferred eukaryotic promoters include, but are not limited to, constitutive promoters, e.g., viral promoters such as CMV, SV40 and RSV promoters, as well as regulatable promoters, e.g., an inducible or repressible promoter such as the tet promoter, the hsp70 promoter and a synthetic promoter regulated by CRE. In one embodiment, vectors for cloning or expression include Flexi® Vectors, such as those disclosed in U.S. published application Nos. 20050074785 and 20050074883, the disclosures of which are incorporated by reference herein, Gateway™ vectors, or any other suitable cloning or expression vector. Vectors for bacterial expression include pGEX-5X-3, and for eukaryotic expression include but are not limited to pCIneo-CMV.

The nucleic acid molecule, expression cassette and/or vector of the invention may be introduced to a cell by any method including, but not limited to, calcium-mediated transformation, electroporation, microinjection, lipofection, particle bombardment and the like.

Functional Groups

Functional groups useful in the substrates and methods of the invention are molecules that are detectable or capable of detection. A functional group within the scope of the invention is capable of being covalently linked to one reactive substituent of a bifunctional linker or a substrate for a hydrolase, and, as part of a substrate of the invention, has substantially the same activity as a functional group which is not linked to a substrate found in nature and is capable of forming a stable complex with a mutant hydrolase. Functional groups thus have one or more properties that facilitate detection, and optionally the isolation, of stable complexes between a substrate having that functional group and a mutant hydrolase. For instance, functional groups include those with a characteristic electromagnetic spectral property such as emission or absorbance, magnetism, electron spin resonance, electrical capacitance, dielectric constant or electrical conductivity as well as functional groups which are ferromagnetic, paramagnetic, diamagnetic, luminescent, electrochemiluminescent, fluorescent, phosphorescent, chromatic, antigenic, or have a distinctive mass. A functional group includes, but is not limited to, a nucleic acid molecule, i.e., DNA or RNA, e.g., an oligonucleotide or nucleotide, such as one having nucleotide analogs, DNA which is capable of binding a protein, single stranded DNA corresponding to a gene of interest, RNA corresponding to a gene of interest, mRNA which lacks a stop codon, an aminoacylated initiator tRNA, an aminoacylated amber suppressor tRNA, or double stranded RNA for RNAi, a protein, e.g., a luminescent protein, a peptide, a peptide nucleic acid, an epitope recognized by a ligand, e.g., biotin or streptavidin, a hapten, an amino acid, a lipid, a lipid bilayer, a solid support, a fluorophore, a chromophore, a reporter molecule, a radionuclide, such as a radioisotope for use in, for instance, radioactive measurements or a stable isotope for use in methods such as isotope coded affinity tag (ICAT), an electron opaque molecule, an X-ray contrast reagent, a MRI contrast agent, e.g., manganese, gadolinium (III) or iron-oxide particles, and the like. In one embodiment, the functional group is an amino acid, protein, glycoprotein, polysaccharide, triplet sensitizer, e.g., CALI, nucleic acid molecule, drug, toxin, lipid, biotin, or solid support, such as self-assembled monolayers (see, e.g., Kwon et al., 2004), binds $Ca^{2+}$, binds $K^+$, binds $Na^+$, is pH sensitive, is electron opaque, is a chromophore, is a MRI contrast agent, fluoresces in the presence of NO or is sensitive to a reactive oxygen, a nanoparticle, an enzyme, a substrate for an enzyme, an inhibitor of an enzyme, for instance, a suicide substrate (see, e.g., Kwon et al., 2004), a cofactor, e.g., NADP, a coenzyme, a succinimidyl ester or aldehyde, luciferin, glutathione, NTA, biotin, cAMP, phosphatidylinositol, a ligand for cAMP, a metal, a nitroxide or nitrone for use as a spin trap (detected by electron spin resonance (ESR), a metal chelator, e.g., for use as a contrast agent, in time resolved fluorescence or to capture metals, a photocaged compound, e.g., where irradiation liberates the caged compound such as a fluorophore, an intercalator, e.g., such as psoralen or another intercalator useful to bind DNA or as a photoactivatable molecule, a triphosphate or a phosphoramidite, e.g., to allow for incorporation of the substrate into DNA or RNA, an antibody, or a heterobifunctional cross-linker such as one useful to conjugate proteins or other molecules, cross-linkers including but not limited to hydrazide, aryl azide, maleimide, iodoacetamide/bromoacetamide, N-hydroxysuccinimidyl ester, mixed disulfide such as pyridyl disulfide, glyoxal/phenylglyoxal, vinyl sulfone/vinyl sulfonamide, acrylamide, boronic ester, hydroxamic acid, imidate ester, isocyanate/isothiocyanate, or chlorotriazine/dichlorotriazine.

For instance, a functional group includes but is not limited to one or more amino acids, e.g., a naturally occurring amino acid or a non-natural amino acid, a peptide or polypeptide (protein) including an antibody or a fragment thereof, a His-tag, a FLAG tag, a Streptag, an enzyme, a cofactor, a coenzyme, a peptide or protein substrate for an enzyme, for instance, a branched peptide substrate (e.g., Z-aminobenzoyl (Abz)-Gly-Pro-Ala-Leu-Ala-4-nitrobenzyl amide (NBA), a suicide substrate, or a receptor, one or more nucleotides (e.g., ATP, ADP, AMP, GTP or GDP) including analogs thereof, e.g., an oligonucleotide, double stranded or single stranded DNA corresponding to a gene or a portion thereof, e.g., DNA capable of binding a protein such as a transcription factor, RNA corresponding to a gene, for instance, mRNA which lacks a stop codon, or a portion thereof, double stranded RNA for RNAi or vectors therefor, a glycoprotein, a polysaccharide, a peptide-nucleic acid (PNA), lipids including lipid bilayers; or is a solid support, e.g., a sedimental particle such as a magnetic particle, a sepharose or cellulose bead, a membrane, glass, e.g., glass slides, cellulose, alginate, plastic or other synthetically prepared polymer, e.g., an eppendorf tube or a well of a multi-well plate, self assembled monolayers, a surface plasmon resonance chip, or a solid support with an electron conducting surface, and includes a drug, for instance, a chemotherapeutic such as doxorubicin, 5-fluorouracil, or camptosar (CPT-11; Irinotecan), an aminoacylated tRNA such as an aminoacylated initiator tRNA or an aminoacylated amber suppressor tRNA, a molecule which binds $Ca^{2+}$, a molecule which binds $K^+$, a molecule which binds $Na^+$, a molecule which is pH sensitive, a radionuclide, a molecule which is electron opaque, a contrast agent, e.g., barium, iodine or other MRI or X-ray contrast agent, a molecule which fluoresces in the presence of NO or is sensitive to a reactive oxygen, a nanoparticle, e.g., an immunogold particle, paramagnetic nanoparticle, upconverting nanoparticle, or a quantum dot, a nonprotein substrate for an enzyme, an inhibitor of an enzyme, either a reversible or irreversible inhibitor, a chelating agent, a cross-linking group, for example, a succinimidyl ester or aldehyde, glutathione, biotin or other avidin binding molecule, avidin, streptavidin, cAMP, phosphatidylinositol, heme, a ligand for cAMP, a metal, NTA, and, in one embodiment, includes one or more dyes, e.g., a xanthene dye, a calcium sensitive dye, e.g., 1-[2-amino-5-(2,7-dichloro-6-hydroxy-3-oxy-9-xanthenyl)-phenoxy]-2-(2'-amino-5'-methylphenoxy)ethane-N,N,N',N'-tetraacetic acid (Fluo-3), a sodium sensitive dye, e.g., 1,3-benzenedicarboxylic acid, 4,4'-[1,4,10,13-tetraoxa-7,16-diazacyclooctadecane-7,16-diylbis(5-methoxy-6,2-benzofurandiyl)]bis (PBFI), a NO sensitive dye, e.g., 4-amino-5-methylamino-2',7'-difluorescein, or other fluorophore. In one embodiment, the functional group is a hapten or an immunogenic molecule, i.e., one which is bound by antibodies specific for that molecule. In one embodiment, the functional group is not a radionuclide. In another embodiment, the functional group is a radionuclide, e.g., $^3H$, $^{14}C$, $^{35}S$, $^{125}I$, $^{131}I$, including a molecule useful in diagnostic methods.

Methods to detect a particular functional group are known to the art. For example, a nucleic acid molecule can be detected by hybridization, amplification, binding to a nucleic acid binding protein specific for the nucleic acid molecule, enzymatic assays (e.g., if the nucleic acid molecule is a ribozyme), or, if the nucleic acid molecule itself comprises a molecule which is detectable or capable of detection, for instance, a radiolabel or biotin, it can be detected by an assay suitable for that molecule.

Exemplary functional groups include haptens, e.g., molecules useful to enhance immunogenicity such as keyhole limpet hemacyanin (KLH), cleavable labels, for instance, photocleavable biotin, and fluorescent labels, e.g., N-hydroxysuccinimide (NHS) modified coumarin and succinimide or sulfonosuccinimide modified BODIPY (which can be detected by UV and/or visible excited fluorescence detection), rhodamine, e.g., R110, rhodols, CRG6, Texas Methyl Red (carboxytetramethylrhodamine), 5-carboxy-X-rhodamine, or fluoroscein, coumarin derivatives, e.g., 7 aminocoumarin, and 7-hydroxycoumarin, 2-amino-4-methoxynapthalene, 1-hydroxypyrene, resorufin, phenalenones or benzphenalenones (U.S. Pat. No. 4,812,409), acridinones (U.S. Pat. No. 4,810,636), anthracenes, and derivatives of α- and β-napthol, fluorinated xanthene derivatives including fluorinated fluoresceins and rhodols (e.g., U.S. Pat. No. 6,162,931), bioluminescent molecules, e.g., luciferin, coelenterazine, luciferase, chemiluminescent molecules, e.g., stabilized dioxetanes, and electrochemiluminescent molecules. A fluorescent (or luminescent) functional group linked to a mutant hydrolase by virtue of being linked to a substrate for a corresponding wild-type hydrolase, may be used to sense changes in a system, like phosphorylation, in real time. Moreover, a fluorescent molecule, such as a chemosensor of metal ions, e.g., a 9-carbonylanthracene modified glycyl-histidyl-lysine (GHK) for Cu2+, in a substrate of the invention may be employed to label proteins which bind the substrate. A luminescent or fluorescent functional group such as BODIPY, rhodamine green, GFP, or infrared dyes, also finds use as a functional group and may, for instance, be employed in interaction studies, e.g., using BRET, FRET, LRET or electrophoresis.

Another class of functional group is a molecule that selectively interacts with molecules containing acceptor groups (an "affinity" molecule). Thus, a substrate for a hydrolase which includes an affinity molecule can facilitate the separation of complexes having such a substrate and a mutant hydrolase, because of the selective interaction of the affinity molecule with another molecule, e.g., an acceptor molecule, that may be biological or non-biological in origin. For example, the specific molecule with which the affinity molecule interacts (referred to as the acceptor molecule) could be a small organic molecule, a chemical group such as a sulfhydryl group (—SH) or a large biomolecule such as an antibody or other naturally occurring ligand for the affinity molecule. The binding is normally chemical in nature and may involve the formation of covalent or non-covalent bonds or interactions such as ionic or hydrogen bonding. The acceptor molecule might be free in solution or itself bound to a solid or semi-solid surface, a polymer matrix, or reside on the surface of a solid or semi-solid substrate. The interaction may also be triggered by an external agent such as light, temperature, pressure or the addition of a chemical or biological molecule that acts as a catalyst. The detection and/or separation of the complex from the reaction mixture occurs because of the interaction, normally a type of binding, between the affinity molecule and the acceptor molecule.

Examples of affinity molecules include molecules such as immunogenic molecules, e.g., epitopes of proteins, peptides, carbohydrates or lipids, i.e., any molecule which is useful to prepare antibodies specific for that molecule; biotin, avidin, streptavidin, and derivatives thereof; metal binding molecules; and fragments and combinations of these molecules. Exemplary affinity molecules include His5 (HHHHH) (SEQ ID NO:3), HisX6 (HHHHHH) (SEQ ID NO:4), C-myc (EQKLISEEDL) (SEQ ID NO:5), Flag (DYKDDDDK) (SEQ ID NO:6), SteptTag (WSHPQFEK) (SEQ ID NO:7), HA Tag (YPYDVPDYA) (SEQ ID NO:8), thioredoxin, cellulose binding domain, chitin binding domain, S-peptide, T7 peptide, calmodulin binding peptide, C-end RNA tag, metal binding domains, metal binding reactive groups, amino acid reactive groups, inteins, biotin, streptavidin, and maltose binding protein. For example, a substrate for a hydrolase which includes biotin is contacted with a mutant hydrolase. The presence of the biotin in a complex between the mutant hydrolase and the substrate permits selective binding of the complex to avidin molecules, e.g., streptavidin molecules coated onto a surface, e.g., beads, microwells, nitrocellulose and the like. Suitable surfaces include resins for chromatographic separation, plastics such as tissue culture surfaces or binding plates, microtiter dishes and beads, ceramics and glasses, particles including magnetic particles, polymers and other matrices. The treated surface is washed with, for example, phosphate buffered saline (PBS), to remove molecules that lack biotin and the biotin-containing complexes isolated. In some case these materials may be part of biomolecular sensing devices such as optical fibers, chemfets, and plasmon detectors.

Another example of an affinity molecule is dansyllysine. Antibodies which interact with the dansyl ring are commercially available (Sigma Chemical; St. Louis, Mo.) or can be prepared using known protocols such as described in Antibodies: A Laboratory Manual (Harlow and Lane, 1988). For example, the anti-dansyl antibody is immobilized onto the packing material of a chromatographic column. This method, affinity column chromatography, accomplishes separation by causing the complex between a mutant hydrolase and a substrate of the invention to be retained on the column due to its interaction with the immobilized antibody, while other molecules pass through the column. The complex may then be released by disrupting the antibody-antigen interaction. Specific chromatographic column materials such as ion-exchange or affinity Sepharose, Sephacryl, Sephadex and other chromatography resins are commercially available (Sigma Chemical; St. Louis, Mo.; Pharmacia Biotech; Piscataway, N.J.). Dansyllysine may conveniently be detected because of its fluorescent properties.

When employing an antibody as an acceptor molecule, separation can also be performed through other biochemical separation methods such as immunoprecipitation and immobilization of antibodies on filters or other surfaces such as beads, plates or resins. For example, complexes of a mutant hydrolase and a substrate of the invention may be isolated by coating magnetic beads with an affinity molecule-specific or a hydrolase-specific antibody. Beads are oftentimes separated from the mixture using magnetic fields.

Another class of functional molecules includes molecules detectable using electromagnetic radiation and includes but is not limited to xanthene fluorophores, dansyl fluorophores, coumarins and coumarin derivatives, fluorescent acridinium moieties, benzopyrene based fluorophores, as well as 7-nitrobenz-2-oxa-1,3-diazole, and 3-N-(7-nitrobenz-2-oxa-1,3-diazol-4-yl)-2,3-diamino-propionic acid. Preferably, the fluorescent molecule has a high quantum yield of fluorescence at a wavelength different from native amino acids and more preferably has high quantum yield of fluorescence that can be excited in the visible, or in both the UV and visible, portion of the spectrum. Upon excitation at a preselected wavelength, the molecule is detectable at low concentrations either visually or using conventional fluorescence detection methods. Electrochemiluminescent molecules such as ruthenium chelates and its derivatives or nitroxide amino acids and their derivatives are detectable at femtomolar ranges and below.

In one embodiment, an optionally detectable functional group includes one of:

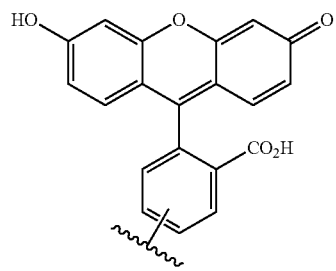

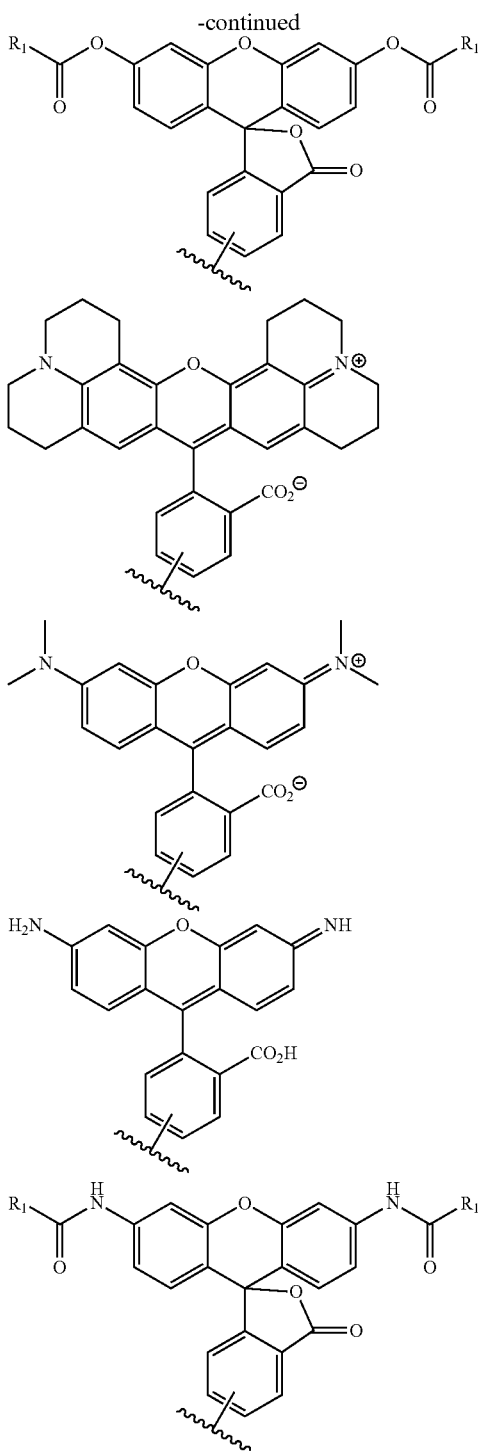

wherein $R_1$ is $C_1$-$C_8$.

In addition to fluorescent molecules, a variety of molecules with physical properties based on the interaction and response of the molecule to electromagnetic fields and radiation can be used to detect complexes between a mutant hydrolase and a substrate of the invention. These properties include absorption in the UV, visible and infrared regions of the electromagnetic spectrum, presence of chromophores which are Raman active, and can be further enhanced by resonance Raman spectroscopy, electron spin resonance activity and nuclear magnetic resonances and molecular mass, e.g., via a mass spectrometer.

Methods to detect and/or isolate complexes having affinity molecules include chromatographic techniques including gel filtration, fast-pressure or high-pressure liquid chromatography, reverse-phase chromatography, affinity chromatography and ion exchange chromatography. Other methods of protein separation are also useful for detection and subsequent isolation of complexes between a mutant hydrolase and a substrate of the invention, for example, electrophoresis, isoelectric focusing and mass spectrometry.

Linkers

The term "linker", which is also identified by the symbol >L=, refers to a group or groups that covalently attach one or more functional groups to a substrate which includes a reactive group or to a reactive group. A linker, as used herein, is not a single covalent bond. The structure of the linker is not crucial, provided it yields a substrate that can be bound by its target enzyme. In one embodiment, the linker can be a divalent group that separates a functional group (R) and the reactive group by about 5 angstroms to about 1000 angstroms, inclusive, in length. Other suitable linkers include linkers that separate R and the reactive group by about 5 angstroms to about 100 angstroms, as well as linkers that separate R and the substrate by about 5 angstroms to about 50 angstroms, by about 5 angstroms to about 25 angstroms, by about 5 angstroms to about 500 angstroms, or by about 30 angstroms to about 100 angstroms.

In one embodiment the linker is an amino acid.

In another embodiment, the linker is a peptide.

In another embodiment, the linker is a divalent branched or unbranched carbon chain comprising from about 2 to about 30 carbon atoms, which chain optionally includes one or more (e.g., 1, 2, 3, or 4) double or triple bonds, and which chain is optionally substituted with one or more (e.g., 2, 3, or 4) hydroxy or oxo (=O) groups, wherein one or more (e.g., 1, 2, 3, or 4) of the carbon atoms in the chain is optionally replaced with a non-peroxide —O—, —S— or —NH— and wherein one or more (e.g., 1, 2, 3, or 4) of the carbon atoms in the chain is replaced with an aryl or heteroaryl ring.

In another embodiment, the linker is a divalent branched or unbranched carbon chain comprising from about 2 to about 30 carbon atoms, which chain optionally includes one or more (e.g., 1, 2, 3, or 4) double or triple bonds, and which chain is optionally substituted with one or more (e.g., 2, 3, or 4) hydroxy or oxo (=O) groups, wherein one or more (e.g., 1, 2, 3, or 4) of the carbon atoms in the chain is replaced with a non-peroxide —O—, —S— or —NH— and wherein one or more (e.g., 1, 2, 3, or 4) of the carbon atoms in the chain is replaced with one or more (e.g., 1, 2, 3, or 4) aryl or heteroaryl rings.

In another embodiment, the linker is a divalent branched or unbranched carbon chain comprising from about 2 to about 30 carbon atoms, which chain optionally includes one or more (e.g., 1, 2, 3, or 4) double or triple bonds, and which chain is optionally substituted with one or more (e.g., 2, 3, or 4) hydroxy or oxo (=O) groups, wherein one or more (e.g., 1, 2, 3, or 4) of the carbon atoms in the chain is replaced with a non-peroxide —O—, —S— or —NH— and wherein one or more (e.g., 1, 2, 3, or 4) of the carbon atoms in the chain is replaced with one or more (e.g., 1, 2, 3, or 4) heteroaryl rings.

In another embodiment, the linker is a divalent branched or unbranched carbon chain comprising from about 2 to about 30 carbon atoms, which chain optionally includes one or more (e.g., 1, 2, 3, or 4) double or triple bonds, and which chain is optionally substituted with one or more (e.g., 2, 3, or 4) hydroxy or oxo (=O) groups, wherein one or more (e.g., 1, 2, 3, or 4) of the carbon atoms in the chain is optionally replaced with a non-peroxide —O—, —S— or —NH—.

In another embodiment, the linker is a divalent group of the formula —W—F—W— wherein F is $(C_1-C_{30})$alkyl, $(C_2-C_{30})$alkenyl, $(C_2-C_{30})$alkynyl, $(C_3-C_8)$cycloalkyl, or $(C_6-C_{10})$, wherein W is —N(Q)C(=O)—, —C(=O)N(Q)-, —OC(=O)—, —C(=O)O—, —O—, —S—, —S(O)—, —S(O)$_2$—, —N(Q)-, —C(=O)—, or a direct bond; wherein each Q is independently H or $(C_1-C_6)$alkyl In another embodiment, the linker is a divalent branched or unbranched carbon chain comprising from about 2 to about 30 carbon atoms, which chain optionally includes one or more (e.g., 1, 2, 3, or 4) double or triple bonds, and which chain is optionally substituted with one or more (e.g., 2, 3, or 4) hydroxy or oxo (=O) groups.

In another embodiment, the linker is a divalent branched or unbranched carbon chain comprising from about 2 to about 30 carbon atoms, which chain optionally includes one or more (e.g., 1, 2, 3, or 4) double or triple bonds.

In another embodiment, the linker is a divalent branched or unbranched carbon chain comprising from about 2 to about 30 carbon atoms.

In another embodiment, the linker is a divalent branched or unbranched carbon chain comprising from about 2 to about 20 carbon atoms, which chain optionally includes one or more (e.g., 1, 2, 3, or 4) double or triple bonds, and which chain is optionally substituted with one or more (e.g., 2, 3, or 4) hydroxy or oxo (=O) groups.

In another embodiment, the linker is a divalent branched or unbranched carbon chain comprising from about 2 to about 20 carbon atoms, which chain optionally includes one or more (e.g., 1, 2, 3, or 4) double or triple bonds.

In another embodiment, the linker is a divalent branched or unbranched carbon chain comprising from about 2 to about 20 carbon atoms.

In another embodiment, the linker is —(CH$_2$CH$_2$O)—$_{1-10}$.

In another embodiment, the linker is —C(=O)NH(CH$_2$)$_3$—; —C(=O)NH(CH$_2$)$_5$C(=O)NH(CH$_2$)—; —CH$_2$OC(=O)NH(CH$_2$)$_2$O(CH$_2$)$_2$O(CH$_2$)—; —C(=O)NH(CH$_2$)$_2$O(CH$_2$)$_2$O(CH$_2$)$_3$—; —CH$_2$OC(=O)NH(CH$_2$)$_2$O(CH$_2$)$_2$O(CH$_2$)$_3$—; —(CH$_2$)$_4$C(=O)NH(CH$_2$)$_2$O(CH$_2$)$_2$O(CH$_2$)$_3$—; —C(=O)NH(CH$_2$)$_5$C(=O)NH(CH$_2$)$_2$O(CH$_2$)$_2$O(CH$_2$)$_3$—.

In another embodiment, the linker comprises one or more divalent heteroaryl groups.

Specifically, $(C_1-C_{30})$alkyl can be methyl, ethyl, propyl, isopropyl, butyl, iso-butyl, sec-butyl, pentyl, 3-pentyl, hexyl, heptyl, octyl, nonyl, or decyl; $(C_3-C_8)$cycloalkyl can be cyclopropyl, cyclobutyl, cyclopentyl, or cyclohexyl; $(C_2-C_{30})$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, 5-hexenyl, heptenyl, octenyl, nonenyl, or decenyl; $(C_2-C_{30})$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, heptynyl, octynyl, nonynyl, or decynyl; $(C_6-C_{10})$aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

The term aromatic includes aryl and heteroaryl groups.

Aryl denotes a phenyl radical or an ortho-fused bicyclic carbocyclic radical having about nine to ten ring atoms in which at least one ring is aromatic.

Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

The term "amino acid," when used with reference to a linker, comprises the residues of the natural amino acids (e.g., Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g., phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also includes natural and unnatural amino acids bearing a conventional amino protecting group (e.g., acetyl or benzyloxycarbonyl), as well as natural and unnatural amino acids protected at the carboxy terminus (e.g. as a $(C_1-C_6)$alkyl, phenyl or benzyl ester or amide). Other suitable amino and carboxy protecting groups are known to those skilled in the art (see for example, Greene, *Protecting Groups In Organic Synthesis*; Wiley: New York, 1981, and references cited therein). An amino acid can be linked to another molecule through the carboxy terminus, the amino terminus, or through any other convenient point of attachment, such as, for example, through the sulfur of cysteine.

The term "peptide" when used with reference to a linker, describes a sequence of 2 to 25 amino acids (e.g. as defined hereinabove) or peptidyl residues. The sequence may be linear or cyclic. For example, a cyclic peptide can be prepared or may result from the formation of disulfide bridges between two cysteine residues in a sequence. A peptide can be linked to another molecule through the carboxy terminus, the amino terminus, or through any other convenient point of attachment, such as, for example, through the sulfur of a cysteine. Preferably a peptide comprises 3 to 25, or 5 to 21 amino acids. Peptide derivatives can be prepared as disclosed in U.S. Pat. Nos. 4,612,302; 4,853,371; and 4,684,620. Peptide sequences specifically recited herein are written with the amino terminus on the left and the carboxy terminus on the right.

Exemplary Substrates

In one embodiment, the hydrolase substrate has a compound of formula (I): R-linker-A-X, wherein R is one or more functional groups, wherein the linker is a multiatom straight or branched chain including C, N, S, or O, or a group that comprises one or more rings, e.g., saturated or unsaturated rings, such as one or more aryl rings, heteroaryl rings, or any combination thereof, wherein A-X is a substrate for a dehalogenase, e.g., a haloalkane dehalogenase or a dehalogenase that cleaves carbon-halogen bonds in an aliphatic or aromatic halogenated substrate, such as a substrate for *Rhodococcus, Sphingomonas, Staphylococcus, Pseudomonas, Burkholderia, Agrobacterium* or *Xanthobacter* dehalogenase, and wherein X is a halogen. In one embodiment, an alkylhalide is covalently attached to a linker, L, which is a group or groups that covalently attach one or more functional groups to form a substrate for a dehalogenase.

In one embodiment, a substrate of the invention for a dehalogenase which has a linker has the formula (I):

R-linker-A-X                             (I)

wherein R is one or more functional groups (such as a fluorophore, biotin, luminophore, or a fluorogenic or luminogenic molecule, or is a solid support, including microspheres, membranes, polymeric plates, glass beads, glass slides, and the like), wherein the linker is a multiatom straight or branched chain including C, N, S, or O, wherein A-X is a substrate for a dehalogenase, and wherein X is a halogen. In one embodiment, A-X is a haloaliphatic or haloaromatic substrate for a dehalogenase. In one embodiment, the linker is a divalent branched or unbranched carbon chain comprising from about 12 to about 30 carbon atoms, which chain optionally includes one or more (e.g., 1, 2, 3, or 4) double or triple bonds, and which chain is optionally substituted with one or more (e.g., 2, 3, or 4) hydroxy or oxo (=O) groups, wherein one or more (e.g., 1, 2, 3, or 4) of the carbon atoms in the chain is optionally replaced with a non-peroxide —O—, —S— or —NH—. In one embodiment, the linker comprises 3 to 30 atoms, e.g., 11 to 30 atoms. In one embodiment, the linker comprises $(CH_2CH_2O)_y$ and y=2 to 8. In one embodiment, A is $(CH_2)_n$ and n=2 to 10, e.g., 4 to 10. In one embodiment, A is $CH_2CH_2$ or $CH_2CH_2CH_2$. In another embodiment, A comprises an aryl or heteroaryl group. In one embodiment, a linker in a substrate for a dehalogenase such as a *Rhodococcus* dehalogenase, is a multiatom straight or branched chain including C, N, S, or O, and preferably 11-30 atoms when the functional group R includes an aromatic ring system or is a solid support.

In another embodiment, a substrate of the invention for a dehalogenase which has a linker has formula (II):

R-linker-$CH_2$—$CH_2$—$CH_2$—X             (II)

where X is a halogen, preferably chloride. In one embodiment, R is one or more functional groups, such as a fluorophore, biotin, luminophore, or a fluorogenic or luminogenic molecule, or is a solid support, including microspheres, membranes, glass beads, and the like. When R is a radiolabel, or a small detectable atom such as a spectroscopically active isotope, the linker can be 0-30 atoms.

Exemplary dehalogenase substrates are described in U.S. published application numbers 2006/0024808 and 2005/0272114, which are incorporated by reference herein.

Exemplary Methods

The invention provides methods to monitor the expression, location and/or trafficking of molecules in a cell, as well as to monitor changes in microenvironments within a cell, e.g., to image, identify, localize, display or detect one or more molecules which may be present in a sample, e.g., in a cell, or to capture, purify or isolate molecules, such as those in cells, which methods employ a hydrolase substrate and mutant hydrolase of the invention. The hydrolase substrates employed in the methods of the invention are preferably soluble in an aqueous or mostly aqueous solution, including water and aqueous solutions having a pH greater than or equal to about 6. Stock solutions of substrates, however, may be dissolved in organic solvent before diluting into aqueous solution or buffer. Preferred organic solvents are aprotic polar solvents such as DMSO, DMF, N-methylpyrrolidone, acetone, acetonitrile, dioxane, tetrahydrofuran and other nonhydroxylic, completely water-miscible solvents. The concentration of a hydrolase substrate and a mutant hydrolase to be used is dependent upon the experimental conditions and the desired results, e.g., to obtain results within a reasonable time, with minimal background or undesirable labeling. The concentration of a hydrolase substrate typically ranges from nanomolar to micromolar. The required concentration for the hydrolase substrate with a corresponding mutant hydrolase is determined by systematic variation in substrate until satisfactory labeling is accomplished. The starting ranges are readily determined from methods known in the art.

In one embodiment, a substrate which includes a functional group with optical properties is employed to detect an interaction between a cellular molecule and a fusion partner of a fusion having a mutant hydrolase. Such a substrate is combined with the sample of interest comprising the fusion fragment for a period of time sufficient for the fusion partner to bind the cellular molecule, and the mutant hydrolase to bind the substrate, after which the sample is illuminated at a wavelength selected to elicit the optical response of the functional group. Optionally, the sample is washed to remove residual, excess or unbound substrate. In one embodiment, the labeling is used to determine a specified characteristic of the sample by further comparing the optical response with a standard or expected response. For example, the mutant hydrolase bound substrate is used to monitor specific components of the sample with respect to their spatial and temporal distribution in the sample. Alternatively, the mutant hydrolase bound substrate is employed to determine or detect the presence or quantity of a certain molecule.

In contrast to intrinsically fluorescent proteins, e.g., GFP, mutant hydrolase bound to a fluorescent substrate does not require a native protein structure to retain fluorescence. After the fluorescent substrate is bound, the mutant hydrolase may be detected, for example, in denaturing electrophoretic gels, e.g., SDS-PAGE, or in cells fixed with organic solvents, e.g., paraformaldehyde.

A detectable optical response means a change in, or occurrence of, a parameter in a test system that is capable of being perceived, either by direct observation or instrumentally. Such detectable responses include the change in, or appearance of, color, fluorescence, reflectance, chemiluminescence, light polarization, light scattering, or X-ray scattering. Typically the detectable response is a change in fluorescence, such as a change in the intensity, excitation or emission wavelength distribution of fluorescence, fluorescence lifetime, fluorescence polarization, or a combination thereof. The detectable optical response may occur throughout the sample or in a localized portion of the sample having the substrate bound to the mutant hydrolase. Comparison of the degree of optical response with a standard or expected response can be used to determine whether and to what degree the sample possesses a given characteristic.

A sample comprising a mutant hydrolase is typically labeled by passive means, i.e., by incubation with the substrate. However, any method of introducing the substrate into the sample such as microinjection of a substrate into a cell or organelle, can be used to introduce the substrate into the sample. The substrates of the present invention are generally non-toxic to living cells and other biological components, within the concentrations of use.

A sample comprising a mutant hydrolase can be observed immediately after contact with a substrate of the invention. The sample comprising a mutant hydrolase or a fusion thereof is optionally combined with other solutions in the course of labeling, including wash solutions, permeabilization and/or fixation solutions, and other solutions containing additional detection reagents. Washing following contact with the substrate may improve the detection of the optical response due to the decrease in non-specific background after washing. Satisfactory visualization is possible without washing by using lower labeling concentrations. A number of fixatives and fixation conditions are known in the art, including formaldehyde, paraformaldehyde, formalin, glutaraldehyde, cold methanol and 3:1 methanol:acetic acid. Fixation is typically used to preserve cellular morphology and to reduce biohazards when working with pathogenic samples. Selected embodiments of the substrates are well retained in cells. Fixation is optionally followed or accompanied by permeabilization, such as with acetone, ethanol, DMSO or various detergents, to allow bulky substrates of the invention, to cross cell membranes, according to methods generally known in the art. Optionally, the use of a substrate may be combined with the use of an additional detection reagent that produces a detectable response due to the presence of a specific cell component, intracellular substance, or cellular condition, in a sample comprising a mutant hydrolase or a fusion thereof. Where the additional detection reagent has spectral properties that differ from those of the substrate, multi-color applications are possible.

At any time after or during contact with the substrate having a functional group with optical properties, the sample comprising a mutant hydrolase or a fusion thereof is illuminated with a wavelength of light that results in a detectable optical response, and observed with a means for detecting the optical response. While some substrates are detectable colorimetrically, using ambient light, other substrates are detected by the fluorescence properties of the parent fluorophore. Upon illumination, such as by an ultraviolet or visible wavelength emission lamp, an arc lamp, a laser, or even sunlight or ordinary room light, the substrates, including substrates bound to the complementary specific binding pair member, display intense visible absorption as well as fluorescence emission. Selected equipment that is useful for illuminating the substrates of the invention includes, but is not limited to, hand-held ultraviolet lamps, mercury arc lamps, xenon lamps, argon lasers, laser diodes, and YAG lasers. These illumination sources are optionally integrated into laser scanners, fluorescence microplate readers, standard or mini fluorometers, or chromatographic detectors. This colorimetric absorbance or fluorescence emission is optionally detected by visual inspection, or by use of any of the following devices: CCD cameras, video cameras, photographic film, laser scanning devices, fluorometers, photodiodes, quantum counters, epifluorescence microscopes, scanning microscopes, flow cytometers, fluorescence microplate readers, or by means for amplifying the signal such as photomultiplier tubes. Where the sample comprising a mutant hydrolase or a fusion thereof is examined using a flow cytometer, a fluorescence microscope or a fluorometer, the instrument is optionally used to distinguish and discriminate between the substrate comprising a functional group which is a fluorophore and a second fluorophore with detectably different optical properties, typically by distinguishing the fluorescence response of the substrate from that of the second fluorophore. Where the sample is examined using a flow cytometer, examination of the sample optionally includes isolation of particles within the sample based on the fluorescence response of the substrate by using a sorting device.

Exemplary Mutant Hydrolases and Methods of Using Those Hydrolases

In one embodiment, the invention provides a first mutant dehalogenase comprising at least one amino acid substitution relative to a second mutant dehalogenase. The first and second mutant dehalogenases form a bond with a dehalogenase substrate which comprises one or more functional groups, which bond is more stable than the bond formed between a corresponding wild-type dehalogenase and the substrate. At least one amino acid substitution in the first mutant dehalogenase that is not in the second mutant dehalogenase is a substitution that improves functional expression or binding kinetics. The first and second mutant dehalogenases have at least one amino acid substitution in a residue that in the corresponding wild-type dehalogenase is associated with activating a water molecule which cleaves the bond formed between the corresponding wild-type dehalogenase and the substrate or at an amino acid residue that in the wild-type dehalogenase forms an ester intermediate with the substrate.

At least one substitution that improves functional expression or binding kinetics is at position corresponding to position 5, 11, 20, 30, 32, 47, 58, 60, 65, 78, 80, 87, 88, 94, 109, 113, 117, 118, 124, 128, 134, 136, 150, 151, 155, 157, 160, 167, 172, 187, 195, 204, 221, 224, 227, 231, 250, 256, 257, 263, 264, 277, 282, 291 or 292 in SEQ ID NO:1. In one embodiment, the first mutant dehalogenase has at least two substitutions at positions corresponding to positions 5, 11, 20, 30, 32, 58, 60, 65, 78, 80 87, 94, 109, 113, 117, 118, 124, 134, 136, 150, 151, 155, 157, 172, 187, 204, 221, 224, 227, 231, 250, 256, 263, 277, 282, 291 and 292 in SEQ ID NO:1.

In one embodiment, the first mutant dehalogenase has a substitution at position corresponding to position 58, 78, 87, 155, 172, 224, 227, 291, or 292 in SEQ ID NO:1, or a plurality thereof, and a substitution at a position corresponding to position 175, 176, 272 or 273 in SEQ ID NO: 1, or a plurality thereof.

In one embodiment, the first mutant dehalogenase has a substitution at a position corresponding to 58, 78, 155, 172, 224, 291, or 292 in SEQ ID NO:1, or a plurality thereof, and a substitution at a position corresponding to position 175, 176, 272 or 273 in SEQ ID NO: 1, or a plurality thereof. For instance, the substituted amino acid in the first mutant dehalogenase at a position corresponding to position 291 is G, S or Q, or the substituted amino acid at a position corresponding to position 80 is Q, N, K or T. In one embodiment, the second mutant dehalogenase has a substitution at a residue corresponding to position 272, and further comprises one or more substitutions at a position corresponding to position 175, 176 or 273, in SEQ ID NO:1, e.g., has SEQ ID NO:18.

In one embodiment, at least one substitution in the first and second mutant dehalogenases is at an amino acid residue in the wild-type dehalogenase that is within the active site cavity and one atom of that residue is within 5 Å of a dehalogenase substrate bound to the wild-type dehalogenase. In one embodiment, at least one substitution in the first and second mutant dehalogenases is at a position corresponding to amino acid residue 272 of a *Rhodococcus rhodochrous* dehalogenase, e.g., the substituted amino acid at the position corresponding to amino acid residue 272 is asparagine, glutamine, phenylalanine, glycine or alanine, and optionally another substitution at position 273.

In one embodiment, the first mutant dehalogenase further comprises a protein of interest, thereby yielding a fusion protein, e.g., a selectable marker protein, membrane protein, cytosolic protein, nuclear protein, structural protein, an enzyme, an enzyme substrate, a receptor protein, a transporter protein, a transcription factor, a channel protein, a phospho-protein, a kinase, a signaling protein, a metabolic protein, a mitochondrial protein, a receptor associated protein, a nucleic acid binding protein, an extracellular matrix protein, a secreted protein, a receptor ligand, a serum protein, an immunogenic protein, a fluorescent protein, or a protein with reactive cysteine.

Also provided is an isolated polynucleotide encoding the first mutant dehalogenase. In one embodiment, the isolated polynucleotide encodes a fusion polypeptide comprising the first mutant dehalogenase and a nondehalogenase polypeptide. In one embodiment, the first mutant dehalogenase is C-terminal to the nondehalogenase polypeptide. In one embodiment, the fusion comprises a connector sequence having a protease recognition sequence between the first mutant dehalogenase and the nondehalogenase polypeptide, e.g., the connector sequence includes EPTTEDLYFQS/C (SEQ ID NO:31) or EPTTEDLYFQS/CDN (SEQ ID NO:38).

Mutant hydrolases of the invention are useful in a variety of methods.

In one embodiment, the invention provides a method to detect or determine the presence or amount of a mutant hydrolase. The method includes contacting a sample having a mutant hydrolase with a hydrolase substrate which comprises one or more functional groups, wherein the mutant hydrolase comprises at least two amino acid substitutions relative to a corresponding wild-type hydrolase, wherein one amino acid substitution results in the mutant hydrolase forming a bond with the substrate which is more stable than the bond formed between the corresponding wild-type hydrolase and the substrate and is at an amino acid residue in the corresponding wild-type hydrolase that is associated with activating a water molecule which cleaves the bond formed between the corresponding wild-type hydrolase and the substrate or at an amino acid residue in the corresponding wild-type hydrolase that forms an ester intermediate with the substrate.

In one embodiment, the second substitution is at position corresponding to position 5, 11, 20, 30, 32, 47, 58, 60, 65, 78, 80, 87, 88, 94, 109, 113, 117, 118, 124, 128, 134, 136, 150, 151, 155, 157, 160, 167, 172, 187, 195, 204, 221, 224, 227, 231, 250, 256, 257, 263, 264, 277, 282, 291 or 292 in SEQ ID NO:1. In one embodiment, the mutant hydrolase has a plurality of substitutions at positions corresponding to positions 5, 11, 20, 30, 32, 58, 60, 65, 78, 80, 87, 94, 109, 113, 117, 118, 124, 134, 136, 150, 151, 155, 157, 172, 187, 204, 221, 224, 227, 231, 250, 256, 263, 277, 282, 291, or 292 in SEQ ID NO:1.

In one embodiment, the mutant hydrolase has at least one substitution at a position corresponding to amino acid residue 272 of a *Rhodococcus rhodochrous* dehalogenase, e.g., wherein the substituted amino acid at the position corresponding to amino acid residue 272 is asparagine, glutamine, phenylalanine, glycine or alanine. In one embodiment, the mutant hydrolase further comprises one or more substitutions at a position corresponding to position 175, 176 or 273 in SEQ ID NO:1. In one embodiment, the mutant hydrolase has at least 80%, e.g., at least 85%, amino acid sequence identity to the corresponding wild-type hydrolase. The presence or amount of the functional group is detected or determined, thereby detecting or determining the presence or amount of the mutant hydrolase. In one embodiment, the mutant hydrolase is fused to a molecule of interest, e.g., a protein of interest.

In one embodiment, the invention provides a method to label a cell. The method includes contacting a sample having a cell comprising a mutant hydrolase with a hydrolase substrate which comprises one or more functional groups, wherein the mutant hydrolase comprises at least two amino acid substitutions relative to a corresponding wild-type hydrolase. One amino acid substitution results in the mutant hydrolase forming a bond with the substrate which is more stable than the bond formed between the corresponding wild-type hydrolase and the substrate and the substitution is at an amino acid residue in the corresponding wild-type hydrolase that is associated with activating a water molecule which cleaves a bond formed between the corresponding wild-type hydrolase and the substrate or at an amino acid residue in the corresponding wild-type hydrolase that forms an ester intermediate with the substrate. The second substitution is at position corresponding to position 5, 11, 20, 30, 32, 47, 58, 60, 65, 78, 80, 87, 88, 94, 109, 113, 117, 118, 124, 128, 134, 136, 150, 151, 155, 157, 160, 167, 172, 187, 195, 204, 221, 224, 227, 231, 250, 256, 257, 263, 264, 277, 282, 291 or 292 in SEQ ID NO:1.

In one embodiment, the mutant hydrolase has a plurality of substitutions at positions corresponding to positions 5, 11, 20, 30, 32, 58, 60, 65, 78, 80, 87, 94, 109, 113, 117, 118, 124, 134, 136, 150, 151, 155, 157, 172, 187, 204, 221, 224, 227, 231, 250, 256, 263, 277, 282, 291, or 292 in SEQ ID NO:1. In one embodiment, the mutant hydrolase has at least one substitution at a position corresponding to amino acid residue 272 of a *Rhodococcus rhodochrous* dehalogenase, e.g., wherein the substituted amino acid at the position corresponding to amino acid residue 272 is asparagine, glutamine, phenylalanine, glycine or alanine. In one embodiment, the mutant hydrolase further comprises one or more substitutions at a position corresponding to position 175, 176 or 273 in SEQ ID NO:1. In one embodiment, the mutant hydrolase has at least 80%, e.g., at least 85%, amino acid sequence identity to the corresponding wild-type hydrolase. The presence or amount of the functional group in the sample is then detected or determined. In one embodiment, the cell is a bacterial cell. In another embodiment, the cell is a mammalian cell. In one embodiment, the mutant hydrolase is fused to a molecule of interest, e.g., a protein of interest.

In one embodiment, the invention provides a method to isolate a protein of interest. The method includes providing a sample comprising one or more fusion proteins at least one of which comprises a mutant hydrolase and a protein of interest and a solid support comprising one or more hydrolase substrates. The mutant hydrolase comprises at least two amino acid substitutions relative to a corresponding wild-type hydrolase, wherein one amino acid substitution results in the mutant hydrolase forming a bond with the substrate which is more stable than the bond formed between the corresponding wild-type hydrolase and the substrate and the substitution is at an amino acid residue in the corresponding wild-type hydrolase that is associated with activating a water molecule which cleaves the bond formed between the corresponding wild-type hydrolase and the substrate or at an amino acid residue in the corresponding wild-type hydrolase that forms an ester intermediate with the substrate. The second substitution is at position corresponding to position 5, 11, 20, 30, 32, 47, 58, 60, 65, 78, 80, 87, 88, 94, 109, 113, 117, 118, 124, 128, 134, 136, 150, 151, 155, 157, 160, 167, 172, 187, 195, 204, 221, 224, 227, 231, 250, 256, 257, 263, 264, 277, 282, 291 or 292 in SEQ ID NO:1.

In one embodiment, the mutant hydrolase has a plurality of substitutions at positions corresponding to positions 5, 11, 20, 30, 32, 58, 60, 65, 78, 80, 87, 94, 109, 113, 117, 118, 124, 134, 136, 150, 151, 155, 157, 172, 187, 204, 221, 224, 227, 231, 250, 256, 263, 277, 282, 291, or 292 in SEQ ID NO:1. In one embodiment, the mutant hydrolase has at least one substitution at a position corresponding to amino acid residue 272 of a *Rhodococcus rhodochrous* dehalogenase, e.g., wherein the substituted amino acid at the position corresponding to amino acid residue 272 is asparagine, glutamine, phenylalanine, glycine or alanine. In one embodiment, the mutant hydrolase further comprises one or more substitutions at a position corresponding to position 175, 176 or 273 in SEQ ID NO:1. In one embodiment, the mutant hydrolase has at least 80%, e.g., at least 85%, amino acid sequence identity to the corresponding wild-type hydrolase. The sample and the solid support are contacted so as to isolate the protein of interest. In one embodiment, the protein of interest binds to a molecule of interest. In one embodiment, the molecule of interest which is bound to the protein of interest is isolated.

The methods of the invention employ a compound that includes a substrate for the hydrolase. In one embodiment, the mutant hydrolase is a mutant dehalogenase and the substrate is a compound of formula (I): R-linker-A-X, wherein R is one or more functional groups; linker is a group that separates R and A; A-X is a substrate for a dehalogenase; and X is a halogen, e.g., Cl or Br. In one embodiment, the linker is a multiatom straight or branched chain including C, N, S, or O. In one embodiment, the linker is a divalent branched or unbranched carbon chain comprising from about 2 to about 30 carbon atoms, which chain optionally includes one or more double or triple bonds, and which chain is optionally substituted with one or more hydroxy or oxo (=O) groups, wherein one or more of the carbon atoms in the chain is optionally replaced with a non-peroxide —O—, —S— or —NH—. In one embodiment, the linker separates R and A by at least 12 atoms in the carbon chain. In one embodiment, one or more of the carbon atoms in the chain is replaced with an aryl or heteroaryl ring.

In one embodiment, A is $(CH_2)_n$ and n=2-10 or n=4-10. In one embodiment, R comprises biotin or other avidin binding molecule, a solid support, e.g., a magnetic particle, a sepharose bead, a cellulose bead, glass slide, or well of a multiwell plate, or a fluorophore, such as a xanthene, coumarin, chromene, indole, isoindole, oxazole, BODIPY, a BODIPY derivative, imidazole, pyrimidine, thiophene, pyrene, benzopyrene, benzofuran, fluorescein, rhodamine, rhodol, phenalenone, acridinone, resorufin, naphthalene, anthracene, acridinium, ca-napthol, (3-napthol, dansyl, cyanines, oxazines, nitrobenzoxazole (NBD), dapoxyl, naphthalene imides, styryls, and the like.

The invention will be further described by the following non-limiting examples.

EXAMPLE 1

In the absence of a fusion partner, expression of HT2 in E. coli or cell free systems was robust. However, when fused to another gene, production of soluble and functional HT2 was lower, possibly due to structural incompatibility between the two components of the fusion. In general, the problem was more pronounced when HT2 was the C-terminal component of a fusion. To improve the structural compatibility between mutant hydrolases such as mutant dehalogenases with a substitution at a position corresponding to position 272 in SEQ ID NO: 1, and a fusion partner, and to improve the relative labeling kinetics for hydrolase substrates other than those with a TMR functional group, an evolution process was employed. The FAM ligand was used in screens for further optimized mutant DhaAs, with the intention that some of the mutations identified would provide improved FAM ligand kinetics. Candidates were then examined with the TMR ligand to ensure that the mutations did not substantiate alter the kinetics with this ligand.

The following site-directed changes to DNA for DhaA.H272F H11YL (FIG. 4; "HT2, SEQ ID NO:20) were made and found to improve functional expression in *E. coli*: D78G, F80S, P291A, and P291G, relative to DhaA.H272F H11YL.

Site-saturation mutagenesis at codons 80, 272, and 273 in DhaA.H272F H11YL was employed to create libraries containing all possible amino acids at each of these positions. The libraries were overexpressed in *E. coli* and screened for functional expression/improved kinetics using a carboxyfluoroscein (FAM) containing dehalogenase substrate ($C_{31}H_{31}ClNO_8$) and fluorescence polarization (FP). The nature of the screen allowed the identification of protein with improved expression as well as improved kinetics. In particular, the screen excluded mutants with slower intrinsic kinetics. Substitutions with desirable properties included the following: F80Q, F80N, F80K, F80H, F80T, H272N, H272Y, Y273F, Y273M, and Y273L. Of these, Y273F showed improved intrinsic kinetics.

The Phe at 272 in HT2 lacks the ability to hydrogen bond with Glu-130. The interaction between His-272 and Glu-130 is thought to play a structural role, and so the absence of this bond may destabilize HT2. Moreover, the proximity of the Phe to the Tyr->Leu change at position 273 may provide for potentially cooperative interactions between side chains from these adjacent residues. Asn was identified as a better residue for position 272 in the context of either Leu or Phe at position 273. When the structure of HT2 containing Asn-272 was modeled, it was evident that 1) Asn fills space with similar geometry compared to His, and 2) Asn can hydrogen bond with Glu-130. HT2 with a substitution of Asn at position 272 was found to produce higher levels of functional protein in *E. coli*, cell-free systems, and mammalian cells, likely as a result of improving the overall stability of the protein.

Two rounds of mutagenic PCR were used to introduce mutations across the entire coding sequence for HT2 at a frequency of 1-2 amino acid substitutions per sequence. This approach allowed targeting of the whole sequence and did not rely on any a priori knowledge of HT2 structure/function. In the first round of mutagenesis, Asn-272, Phe-273, and Gly-78 were fixed in the context of an N-terminal HT2 fusion to a humanized *Renilla* luciferase as a template. Six mutations were identified that were beneficial to improved FP signal for the FAM ligand (S58T, A155T, A172T, A224E, P291S, A292T; V2), and it was determined that each substitution, with the exception of A172T provided increased protein production in *E. coli*. However, the A172T change provided improved intrinsic kinetics. The 6 substitutions (including Leu+/−273) were then combined to give a composite sequence (V3/V2) that provided significantly improved protein production and intrinsic labeling kinetics when fused to multiple partners and in both orientations.

In the second round of mutagenesis, 6 different templates were used: V3 or V2 were fused at the C-terminus to humanized *Renilla* luciferase (RL), firefly luciferase, or Id. Mutagenic PCR was carried out as above, and mutations identified as beneficial to at least 2 of the 3 partners were combined to give V6 (Leu-273). In the second round of mutagenic PCR, protein expression was induced using elevated temperature (30° C.) in an attempt to select for sequences conferring thermostability. Increasing the intrinsic structural stability of mutant DhaA fusions may result in more efficient production of protein.

Random mutations associated with desirable properties included the following: G5C, G5R, D11N, E20K, R30S, G32S, L47V, S58T, R60H, D65Y, Y87F, L88M, A94V, S109A, F113L, K117M, R118H, K124I, C128F, P134H, P136T, Q150H, A151T, A155T, V157I, E160K, A167V, A172T, D187G, K195N, R204S, L221M, A224E, N227E, N227S, N227D, Q231H, A250V, A256D, E257K, K263T, T264A, D277N, I282F, P291S, P291Q, A292T, and A292E.

In addition to the substitutions above, substitutions in a connector sequence between the mutant DhaA and the downstream C-terminal partner, *Renilla* luciferase, were identified. The parental connector sequence (residues 294-320) is: QYSGGGGSGGGGSGGGGENLYFQAIEL (SEQ ID NO: 19). The substitutions identified in the connector which were associated with improved FP signal were Y295N, G298C, G302D, G304D, G308D, G310D, L313P, L313Q, and A317E. Notably, five out of nine were negatively charged.

With the exception of A172T and Y273F (in the context of H272N), all of the above substitutions provided improved functional expression in *E. coli* as N-terminal fusions. Nevertheless, A172T and Y273F improved intrinsic kinetics for labeling.

Exemplary combined substitutions in mutant DhaAs with generally improved properties were:

DhaA 2.3 (V3): S58T, D78G, A155T, A172T, A224E, F272N, P291S, and A292T.

DhaA 2.4 (V4): S58T, D78G, Y87F, A155T, A172T, A224E, N227D, F272N, Y273F, P291Q, and A292E.

DhaA 2.5 (V5): G32S, S58T, D78G, Y87F, A155T, A172T, A224E, N227D, F272N, P291Q, and A292E.

DhaA 2.6 (V6): L47V, S58T, D78G, Y87F, L88M, C128F, A155T, E160K, A167V, A172T, K195N, A224E, N227D, E257K, T264A, F272N, P291S, and A292T.

Of the substitutions found in DhaA 2.6, all improved functional expression in *E. coli* with the exception of A167V, which improved intrinsic kinetics.

FIG. 5 provides additional substitutions which improve functional expression in *E. coli*.

EXAMPLE 2

Figure 6A:
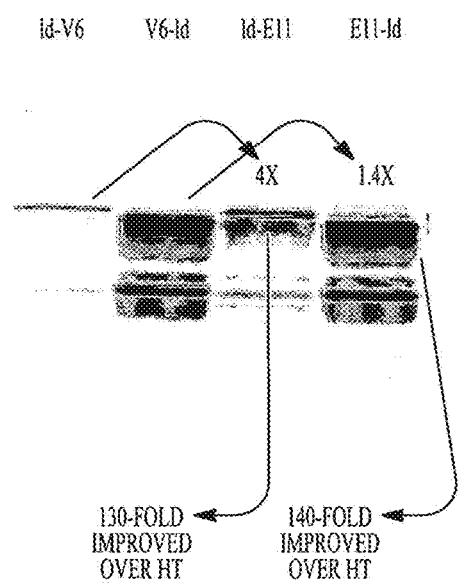
FIGS. 6A-6B show (A) TMR ligand labeling and (B) kinetics for a mutant dehalogenase "V7" expressed as a N-terminal fusion in *E. coli* (SEQ ID NO: 19, which has a sequence identical to SEQ ID NO: 16, i.e., "V6", with the exception that the C-terminal residues in SEQ ID NO: 17 are different that those in SEQ ID NO: 16; see FIG. 8).
Figure 6B:
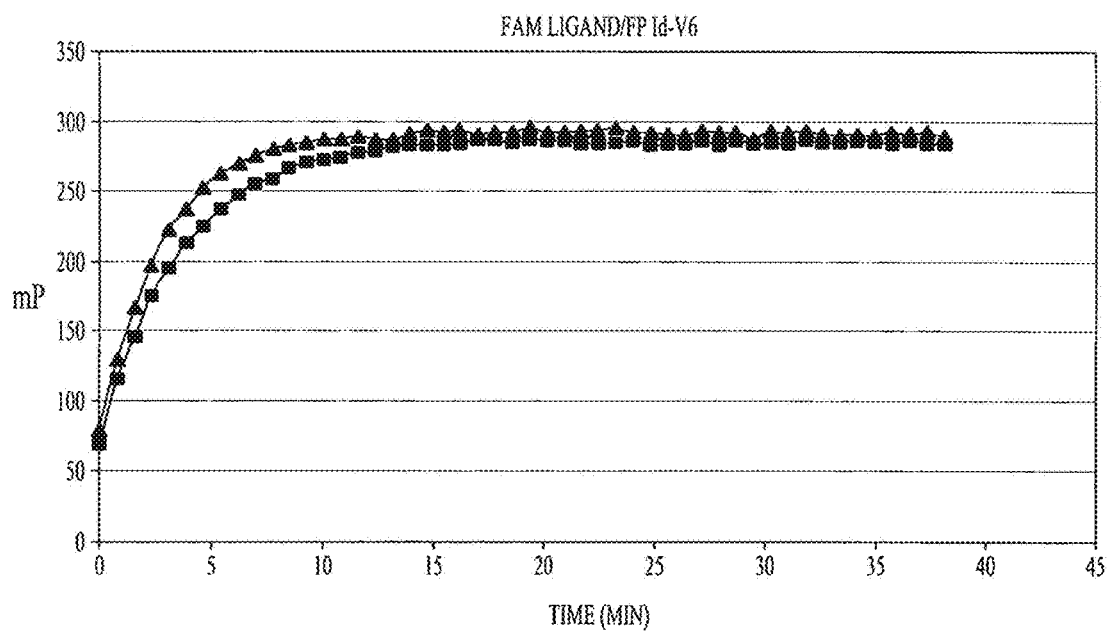
Figure 8:
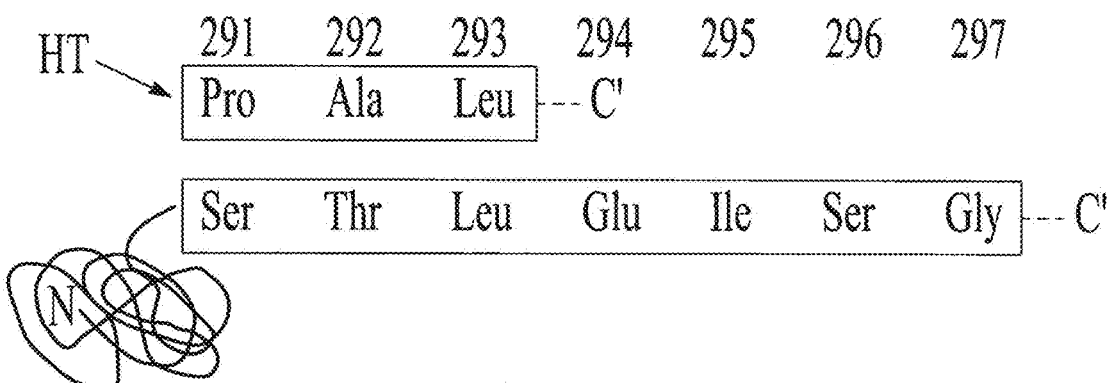
FIG. 8 provides an alignment of the C-termini of HT and V7 (SEQ ID NO:2).

The V6 sequence was used as a template for mutagenesis at the C-terminus. A library of mutants was prepared containing random, two-residue extensions (tails) in the context of an Id-V6 fusion (V6 is the C-terminal partner), and screened with the FAM ligand. Mutants with improved protein production and less non-specific cleavage (as determined by TMR ligand labeling and gel analysis) were identified. The two C-terminal residues in DhaA 2.6 ("V6") were replaced with Glu-Ile-Ser-Gly to yield V7 (FIG. 8). The expression of V7 was compared to V6 as both an N- and C-terminal fusion to Id. Fusions were overexpressed in *E. coli* and labeled to completion with 10 μM TMR ligand, then resolved by SDS-PAGE+fluorimaging (FIG. 6). The data shows that more functional fusion protein was made from the V7 sequence. In addition, labeling kinetics with a FAM ligand over time for V7 were similar to that for V6 (FIG. 6), although V7 had faster kinetics than V6 when purified nonfused protein was tested.

Figures 7A, 7B:
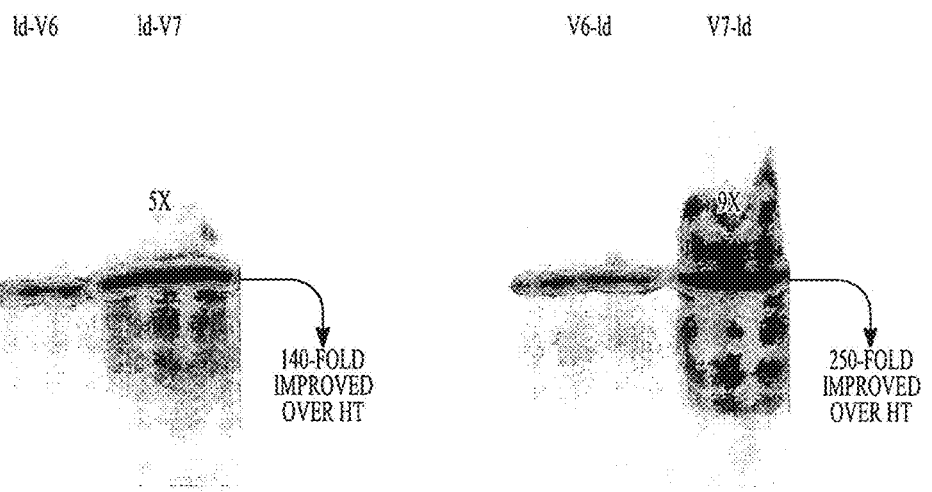
FIGS. 7A-7B provide replicates (A and B) of expression data for V7 in a rabbit reticulocyte transcription/translation reaction.
Figures 9A, 9B:
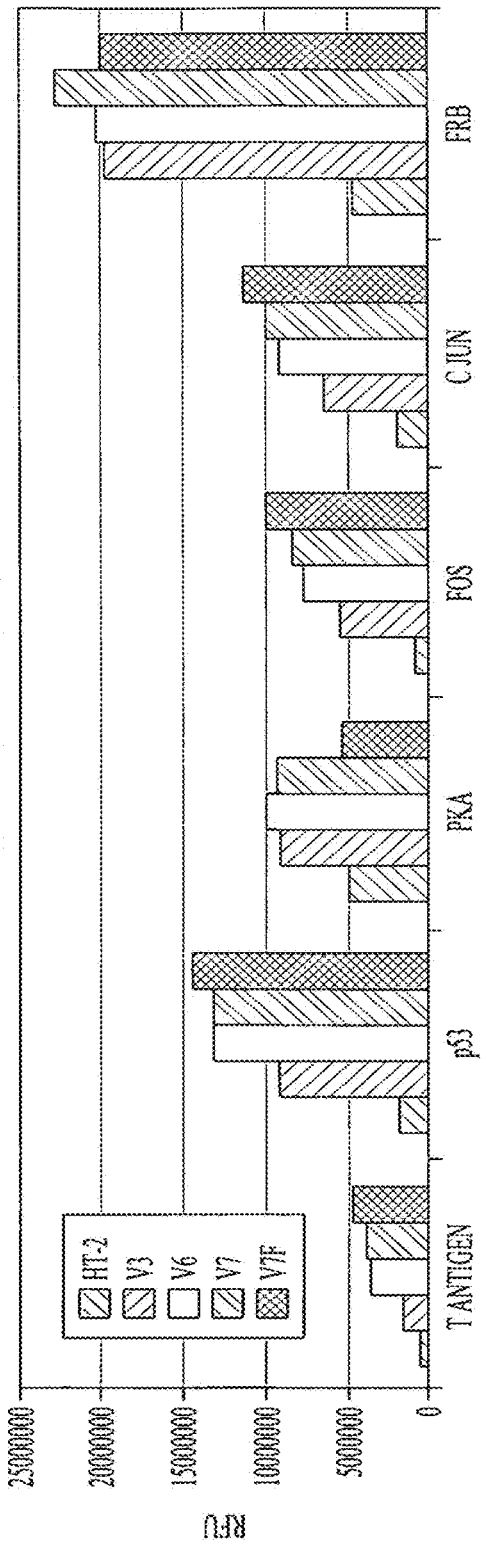
FIGS. 9A-9B show functional expression of V7 in a wheat germ transcription/translation reaction depicted by (A) graph and (B) table.

V7 was also expressed in a rabbit reticulocyte TNT cell-free expression system (FIG. 7). Lysates were labeled to completion with 10 μM TMR ligand and analyzed for functional expression by SDS-PAGE+fluorimaging. As with expression in *E. coli*, more functional protein resulted from expression of the V7 sequence in the rabbit lysates. The expression for V7 was improved by about 140- to 250-fold over SEQ ID NO:20 ("HT2"). Expression of V7 was also improved relative to HT2 in a wheat germ transcription/translation system (FIG. 9).

To test for in vivo labeling, 24 hours after HeLa cells were transfected with vectors for HT2, V3, V7 and V7F (V7F has a single amino acid difference relative to V7; V7F has Phe at position 273 rather than Leu), cells were labeled in vivo with 0.2 μM TMR ligand for 5 minutes, 15 minutes, 30 minutes or 2 hours. Samples were analyzed by SDS-PAGE/fluorimaging and quantitated by ImageQuant. V7 and V7F resulted in better functional expression than HT2 and V3, and V7, V7F and V3 had improved kinetics in vivo in mammalian cells relative to HT2 (FIG. 10).

Figures 12A, 12B, 13:
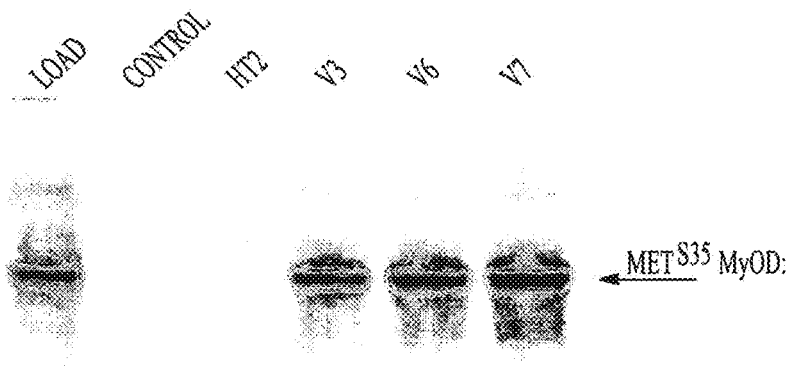
FIGS. 12A-12B show (A) results from a pull-down assay, and (B) a table summarizing the results.
FIG. 13 summarizes 2nd order rate constant data for a TMR-ligand and a FAM-ligand using purified protein. The data was generated by following labeling over time using FP.

Moreover, V7 has improved functional expression as an N- or C-terminal fusion (FIG. 11), and was more efficient in pull down assays (FIG. 12) than other mutant DhaAs. The results showed that V7>V6>V3 for the quantity of MyoD that can be pulled down using HaloLink™-immobilized mutant DhaA-Id fusions. V7 and V7F had improved labeling kinetics (FIG. 13). In particular, V7F had about 1.5- to about 3-fold faster labeling than V7.

Figure 14:
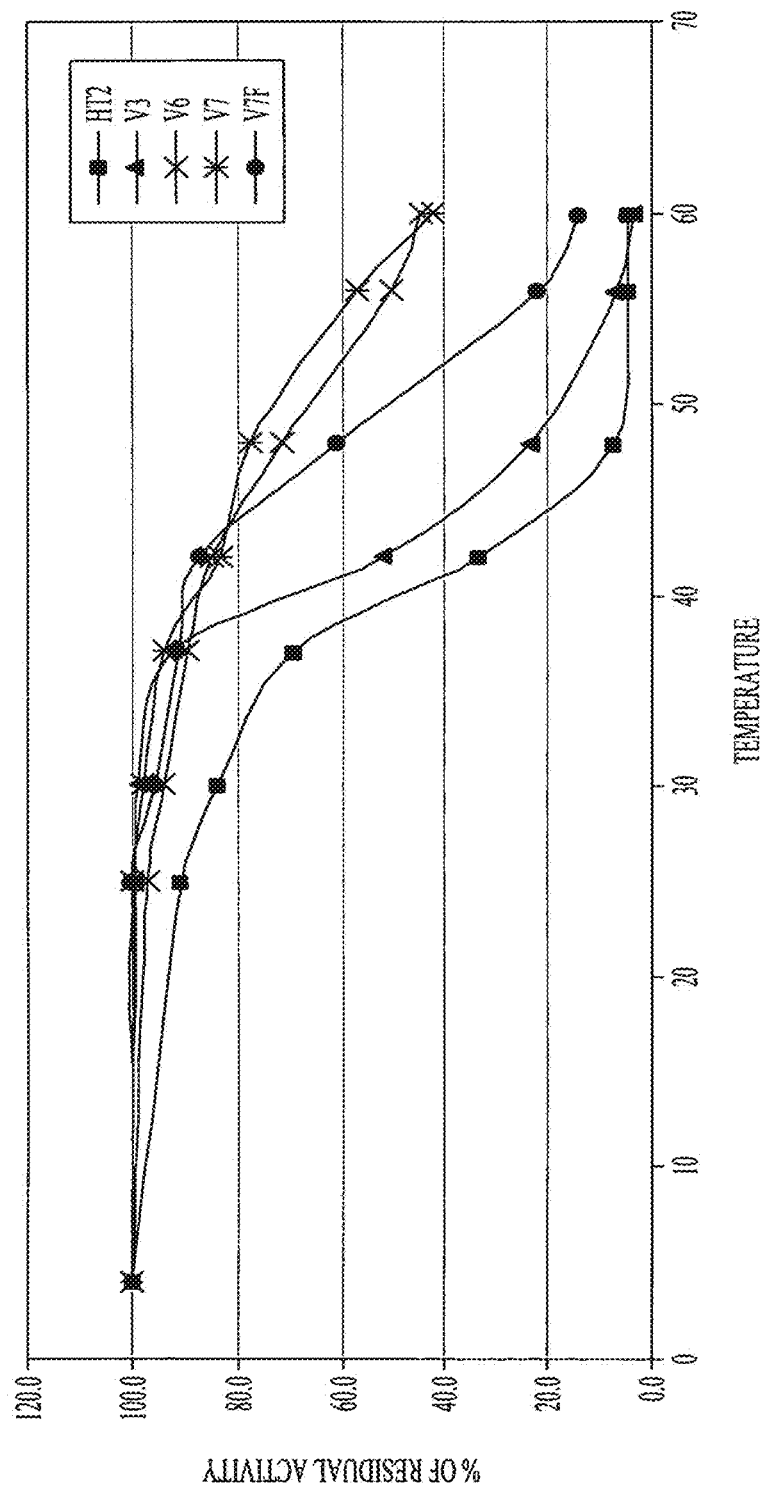
FIG. 14 shows residual activity at various temperatures for selected proteins. Proteins were exposed to the temperatures indicated for 30 minutes and then analyzed for FAM-ligand binding by FP. Data is expressed as the residual activity, normalized for the amount of activity each protein has in the absence of exposure to elevated temperature.

FIG. 14 shows thermostability data for various mutant DhaA proteins. The data was generated using purified protein and shows that V7>V6>V7F>V3>HT2 for thermostability. For example, under some conditions (30 minute exposure to 48° C.) purified V7F loses 50% of its activity, while V7 still maintains 80% activity. The thermostability discrepancy between the two is more dramatic when they V7 and V7F are expressed in *E. coli* and analyzed as lysates.

Figure 15A:
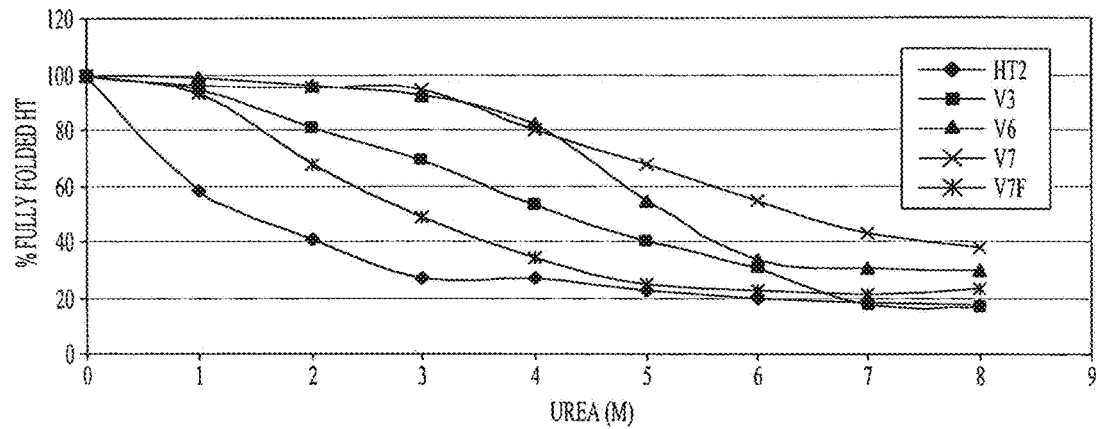
FIGS. 15A-B illustrate the stability of various DhaA mutants (320 nM) in the presence of urea (A) or guanidine-HCl (B) overnight at room temperature.
Figure 15B:
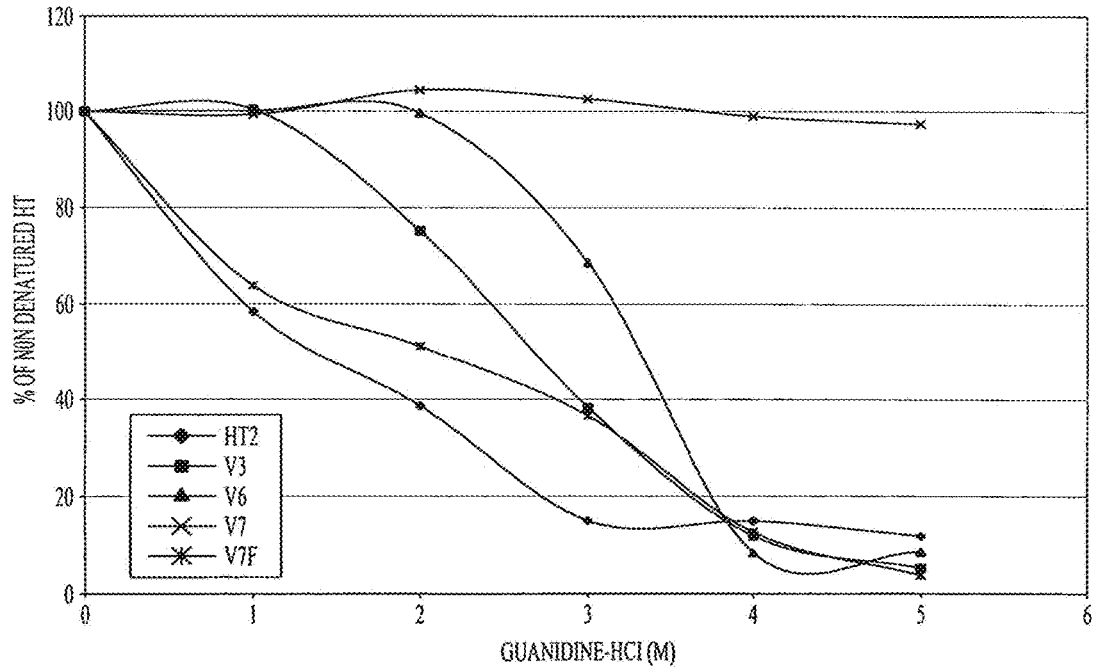
Figures 16A, 16B:
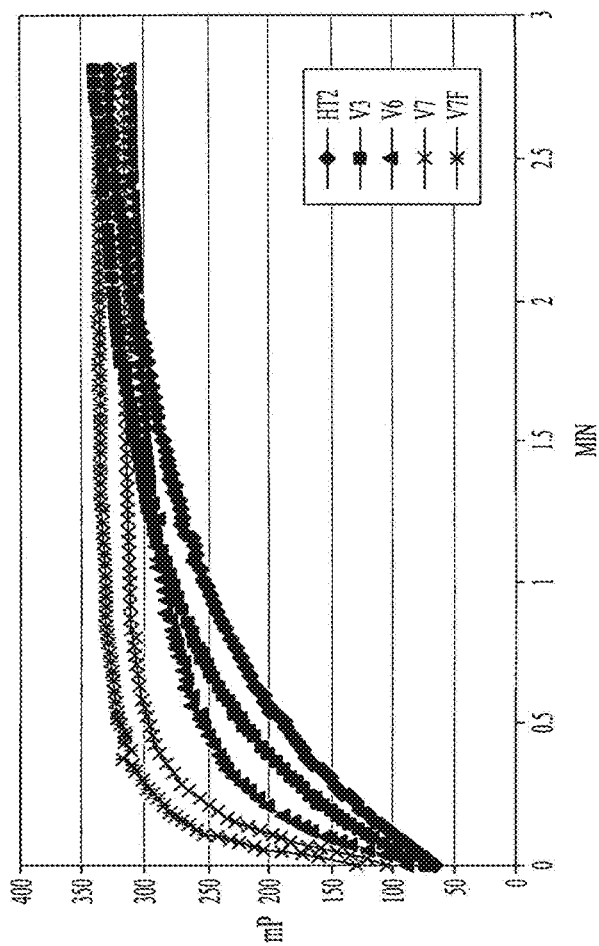
FIGS. 16A-16B shows a (A) graph and (B) table illustrating labeling kinetics for various DhaA mutants with a TMR ligand.
Figures 17A, 17B:
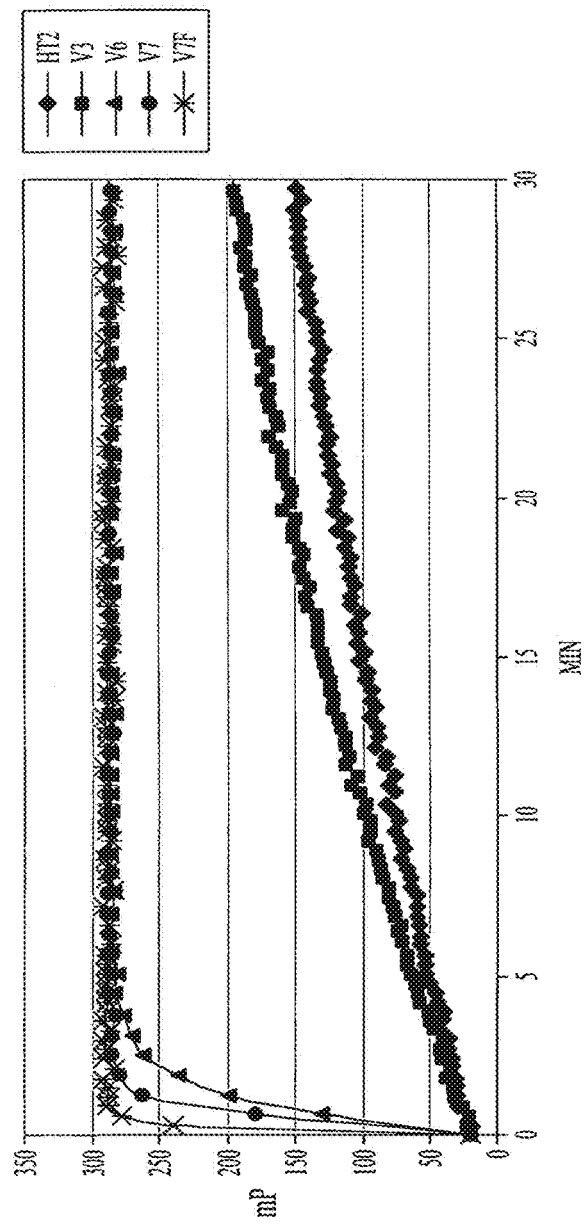
FIGS. 17A-17B shows a (A) graph and (B) table illustrating labeling kinetics for various DhaA mutants with a FAM ligand.
Figures 18A, 18B:
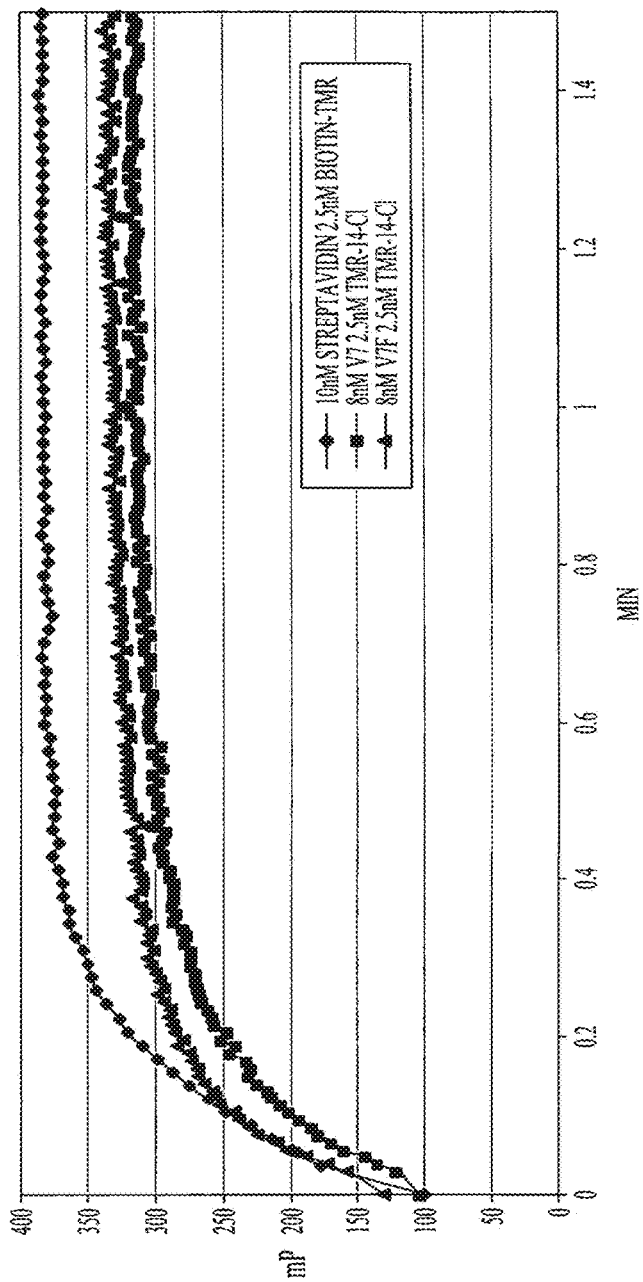
FIGS. 18A-18B provides a (A) graph and (B) table depicting a comparison of labeling rates for two DhaA mutants.

FIGS. 15A-B show stability following exposure to urea and guanidine-HCl. FIGS. 16-17 show labeling kinetics for various DhaA mutants with two different ligands. FIG. 18 is a comparison of labeling rates for two DhaA mutants versus streptavidin-biotin.

FIG. 19 provides nucleotide and amino acid sequences for various DhaA mutants including those useful as N- or C-terminal fusions. Note that the ends of these mutants can accommodate various sequences including tail and connector sequences, as well as substitutions. For instance, the N-terminus of a mutant DhaA may be M/GA/SETG (SEQ ID NO:39), and the C-terminus may include substitutions and additions ("tail"), e.g., P/S/QA/T/ELQ/EY/I (SEQ ID NO:40), and optionally SG. For instance, the C-terminus can be either EISG (SEQ ID NO:41), EI, QY or Q. For the N-vectors, the N-terminus may be MAE, and in the C-vectors the N-terminal sequence or the mutant DhaA may be GSE or MAE. Tails include but are not limited to QY and EISG.

Sequences between two proteins (connector sequences) may include sequences recognized by a protease. In one embodiment, the connector sequence may include a TEV protease site (Doherty et al., 1989), an upstream region of about 4 amino acids (P10 to P7), and a downstream region of about 2 or 3 amino acids (P'2-P'4). Inclusion of a TEV site may decrease solubility of recombinant expression in *E. coli* (Kurz et al., 2006), and may reduce mammalian expression (data not shown). To address this, the TEV site was optimized to maintain expression levels in mammalian cells, cell free expression systems or *E. coli*, without reducing the ability of TEV protease to cleave the sequence. To enhance mammalian expression, the following changes in the TEV protease site were made: at P5, N to D, and in the upstream region sequence at P10, I to E. P'2 D, P'3 N and optionally P'4 D. These changes improved TEV cleavage, reduced nonspecific truncation in *E. coli* cells, and improved expression in mammalian cells and cell free expression systems. For use with the DhaA mutants, the N-terminal sequence includes EPTT-EDLYFQ(S/C)-DN (SEQ ID NO:38) and the C-terminal sequence includes EPTT-EDLYFQS-DND (SEQ ID NO:50). These sequences do not reduce expression or solubility of DhaA mutant fusion protein expression in mammalian cells, cell free systems, or *E. coli* cells. These sequences may be used with any fusion.

Vectors harboring p65-HT2, p65-HTv3, p65-HTv6, p65-HTv7 and p65-HTv7f were introduced to HeLa cells plated in 24 well plates (2 well for each time point or ligand concentration) using LT1 (Mirus) according manufacturer's recommendations. 24 hours post transfection cells were labeled with different concentrations of TMR ligand (5 µM for 15 minutes) for different periods of time indicated in FIG. 20. Unbound ligand was washed out and cells were collected with SDS-PAGE sample buffer. Fluorescently labeled proteins were resolved on SDS-PAGE and analyzed on fluorimaging (Typhoon-9410, Amersham).

Figure 21A:
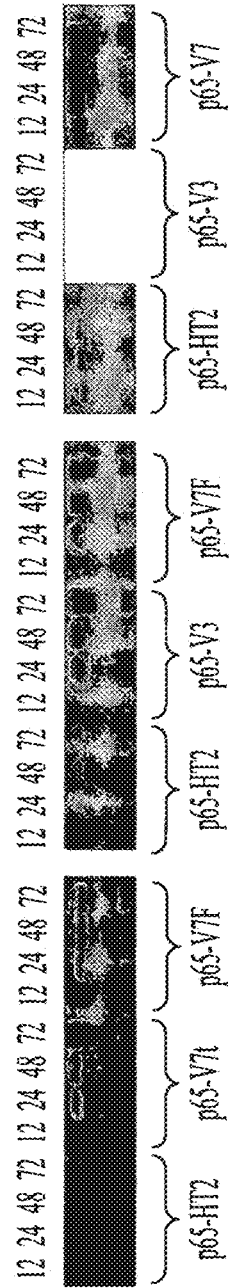
FIGS. 21A-21B show replicates (A-B) of detection of p65-mutant DhaA fusion proteins at different times after transfection (Western Blot analysis). HeLa cells were transiently transfected with p65-HT2 (green), p65-V3 (pink), p65-V7 (blue/white), p65-V7F (yellow), lysed and probed with p65 AB (upper panel) and IkB AB (lower panel).
Figure 21B:
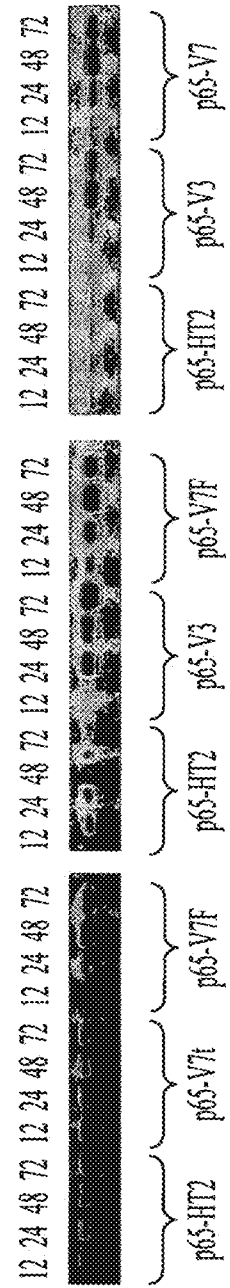
Figure 22:
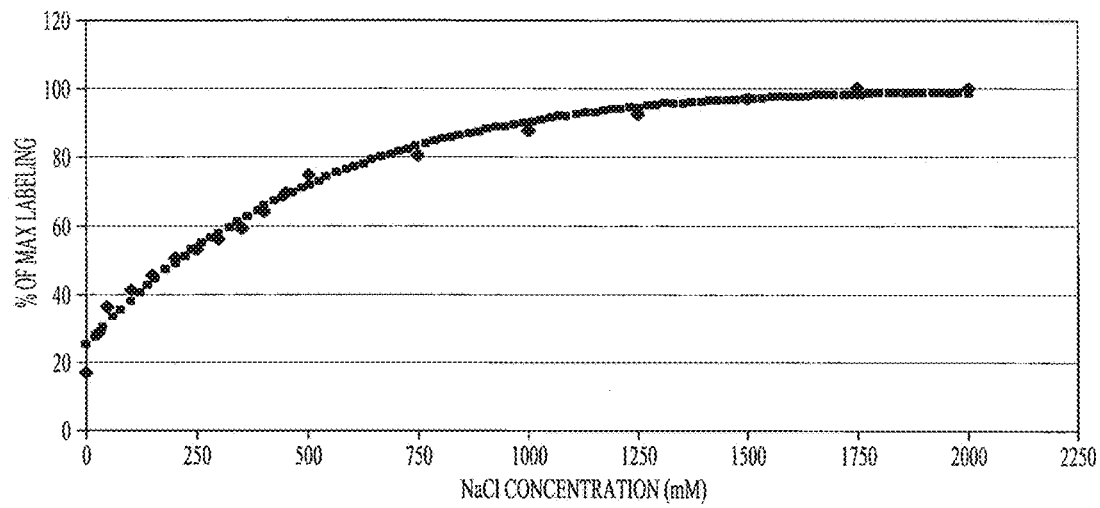
FIG. 22 illustrates the dependence of labeling kinetics in salt. Labeling rate of V7 (16.5 nM) to FAM ligand (7.5 nM) was measured and calculated in 20 mM HEPES pH 7.2+0-2 M NaCl. There is a positive correlation between salt concentration and labeling rates.
Figure 23:
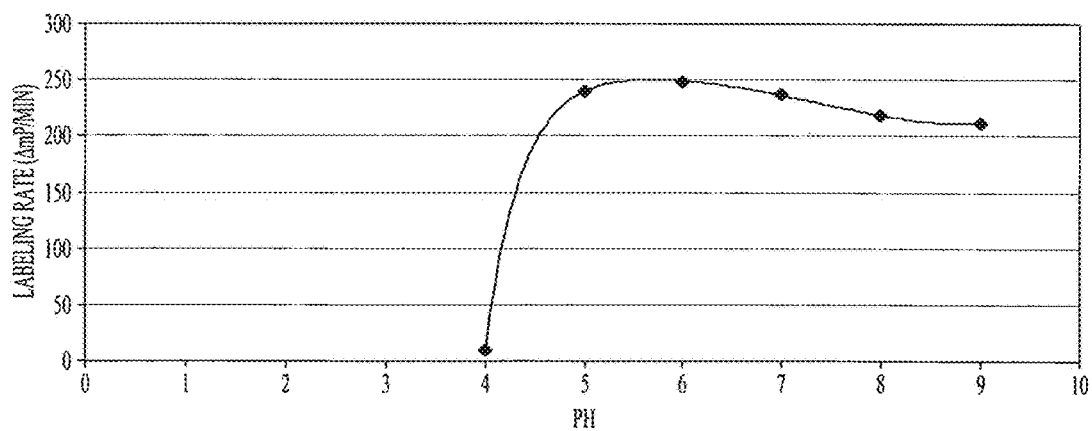
FIG. 23 shows pH effect on labeling kinetics. Buffers included 25 mM NaAcetate (useful buffering range of pH 3.6-5.6), 25 mM MES (pH 5.5-6.7), 50 mM Tris (pH 7.0-9.0) and 150 mM NaCl. Acidic adjustment: acetic acid, alkali adjustment: tetramethyl ammonium hydroxide.
Figures 26A, 26B:
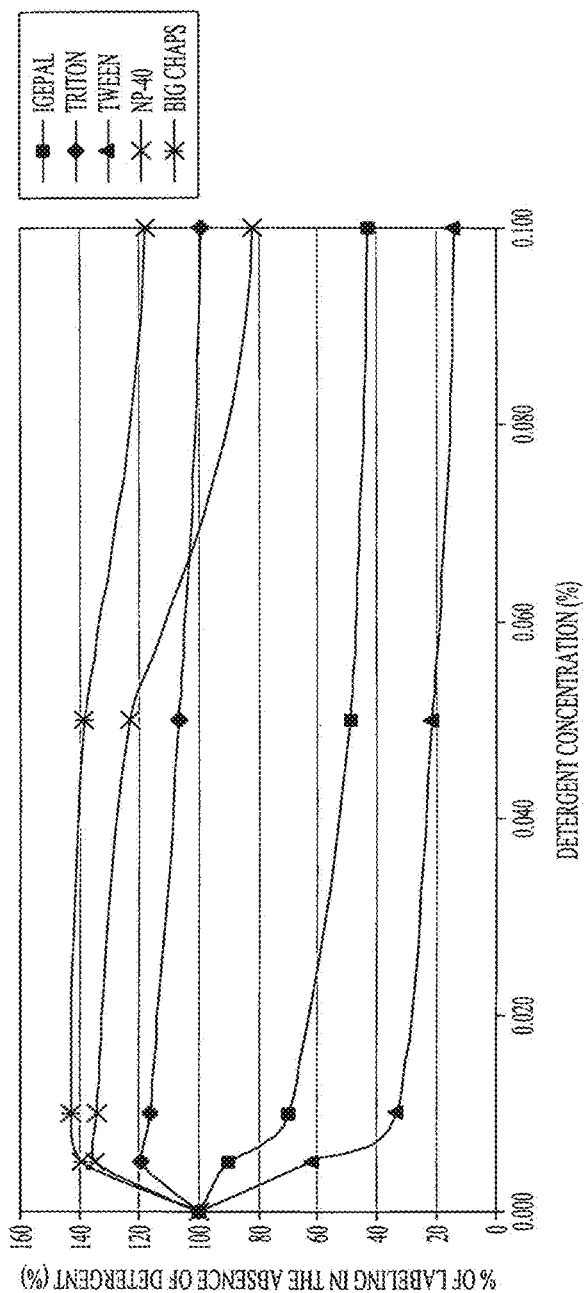
FIGS. 26A-26B show a (A) graph and (B) table depicting the effect of nonionic detergents on labeling kinetics.
Figures 27A, 27B:
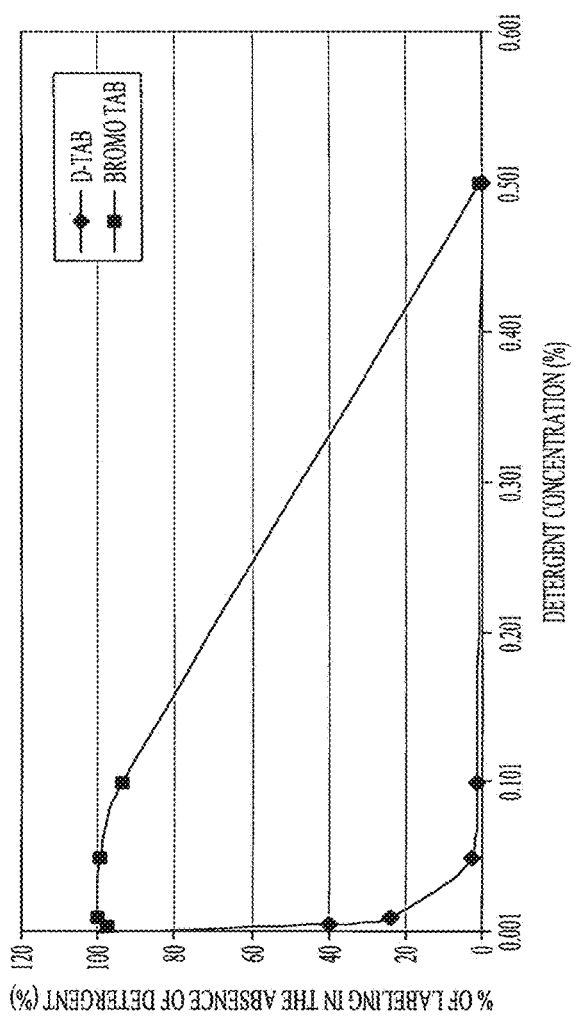
FIGS. 27A-27B shows a (A) graph and (B) table depicting the effect of cationic detergents on labeling kinetics.
Figures 29A, 29B:
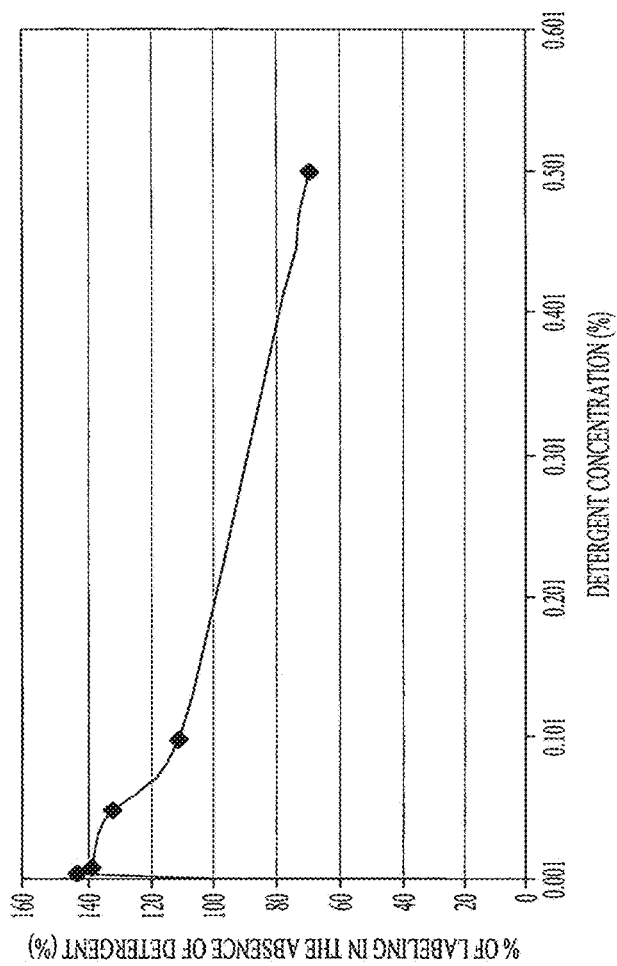
FIGS. 29A-29B show a (A) graph and (B) table depicting the effect of zwitterionic detergents on labeling kinetics.

Western blot analysis of HeLa cells transiently transfected with p65-HT2, p65-V3, p65-V7, or p65-V7F, lysed and probed with p65 AB and IkB AB is shown in FIG. 21.

To further explore the labeling kinetics of mutant DhaAs under various conditions, reactions were conducted in the presence of increasing salt concentration, a nondetergent reagent found in lysis buffers, different buffers and different detergents (FIGS. 22-29) The disclosed mutant DhaAs provide for improved production of functional fusion protein which allows for efficient pull-down of protein-protein interactions using an appropriate ligand linked substrate or glass slides.

REFERENCES

Ausubel et al., Current Protocols in Molecular Biology, Vol. III, A. 1(3-4), Supplement 38 (1997).
Chalfie, M. and Kain, S. R., eds., GFP: Green Fluorescent Protein Strategies and Applications (Wiley, New York, 1998).
Cubitt et al., Trends Biochem. Sci., 20:448 (1995).
Doherty et al., Virol., 171:356 (1989).
Einbond et al., FEBS Lett., 384:1 (1996).
Farinas et al., J. Biol. Chem., 274:7603 (1999).
Griffin et al., Science, 281:269 (1998).
Hanks and Hunter, FASEB J, 9:576-595 (1995).
Harlow and Lane, In: *Antibodies: A Laboratory Manual*, Cold Spring Harbor Laboratory Press, p. 726 (1988)
Ilsley et al., Cell Signaling, 14:183 (2002).
Hermanson, Bioconjugate Techniques, Academic Press, San Diego, Calif. (1996).
Janssen et al., J. Bacteriol., 171:6791 (1989).
Keuning et al., J. Bacteriol., 163:635 (1985).
Kneen et al., Biophys. J., 74:1591 (1998).
Kulakova et al., Microbiology, 143:109 (1997).
Kurz et al., Protein Expression and Purification, 50:68 (2006).
Llopis et al., Proc. Natl. Acad. Sci. USA, 95:6803 (1998).
Mayer and Baltimore, Trends Cell. Biol., 3:8 (1993).
Miesenböck et al., Nature, 394:192 (1998).
Mils et al., Oncogene, 19:1257 (2000).
Miyawaki et al., Nature, 388:882 (1967).
Nagata et al., Appl. Environ. Microbiol., 63:3707 (1997).
Ormö et al., Science, 273:1392 (1996).
Rosomer et al., J. Biol. Chem., 272:13270 (1997).
Sadowski, et al., Mol. Cell. Bio., 6:4396 (1986).
Sallis et al., J. Gen. Microbiol., 136:115 (1990).
Scholtz et al., J. Bacteriol., 169:5016 (1987).
Stroffekova et al., Eur. J. Physiol., 442:859 (2001).
Tsien, Ann. Rev. Biochem., 67:509 (1998).
Wada et al., Nucleic Acids Res., 18 Suppl:2367 (1990).
Yokota et al., J. Bacteriol., 169:4049 (1987).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A polypeptide comprising a mutant dehalogenase that is capable of catalyzing hydrolytic dehalogenation of an alkylhalide substrate and forming a covalent ester intermediate with the substrate, said mutant dehalogenase having at least 85% sequence identity with the polypeptide of SEQ ID NO: 1; wherein said mutant dehalogenase comprises substitutions at:

(a) one or more positions corresponding to positions in SEQ ID NO: 1 selected from the group consisting of positions 106 and 272; and (b) positions corresponding to positions 58, 78, 155, 167, 172, 224, and 291 of SEQ ID NO: 1.

2. A fusion polypeptide comprising the polypeptide of claim 1 and a polypeptide of interest.

3. The fusion polypeptide of claim 2, wherein the polypeptide of interest is at the C-terminus of the fusion polypeptide.

4. The fusion polypeptide of claim 2, wherein the polypeptide of interest is at the N-terminus of the fusion polypeptide.

5. The fusion polypeptide of claim 2, further comprising a polypeptide linker linking the polypeptide of claim 1 and the polypeptide of interest.

6. The fusion polypeptide of claim 5, wherein the linker comprises a protease recognition sequence.

* * * * *

SEQUENCE LISTING

```
<160> NUMBER OF SEQ ID NOS: 73

<210> SEQ ID NO 1
<211> LENGTH: 293
<212> TYPE: PRT
<213> ORGANISM: Rhodococcus rhodochrous

<400> SEQUENCE: 1

Met Ser Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
            20                  25                  30

Thr Pro Val Leu Phe Leu His Gly Asn Pro Thr Ser Ser Tyr Leu Trp
        35                  40                  45

Arg Asn Ile Ile Pro His Val Ala Pro Ser His Arg Cys Ile Ala Pro
    50                  55                  60

Asp Leu Ile Gly Met Gly Lys Ser Asp Lys Pro Asp Leu Asp Tyr Phe
65                  70                  75                  80

Phe Asp Asp His Val Arg Tyr Leu Asp Ala Phe Ile Glu Ala Leu Gly
                85                  90                  95

Leu Glu Glu Val Val Leu Val Ile His Asp Trp Gly Ser Ala Leu Gly
            100                 105                 110
```

```
Phe His Trp Ala Lys Arg Asn Pro Glu Arg Val Lys Gly Ile Ala Cys
            115                 120                 125

Met Glu Phe Ile Arg Pro Ile Pro Thr Trp Asp Glu Trp Pro Glu Phe
    130                 135                 140

Ala Arg Glu Thr Phe Gln Ala Phe Arg Thr Ala Asp Val Gly Arg Glu
145                 150                 155                 160

Leu Ile Ile Asp Gln Asn Ala Phe Ile Glu Gly Ala Leu Pro Lys Cys
                165                 170                 175

Val Val Arg Pro Leu Thr Glu Val Glu Met Asp His Tyr Arg Glu Pro
            180                 185                 190

Phe Leu Lys Pro Val Asp Arg Glu Pro Leu Trp Arg Phe Pro Asn Glu
        195                 200                 205

Leu Pro Ile Ala Gly Glu Pro Ala Asn Ile Val Ala Leu Val Glu Ala
    210                 215                 220

Tyr Met Asn Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255

Glu Ser Leu Pro Asn Cys Lys Thr Val Asp Ile Gly Pro Gly Leu His
            260                 265                 270

Tyr Leu Gln Glu Asp Asn Pro Asp Leu Ile Gly Ser Glu Ile Ala Arg
        275                 280                 285

Trp Leu Pro Ala Leu
    290

<210> SEQ ID NO 2
<211> LENGTH: 7
<212> TYPE: PRT
<213> ORGANISM: Artificial Sequence
<220> FEATURE:
<223> OTHER INFORMATION: A synthetic DhaA C-termini sequence

<400> SEQUENCE: 2

Ser Thr Leu Glu Ile Ser Gly
1               5

<210> SEQ ID NO 3
<211> LENGTH: 5
<212> TYPE: PRT
<213> ORGANISM: Artificial Sequence
<220> FEATURE:
<223> OTHER INFORMATION: A synthetic affinity domain

<400> SEQUENCE: 3

His His His His His
1               5

<210> SEQ ID NO 4
<211> LENGTH: 6
<212> TYPE: PRT
<213> ORGANISM: Artificial Sequence
<220> FEATURE:
<223> OTHER INFORMATION: A synthetic affinity domain

<400> SEQUENCE: 4

His His His His His His
1               5

<210> SEQ ID NO 5
<211> LENGTH: 10
<212> TYPE: PRT
```

```
<213> ORGANISM: Artificial Sequence
<220> FEATURE:
<223> OTHER INFORMATION: A synthetic affinity domain

<400> SEQUENCE: 5

Glu Gln Lys Leu Ile Ser Glu Glu Asp Leu
1               5                   10

<210> SEQ ID NO 6
<211> LENGTH: 8
<212> TYPE: PRT
<213> ORGANISM: Artificial Sequence
<220> FEATURE:
<223> OTHER INFORMATION: A synthetic affinity domain

<400> SEQUENCE: 6

Asp Tyr Lys Asp Asp Asp Asp Lys
1               5

<210> SEQ ID NO 7
<211> LENGTH: 8
<212> TYPE: PRT
<213> ORGANISM: Artificial Sequence
<220> FEATURE:
<223> OTHER INFORMATION: A synthetic affinity domain

<400> SEQUENCE: 7

Trp Ser His Pro Gln Phe Glu Lys
1               5

<210> SEQ ID NO 8
<211> LENGTH: 9
<212> TYPE: PRT
<213> ORGANISM: Artificial Sequence
<220> FEATURE:
<223> OTHER INFORMATION: A synthetic affinity domain

<400> SEQUENCE: 8

Tyr Pro Tyr Asp Val Pro Asp Tyr Ala
1               5

<210> SEQ ID NO 9
<211> LENGTH: 5
<212> TYPE: PRT
<213> ORGANISM: Artificial Sequence
<220> FEATURE:
<223> OTHER INFORMATION: A synthetic affinity domain

<400> SEQUENCE: 9

Arg Tyr Ile Arg Ser
1               5

<210> SEQ ID NO 10
<211> LENGTH: 4
<212> TYPE: PRT
<213> ORGANISM: Artificial Sequence
<220> FEATURE:
<223> OTHER INFORMATION: A synthetic affinity domain

<400> SEQUENCE: 10

Phe His His Thr
1

<210> SEQ ID NO 11
<211> LENGTH: 17
<212> TYPE: PRT
<213> ORGANISM: Artificial Sequence
```

<220> FEATURE:
<223> OTHER INFORMATION: A synthetic affinity domain

<400> SEQUENCE: 11

Trp Glu Ala Ala Ala Arg Glu Ala Cys Cys Arg Glu Cys Cys Ala Arg
1               5                   10                  15
Ala

<210> SEQ ID NO 12
<211> LENGTH: 885
<212> TYPE: DNA
<213> ORGANISM: Artificial Sequence
<220> FEATURE:
<223> OTHER INFORMATION: A synthetic mutant dehalogenase

<400> SEQUENCE: 12

| | | |
|---|---|---|
| atggcagaaa tcggtactgg ctttccattc gaccccatt atgtggaagt cctgggcgag | 60 |
| cgcatgcact acgtcgatgt tggtccgcgc gatggcaccc tgtgctgtt cctgcacggt | 120 |
| aacccgacct cctcctacct gtggcgcaac atcatcccgc atgttgcacc gacccatcgc | 180 |
| tgcattgctc cagacctgat cggtatgggc aaatccgaca accagacct gggttatttc | 240 |
| ttcgacgacc acgtccgcta cctggatgcc ttcatcgaag ccctgggtct ggaagaggtc | 300 |
| gtcctggtca ttcacgactg gggctccgct ctgggtttcc actgggccaa gcgcaatcca | 360 |
| gagcgcgtca aggtattgc atgtatggag ttcatccgcc tatcccgac ctgggacgaa | 420 |
| tggccagaat tgcccgcga gaccttccag gccttccgca ccaccgacgt cggccgcgag | 480 |
| ctgatcatcg atcagaacgc ttttatcgag ggtacgctgc cgatgggtgt cgtccgcccg | 540 |
| ctgactgaag tcgagatgga ccattaccgc gagccgttcc tgaagcctgt tgaccgcgag | 600 |
| ccactgtggc gcttcccaaa cgagctgcca atcgccggtg agccagcgaa catcgtcgcg | 660 |
| ctggtcgaag aatacatgaa ctggctgcac cagtcccctg tcccgaagct gctgttctgg | 720 |
| ggcaccccag gcgttctgat cccaccggcc gaagccgctc gcctggccga agcctgcct | 780 |
| aactgcaaga ctgtggacat cggcccgggt ctgaattttc tgcaagaaga caacccggac | 840 |
| ctgatcggca gcgagatcgc gcgctggctg tcgacgctgc aatat | 885 |

<210> SEQ ID NO 13
<211> LENGTH: 885
<212> TYPE: DNA
<213> ORGANISM: Artificial Sequence
<220> FEATURE:
<223> OTHER INFORMATION: A synthetic mutant dehalogenase

<400> SEQUENCE: 13

| | | |
|---|---|---|
| atggcagaaa tcggtactgg ctttccattc gaccccatt atgtggaagt cctgggcgag | 60 |
| cgcatgcact acgtcgatgt tggtccgcgc gatggcaccc tgtgctgtt cctgcacggt | 120 |
| aacccgacct cctcctacct gtggcgcaac atcatcccgc atgttgcacc gacccatcgc | 180 |
| tgcattgctc cagacctgat cggtatgggc aaatccgaca accagacct gggttatttc | 240 |
| ttcgacgacc acgtccgcta cctggatgcc ttcatcgaag ccctgggtct ggaagaggtc | 300 |
| gtcctggtca ttcacgactg gggctccgct ctgggtttcc actgggccaa gcgcaatcca | 360 |
| gagcgcgtca aggtattgc atgtatggag ttcatccgcc tatcccgac ctgggacgaa | 420 |
| tggccagaat tgcccgcga gaccttccag gccttccgca ccaccgacgt cggccgcgag | 480 |
| ctgatcatcg atcagaacgc ttttatcgag ggtacgctgc cgatgggtgt cgtccgcccg | 540 |
| ctgactgaag tcgagatgga ccattaccgc gagccgttcc tgaagcctgt tgaccgcgag | 600 |

```
ccactgtggc gcttcccaaa cgagctgcca atcgccggtg agccagcgaa catcgtcgcg    660
ctggtcgaag aatacatgaa ctggctgcac cagtcccctg tcccgaagct gctgttctgg    720
ggcaccccag gcgttctgat cccaccggcc gaagccgctc gcctggccga aagcctgcct    780
aactgcaaga ctgtggacat cggcccgggt ctgaatctgc tgcaagaaga caacccggac    840
ctgatcggca gcgagatcgc gcgctggctg tcgacgctgc aatat                    885
```

<210> SEQ ID NO 14
<211> LENGTH: 885
<212> TYPE: DNA
<213> ORGANISM: Artificial Sequence
<220> FEATURE:
<223> OTHER INFORMATION: A synthetic mutant dehalogenase

<400> SEQUENCE: 14

```
atggcagaaa tcggtactgg cttcccattc gaccccatt atgtggaagt cctgggcgag     60
cgcatgcact acgtcgatgt tggtccgcgc gatggcaccc ctgtgctgtt cctgcacggt    120
aacccgacct cctcctacct gtggcgcaac atcatcccgc atgttgcacc gacccatcgc    180
tgcattgctc cagacctgat cggtatgggc aaatccgaca accagacct gggttatttc     240 ttcgacgacc acgtccgctt cctggatgcc ttcatcgaag ccctgggtct ggaagaggtc    300
gtcctggtca ttcacgactg gggctccgct ctgggtttcc actgggccaa gcgcaatcca    360
gagcgcgtca aggtattgc atgtatggag ttcatccgcc ctatcccgac ctgggacgaa    420
tggccagaat ttgcccgcga gaccttccag gccttccgca ccaccgacgt cggccgcgag    480
ctgatcatcg atcagaacgc ttttatcgag ggtacgctgc cgatgggtgt cgtccgcccg    540
ctgactgaag tcgagatgga ccattaccgc gagccgttcc tgaagcctgt gaccgcgag     600 ccactgtggc gcttcccaaa cgagctgcca atcgccggtg agccagcgaa catcgtcgcg    660
ctggtcgaag aatacatgga ctggctgcac cagtcccctg tcccgaagct gctgttctgg    720
ggcaccccag gcgttctgat cccaccggcc gaagccgctc gcctggccga aagcctgcct    780
aactgcaaga ctgtggacat cggcccgggt ctgaatttc tgcaagaaga caacccggac     840
ctgatcggca gcgagatcgc gcgctggctg caggagctgc aatat                    885
```

<210> SEQ ID NO 15
<211> LENGTH: 885
<212> TYPE: DNA
<213> ORGANISM: Artificial Sequence
<220> FEATURE:
<223> OTHER INFORMATION: A synthetic mutant dehalogenase

<400> SEQUENCE: 15

```
atggcagaaa tcggtactgg cttcccattc gaccccatt atgtggaagt cctgggcgag     60
cgcatgcact acgtcgatgt tggtccgcgc gatagcaccc ctgtgctgtt cctgcacggt    120
aacccgacct cctcctacct gtggcgcaac atcatcccgc atgttgcacc gacccatcgc    180
tgcattgctc cagacctgat cggtatgggc aaatccgaca accagacct gggttatttc     240 ttcgacgacc acgtccgctt cctggatgcc ttcatcgaag ccctgggtct ggaagaggtc    300
gtcctggtca ttcacgactg gggctccgct ctgggtttcc actgggccaa gcgcaatcca    360
gagcgcgtca aggtattgc atgtatggag ttcatccgcc ctatcccgac ctgggacgaa    420
tggccagaat ttgcccgcga gaccttccag gccttccgca ccaccgacgt cggccgcgag    480
ctgatcatcg atcagaacgc ttttatcgag ggtacgctgc cgatgggtgt cgtccgcccg    540
```

```
ctgactgaag tcgagatgga ccattaccgc gagccgttcc tgaagcctgt tgaccgcgag    600
ccactgtggc gcttcccaaa cgagctgcca atcgccggtg agccagcgaa catcgtcgcg    660
ctggtcgaag aatacatgga ctggctgcac cagtcccctg tcccgaagct gctgttctgg    720
ggcaccccag gcgttctgat cccaccggcc gaagccgctc gcctggccga agcctgcct     780 aactgcaaga ctgtggacat cggcccgggt ctgaatctgc tgcaagaaga caacccggac    840
ctgatcggca gcgagatcgc gcgctggctg caggagctgc aatat                    885
```

<210> SEQ ID NO 16
<211> LENGTH: 885
<212> TYPE: DNA
<213> ORGANISM: Artificial Sequence
<220> FEATURE:
<223> OTHER INFORMATION: A synthetic mutant dehalogenase

<400> SEQUENCE: 16

```
atggcagaaa tcggtactgg ctttccattc gaccccccatt atgtggaagt cctgggcgag     60
cgcatgcact acgtcgatgt tggtccgcgc gatggcaccc tgtgctgtt cctgcacggt    120 aacccgacct cctcctacgt gtggcgcaac atcatcccgc atgttgcacc gacccatcgc    180
tgcattgctc cagacctgat cggtatgggc aaatccgaca accagacct gggttatttc    240 ttcgacgacc acgtccgctt catggatgcc ttcatcgaag ccctgggtct ggaagaggtc    300
gtcctggtca ttcacgactg gggctccgct ctgggtttcc actgggccaa gcgcaatcca    360
gagcgcgtca aggtattgc atttatggag ttcatccgcc ctatcccgac ctgggacgaa    420
tggccagaat ttgcccgcga gaccttccag gccttccgca ccaccgacgt cggccgcaag    480
ctgatcatcg atcagaacgt ttttatcgag ggtacgctgc cgatgggtgt cgtccgcccg    540
ctgactgaag tcgagatgga ccattaccgc gagccgttcc tgaatcctgt tgaccgcgag    600
ccactgtggc gcttcccaaa cgagctgcca atcgccggtg agccagcgaa catcgtcgcg    660
ctggtcgaag aatacatgga ctggctgcac cagtcccctg tcccgaagct gctgttctgg    720
ggcaccccag gcgttctgat cccaccggcc gaagccgctc gcctggccaa aagcctgcct    780
aactgcaagg ctgtggacat cggcccgggt ctgaatctgc tgcaagaaga caacccggac    840
ctgatcggca gcgagatcgc gcgctggctg tcgacgctgc aatat                    885
```

<210> SEQ ID NO 17
<211> LENGTH: 876
<212> TYPE: DNA
<213> ORGANISM: Artificial Sequence
<220> FEATURE:
<223> OTHER INFORMATION: A synthetic DhaA mutant

<400> SEQUENCE: 17

```
tccgaaatcg gtacaggctt ccccttcgac ccccattatg tggaagtcct gggcgagcgt     60
atgcactacg tcgatgttgg accgcgggat ggcacgcctg tgctgttcct gcacggtaac    120
ccgacctcgt cctacctgtg cgcaacatc atcccgcatg tagcaccgag tcatcggtgc    180
attgctccag acctgatcgg gatgggaaaa tcggacaaac cagacctcga ttatttcttc    240
gacgaccacg tccgctacct cgatgccttc atcgaagcct gggtttgga agaggtcgtc    300 ctggtcatcc acgactgggg ctcagctctc ggattccact gggccaagcg caatccggaa    360
cgggtcaaag gtattgcatg tatggaattc atccggccta tccgacgtg gacgaatgg    420 ccagaattcg cccgtgagac cttccaggcc ttccggaccg ccgacgtcgg ccgagagttg    480
atcatcgatc agaacgcttt catcgagggt gcgctcccga tggggtcgt ccgtccgctt    540
```

```
acggaggtcg agatggacca ctatcgcgag cccttcctca agcctgttga ccgagagcca    600
ctgtggcgat tccccaacga gctgccatc gccggtgagc ccgcgaacat cgtcgcgctc     660
gtcgaggcat acatgaactg gctgcaccag tcacctgtcc cgaagttgtt gttctggggc    720
acacccggcg tactgatccc cccggccgaa gccgcgagac ttgccgaaag cctccccaac    780
tgcaagacag tggacatcgg cccgggattg ttcttgctcc aggaagacaa cccggacctt    840
atcggcagtg agatcgcgcg ctggctcccg gcactc                               876
```

<210> SEQ ID NO 18
<211> LENGTH: 292
<212> TYPE: PRT
<213> ORGANISM: Artificial Sequence
<220> FEATURE:
<223> OTHER INFORMATION: A synthetic DhaA mutant

<400> SEQUENCE: 18

```
Ser Glu Ile Gly Thr Gly Phe Pro Phe Asp Pro His Tyr Val Glu Val
1               5                   10                  15

Leu Gly Glu Arg Met His Tyr Val Asp Val Gly Pro Arg Asp Gly Thr
            20                  25                  30

Pro Val Leu Phe Leu His Gly Asn Pro Thr Ser Ser Tyr Leu Trp Arg
        35                  40                  45

Asn Ile Ile Pro His Val Ala Pro Ser His Arg Cys Ile Ala Pro Asp
    50                  55                  60

Leu Ile Gly Met Gly Lys Ser Asp Lys Pro Asp Leu Asp Tyr Phe Phe
65                  70                  75                  80

Asp Asp His Val Arg Tyr Leu Asp Ala Phe Ile Glu Ala Leu Gly Leu
                85                  90                  95

Glu Glu Val Val Leu Val Ile His Asp Trp Gly Ser Ala Leu Gly Phe
            100                 105                 110

His Trp Ala Lys Arg Asn Pro Glu Arg Val Lys Gly Ile Ala Cys Met
        115                 120                 125

Glu Phe Ile Arg Pro Ile Pro Thr Trp Asp Glu Trp Pro Glu Phe Ala
130                 135                 140

Arg Glu Thr Phe Gln Ala Phe Arg Thr Ala Asp Val Gly Arg Glu Leu
145                 150                 155                 160

Ile Ile Asp Gln Asn Ala Phe Ile Glu Gly Ala Leu Pro Met Gly Val
                165                 170                 175

Val Arg Pro Leu Thr Glu Val Glu Met Asp His Tyr Arg Glu Pro Phe
            180                 185                 190

Leu Lys Pro Val Asp Arg Glu Pro Leu Trp Arg Phe Pro Asn Glu Leu
        195                 200                 205

Pro Ile Ala Gly Glu Pro Ala Asn Ile Val Ala Leu Val Glu Ala Tyr
    210                 215                 220

Met Asn Trp Leu His Gln Ser Pro Val Pro Lys Leu Leu Phe Trp Gly
225                 230                 235                 240

Thr Pro Gly Val Leu Ile Pro Pro Ala Glu Ala Ala Arg Leu Ala Glu
                245                 250                 255

Ser Leu Pro Asn Cys Lys Thr Val Asp Ile Gly Pro Gly Leu Phe Leu
            260                 265                 270

Leu Gln Glu Asp Asn Pro Asp Leu Ile Gly Ser Glu Ile Ala Arg Trp
        275                 280                 285

Leu Pro Ala Leu
    290
```

<210> SEQ ID NO 19
<211> LENGTH: 27
<212> TYPE: PRT
<213> ORGANISM: Artificial Sequence
<220> FEATURE:
<223> OTHER INFORMATION: A synthetic connector sequence

<400> SEQUENCE: 19

```
Gln Tyr Ser Gly Gly Gly Gly Ser Gly Gly Gly Gly Ser Gly Gly Gly
1               5                   10                  15

Gly Glu Asn Leu Tyr Phe Gln Ala Ile Glu Leu
            20                  25
```

<210> SEQ ID NO 20
<211> LENGTH: 943
<212> TYPE: DNA
<213> ORGANISM: Artificial Sequence
<220> FEATURE:
<223> OTHER INFORMATION: A synthetic HT2 sequence

<400> SEQUENCE: 20

```
gctagccagc tggcgcggat atcgccacca tgggatccga aatcggtaca ggcttcccct     60
tcgaccccca ttatgtggaa gtcctgggcg agcgtatgca ctacgtcgat gttggaccgc    120
gggatggcac gcctgtgctg ttcctgcacg gtaacccgac ctcgtcctac ctgtggcgca    180
acatcatccc gcatgtagca ccgagtcatc ggtgcattgc tccagacctg atcgggatgg    240
gaaaatcgga caaaccagac ctcgattatt tcttcgacga ccacgtccgc tacctcgatg    300
ccttcatcga agccttgggt ttggaagagg tcgtcctggt catccacgac tggggctcag    360
ctctcggatt ccactgggcc aagcgcaatc cggaacgggt caaaggtatt gcatgtatgg    420
aattcatccg gcctatcccg acgtgggacg aatggccaga attcgcccgt gagaccttcc    480
aggccttccg gaccgccgac gtcggccgag agttgatcat cgatcagaac gctttcatcg    540
agggtgcgct cccgatgggg gtcgtccgtc cgcttacgga ggtcgagatg gaccactatc    600
gcgagccctt cctcaagcct gttgaccgag agccactgtg gcgattcccc aacgagctgc    660
ccatcgccgg tgagcccgcg aacatcgtcg cgctcgtcga ggcatacatg aactggctgc    720
accagtcacc tgtcccgaag ttgttgttct ggggcacacc cggcgtactg atccccccgg    780
ccgaagccgc gagacttgcc gaaagcctcc ccaactgcaa gacagtggac atcggcccgg    840
gattgttctt gctccaggaa gacaacccgg accttatcgg cagtgagatc gcgcgctggc    900
tccccgggct ggccggctaa tagttaatta agtaggcggc cgc                      943
```

<210> SEQ ID NO 21
<211> LENGTH: 301
<212> TYPE: PRT
<213> ORGANISM: Artificial Sequence
<220> FEATURE:
<223> OTHER INFORMATION: A synthetic HT2 sequence

<400> SEQUENCE: 21

```
Met Gly Ser Glu Ile Gly Thr Gly Phe Pro Phe Pro His Tyr Val Glu
1               5                   10                  15

Val Leu Gly Glu Arg Met His His Tyr Val Asp Val Gly Pro Arg Asp
            20                  25                  30

Gly Thr Pro Val Leu Phe Leu His Gly Asn Pro Thr Ser Ser Tyr Leu
        35                  40                  45

Trp Arg Asn Ile Ile Pro His Val Ala Pro Ser His Arg Cys Ile Ala
```

```
            50                  55                  60
Pro Asp Leu Ile Gly Met Gly Lys Ser Asp Ala Lys Pro Asp Leu Asp
 65                  70                  75                  80

Tyr Phe Phe Asp Asp His Val Arg Tyr Leu Asp Ala Phe Ile Glu Ala
                 85                  90                  95

Leu Gly Leu Glu Glu Val Val Leu Val Ile His Asp Trp Gly Ser Ala
                100                 105                 110

Leu Gly Phe His Trp Ala Lys Arg Asn Pro Glu Arg Val Val Lys Gly
            115                 120                 125

Ile Ala Cys Met Glu Phe Ile Arg Pro Ile Pro Thr Trp Asp Glu Trp
        130                 135                 140

Pro Glu Phe Ala Arg Glu Thr Phe Gln Ala Phe Arg Thr Ala Asp Val
145                 150                 155                 160

Gly Arg Glu Leu Ile Ile Asp Gln Asn Ala Phe Ile Glu Gly Ala Leu
                165                 170                 175

Leu Pro Met Gly Val Val Arg Pro Leu Thr Glu Val Glu Met Asp His
            180                 185                 190

Tyr Arg Glu Pro Phe Leu Lys Pro Val Asp Arg Glu Pro Leu Trp Arg
        195                 200                 205

Phe Pro Asn Glu Leu Pro Ile Ala Gly Glu Pro Ala Asn Ile Val Ala
    210                 215                 220

Leu Val Glu Gly Ala Tyr Met Asn Trp Leu His Gln Ser Pro Val Pro
225                 230                 235                 240

Lys Leu Leu Phe Trp Gly Thr Pro Gly Val Leu Ile Pro Pro Ala Glu
                245                 250                 255

Ala Ala Arg Leu Ala Glu Ser Leu Pro Asn Cys Lys Thr Val Asp Ile
            260                 265                 270

Gly Pro Gly Leu Phe Leu Leu Gln Glu Asp Asn Pro Asp Leu Ile
        275                 280                 285

Gly Ser Glu Ile Ala Arg Trp Leu Pro Gly Leu Ala Gly
    290                 295                 300

<210> SEQ ID NO 22
<211> LENGTH: 295
<212> TYPE: PRT
<213> ORGANISM: Artificial Sequence
<220> FEATURE:
<223> OTHER INFORMATION: A synthetic DhaA mutant

<400> SEQUENCE: 22

Met Ala Glu Ile Gly Thr Gly Phe Pro Phe Asp Pro His Tyr Val Glu
  1               5                  10                  15

Val Leu Gly Glu Arg Met His Tyr Val Asp Val Gly Pro Arg Asp Gly
                 20                  25                  30

Thr Pro Val Leu Phe Leu His Gly Asn Pro Thr Ser Ser Tyr Leu Trp
             35                  40                  45

Arg Asn Ile Ile Pro His Val Ala Pro Thr His Arg Cys Ile Ala Pro
         50                  55                  60

Asp Leu Ile Gly Met Gly Lys Ser Asp Lys Pro Asp Leu Gly Tyr Phe
 65                  70                  75                  80

Phe Asp Asp His Val Arg Tyr Leu Asp Ala Phe Ile Glu Ala Leu Gly
                 85                  90                  95

Leu Glu Glu Val Val Leu Val Ile His Asp Trp Gly Ser Ala Leu Gly
                100                 105                 110

Phe His Trp Ala Lys Arg Asn Pro Glu Arg Val Lys Gly Ile Ala Cys
            115                 120                 125
```

```
            115                 120                 125
Met Glu Phe Ile Arg Pro Ile Pro Thr Trp Asp Glu Trp Pro Glu Phe
        130                 135                 140

Ala Arg Glu Thr Phe Gln Ala Phe Arg Thr Thr Asp Val Gly Arg Glu
145                 150                 155                 160

Leu Ile Ile Asp Gln Asn Ala Phe Ile Glu Gly Thr Leu Pro Met Gly
                165                 170                 175

Val Val Arg Pro Leu Thr Glu Val Glu Met Asp His Tyr Arg Glu Pro
            180                 185                 190

Phe Leu Lys Pro Val Asp Arg Glu Pro Leu Trp Arg Phe Pro Asn Glu
        195                 200                 205

Leu Pro Ile Ala Gly Glu Pro Ala Asn Ile Val Ala Leu Val Glu Glu
    210                 215                 220

Tyr Met Asn Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255

Glu Ser Leu Pro Asn Cys Lys Thr Val Asp Ile Gly Pro Gly Leu Asn
            260                 265                 270

Phe Leu Gln Glu Asp Asn Pro Asp Leu Ile Gly Ser Glu Ile Ala Arg
        275                 280                 285

Trp Leu Ser Thr Leu Gln Tyr
    290                 295

<210> SEQ ID NO 23
<211> LENGTH: 295
<212> TYPE: PRT
<213> ORGANISM: Artificial Sequence
<220> FEATURE:
<223> OTHER INFORMATION: A synthetic DhaA mutant

<400> SEQUENCE: 23

Met Ala Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
            20                  25                  30

Thr Pro Val Leu Phe Leu His Gly Asn Pro Thr Ser Ser Tyr Leu Trp
        35                  40                  45

Arg Asn Ile Ile Pro His Val Ala Pro Thr His Arg Cys Ile Ala Pro
    50                  55                  60

Asp Leu Ile Gly Met Gly Lys Ser Asp Lys Pro Asp Leu Gly Tyr Phe
65                  70                  75                  80

Phe Asp Asp His Val Arg Tyr Leu Asp Ala Phe Ile Glu Ala Leu Gly
                85                  90                  95

Leu Glu Glu Val Val Leu Val Ile His Asp Trp Gly Ser Ala Leu Gly
            100                 105                 110

Phe His Trp Ala Lys Arg Asn Pro Glu Arg Val Lys Gly Ile Ala Cys
        115                 120                 125

Met Glu Phe Ile Arg Pro Ile Pro Thr Trp Asp Glu Trp Pro Glu Phe
    130                 135                 140

Ala Arg Glu Thr Phe Gln Ala Phe Arg Thr Thr Asp Val Gly Arg Glu
145                 150                 155                 160

Leu Ile Ile Asp Gln Asn Ala Phe Ile Glu Gly Thr Leu Pro Met Gly
                165                 170                 175

Val Val Arg Pro Leu Thr Glu Val Glu Met Asp His Tyr Arg Glu Pro
```

```
            180                 185                 190
Phe Leu Lys Pro Val Asp Arg Glu Pro Leu Trp Arg Phe Pro Asn Glu
            195                 200                 205
Leu Pro Ile Ala Gly Glu Pro Ala Asn Ile Val Ala Leu Val Glu Glu
            210                 215                 220
Tyr Met Asn Trp Leu His Gln Ser Pro Val Pro Lys Leu Leu Phe Trp
225                 230                 235                 240
Gly Thr Pro Gly Val Leu Ile Pro Pro Ala Glu Ala Ala Arg Leu Ala
                245                 250                 255
Glu Ser Leu Pro Asn Cys Lys Thr Val Asp Ile Gly Pro Gly Leu Asn
                260                 265                 270
Leu Leu Gln Glu Asp Asn Pro Asp Leu Ile Gly Ser Glu Ile Ala Arg
                275                 280                 285
Trp Leu Ser Thr Leu Gln Tyr
                290                 295

<210> SEQ ID NO 24
<211> LENGTH: 295
<212> TYPE: PRT
<213> ORGANISM: Artificial Sequence
<220> FEATURE:
<223> OTHER INFORMATION: A synthetic DhaA mutant

<400> SEQUENCE: 24

Met Ala Glu Ile Gly Thr Gly Phe Pro Phe Asp Pro His Tyr Val Glu
1               5                   10                  15
Val Leu Gly Glu Arg Met His Tyr Val Asp Val Gly Pro Arg Asp Gly
            20                  25                  30
Thr Pro Val Leu Phe Leu His Gly Asn Pro Thr Ser Ser Tyr Leu Trp
        35                  40                  45
Arg Asn Ile Ile Pro His Val Ala Pro Thr His Arg Cys Ile Ala Pro
    50                  55                  60
Asp Leu Ile Gly Met Gly Lys Ser Asp Lys Pro Asp Leu Gly Tyr Phe
65                  70                  75                  80
Phe Asp Asp His Val Arg Phe Leu Asp Ala Phe Ile Glu Ala Leu Gly
                85                  90                  95
Leu Glu Glu Val Val Leu Val Ile His Asp Trp Gly Ser Ala Leu Gly
            100                 105                 110
Phe His Trp Ala Lys Arg Asn Pro Glu Arg Val Lys Gly Ile Ala Cys
        115                 120                 125
Met Glu Phe Ile Arg Pro Ile Pro Thr Trp Asp Glu Trp Pro Glu Phe
    130                 135                 140
Ala Arg Glu Thr Phe Gln Ala Phe Arg Thr Thr Asp Val Gly Arg Glu
145                 150                 155                 160
Leu Ile Ile Asp Gln Asn Ala Phe Ile Glu Gly Thr Leu Pro Met Gly
                165                 170                 175
Val Val Arg Pro Leu Thr Glu Val Glu Met Asp His Tyr Arg Glu Pro
            180                 185                 190
Phe Leu Lys Pro Val Asp Arg Glu Pro Leu Trp Arg Phe Pro Asn Glu
            195                 200                 205
Leu Pro Ile Ala Gly Glu Pro Ala Asn Ile Val Ala Leu Val Glu Glu
            210                 215                 220
Tyr Met Asp Trp Leu His Gln Ser Pro Val Pro Lys Leu Leu Phe Trp
225                 230                 235                 240
Gly Thr Pro Gly Val Leu Ile Pro Pro Ala Glu Ala Ala Arg Leu Ala
```

245                 250                 255
Glu Ser Leu Pro Asn Cys Lys Thr Val Asp Ile Gly Pro Gly Leu Asn
            260                 265                 270

Phe Leu Gln Glu Asp Asn Pro Asp Leu Ile Gly Ser Glu Ile Ala Arg
        275                 280                 285

Trp Leu Gln Glu Leu Gln Tyr
    290                 295

<210> SEQ ID NO 25
<211> LENGTH: 295
<212> TYPE: PRT
<213> ORGANISM: Artificial Sequence
<220> FEATURE:
<223> OTHER INFORMATION: A synthetic DhaA mutant

<400> SEQUENCE: 25

Met Ala Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Ser
            20                  25                  30

Thr Pro Val Leu Phe Leu His Gly Asn Pro Thr Ser Ser Tyr Leu Trp
        35                  40                  45

Arg Asn Ile Ile Pro His Val Ala Pro Thr His Arg Cys Ile Ala Pro
    50                  55                  60

Asp Leu Ile Gly Met Gly Lys Ser Asp Lys Pro Asp Leu Gly Tyr Phe
65                  70                  75                  80

Phe Asp Asp His Val Arg Phe Leu Asp Ala Phe Ile Glu Ala Leu Gly
                85                  90                  95

Leu Glu Glu Val Val Leu Val Ile His Asp Trp Gly Ser Ala Leu Gly
            100                 105                 110

Phe His Trp Ala Lys Arg Asn Pro Glu Arg Val Lys Gly Ile Ala Cys
        115                 120                 125

Met Glu Phe Ile Arg Pro Ile Pro Thr Trp Asp Glu Trp Pro Glu Phe
    130                 135                 140

Ala Arg Glu Thr Phe Gln Ala Phe Arg Thr Thr Asp Val Gly Arg Glu
145                 150                 155                 160

Leu Ile Ile Asp Gln Asn Ala Phe Ile Glu Gly Thr Leu Pro Met Gly
                165                 170                 175

Val Val Arg Pro Leu Thr Glu Val Glu Met Asp His Tyr Arg Glu Pro
            180                 185                 190

Phe Leu Lys Pro Val Asp Arg Glu Pro Leu Trp Arg Phe Pro Asn Glu
        195                 200                 205

Leu Pro Ile Ala Gly Glu Pro Ala Asn Ile Val Ala Leu Val Glu Glu
    210                 215                 220

Tyr Met Asp Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255

Glu Ser Leu Pro Asn Cys Lys Thr Val Asp Ile Gly Pro Gly Leu Asn
            260                 265                 270

Leu Leu Gln Glu Asp Asn Pro Asp Leu Ile Gly Ser Glu Ile Ala Arg
        275                 280                 285

Trp Leu Gln Glu Leu Gln Tyr
    290                 295

<210> SEQ ID NO 26
<211> LENGTH: 295
<212> TYPE: PRT
<213> ORGANISM: Artificial Sequence
<220> FEATURE:
<223> OTHER INFORMATION: A synthetic DhaA mutant

<400> SEQUENCE: 26

```
Met Ala Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
                20                  25                  30

Thr Pro Val Leu Phe Leu His Gly Asn Pro Thr Ser Ser Tyr Val Trp
            35                  40                  45

Arg Asn Ile Ile Pro His Val Ala Pro Thr His Arg Cys Ile Ala Pro
        50                  55                  60

Asp Leu Ile Gly Met Gly Lys Ser Asp Lys Pro Asp Leu Gly Tyr Phe
65                  70                  75                  80

Phe Asp Asp His Val Arg Phe Met Asp Ala Phe Ile Glu Ala Leu Gly
                85                  90                  95

Leu Glu Glu Val Val Leu Val Ile His Asp Trp Gly Ser Ala Leu Gly
                100                 105                 110

Phe His Trp Ala Lys Arg Asn Pro Glu Arg Val Lys Gly Ile Ala Phe
            115                 120                 125

Met Glu Phe Ile Arg Pro Ile Pro Thr Trp Asp Glu Trp Pro Glu Phe
130                 135                 140

Ala Arg Glu Thr Phe Gln Ala Phe Arg Thr Thr Asp Val Gly Arg Lys
145                 150                 155                 160

Leu Ile Ile Asp Gln Asn Val Phe Ile Glu Gly Thr Leu Pro Met Gly
                165                 170                 175

Val Val Arg Pro Leu Thr Glu Val Glu Met Asp His Tyr Arg Glu Pro
            180                 185                 190

Phe Leu Asn Pro Val Asp Arg Glu Pro Leu Trp Arg Phe Pro Asn Glu
        195                 200                 205

Leu Pro Ile Ala Gly Glu Pro Ala Asn Ile Val Ala Leu Val Glu Glu
    210                 215                 220

Tyr Met Asp Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255

Lys Ser Leu Pro Asn Cys Lys Ala Val Asp Ile Gly Pro Gly Leu Asn
            260                 265                 270

Leu Leu Gln Glu Asp Asn Pro Asp Leu Ile Gly Ser Glu Ile Ala Arg
        275                 280                 285

Trp Leu Ser Thr Leu Gln Tyr
    290                 295
```

<210> SEQ ID NO 27
<211> LENGTH: 297
<212> TYPE: PRT
<213> ORGANISM: Artificial Sequence
<220> FEATURE:
<223> OTHER INFORMATION: A synthetic DhaA mutant

<400> SEQUENCE: 27

```
Met Ala Glu Ile Gly Thr Gly Phe Pro Phe Asp Pro His Tyr Val Glu
1               5                   10                  15
```

Val Leu Gly Glu Arg Met His Tyr Val Asp Val Gly Pro Arg Asp Gly
            20                  25                  30

Thr Pro Val Leu Phe Leu His Gly Asn Pro Thr Ser Ser Tyr Val Trp
        35                  40                  45

Arg Asn Ile Ile Pro His Val Ala Pro Thr His Arg Cys Ile Ala Pro
 50                  55                  60

Asp Leu Ile Gly Met Gly Lys Ser Asp Lys Pro Asp Leu Gly Tyr Phe
 65                  70                  75                  80

Phe Asp Asp His Val Arg Phe Met Asp Ala Phe Ile Glu Ala Leu Gly
                85                  90                  95

Leu Glu Glu Val Val Leu Val Ile His Asp Trp Gly Ser Ala Leu Gly
            100                 105                 110

Phe His Trp Ala Lys Arg Asn Pro Glu Arg Val Lys Gly Ile Ala Phe
        115                 120                 125

Met Glu Phe Ile Arg Pro Ile Pro Thr Trp Asp Glu Trp Pro Glu Phe
    130                 135                 140

Ala Arg Glu Thr Phe Gln Ala Phe Arg Thr Thr Asp Val Gly Arg Lys
145                 150                 155                 160

Leu Ile Ile Asp Gln Asn Val Phe Ile Glu Gly Thr Leu Pro Met Gly
                165                 170                 175

Val Val Arg Pro Leu Thr Glu Val Glu Met Asp His Tyr Arg Glu Pro
            180                 185                 190

Phe Leu Asn Pro Val Asp Arg Glu Pro Leu Trp Arg Phe Pro Asn Glu
        195                 200                 205

Leu Pro Ile Ala Gly Glu Pro Ala Asn Ile Val Ala Leu Val Glu Glu
    210                 215                 220

Tyr Met Asp Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255

Lys Ser Leu Pro Asn Cys Lys Ala Val Asp Ile Gly Pro Gly Leu Asn
            260                 265                 270

Leu Leu Gln Glu Asp Asn Pro Asp Leu Ile Gly Ser Glu Ile Ala Arg
        275                 280                 285

Trp Leu Ser Thr Leu Glu Ile Ser Gly
    290                 295

<210> SEQ ID NO 28
<211> LENGTH: 16
<212> TYPE: PRT
<213> ORGANISM: Artificial Sequence
<220> FEATURE:
<223> OTHER INFORMATION: A synthetic connector sequence

<400> SEQUENCE: 28

Glu Pro Thr Thr Glu Asp Leu Tyr Phe Gln Ser Asp Asn Ala Ile Ala
1               5                   10                  15

<210> SEQ ID NO 29
<211> LENGTH: 17
<212> TYPE: PRT
<213> ORGANISM: Artificial Sequence
<220> FEATURE:
<223> OTHER INFORMATION: A synthetic connector sequence

<400> SEQUENCE: 29

Val Ser Leu Glu Pro Thr Thr Glu Asp Leu Tyr Phe Gln Ser Asp Asn
1               5                   10                  15

Asp

<210> SEQ ID NO 30
<211> LENGTH: 879
<212> TYPE: DNA
<213> ORGANISM: Artificial Sequence
<220> FEATURE:
<223> OTHER INFORMATION: A synthetic mutant DhaA sequence

<400> SEQUENCE: 30

```
atggcagaaa tcggtactgg ctttccattc gaccccatt atgtggaagt cctgggcgag      60
cgcatgcact acgtcgatgt tggtccgcgc gatggcaccc ctgtgctgtt cctgcacggt     120
aacccgacct cctcctacct gtggcgcaac atcatcccgc atgttgcacc gagccatcgc     180
tgcattgctc cagacctgat cggtatgggc aaatccgaca accagacct gggttatttc      240
ttcgacgacc acgtccgcta cctggatgcc ttcatcgaag ccctgggtct ggaagaggtc     300
gtcctggtca ttcacgactg ggctccgct ctgggtttcc actgggccaa gcgcaatcca      360
gagcgcgtca aggtattgc atgtatggag ttcatccgcc ctatcccgac ctgggacgaa      420
tggccagaat tgcccgcga gaccttccag gccttccgca cgccgacgt cggccgcgag      480
ctgatcatcg atcagaacgc ttttatcgag ggtgcgctgc cgatgggtgt cgtccgcccg     540
ctgactgaag tcgagatgga ccattaccgc gagccgttcc tgaagcctgt tgaccgcgag     600
ccactgtggc gcttcccaaa cgagctgcca atcgccggtg agccagcgaa catcgtcgcg     660
ctggtcgaag catacatgaa ctggctgcac cagtcccctg tcccgaagct gctgttctgg     720
ggcacccag gcgttctgat cccaccggcc gaagccgctc gcctggccga agcctgcct      780
aactgcaaga ctgtggacat cggcccgggt ctgaatttc tgcaagaaga caacccggac     840
ctgatcggca gcgagatcgc gcgctggctg ccggcgctg                           879
```

<210> SEQ ID NO 31
<211> LENGTH: 11
<212> TYPE: PRT
<213> ORGANISM: Artificial Sequence
<220> FEATURE:
<223> OTHER INFORMATION: A synthetic connector sequence
<220> FEATURE:
<221> NAME/KEY: SITE
<222> LOCATION: (11)..(11)
<223> OTHER INFORMATION: Xaa = S or C

<400> SEQUENCE: 31

Glu Pro Thr Thr Glu Asp Leu Tyr Phe Gln Xaa
1               5                   10

<210> SEQ ID NO 32
<211> LENGTH: 885
<212> TYPE: DNA
<213> ORGANISM: Artificial Sequence
<220> FEATURE:
<223> OTHER INFORMATION: A synthetic DhaA mutant

<400> SEQUENCE: 32

```
atggcagaaa tcggtactgg ctttccattc gaccccatt atgtggaagt cctgggcgag      60
cgcatgcact acgtcgatgt tggtccgcgc gatggcaccc ctgtgctgtt cctgcacggt     120
aacccgacct cctcctacct gtggcgcaac atcatcccgc atgttgcacc gacccatcgc     180
tgcattgctc cagacctgat cggtatgggc aaatccgaca accagacct gggttatttc      240
ttcgacgacc acgtccgcta cctggatgcc ttcatcgaag ccctgggtct ggaagaggtc     300
```

```
gtcctggtca ttcacgactg gggctccgct ctgggtttcc actgggccaa gcgcaatcca    360
gagcgcgtca aaggtattgc atgtatggag ttcatccgcc ctatcccgac ctgggacgaa    420
tggccagaat ttgcccgcga gaccttccag gccttccgca ccaccgacgt cggccgcgag    480
ctgatcatcg atcagaacgc ttttatcgag ggtacgctgc cgatgggtgt cgtccgcccg    540
ctgactgaag tcgagatgga ccattaccgc gagccgttcc tgaagcctgt tgaccgcgag    600
ccactgtggc gcttcccaaa cgagctgcca atcgccggtg agccagcgaa catcgtcgcg    660
ctggtcgaag aatacatgaa ctggctgcac cagtcccctg tcccgaagct gctgttctgg    720
ggcaccccag gcgttctgat cccaccggcc gaagccgctc gcctggccga aagcctgcct    780
aactgcaaga ctgtggacat cggcccgggt ctgaattttc tgcaagaaga caacccggac    840
ctgatcggca gcgagatcgc gcgctggctg tcgacgctgc aatat                   885
```

<210> SEQ ID NO 33
<211> LENGTH: 885
<212> TYPE: DNA
<213> ORGANISM: Artificial Sequence
<220> FEATURE:
<223> OTHER INFORMATION: A synthetic DhaA mutant

<400> SEQUENCE: 33

```
atggcagaaa tcggtactgg ctttccattc gacccccatt atgtggaagt cctgggcgag     60
cgcatgcact acgtcgatgt tggtccgcgc gatggcaccc ctgtgctgtt cctgcacggt    120
aacccgacct cctcctacct gtggcgcaac atcatcccgc atgttgcacc gacccatcgc    180
tgcattgctc cagacctgat cggtatgggc aaatccgaca accagacct gggttatttc    240 ttcgacgacc acgtccgcta cctggatgcc ttcatcgaag ccctgggtct ggaagaggtc    300
gtcctggtca ttcacgactg gggctccgct ctgggtttcc actgggccaa gcgcaatcca    360
gagcgcgtca aaggtattgc atgtatggag ttcatccgcc ctatcccgac ctgggacgaa    420
tggccagaat ttgcccgcga gaccttccag gccttccgca ccaccgacgt cggccgcgag    480
ctgatcatcg atcagaacgc ttttatcgag ggtacgctgc cgatgggtgt cgtccgcccg    540
ctgactgaag tcgagatgga ccattaccgc gagccgttcc tgaagcctgt tgaccgcgag    600
ccactgtggc gcttcccaaa cgagctgcca atcgccggtg agccagcgaa catcgtcgcg    660
ctggtcgaag aatacatgaa ctggctgcac cagtcccctg tcccgaagct gctgttctgg    720
ggcaccccag gcgttctgat cccaccggcc gaagccgctc gcctggccga aagcctgcct    780
aactgcaaga ctgtggacat cggcccgggt ctgaatctgc tgcaagaaga caacccggac    840
ctgatcggca gcgagatcgc gcgctggctg tcgacgctgc aatat                   885
```

<210> SEQ ID NO 34
<211> LENGTH: 885
<212> TYPE: DNA
<213> ORGANISM: Artificial Sequence
<220> FEATURE:
<223> OTHER INFORMATION: A synthetic DhaA mutant

<400> SEQUENCE: 34

```
atggcagaaa tcggtactgg ctttccattc gacccccatt atgtggaagt cctgggcgag     60
cgcatgcact acgtcgatgt tggtccgcgc gatggcaccc ctgtgctgtt cctgcacggt    120
aacccgacct cctcctacct gtggcgcaac atcatcccgc atgttgcacc gacccatcgc    180
tgcattgctc cagacctgat cggtatgggc aaatccgaca accagacct gggttatttc    240
```

```
ttcgacgacc acgtccgctt cctggatgcc ttcatcgaag ccctgggtct ggaagaggtc      300
gtcctggtca ttcacgactg gggctccgct ctgggtttcc actgggccaa gcgcaatcca      360
gagcgcgtca aggtattgc atgtatggag ttcatccgcc ctatcccgac ctgggacgaa       420
tggccagaat tgcccgcga gaccttccag gccttccgca ccaccgacgt cggccgcgag       480
ctgatcatcg atcagaacgc ttttatcgag ggtacgctgc cgatgggtgt cgtccgcccg      540
ctgactgaag tcgagatgga ccattaccgc gagccgttcc tgaagcctgt tgaccgcgag      600
ccactgtggc gcttcccaaa cgagctgcca atcgccggtg agccagcgaa catcgtcgcg      660
ctggtcgaag aatacatgga ctggctgcac cagtcccctg tcccgaagct gctgttctgg      720
ggcaccccag gcgttctgat cccaccggcc gaagccgctc gcctggccga aagcctgcct      780
aactgcaaga ctgtggacat cggcccgggt ctgaattttc tgcaagaaga caacccggac      840
ctgatcggca gcgagatcgc gcgctggctg caggagctgc aatat                     885
```

<210> SEQ ID NO 35
<211> LENGTH: 885
<212> TYPE: DNA
<213> ORGANISM: Artificial Sequence
<220> FEATURE:
<223> OTHER INFORMATION: A synthetic DhaA mutant

<400> SEQUENCE: 35

```
atggcagaaa tcggtactgg ctttccattc gaccccatt atgtggaagt cctgggcgag       60
cgcatgcact acgtcgatgt tggtccgcgc gatagcaccc ctgtgctgtt cctgcacggt      120
aacccgacct cctcctacct gtggcgcaac atcatcccgc atgttgcacc gacccatcgc      180
tgcattgctc cagacctgat cggtatgggc aaatccgaca accagacct gggttatttc      240 ttcgacgacc acgtccgctt cctggatgcc ttcatcgaag ccctgggtct ggaagaggtc      300
gtcctggtca ttcacgactg gggctccgct ctgggtttcc actgggccaa gcgcaatcca      360
gagcgcgtca aggtattgc atgtatggag ttcatccgcc ctatcccgac ctgggacgaa       420
tggccagaat tgcccgcga gaccttccag gccttccgca ccaccgacgt cggccgcgag       480
ctgatcatcg atcagaacgc ttttatcgag ggtacgctgc cgatgggtgt cgtccgcccg      540
ctgactgaag tcgagatgga ccattaccgc gagccgttcc tgaagcctgt tgaccgcgag      600
ccactgtggc gcttcccaaa cgagctgcca atcgccggtg agccagcgaa catcgtcgcg      660
ctggtcgaag aatacatgga ctggctgcac cagtcccctg tcccgaagct gctgttctgg      720
ggcaccccag gcgttctgat cccaccggcc gaagccgctc gcctggccga aagcctgcct      780
aactgcaaga ctgtggacat cggcccgggt ctgaatctgc tgcaagaaga caacccggac      840
ctgatcggca gcgagatcgc gcgctggctg caggagctgc aatat                     885
```

<210> SEQ ID NO 36
<211> LENGTH: 885
<212> TYPE: DNA
<213> ORGANISM: Artificial Sequence
<220> FEATURE:
<223> OTHER INFORMATION: A synthetic DhaA mutant

<400> SEQUENCE: 36

```
atggcagaaa tcggtactgg ctttccattc gaccccatt atgtggaagt cctgggcgag       60
cgcatgcact acgtcgatgt tggtccgcgc gatggcaccc ctgtgctgtt cctgcacggt      120
aacccgacct cctcctacgt gtggcgcaac atcatcccgc atgttgcacc gacccatcgc      180
tgcattgctc cagacctgat cggtatgggc aaatccgaca accagacct gggttatttc      240
```

```
ttcgacgacc acgtccgctt catggatgcc ttcatcgaag ccctgggtct ggaagaggtc    300
gtcctggtca ttcacgactg gggctccgct ctgggtttcc actgggccaa gcgcaatcca    360
gagcgcgtca aggtattgc atttatggag ttcatccgcc ctatcccgac ctgggacgaa     420
tggccagaat tgcccgcga gaccttccag gccttccgca ccaccgacgt cggccgcaag     480
ctgatcatcg atcagaacgt ttttatcgag ggtacgctgc cgatgggtgt cgtccgcccg    540
ctgactgaag tcgagatgga ccattaccgc gagccgttcc tgaatcctgt tgaccgcgag    600
ccactgtggc gcttcccaaa cgagctgcca atcgccggtg agccagcgaa catcgtcgcg    660
ctggtcgaag aatacatgga ctggctgcac cagtcccctg tcccgaagct gctgttctgg    720
ggcaccccag gcgttctgat cccaccggcc gaagccgctc gcctggccaa aagcctgcct    780
aactgcaagg ctgtggacat cggcccgggt ctgaatctgc tgcaagaaga caacccggac    840
ctgatcggca gcgagatcgc gcgctggctg tcgacgctgc aatat                    885
```

<210> SEQ ID NO 37
<211> LENGTH: 891
<212> TYPE: DNA
<213> ORGANISM: Artificial Sequence
<220> FEATURE:
<223> OTHER INFORMATION: A synthetic DhaA mutant

<400> SEQUENCE: 37

```
atggcagaaa tcggtactgg ctttccattc gaccccatt atgtggaagt cctgggcgag    60
cgcatgcact acgtcgatgt tggtccgcgc gatggcaccc ctgtgctgtt cctgcacggt    120
aacccgacct cctcctacgt gtggcgcaac atcatcccgc atgttgcacc gacccatcgc    180
tgcattgctc cagacctgat cggtatgggc aaatccgaca accagacct gggttatttc    240 ttcgacgacc acgtccgctt catggatgcc ttcatcgaag ccctgggtct ggaagaggtc    300
gtcctggtca ttcacgactg gggctccgct ctgggtttcc actgggccaa gcgcaatcca    360
gagcgcgtca aggtattgc atttatggag ttcatccgcc ctatcccgac ctgggacgaa     420
tggccagaat tgcccgcga gaccttccag gccttccgca ccaccgacgt cggccgcaag     480
ctgatcatcg atcagaacgt ttttatcgag ggtacgctgc cgatgggtgt cgtccgcccg    540
ctgactgaag tcgagatgga ccattaccgc gagccgttcc tgaatcctgt tgaccgcgag    600
ccactgtggc gcttcccaaa cgagctgcca atcgccggtg agccagcgaa catcgtcgcg    660
ctggtcgaag aatacatgga ctggctgcac cagtcccctg tcccgaagct gctgttctgg    720
ggcaccccag gcgttctgat cccaccggcc gaagccgctc gcctggccaa aagcctgcct    780
aactgcaagg ctgtggacat cggcccgggt ctgaatctgc tgcaagaaga caacccggac    840
ctgatcggca gcgagatcgc gcgctggctg tcgacgctgg agatttccgg a             891
```

<210> SEQ ID NO 38
<211> LENGTH: 13
<212> TYPE: PRT
<213> ORGANISM: Artificial Sequence
<220> FEATURE:
<223> OTHER INFORMATION: A synthetic connector sequence
<220> FEATURE:
<221> NAME/KEY: SITE
<222> LOCATION: (11)..(11)
<223> OTHER INFORMATION: Xaa = S or C

<400> SEQUENCE: 38

Glu Pro Thr Thr Glu Asp Leu Tyr Phe Gln Xaa Asp Asn
1               5                   10

```
<210> SEQ ID NO 39
<211> LENGTH: 5
<212> TYPE: PRT
<213> ORGANISM: Artificial Sequence
<220> FEATURE:
<223> OTHER INFORMATION: A synthetic N-terminus mutant DhaA sequence
<220> FEATURE:
<221> NAME/KEY: SITE
<222> LOCATION: (1)..(1)
<223> OTHER INFORMATION: Xaa = M or G
<220> FEATURE:
<221> NAME/KEY: SITE
<222> LOCATION: (2)..(2)
<223> OTHER INFORMATION: Xaa = A or S

<400> SEQUENCE: 39

Xaa Xaa Glu Thr Gly
1               5

<210> SEQ ID NO 40
<211> LENGTH: 5
<212> TYPE: PRT
<213> ORGANISM: Artificial Sequence
<220> FEATURE:
<223> OTHER INFORMATION: A synthetic C-terminus mutant DhaA sequence
<220> FEATURE:
<221> NAME/KEY: SITE
<222> LOCATION: (1)..(1)
<223> OTHER INFORMATION: Xaa = P, S or Q
<220> FEATURE:
<221> NAME/KEY: SITE
<222> LOCATION: (2)..(2)
<223> OTHER INFORMATION: Xaa = A, T or E
<220> FEATURE:
<221> NAME/KEY: SITE
<222> LOCATION: (4)..(4)
<223> OTHER INFORMATION: Xaa = Q or E
<220> FEATURE:
<221> NAME/KEY: SITE
<222> LOCATION: (5)..(5)
<223> OTHER INFORMATION: Xaa = Y or I

<400> SEQUENCE: 40

Xaa Xaa Leu Xaa Xaa
1               5

<210> SEQ ID NO 41
<211> LENGTH: 4
<212> TYPE: PRT
<213> ORGANISM: Artificial Sequence
<220> FEATURE:
<223> OTHER INFORMATION: A synthetic C-terminus mutant DhaA sequence

<400> SEQUENCE: 41

Glu Ile Ser Gly
1

<210> SEQ ID NO 42
<211> LENGTH: 294
<212> TYPE: PRT
<213> ORGANISM: Artificial Sequence
<220> FEATURE:
<223> OTHER INFORMATION: A synthetic DhaA mutant

<400> SEQUENCE: 42

Ser Glu Ile Gly Thr Gly Phe Pro Phe Asp Pro His Tyr Val Glu Val
1               5                   10                  15

Leu Gly Glu Arg Met His Tyr Val Asp Val Gly Pro Arg Asp Gly Thr
            20                  25                  30
```

Pro Val Leu Phe Leu His Gly Asn Pro Thr Ser Ser Tyr Leu Trp Arg
            35                  40                  45

Asn Ile Ile Pro His Val Ala Pro Thr His Arg Cys Ile Ala Pro Asp
 50                  55                  60

Leu Ile Gly Met Gly Lys Ser Asp Lys Pro Asp Leu Gly Tyr Phe Phe
 65                  70                  75                  80

Asp Asp His Val Arg Tyr Leu Asp Ala Phe Ile Glu Ala Leu Gly Leu
                85                  90                  95

Glu Glu Val Val Leu Val Ile His Asp Trp Gly Ser Ala Leu Gly Phe
               100                 105                 110

His Trp Ala Lys Arg Asn Pro Glu Arg Val Lys Gly Ile Ala Cys Met
               115                 120                 125

Glu Phe Ile Arg Pro Ile Pro Thr Trp Asp Glu Trp Pro Glu Phe Ala
               130                 135                 140

Arg Glu Thr Phe Gln Ala Phe Arg Thr Thr Asp Val Gly Arg Glu Leu
145                 150                 155                 160

Ile Ile Asp Gln Asn Ala Phe Ile Glu Gly Thr Leu Pro Met Gly Val
                165                 170                 175

Val Arg Pro Leu Thr Glu Val Glu Met Asp His Tyr Arg Glu Pro Phe
                180                 185                 190

Leu Lys Pro Val Asp Arg Glu Pro Leu Trp Arg Phe Pro Asn Glu Leu
                195                 200                 205

Pro Ile Ala Gly Glu Pro Ala Asn Ile Val Ala Leu Val Glu Glu Tyr
    210                 215                 220

Met Asn Trp Leu His Gln Ser Pro Val Pro Lys Leu Leu Phe Trp Gly
225                 230                 235                 240

Thr Pro Gly Val Leu Ile Pro Pro Ala Glu Ala Ala Arg Leu Ala Glu
                245                 250                 255

Ser Leu Pro Asn Cys Lys Thr Val Asp Ile Gly Pro Gly Leu Asn Phe
                260                 265                 270

Leu Gln Glu Asp Asn Pro Asp Leu Ile Gly Ser Glu Ile Ala Arg Trp
                275                 280                 285

Leu Ser Thr Leu Gln Tyr
                290

<210> SEQ ID NO 43
<211> LENGTH: 294
<212> TYPE: PRT
<213> ORGANISM: Artificial Sequence
<220> FEATURE:
<223> OTHER INFORMATION: A synthetic DhaA mutant

<400> SEQUENCE: 43

Ser Glu Ile Gly Thr Gly Phe Pro Phe Asp Pro His Tyr Val Glu Val
 1               5                  10                  15

Leu Gly Glu Arg Met His Tyr Val Asp Val Gly Pro Arg Asp Gly Thr
                20                  25                  30

Pro Val Leu Phe Leu His Gly Asn Pro Thr Ser Ser Tyr Leu Trp Arg
            35                  40                  45

Asn Ile Ile Pro His Val Ala Pro Thr His Arg Cys Ile Ala Pro Asp
 50                  55                  60

Leu Ile Gly Met Gly Lys Ser Asp Lys Pro Asp Leu Gly Tyr Phe Phe
 65                  70                  75                  80

Asp Asp His Val Arg Tyr Leu Asp Ala Phe Ile Glu Ala Leu Gly Leu
                85                  90                  95

```
Glu Val Val Leu Val Ile His Asp Trp Gly Ser Ala Leu Gly Phe
    100                 105                 110

His Trp Ala Lys Arg Asn Pro Glu Arg Val Lys Gly Ile Ala Cys Met
        115                 120                 125

Glu Phe Ile Arg Pro Ile Pro Thr Trp Asp Glu Trp Pro Glu Phe Ala
    130                 135                 140

Arg Glu Thr Phe Gln Ala Phe Arg Thr Thr Asp Val Gly Arg Glu Leu
145                 150                 155                 160

Ile Ile Asp Gln Asn Ala Phe Ile Glu Gly Thr Leu Pro Met Gly Val
                165                 170                 175

Val Arg Pro Leu Thr Glu Val Glu Met Asp His Tyr Arg Glu Pro Phe
            180                 185                 190

Leu Lys Pro Val Asp Arg Glu Pro Leu Trp Arg Phe Pro Asn Glu Leu
        195                 200                 205

Pro Ile Ala Gly Glu Pro Ala Asn Ile Val Ala Leu Val Glu Glu Tyr
    210                 215                 220

Met Asn Trp Leu His Gln Ser Pro Val Pro Lys Leu Leu Phe Trp Gly
225                 230                 235                 240

Thr Pro Gly Val Leu Ile Pro Pro Ala Glu Ala Ala Arg Leu Ala Glu
                245                 250                 255

Ser Leu Pro Asn Cys Lys Thr Val Asp Ile Gly Pro Gly Leu Asn Leu
            260                 265                 270

Leu Gln Glu Asp Asn Pro Asp Leu Ile Gly Ser Glu Ile Ala Arg Trp
        275                 280                 285

Leu Ser Thr Leu Gln Tyr
    290
```

<210> SEQ ID NO 44
<211> LENGTH: 294
<212> TYPE: PRT
<213> ORGANISM: Artificial Sequence
<220> FEATURE:
<223> OTHER INFORMATION: A synthetic DhaA mutant

<400> SEQUENCE: 44

```
Ser Glu Ile Gly Thr Gly Phe Pro Phe Asp Pro His Tyr Val Glu Val
1               5                   10                  15

Leu Gly Glu Arg Met His Tyr Val Asp Val Gly Pro Arg Asp Gly Thr
            20                  25                  30

Pro Val Leu Phe Leu His Gly Asn Pro Thr Ser Ser Tyr Leu Trp Arg
        35                  40                  45

Asn Ile Ile Pro His Val Ala Pro Thr His Arg Cys Ile Ala Pro Asp
50                  55                  60

Leu Ile Gly Met Gly Lys Ser Asp Lys Pro Asp Leu Gly Tyr Phe Phe
65                  70                  75                  80

Asp Asp His Val Arg Phe Leu Asp Ala Phe Ile Glu Ala Leu Gly Leu
                85                  90                  95

Glu Glu Val Val Leu Val Ile His Asp Trp Gly Ser Ala Leu Gly Phe
            100                 105                 110

His Trp Ala Lys Arg Asn Pro Glu Arg Val Lys Gly Ile Ala Cys Met
        115                 120                 125

Glu Phe Ile Arg Pro Ile Pro Thr Trp Asp Glu Trp Pro Glu Phe Ala
    130                 135                 140

Arg Glu Thr Phe Gln Ala Phe Arg Thr Thr Asp Val Gly Arg Glu Leu
145                 150                 155                 160
```

```
Ile Ile Asp Gln Asn Ala Phe Ile Glu Gly Thr Leu Pro Met Gly Val
            165                 170                 175

Val Arg Pro Leu Thr Glu Val Glu Met Asp His Tyr Arg Glu Pro Phe
        180                 185                 190

Leu Lys Pro Val Asp Arg Glu Pro Leu Trp Arg Phe Pro Asn Glu Leu
    195                 200                 205

Pro Ile Ala Gly Glu Pro Ala Asn Ile Val Ala Leu Val Glu Glu Tyr
210                 215                 220

Met Asp Trp Leu His Gln Ser Pro Val Pro Lys Leu Leu Phe Trp Gly
225                 230                 235                 240

Thr Pro Gly Val Leu Ile Pro Pro Ala Glu Ala Ala Arg Leu Ala Glu
            245                 250                 255

Ser Leu Pro Asn Cys Lys Thr Val Asp Ile Gly Pro Gly Leu Asn Phe
        260                 265                 270

Leu Gln Glu Asp Asn Pro Asp Leu Ile Gly Ser Glu Ile Ala Arg Trp
    275                 280                 285

Leu Gln Glu Leu Gln Tyr
290

<210> SEQ ID NO 45
<211> LENGTH: 294
<212> TYPE: PRT
<213> ORGANISM: Artificial Sequence
<220> FEATURE:
<223> OTHER INFORMATION: A synthetic DhaA mutant

<400> SEQUENCE: 45

Ser Glu Ile Gly Thr Gly Phe Pro Phe Asp Pro His Tyr Val Glu Val
1               5                   10                  15

Leu Gly Glu Arg Met His Tyr Val Asp Val Gly Pro Arg Asp Ser Thr
            20                  25                  30

Pro Val Leu Phe Leu His Gly Asn Pro Thr Ser Ser Tyr Leu Trp Arg
        35                  40                  45

Asn Ile Ile Pro His Val Ala Pro Thr His Arg Cys Ile Ala Pro Asp
50                  55                  60

Leu Ile Gly Met Gly Lys Ser Asp Lys Pro Asp Leu Gly Tyr Phe Phe
65                  70                  75                  80

Asp Asp His Val Arg Phe Leu Asp Ala Phe Ile Glu Ala Leu Gly Leu
            85                  90                  95

Glu Glu Val Val Leu Val Ile His Asp Trp Gly Ser Ala Leu Gly Phe
        100                 105                 110

His Trp Ala Lys Arg Asn Pro Glu Arg Val Lys Gly Ile Ala Cys Met
    115                 120                 125

Glu Phe Ile Arg Pro Ile Pro Thr Trp Asp Glu Trp Pro Glu Phe Ala
130                 135                 140

Arg Glu Thr Phe Gln Ala Phe Arg Thr Asp Val Gly Arg Glu Leu
145                 150                 155                 160

Ile Ile Asp Gln Asn Ala Phe Ile Glu Gly Thr Leu Pro Met Gly Val
            165                 170                 175

Val Arg Pro Leu Thr Glu Val Glu Met Asp His Tyr Arg Glu Pro Phe
        180                 185                 190

Leu Lys Pro Val Asp Arg Glu Pro Leu Trp Arg Phe Pro Asn Glu Leu
    195                 200                 205

Pro Ile Ala Gly Glu Pro Ala Asn Ile Val Ala Leu Val Glu Glu Tyr
210                 215                 220
```

Met Asp Trp Leu His Gln Ser Pro Val Pro Lys Leu Leu Phe Trp Gly
225                 230                 235                 240

Thr Pro Gly Val Leu Ile Pro Pro Ala Glu Ala Ala Arg Leu Ala Glu
            245                 250                 255

Ser Leu Pro Asn Cys Lys Thr Val Asp Ile Gly Pro Gly Leu Asn Leu
        260                 265                 270

Leu Gln Glu Asp Asn Pro Asp Leu Ile Gly Ser Glu Ile Ala Arg Trp
    275                 280                 285

Leu Gln Glu Leu Gln Tyr
    290

<210> SEQ ID NO 46
<211> LENGTH: 294
<212> TYPE: PRT
<213> ORGANISM: Artificial Sequence
<220> FEATURE:
<223> OTHER INFORMATION: A synthetic DhaA mutant

<400> SEQUENCE: 46

Ser Glu Ile Gly Thr Gly Phe Pro Phe Asp Pro His Tyr Val Glu Val
1               5                   10                  15

Leu Gly Glu Arg Met His Tyr Val Asp Val Gly Pro Arg Asp Gly Thr
            20                  25                  30

Pro Val Leu Phe Leu His Gly Asn Pro Thr Ser Ser Tyr Val Trp Arg
        35                  40                  45

Asn Ile Ile Pro His Val Ala Pro Thr His Arg Cys Ile Ala Pro Asp
50                  55                  60

Leu Ile Gly Met Gly Lys Ser Asp Lys Pro Asp Leu Gly Tyr Phe Phe
65                  70                  75                  80

Asp Asp His Val Arg Phe Met Asp Ala Phe Ile Glu Ala Leu Gly Leu
            85                  90                  95

Glu Glu Val Val Leu Val Ile His Asp Trp Gly Ser Ala Leu Gly Phe
            100                 105                 110

His Trp Ala Lys Arg Asn Pro Glu Arg Val Lys Gly Ile Ala Phe Met
        115                 120                 125

Glu Phe Ile Arg Pro Ile Pro Thr Trp Asp Glu Trp Pro Glu Phe Ala
130                 135                 140

Arg Glu Thr Phe Gln Ala Phe Arg Thr Thr Asp Val Gly Arg Lys Leu
145                 150                 155                 160

Ile Ile Asp Gln Asn Val Phe Ile Glu Gly Thr Leu Pro Met Gly Val
            165                 170                 175

Val Arg Pro Leu Thr Glu Val Glu Met Asp His Tyr Arg Glu Pro Phe
        180                 185                 190

Leu Asn Pro Val Asp Arg Glu Pro Leu Trp Arg Phe Pro Asn Glu Leu
    195                 200                 205

Pro Ile Ala Gly Glu Pro Ala Asn Ile Val Ala Leu Val Glu Glu Tyr
210                 215                 220

Met Asp Trp Leu His Gln Ser Pro Val Pro Lys Leu Leu Phe Trp Gly
225                 230                 235                 240

Thr Pro Gly Val Leu Ile Pro Pro Ala Glu Ala Ala Arg Leu Ala Lys
            245                 250                 255

Ser Leu Pro Asn Cys Lys Ala Val Asp Ile Gly Pro Gly Leu Asn Leu
        260                 265                 270

Leu Gln Glu Asp Asn Pro Asp Leu Ile Gly Ser Glu Ile Ala Arg Trp
    275                 280                 285

Leu Ser Thr Leu Gln Tyr
        290

<210> SEQ ID NO 47
<211> LENGTH: 296
<212> TYPE: PRT
<213> ORGANISM: Artificial Sequence
<220> FEATURE:
<223> OTHER INFORMATION: A synthetic DhaA mutant

<400> SEQUENCE: 47

Ser Glu Ile Gly Thr Gly Phe Pro Phe Asp Pro His Tyr Val Glu Val
1               5                   10                  15

Leu Gly Glu Arg Met His Tyr Val Asp Val Gly Pro Arg Asp Gly Thr
            20                  25                  30

Pro Val Leu Phe Leu His Gly Asn Pro Thr Ser Ser Tyr Val Trp Arg
        35                  40                  45

Asn Ile Ile Pro His Val Ala Pro Thr His Arg Cys Ile Ala Pro Asp
50                  55                  60

Leu Ile Gly Met Gly Lys Ser Asp Lys Pro Asp Leu Gly Tyr Phe Phe
65                  70                  75                  80

Asp Asp His Val Arg Phe Met Asp Ala Phe Ile Glu Ala Leu Gly Leu
                85                  90                  95

Glu Glu Val Val Leu Val Ile His Asp Trp Gly Ser Ala Leu Gly Phe
            100                 105                 110

His Trp Ala Lys Arg Asn Pro Glu Arg Val Lys Gly Ile Ala Phe Met
        115                 120                 125

Glu Phe Ile Arg Pro Ile Pro Thr Trp Asp Glu Trp Pro Glu Phe Ala
130                 135                 140

Arg Glu Thr Phe Gln Ala Phe Arg Thr Thr Asp Val Gly Arg Lys Leu
145                 150                 155                 160

Ile Ile Asp Gln Asn Val Phe Ile Glu Gly Thr Leu Pro Met Gly Val
                165                 170                 175

Val Arg Pro Leu Thr Glu Val Glu Met Asp His Tyr Arg Glu Pro Phe
            180                 185                 190

Leu Asn Pro Val Asp Arg Glu Pro Leu Trp Arg Phe Pro Asn Glu Leu
        195                 200                 205

Pro Ile Ala Gly Glu Pro Ala Asn Ile Val Ala Leu Val Glu Glu Tyr
210                 215                 220

Met Asp Trp Leu His Gln Ser Pro Val Pro Lys Leu Leu Phe Trp Gly
225                 230                 235                 240

Thr Pro Gly Val Leu Ile Pro Pro Ala Glu Ala Ala Arg Leu Ala Lys
                245                 250                 255

Ser Leu Pro Asn Cys Lys Ala Val Asp Ile Gly Pro Gly Leu Asn Leu
            260                 265                 270

Leu Gln Glu Asp Asn Pro Asp Leu Ile Gly Ser Glu Ile Ala Arg Trp
        275                 280                 285

Leu Ser Thr Leu Glu Ile Ser Gly
290                 295

<210> SEQ ID NO 48
<211> LENGTH: 48
<212> TYPE: DNA
<213> ORGANISM: Artificial Sequence
<220> FEATURE:
<223> OTHER INFORMATION: A synthetic connector sequence

<400> SEQUENCE: 48

```
gagccaacca ctgaggatct gtactttcag agcgataacg cgatcgcc         48
```

<210> SEQ ID NO 49
<211> LENGTH: 50
<212> TYPE: DNA
<213> ORGANISM: Artificial Sequence
<220> FEATURE:
<223> OTHER INFORMATION: A synthetic connector sequence

<400> SEQUENCE: 49

```
tttctctcga gccaaccact gaggatctgt actttcagag cgataacgat       50
```

<210> SEQ ID NO 50
<211> LENGTH: 14
<212> TYPE: PRT
<213> ORGANISM: Artificial Sequence
<220> FEATURE:
<223> OTHER INFORMATION: A synthetic connector sequence

<400> SEQUENCE: 50

```
Glu Pro Thr Thr Glu Asp Leu Tyr Phe Gln Ser Asp Asn Asp
1               5                   10
```

<210> SEQ ID NO 51
<211> LENGTH: 13
<212> TYPE: PRT
<213> ORGANISM: Artificial Sequence
<220> FEATURE:
<223> OTHER INFORMATION: A synthetic connector sequence

<400> SEQUENCE: 51

```
Glu Pro Thr Thr Glu Asp Leu Tyr Phe Gln Ser Asp Asn
1               5                   10
```

<210> SEQ ID NO 52
<211> LENGTH: 882
<212> TYPE: DNA
<213> ORGANISM: Artificial Sequence
<220> FEATURE:
<223> OTHER INFORMATION: A synthetic DhaA mutant

<400> SEQUENCE: 52

```
tccgaaatcg gtactggctt tccattcgac ccccattatg tggaagtcct gggcgagcgc    60
atgcactacg tcgatgttgg tccgcgcgat ggcacccctg tgctgttcct gcacggtaac   120
ccgacctcct cctacctgtg gcgcaacatc atcccgcatg ttgcaccgac ccatcgctgc   180
attgctccag acctgatcgg tatgggcaaa tccgacaaac agacctgggg ttatttcttc   240
gacgaccacg tccgctacct ggatgccttc atcgaagccc tgggtctgga agaggtcgtc   300
ctggtcattc acgactgggg ctccgctctg gtttccact  gggccaagcg caatccagag   360
cgcgtcaaag gtattgcatg tatggagttc atccgcccta tcccgacctg ggacgaatgg   420
ccagaatttg cccgcgagac cttccaggcc ttccgcacca ccgacgtcgg ccgcgagctg   480
atcatcgatc agaacgcttt tatcgagggt acgctgccga tgggtgtcgt ccgcccgctg   540
actgaagtcg agatggacca ttaccgcgag ccgttcctga gcctgttga ccgcgagcca   600
ctgtggcgct tcccaaacga gctgccaatc gccggtgagc cagcgaacat cgtcgcgctg   660
gtcgaagaat acatgaactg gctgcaccag tcccctgtcc cgaagctgct gttctggggc   720
accccaggcg ttctgatccc accggccgaa gccgctcgcc tggccgaaag cctgcctaac   780
tgcaagactg tggacatcgg cccgggtctg aattttctgc aagaagacaa cccggacctg   840
```

```
atcggcagcg agatcgcgcg ctggctgtcg acgctgcaat at                882
```

<210> SEQ ID NO 53
<211> LENGTH: 882
<212> TYPE: DNA
<213> ORGANISM: Artificial Sequence
<220> FEATURE:
<223> OTHER INFORMATION: A synthetic DhaA mutant

<400> SEQUENCE: 53

```
tccgaaatcg gtactggctt tccattcgac ccccattatg tggaagtcct gggcgagcgc    60
atgcactacg tcgatgttgg tccgcgcgat ggcacccctg tgctgttcct gcacggtaac   120
ccgacctcct cctacctgtg gcgcaacatc atcccgcatg ttgcaccgac ccatcgctgc   180
attgctccag acctgatcgg tatgggcaaa tccgacaaac cagacctggg ttatttcttc   240
gacgaccacg tccgctacct ggatgccttc atcgaagccc tgggtctgga agaggtcgtc   300
ctggtcattc acgactgggg ctccgctctg ggtttccact gggccaagcg caatccagag   360
cgcgtcaaag gtattgcatg tatggagttc atccgcccta tcccgacctg ggacgaatgg   420
ccagaatttg cccgcgagac cttccaggcc ttccgcacca ccgacgtcgg ccgcgagctg   480
atcatcgatc agaacgcttt tatcgagggt acgctgccga tgggtgtcgt ccgcccgctg   540
actgaagtcg agatggacca ttaccgcgag ccgttcctga gcctgttga ccgcgagcca    600
ctgtggcgct tcccaaacga gctgccaatc gccggtgagc cagcgaacat cgtcgcgctg   660
gtcgaagaat acatgaactg gctgcaccag tcccctgtcc cgaagctgct gttctggggc   720
accccaggcg ttctgatccc accggccgaa gccgctcgcc tggccgaaag cctgcctaac   780
tgcaagactg tggacatcgg cccgggtctg aatctgctgc aagaagacaa cccggacctg   840
atcggcagcg agatcgcgcg ctggctgtcg acgctgcaat at                     882
```

<210> SEQ ID NO 54
<211> LENGTH: 882
<212> TYPE: DNA
<213> ORGANISM: Artificial Sequence
<220> FEATURE:
<223> OTHER INFORMATION: A synthetic DhaA mutant

<400> SEQUENCE: 54

```
tccgaaatcg gtactggctt tccattcgac ccccattatg tggaagtcct gggcgagcgc    60
atgcactacg tcgatgttgg tccgcgcgat ggcacccctg tgctgttcct gcacggtaac   120
ccgacctcct cctacctgtg gcgcaacatc atcccgcatg ttgcaccgac ccatcgctgc   180
attgctccag acctgatcgg tatgggcaaa tccgacaaac cagacctggg ttatttcttc   240
gacgaccacg tccgcttcct ggatgccttc atcgaagccc tgggtctgga agaggtcgtc   300
ctggtcattc acgactgggg ctccgctctg ggtttccact gggccaagcg caatccagag   360
cgcgtcaaag gtattgcatg tatggagttc atccgcccta tcccgacctg ggacgaatgg   420
ccagaatttg cccgcgagac cttccaggcc ttccgcacca ccgacgtcgg ccgcgagctg   480
atcatcgatc agaacgcttt tatcgagggt acgctgccga tgggtgtcgt ccgcccgctg   540
actgaagtcg agatggacca ttaccgcgag ccgttcctga gcctgttga ccgcgagcca    600
ctgtggcgct tcccaaacga gctgccaatc gccggtgagc cagcgaacat cgtcgcgctg   660
gtcgaagaat acatgaactg gctgcaccag tcccctgtcc cgaagctgct gttctggggc   720
accccaggcg ttctgatccc accggccgaa gccgctcgcc tggccgaaag cctgcctaac   780
```

| | |
|---|---|
| tgcaagactg tggacatcgg cccgggtctg aattttctgc aagaagacaa cccggacctg | 840 |
| atcggcagcg agatcgcgcg ctggctgcag gagctgcaat at | 882 |

<210> SEQ ID NO 55
<211> LENGTH: 882
<212> TYPE: DNA
<213> ORGANISM: Artificial Sequence
<220> FEATURE:
<223> OTHER INFORMATION: A synthetic DhaA mutant

<400> SEQUENCE: 55

| | |
|---|---|
| tccgaaatcg gtactggctt tccattcgac ccccattatg tggaagtcct gggcgagcgc | 60 |
| atgcactacg tcgatgttgg tccgcgcgat agcacccctg tgctgttcct gcacggtaac | 120 |
| ccgacctcct cctacctgtg cgcaacatc atcccgcatg ttgcaccgac ccatcgctgc | 180 |
| attgctccag acctgatcgg tatgggcaaa tccgacaaac cagacctggg ttatttcttc | 240 |
| gacgaccacg tccgcttcct ggatgccttc atcgaagccc tgggtctgga agaggtcgtc | 300 |
| ctggtcattc acgactgggg ctccgctctg ggtttccact gggccaagcg caatccagag | 360 |
| cgcgtcaaag gtattgcatg tatggagttc atccgcccta tcccgacctg ggacgaatgg | 420 |
| ccagaatttg cccgcgagac cttccaggcc ttccgcacca ccgacgtcgg ccgcgagctg | 480 |
| atcatcgatc agaacgcttt tatcgagggt acgctgccga tgggtgtcgt ccgcccgctg | 540 |
| actgaagtcg agatggacca ttaccgcgag ccgttcctga gcctgttga ccgcgagcca | 600 |
| ctgtggcgct tcccaaacga gctgccaatc gccggtgagc cagcgaacat cgtcgcgctg | 660 |
| gtcgaagaat acatggactg gctgcaccag tcccctgtcc cgaagctgct gttctggggc | 720 |
| accccaggcg ttctgatccc accggccgaa gccgctcgcc tggccgaaag cctgcctaac | 780 |
| tgcaagactg tggacatcgg cccgggtctg aatctgctgc aagaagacaa cccggacctg | 840 |
| atcggcagcg agatcgcgcg ctggctgcag gagctgcaat at | 882 |

<210> SEQ ID NO 56
<211> LENGTH: 882
<212> TYPE: DNA
<213> ORGANISM: Artificial Sequence
<220> FEATURE:
<223> OTHER INFORMATION: A synthetic DhaA mutant

<400> SEQUENCE: 56

| | |
|---|---|
| tccgaaatcg gtactggctt tccattcgac ccccattatg tggaagtcct gggcgagcgc | 60 |
| atgcactacg tcgatgttgg tccgcgcgat ggcacccctg tgctgttcct gcacggtaac | 120 |
| ccgacctcct cctacgtgtg cgcaacatc atcccgcatg ttgcaccgac ccatcgctgc | 180 |
| attgctccag acctgatcgg tatgggcaaa tccgacaaac cagacctggg ttatttcttc | 240 |
| gacgaccacg tccgcttcat ggatgccttc atcgaagccc tgggtctgga agaggtcgtc | 300 |
| ctggtcattc acgactgggg ctccgctctg ggtttccact gggccaagcg caatccagag | 360 |
| cgcgtcaaag gtattgcatt tatggagttc atccgcccta tcccgacctg ggacgaatgg | 420 |
| ccagaatttg cccgcgagac cttccaggcc ttccgcacca ccgacgtcgg ccgcaagctg | 480 |
| atcatcgatc agaacgtttt tatcgagggt acgctgccga tgggtgtcgt ccgcccgctg | 540 |
| actgaagtcg agatggacca ttaccgcgag ccgttcctga atcctgttga ccgcgagcca | 600 |
| ctgtggcgct tcccaaacga gctgccaatc gccggtgagc cagcgaacat cgtcgcgctg | 660 |
| gtcgaagaat acatggactg gctgcaccag tcccctgtcc cgaagctgct gttctggggc | 720 |
| accccaggcg ttctgatccc accggccgaa gccgctcgcc tggccaaaag cctgcctaac | 780 |

```
tgcaaggctg tggacatcgg cccgggtctg aatctgctgc aagaagacaa cccggacctg      840
atcggcagcg agatcgcgcg ctggctgtcg acgctgcaat at                         882

<210> SEQ ID NO 57
<211> LENGTH: 888
<212> TYPE: DNA
<213> ORGANISM: Artificial Sequence
<220> FEATURE:
<223> OTHER INFORMATION: A synthetic DhaA mutant

<400> SEQUENCE: 57
tccgaaatcg gtactggctt tccattcgac ccccattatg tggaagtcct gggcgagcgc       60
atgcactacg tcgatgttgg tccgcgcgat ggcacccctg tgctgttcct gcacggtaac      120
ccgacctcct cctacgtgtg gcgcaacatc atcccgcatg ttgcaccgac ccatcgctgc      180
attgctccag acctgatcgg tatgggcaaa tccgacaaac cagacctggg ttatttcttc      240
gacgaccacg tccgcttcat ggatgccttc atcgaagccc tgggtctgga agaggtcgtc      300
ctggtcattc acgactgggg ctccgctctg ggtttccact gggccaagcg caatccagag      360
cgcgtcaaag gtattgcatt tatggagttc atccgcccta tcccgacctg ggacgaatgg      420
ccagaatttg cccgcgagac cttccaggcc ttccgcacca ccgacgtcgg ccgcaagctg      480
atcatcgatc agaacgtttt tatcgagggt acgctgccga tgggtgtcgt ccgcccgctg      540
actgaagtcg agatggacca ttaccgcgag ccgttcctga atcctgttga ccgcgagcca      600
ctgtggcgct tcccaaacga gctgccaatc gccggtgagc cagcgaacat cgtcgcgctg      660
gtcgaagaat acatggactg gctgcaccag tcccctgtcc cgaagctgct gttctggggc      720
accccaggcg ttctgatccc accggccgaa gccgctcgcc tggccaaaag cctgcctaac      780
tgcaaggctg tggacatcgg cccgggtctg aatctgctgc aagaagacaa cccggacctg      840
atcggcagcg agatcgcgcg ctggctgtcg acgctggaga tttccgga                   888

<210> SEQ ID NO 58

<400> SEQUENCE: 58

000

<210> SEQ ID NO 59

<400> SEQUENCE: 59

000

<210> SEQ ID NO 60
<211> LENGTH: 293
<212> TYPE: PRT
<213> ORGANISM: Artificial Sequence
<220> FEATURE:
<223> OTHER INFORMATION: A synthetic mutant DhaA sequence
<220> FEATURE:
<221> NAME/KEY: SITE
<222> LOCATION: (1)..(1)
<223> OTHER INFORMATION: Xaa = M or G
<220> FEATURE:
<221> NAME/KEY: SITE
<222> LOCATION: (2)..(2)
<223> OTHER INFORMATION: Xaa = A or S

<400> SEQUENCE: 60

Xaa Xaa Glu Ile Gly Thr Gly Phe Pro Phe Asp Pro His Tyr Val Glu
1               5                   10                  15
```

Val Leu Gly Glu Arg Met His Tyr Val Asp Val Gly Pro Arg Asp Gly
            20                  25                  30

Thr Pro Val Leu Phe Leu His Gly Asn Pro Thr Ser Ser Tyr Leu Trp
            35                  40                  45

Arg Asn Ile Ile Pro His Val Ala Pro Thr His Arg Cys Ile Ala Pro
 50                  55                  60

Asp Leu Ile Gly Met Gly Lys Ser Asp Lys Pro Asp Leu Gly Tyr Phe
 65                  70                  75                  80

Phe Asp Asp His Val Arg Tyr Leu Asp Ala Phe Ile Glu Ala Leu Gly
                85                  90                  95

Leu Glu Glu Val Val Leu Val Ile His Asp Trp Gly Ser Ala Leu Gly
            100                 105                 110

Phe His Trp Ala Lys Arg Asn Pro Glu Arg Val Lys Gly Ile Ala Cys
            115                 120                 125

Met Glu Phe Ile Arg Pro Ile Pro Thr Trp Asp Glu Trp Pro Glu Phe
            130                 135                 140

Ala Arg Glu Thr Phe Gln Ala Phe Arg Thr Thr Asp Val Gly Arg Glu
145                 150                 155                 160

Leu Ile Ile Asp Gln Asn Ala Phe Ile Glu Gly Thr Leu Pro Met Gly
                165                 170                 175

Val Val Arg Pro Leu Thr Glu Val Glu Met Asp His Tyr Arg Glu Pro
            180                 185                 190

Phe Leu Lys Pro Val Asp Arg Glu Pro Leu Trp Arg Phe Pro Asn Glu
            195                 200                 205

Leu Pro Ile Ala Gly Glu Pro Ala Asn Ile Val Ala Leu Val Glu Glu
            210                 215                 220

Tyr Met Asn Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255

Glu Ser Leu Pro Asn Cys Lys Thr Val Asp Ile Gly Pro Gly Leu Asn
            260                 265                 270

Phe Leu Gln Glu Asp Asn Pro Asp Leu Ile Gly Ser Glu Ile Ala Arg
            275                 280                 285

Trp Leu Ser Thr Leu
    290

<210> SEQ ID NO 61
<211> LENGTH: 293
<212> TYPE: PRT
<213> ORGANISM: Artificial Sequence
<220> FEATURE:
<223> OTHER INFORMATION: A synthetic mutant DhaA sequence
<220> FEATURE:
<221> NAME/KEY: SITE
<222> LOCATION: (1)..(1)
<223> OTHER INFORMATION: Xaa = M or G
<220> FEATURE:
<221> NAME/KEY: SITE
<222> LOCATION: (2)..(2)
<223> OTHER INFORMATION: Xaa = A or S

<400> SEQUENCE: 61

Xaa Xaa Glu Ile Gly Thr Gly Phe Pro Phe Asp Pro His Tyr Val Glu
 1               5                  10                  15

Val Leu Gly Glu Arg Met His Tyr Val Asp Val Gly Pro Arg Asp Gly
            20                  25                  30

```
Thr Pro Val Leu Phe Leu His Gly Asn Pro Thr Ser Ser Tyr Leu Trp
        35                  40                  45

Thr Asn Ile Ile Pro His Val Ala Pro Thr His Arg Cys Ile Ala Pro
 50                      55                  60

Asp Leu Ile Gly Met Gly Lys Ser Asp Lys Pro Asp Leu Gly Tyr Phe
65                   70                  75                  80

Phe Asp Asp His Val Arg Tyr Leu Asp Ala Phe Ile Glu Ala Leu Gly
                85                  90                  95

Leu Glu Glu Val Val Leu Val Ile His Asp Trp Gly Ser Ala Leu Gly
            100                 105                 110

Phe His Trp Ala Lys Arg Asn Pro Glu Arg Val Lys Gly Ile Ala Cys
        115                 120                 125

Met Glu Phe Ile Arg Pro Ile Pro Thr Trp Asp Glu Trp Pro Glu Phe
    130                 135                 140

Ala Arg Glu Thr Phe Gln Ala Phe Arg Thr Thr Asp Val Gly Arg Glu
145                 150                 155                 160

Leu Ile Ile Asp Gln Asn Ala Phe Ile Glu Gly Thr Leu Pro Met Gly
                165                 170                 175

Val Val Arg Pro Leu Thr Glu Val Glu Met Asp His Tyr Arg Glu Pro
            180                 185                 190

Phe Leu Lys Pro Val Asp Arg Glu Pro Leu Trp Arg Phe Pro Asn Glu
        195                 200                 205

Leu Pro Ile Ala Gly Glu Pro Ala Asn Ile Val Ala Leu Val Glu Glu
    210                 215                 220

Tyr Met Asn Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255

Glu Ser Leu Pro Asn Cys Lys Thr Val Asp Ile Gly Pro Gly Leu Asn
            260                 265                 270

Leu Leu Gln Glu Asp Asn Pro Asp Leu Ile Gly Ser Glu Ile Ala Arg
        275                 280                 285

Trp Leu Ser Thr Leu
    290

<210> SEQ ID NO 62
<211> LENGTH: 293
<212> TYPE: PRT
<213> ORGANISM: Artificial Sequence
<220> FEATURE:
<223> OTHER INFORMATION: A synthetic mutant DhaA sequence
<220> FEATURE:
<221> NAME/KEY: SITE
<222> LOCATION: (1)..(1)
<223> OTHER INFORMATION: Xaa = M or G
<220> FEATURE:
<221> NAME/KEY: SITE
<222> LOCATION: (2)..(2)
<223> OTHER INFORMATION: Xaa = A or S

<400> SEQUENCE: 62

Xaa Xaa Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
            20                  25                  30

Thr Pro Val Leu Phe Leu His Gly Asn Pro Thr Ser Ser Tyr Leu Trp
        35                  40                  45

Arg Asn Ile Ile Pro His Val Ala Pro Thr His Arg Cys Ile Ala Pro
```

```
                50              55              60
Asp Leu Ile Gly Met Gly Lys Ser Asp Lys Pro Asp Leu Gly Tyr Phe
 65              70              75              80

Phe Asp Asp His Val Arg Phe Leu Asp Ala Phe Ile Glu Ala Leu Gly
                85              90              95

Leu Glu Glu Val Val Leu Val Ile His Asp Trp Gly Ser Ala Leu Gly
                100             105             110

Phe His Trp Ala Lys Arg Asn Pro Glu Arg Val Lys Gly Ile Ala Cys
                115             120             125

Met Glu Phe Ile Arg Pro Ile Pro Thr Trp Asp Glu Trp Pro Glu Phe
                130             135             140

Ala Arg Glu Thr Phe Gln Ala Phe Arg Thr Thr Asp Val Gly Arg Glu
145             150             155             160

Leu Ile Ile Asp Gln Asn Ala Phe Ile Glu Gly Thr Leu Pro Met Gly
                165             170             175

Val Val Arg Pro Leu Thr Glu Val Glu Met Asp His Tyr Arg Glu Pro
                180             185             190

Phe Leu Lys Pro Val Asp Arg Glu Pro Leu Trp Arg Phe Pro Asn Glu
                195             200             205

Leu Pro Ile Ala Gly Glu Pro Ala Asn Ile Val Ala Leu Val Glu Glu
                210             215             220

Tyr Met Asp Trp Leu His Gln Ser Pro Val Pro Lys Leu Leu Phe Trp
225             230             235             240

Gly Thr Pro Gly Val Leu Ile Pro Pro Ala Glu Ala Ala Arg Leu Ala
                245             250             255

Glu Ser Leu Pro Asn Cys Lys Thr Val Asp Ile Gly Pro Gly Leu Asn
                260             265             270

Phe Leu Gln Glu Asp Asn Pro Asp Leu Ile Gly Ser Glu Ile Ala Arg
                275             280             285

Trp Leu Gln Glu Leu
                290

<210> SEQ ID NO 63
<211> LENGTH: 293
<212> TYPE: PRT
<213> ORGANISM: Artificial Sequence
<220> FEATURE:
<223> OTHER INFORMATION: A synthetic mutant DhaA sequence
<220> FEATURE:
<221> NAME/KEY: SITE
<222> LOCATION: (1)..(1)
<223> OTHER INFORMATION: Xaa = M or G
<220> FEATURE:
<221> NAME/KEY: SITE
<222> LOCATION: (2)..(2)
<223> OTHER INFORMATION: Xaa = A or S

<400> SEQUENCE: 63

Xaa Xaa Glu Ile Gly Thr Gly Phe Pro Phe Asp Pro His Tyr Val Glu
 1               5              10              15

Val Leu Gly Glu Arg Met His Tyr Val Asp Val Gly Pro Arg Asp Ser
                20              25              30

Thr Pro Val Leu Phe Leu His Gly Asn Pro Thr Ser Ser Tyr Leu Trp
                35              40              45

Arg Asn Ile Ile Pro His Val Ala Pro Thr His Arg Cys Ile Ala Pro
 50              55              60

Asp Leu Ile Gly Met Gly Lys Ser Asp Lys Pro Asp Leu Gly Tyr Phe
 65              70              75              80
```

```
Phe Asp Asp His Val Arg Phe Leu Asp Ala Phe Ile Glu Ala Leu Gly
                85                  90                  95

Leu Glu Glu Val Val Leu Val Ile His Asp Trp Gly Ser Ala Leu Gly
            100                 105                 110

Phe His Trp Ala Lys Arg Asn Pro Glu Arg Val Lys Gly Ile Ala Cys
        115                 120                 125

Met Glu Phe Ile Arg Pro Ile Pro Thr Trp Asp Glu Trp Pro Glu Phe
    130                 135                 140

Ala Arg Glu Thr Phe Gln Ala Phe Arg Thr Thr Asp Val Gly Arg Glu
145                 150                 155                 160

Leu Ile Ile Asp Gln Asn Ala Phe Ile Glu Gly Thr Leu Pro Met Gly
                165                 170                 175

Val Val Arg Pro Leu Thr Glu Val Glu Met Asp His Tyr Arg Glu Pro
            180                 185                 190

Phe Leu Lys Pro Val Asp Arg Glu Pro Leu Trp Arg Phe Pro Asn Glu
        195                 200                 205

Leu Pro Ile Ala Gly Glu Pro Ala Asn Ile Val Ala Leu Val Glu Glu
    210                 215                 220

Tyr Met Asp Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255

Glu Ser Leu Pro Asn Cys Lys Thr Val Asp Ile Gly Pro Gly Leu Asn
            260                 265                 270

Leu Leu Gln Glu Asp Asn Pro Asp Leu Ile Gly Ser Glu Ile Ala Arg
        275                 280                 285

Trp Leu Gln Glu Leu
    290

<210> SEQ ID NO 64
<211> LENGTH: 293
<212> TYPE: PRT
<213> ORGANISM: Artificial Sequence
<220> FEATURE:
<223> OTHER INFORMATION: A synthetic mutant DhaA sequence
<220> FEATURE:
<221> NAME/KEY: SITE
<222> LOCATION: (1)..(1)
<223> OTHER INFORMATION: Xaa = M or G
<220> FEATURE:
<221> NAME/KEY: SITE
<222> LOCATION: (2)..(2)
<223> OTHER INFORMATION: Xaa = A or S

<400> SEQUENCE: 64

Xaa Xaa Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
            20                  25                  30

Thr Pro Val Leu Phe Leu His Gly Asn Pro Thr Ser Ser Tyr Val Trp
        35                  40                  45

Arg Asn Ile Ile Pro His Val Ala Pro Thr His Arg Cys Ile Ala Pro
    50                  55                  60

Asp Leu Ile Gly Met Gly Lys Ser Asp Lys Pro Asp Leu Gly Tyr Phe
65                  70                  75                  80

Phe Asp Asp His Val Arg Phe Met Asp Ala Phe Ile Glu Ala Leu Gly
                85                  90                  95
```

```
Leu Glu Glu Val Val Leu Val Ile His Asp Trp Gly Ser Ala Leu Gly
            100                 105                 110

Phe His Trp Ala Lys Arg Asn Pro Glu Arg Val Lys Gly Ile Ala Phe
        115                 120                 125

Met Glu Phe Ile Arg Pro Ile Pro Thr Trp Asp Glu Trp Pro Glu Phe
130                 135                 140

Ala Arg Glu Thr Phe Gln Ala Phe Arg Thr Thr Asp Val Gly Arg Lys
145                 150                 155                 160

Leu Ile Ile Asp Gln Asn Val Phe Ile Glu Gly Thr Leu Pro Met Gly
                165                 170                 175

Val Val Arg Pro Leu Thr Glu Val Glu Met Asp His Tyr Arg Glu Pro
            180                 185                 190

Phe Leu Asn Pro Val Asp Arg Glu Pro Leu Trp Arg Phe Pro Asn Glu
        195                 200                 205

Leu Pro Ile Ala Gly Glu Pro Ala Asn Ile Val Ala Leu Val Glu Glu
210                 215                 220

Tyr Met Asp Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255

Lys Ser Leu Pro Asn Cys Lys Ala Val Asp Ile Gly Pro Gly Leu Asn
            260                 265                 270

Leu Leu Gln Glu Asp Asn Pro Asp Leu Ile Gly Ser Glu Ile Ala Arg
        275                 280                 285

Trp Leu Ser Thr Leu
    290

<210> SEQ ID NO 65
<211> LENGTH: 293
<212> TYPE: PRT
<213> ORGANISM: Artificial Sequence
<220> FEATURE:
<223> OTHER INFORMATION: A synthetic mutant DhaA sequence
<220> FEATURE:
<221> NAME/KEY: SITE
<222> LOCATION: (1)..(1)
<223> OTHER INFORMATION: Xaa = M or G
<220> FEATURE:
<221> NAME/KEY: SITE
<222> LOCATION: (2)..(2)
<223> OTHER INFORMATION: Xaa = A or S

<400> SEQUENCE: 65

Xaa Xaa Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
            20                  25                  30

Thr Pro Val Leu Phe Leu His Gly Asn Pro Thr Ser Ser Tyr Val Trp
        35                  40                  45

Arg Asn Ile Ile Pro His Val Ala Pro Thr His Arg Cys Ile Ala Pro
    50                  55                  60

Asp Leu Ile Gly Met Gly Lys Ser Asp Lys Pro Asp Leu Gly Tyr Phe
65                  70                  75                  80

Phe Asp Asp His Val Arg Phe Met Asp Ala Phe Ile Glu Ala Leu Gly
                85                  90                  95

Leu Glu Glu Val Val Leu Val Ile His Asp Trp Gly Ser Ala Leu Gly
            100                 105                 110

Phe His Trp Ala Lys Thr Asn Pro Glu Arg Val Lys Gly Ile Ala Phe
```

-continued

```
                    115                 120                 125
Met Glu Phe Ile Arg Pro Ile Pro Thr Trp Asp Glu Trp Pro Glu Phe
    130                 135                 140

Ala Arg Glu Thr Phe Gln Ala Phe Arg Thr Thr Asp Val Gly Arg Lys
145                 150                 155                 160

Leu Ile Ile Asp Gln Asn Val Phe Ile Glu Gly Thr Leu Pro Met Gly
                    165                 170                 175

Val Val Arg Pro Leu Thr Glu Val Glu Met Asp His Tyr Arg Glu Pro
                180                 185                 190

Phe Leu Asn Pro Val Asp Arg Glu Pro Leu Trp Arg Phe Pro Asn Glu
            195                 200                 205

Leu Pro Ile Ala Gly Glu Pro Ala Asn Ile Val Ala Leu Val Glu Glu
        210                 215                 220

Tyr Met Asp Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                    245                 250                 255

Lys Ser Leu Pro Asn Cys Lys Ala Val Asp Ile Gly Pro Gly Leu Asn
                260                 265                 270

Leu Leu Gln Glu Asp Asn Pro Asp Leu Ile Gly Ser Glu Ile Ala Arg
            275                 280                 285

Trp Leu Ser Thr Leu
        290
```

<210> SEQ ID NO 66
<211> LENGTH: 296
<212> TYPE: PRT
<213> ORGANISM: Artificial Sequence
<220> FEATURE:
<223> OTHER INFORMATION: A synthetic mutant DhaA sequence
<220> FEATURE:
<221> NAME/KEY: SITE
<222> LOCATION: (1)..(1)
<223> OTHER INFORMATION: Xaa = M or G
<220> FEATURE:
<221> NAME/KEY: SITE
<222> LOCATION: (2)..(2)
<223> OTHER INFORMATION: Xaa = A or S
<220> FEATURE:
<221> NAME/KEY: SITE
<222> LOCATION: (290)..(290)
<223> OTHER INFORMATION: Xaa = S, Q or P
<220> FEATURE:
<221> NAME/KEY: SITE
<222> LOCATION: (291)..(291)
<223> OTHER INFORMATION: Xaa = T, E or A
<220> FEATURE:
<221> NAME/KEY: SITE
<222> LOCATION: (293)..(293)
<223> OTHER INFORMATION: Xaa = Q or E
<220> FEATURE:
<221> NAME/KEY: SITE
<222> LOCATION: (294)..(294)
<223> OTHER INFORMATION: Xaa = Y or I
<220> FEATURE:
<221> NAME/KEY: SITE
<222> LOCATION: (295)..(295)
<223> OTHER INFORMATION: Xaa = S or absent
<220> FEATURE:
<221> NAME/KEY: SITE
<222> LOCATION: (296)..(296)
<223> OTHER INFORMATION: Xaa = G or absent

<400> SEQUENCE: 66

```
Xaa Xaa Glu Ile Gly Thr Gly Phe Pro Phe Asp Pro His Tyr Val Glu
1               5                   10                  15
```

```
Val Leu Glu Arg Met His Tyr Val Asp Val Gly Pro Arg Asp Gly Thr
         20                  25                  30

Pro Val Leu Phe Leu His Gly Asn Pro Thr Ser Ser Tyr Leu Trp Arg
         35                  40                  45

Asn Ile Ile Pro His Val Ala Pro Thr His Arg Cys Ile Ala Pro Asp
 50                  55                  60

Leu Ile Gly Met Gly Lys Ser Asp Lys Pro Asp Leu Gly Tyr Phe Phe
 65                  70                  75                  80

Asp Asp His Val Arg Tyr Leu Asp Ala Phe Ile Glu Ala Leu Gly Leu
                 85                  90                  95

Glu Glu Val Val Leu Val Ile His Asp Trp Gly Ser Ala Leu Gly Phe
                100                 105                 110

His Trp Ala Lys Arg Asn Pro Glu Arg Val Lys Gly Ile Ala Cys Met
            115                 120                 125

Glu Phe Ile Arg Pro Ile Pro Thr Trp Asp Glu Trp Pro Glu Phe Ala
130                 135                 140

Arg Glu Thr Phe Gln Ala Phe Arg Thr Thr Asp Val Gly Arg Glu Leu
145                 150                 155                 160

Ile Ile Asp Gln Asn Ala Phe Ile Glu Gly Thr Leu Pro Met Gly Val
                165                 170                 175

Val Arg Pro Leu Thr Glu Val Glu Met Asp His Tyr Arg Glu Pro Phe
            180                 185                 190

Leu Lys Pro Val Asp Arg Glu Pro Leu Trp Arg Phe Pro Asn Glu Leu
        195                 200                 205

Pro Ile Ala Gly Glu Pro Ala Asn Ile Val Ala Leu Val Glu Glu Tyr
210                 215                 220

Met Asn Trp Leu His Gln Ser Pro Val Pro Lys Leu Leu Phe Trp Gly
225                 230                 235                 240

Thr Pro Gly Val Leu Ile Pro Pro Ala Glu Ala Ala Arg Leu Ala Glu
                245                 250                 255

Ser Leu Pro Asn Cys Lys Thr Val Asp Ile Gly Pro Gly Leu Asn Phe
            260                 265                 270

Leu Gln Glu Asp Asn Pro Asp Leu Ile Gly Ser Glu Ile Ala Arg Trp
        275                 280                 285

Leu Xaa Xaa Leu Xaa Xaa Xaa Xaa
        290                 295
```

```
<210> SEQ ID NO 67
<211> LENGTH: 297
<212> TYPE: PRT
<213> ORGANISM: Artificial Sequence
<220> FEATURE:
<223> OTHER INFORMATION: A synthetic mutant DhaA sequence
<220> FEATURE:
<221> NAME/KEY: SITE
<222> LOCATION: (1)..(1)
<223> OTHER INFORMATION: Xaa = M or G
<220> FEATURE:
<221> NAME/KEY: SITE
<222> LOCATION: (2)..(2)
<223> OTHER INFORMATION: Xaa = A or S
<220> FEATURE:
<221> NAME/KEY: SITE
<222> LOCATION: (291)..(291)
<223> OTHER INFORMATION: Xaa = S, Q or P
<220> FEATURE:
<221> NAME/KEY: SITE
<222> LOCATION: (292)..(292)
<223> OTHER INFORMATION: Xaa = T, E or A
<220> FEATURE:
```

<221> NAME/KEY: SITE
<222> LOCATION: (294)..(294)
<223> OTHER INFORMATION: Xaa = Q or E
<220> FEATURE:
<221> NAME/KEY: SITE
<222> LOCATION: (295)..(295)
<223> OTHER INFORMATION: Xaa = Y or I
<220> FEATURE:
<221> NAME/KEY: SITE
<222> LOCATION: (296)..(296)
<223> OTHER INFORMATION: Xaa = S or absent
<220> FEATURE:
<221> NAME/KEY: SITE
<222> LOCATION: (297)..(297)
<223> OTHER INFORMATION: Xaa = G or absent

<400> SEQUENCE: 67

```
Xaa Xaa Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
                20                  25                  30

Thr Pro Val Leu Phe Leu His Gly Asn Pro Thr Ser Ser Tyr Leu Trp
            35                  40                  45

Arg Asn Ile Ile Pro His Val Ala Pro Thr His Arg Cys Ile Ala Pro
50                  55                  60

Asp Leu Ile Gly Met Gly Lys Ser Asp Lys Pro Asp Leu Gly Tyr Phe
65                  70                  75                  80

Phe Asp Asp His Val Arg Tyr Leu Asp Ala Phe Ile Glu Ala Leu Gly
                85                  90                  95

Leu Glu Glu Val Val Leu Val Ile His Asp Trp Gly Ser Ala Leu Gly
            100                 105                 110

Phe His Trp Ala Lys Arg Asn Pro Glu Arg Val Lys Gly Ile Ala Cys
        115                 120                 125

Met Glu Phe Ile Arg Pro Ile Pro Thr Trp Asp Glu Trp Pro Glu Phe
130                 135                 140

Ala Arg Glu Thr Phe Gln Ala Phe Arg Thr Thr Asp Val Gly Arg Glu
145                 150                 155                 160

Leu Ile Ile Asp Gln Asn Ala Phe Ile Glu Gly Thr Leu Pro Met Gly
                165                 170                 175

Val Val Arg Pro Leu Thr Glu Val Glu Met Asp His Tyr Arg Glu Pro
            180                 185                 190

Phe Leu Lys Pro Val Asp Arg Glu Pro Leu Trp Arg Phe Pro Asn Glu
        195                 200                 205

Leu Pro Ile Ala Gly Glu Pro Ala Asn Ile Val Ala Leu Val Glu Glu
210                 215                 220

Tyr Met Asn Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255

Glu Ser Leu Pro Asn Cys Lys Thr Val Asp Ile Gly Pro Gly Leu Asn
            260                 265                 270

Leu Leu Gln Glu Asp Asn Pro Asp Leu Ile Gly Ser Glu Ile Ala Arg
        275                 280                 285

Trp Leu Xaa Xaa Leu Xaa Xaa Xaa Xaa
        290                 295
```

<210> SEQ ID NO 68
<211> LENGTH: 297
<212> TYPE: PRT

```
<213> ORGANISM: Artificial Sequence
<220> FEATURE:
<223> OTHER INFORMATION: A synthetic mutant DhaA sequence
<220> FEATURE:
<221> NAME/KEY: SITE
<222> LOCATION: (1)..(1)
<223> OTHER INFORMATION: Xaa = M or G
<220> FEATURE:
<221> NAME/KEY: SITE
<222> LOCATION: (2)..(2)
<223> OTHER INFORMATION: Xaa = A or S
<220> FEATURE:
<221> NAME/KEY: SITE
<222> LOCATION: (291)..(291)
<223> OTHER INFORMATION: Xaa = S, Q or P
<220> FEATURE:
<221> NAME/KEY: SITE
<222> LOCATION: (292)..(292)
<223> OTHER INFORMATION: Xaa = T, E or A
<220> FEATURE:
<221> NAME/KEY: SITE
<222> LOCATION: (294)..(294)
<223> OTHER INFORMATION: Xaa = Q or E
<220> FEATURE:
<221> NAME/KEY: SITE
<222> LOCATION: (295)..(295)
<223> OTHER INFORMATION: Xaa = Y or I
<220> FEATURE:
<221> NAME/KEY: SITE
<222> LOCATION: (296)..(296)
<223> OTHER INFORMATION: Xaa = S or absent
<220> FEATURE:
<221> NAME/KEY: SITE
<222> LOCATION: (297)..(297)
<223> OTHER INFORMATION: Xaa = G or absent

<400> SEQUENCE: 68

Xaa Xaa Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
            20                  25                  30

Thr Pro Val Leu Phe Leu His Gly Asn Pro Thr Ser Ser Tyr Leu Trp
        35                  40                  45

Arg Asn Ile Ile Pro His Val Ala Pro Thr His Arg Cys Ile Ala Pro
50                  55                  60

Asp Leu Ile Gly Met Gly Lys Ser Asp Lys Pro Asp Leu Gly Tyr Phe
65                  70                  75                  80

Phe Asp Asp His Val Arg Phe Leu Asp Ala Phe Ile Glu Ala Leu Gly
                85                  90                  95

Leu Glu Glu Val Val Leu Val Ile His Asp Trp Gly Ser Ala Leu Gly
            100                 105                 110

Phe His Trp Ala Lys Arg Asn Pro Glu Arg Val Lys Gly Ile Ala Cys
        115                 120                 125

Met Glu Phe Ile Arg Pro Ile Pro Thr Trp Asp Glu Trp Pro Glu Phe
130                 135                 140

Ala Arg Glu Thr Phe Gln Ala Phe Arg Thr Thr Asp Val Gly Arg Glu
                150                 155                 160
145

Leu Ile Ile Asp Gln Asn Ala Phe Ile Glu Gly Thr Leu Pro Met Gly
            165                 170                 175

Val Val Arg Pro Leu Thr Glu Val Glu Met Asp His Tyr Arg Glu Pro
        180                 185                 190

Phe Leu Lys Pro Val Asp Arg Glu Pro Leu Trp Arg Phe Pro Asn Glu
    195                 200                 205

Leu Pro Ile Ala Gly Glu Pro Ala Asn Ile Val Ala Leu Val Glu Glu
210                 215                 220
```

-continued

```
Tyr Met Asp Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
            245                 250                 255

Glu Ser Leu Pro Asn Cys Lys Thr Val Asp Ile Gly Pro Gly Leu Asn
        260                 265                 270

Phe Leu Gln Glu Asp Asn Pro Asp Leu Ile Gly Ser Glu Ile Ala Arg
    275                 280                 285

Trp Leu Xaa Xaa Leu Xaa Xaa Xaa Xaa
    290                 295
```

<210> SEQ ID NO 69
<211> LENGTH: 297
<212> TYPE: PRT
<213> ORGANISM: Artificial Sequence
<220> FEATURE:
<223> OTHER INFORMATION: A synthetic mutant DhaA sequence
<220> FEATURE:
<221> NAME/KEY: SITE
<222> LOCATION: (1)..(1)
<223> OTHER INFORMATION: Xaa = M or G
<220> FEATURE:
<221> NAME/KEY: SITE
<222> LOCATION: (2)..(2)
<223> OTHER INFORMATION: Xaa = A or S
<220> FEATURE:
<221> NAME/KEY: SITE
<222> LOCATION: (291)..(291)
<223> OTHER INFORMATION: Xaa = S, Q or P
<220> FEATURE:
<221> NAME/KEY: SITE
<222> LOCATION: (292)..(292)
<223> OTHER INFORMATION: Xaa = T, E or A
<220> FEATURE:
<221> NAME/KEY: SITE
<222> LOCATION: (294)..(294)
<223> OTHER INFORMATION: Xaa = Q or E
<220> FEATURE:
<221> NAME/KEY: SITE
<222> LOCATION: (295)..(295)
<223> OTHER INFORMATION: Xaa = Y or I
<220> FEATURE:
<221> NAME/KEY: SITE
<222> LOCATION: (296)..(296)
<223> OTHER INFORMATION: Xaa = S or absent
<220> FEATURE:
<221> NAME/KEY: SITE
<222> LOCATION: (297)..(297)
<223> OTHER INFORMATION: Xaa = G or absent

<400> SEQUENCE: 69

```
Xaa Xaa Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Ser
            20                  25                  30

Thr Pro Val Leu Phe Leu His Gly Asn Pro Thr Ser Ser Tyr Leu Trp
        35                  40                  45

Arg Asn Ile Ile Pro His Val Ala Pro Thr His Arg Cys Ile Ala Pro
    50                  55                  60

Asp Leu Ile Gly Met Gly Lys Ser Asp Lys Pro Asp Leu Gly Tyr Phe
65                  70                  75                  80

Phe Asp Asp His Val Arg Phe Leu Asp Ala Phe Ile Glu Ala Leu Gly
                85                  90                  95

Leu Glu Glu Val Val Leu Val Ile His Asp Trp Gly Ser Ala Leu Gly
            100                 105                 110
```

-continued

```
Phe His Trp Ala Lys Arg Asn Pro Glu Arg Val Lys Gly Ile Ala Cys
            115                 120                 125
Met Glu Phe Ile Arg Pro Ile Pro Thr Trp Asp Glu Trp Pro Glu Phe
    130                 135                 140
Ala Arg Glu Thr Phe Gln Ala Phe Arg Thr Thr Asp Val Gly Arg Glu
145                 150                 155                 160
Leu Ile Ile Asp Gln Asn Ala Phe Ile Glu Gly Thr Leu Pro Met Gly
                165                 170                 175
Val Val Arg Pro Leu Thr Glu Val Glu Met Asp His Tyr Arg Glu Pro
            180                 185                 190
Phe Leu Lys Pro Val Asp Arg Glu Pro Leu Trp Arg Phe Pro Asn Glu
        195                 200                 205
Leu Pro Ile Ala Gly Glu Pro Ala Asn Ile Val Ala Leu Val Glu Glu
    210                 215                 220
Tyr Met Asp Trp Leu His Gln Ser Pro Val Pro Lys Leu Leu Phe Trp
225                 230                 235                 240
Gly Thr Pro Gly Val Leu Ile Pro Pro Ala Glu Ala Ala Arg Leu Ala
                245                 250                 255
Glu Ser Leu Pro Asn Cys Lys Thr Val Asp Ile Gly Pro Gly Leu Asn
            260                 265                 270
Leu Leu Gln Glu Asp Asn Pro Asp Leu Ile Gly Ser Glu Ile Ala Arg
        275                 280                 285
Trp Leu Xaa Xaa Leu Xaa Xaa Xaa Xaa
        290                 295
```

<210> SEQ ID NO 70
<211> LENGTH: 297
<212> TYPE: PRT
<213> ORGANISM: Artificial Sequence
<220> FEATURE:
<223> OTHER INFORMATION: A synthetic mutant DhaA sequence
<220> FEATURE:
<221> NAME/KEY: SITE
<222> LOCATION: (1)..(1)
<223> OTHER INFORMATION: Xaa = M or G
<220> FEATURE:
<221> NAME/KEY: SITE
<222> LOCATION: (2)..(2)
<223> OTHER INFORMATION: Xaa = A or S
<220> FEATURE:
<221> NAME/KEY: SITE
<222> LOCATION: (7)..(297)
<223> OTHER INFORMATION: Xaa = G or absent
<220> FEATURE:
<221> NAME/KEY: SITE
<222> LOCATION: (291)..(291)
<223> OTHER INFORMATION: Xaa = S, Q or P
<220> FEATURE:
<221> NAME/KEY: SITE
<222> LOCATION: (292)..(292)
<223> OTHER INFORMATION: Xaa = T, E or A
<220> FEATURE:
<221> NAME/KEY: SITE
<222> LOCATION: (294)..(294)
<223> OTHER INFORMATION: Xaa = Q or E
<220> FEATURE:
<221> NAME/KEY: SITE
<222> LOCATION: (295)..(295)
<223> OTHER INFORMATION: Xaa = Y or I
<220> FEATURE:
<221> NAME/KEY: SITE
<222> LOCATION: (296)..(296)
<223> OTHER INFORMATION: Xaa = S or absent

<400> SEQUENCE: 70

```
Xaa Xaa Glu Ile Gly Thr Gly Phe Pro Phe Asp Pro His Tyr Val Glu
```

```
              1               5                  10                 15
            Val Leu Gly Glu Arg Met His Tyr Val Asp Val Gly Pro Arg Asp Gly
                           20                 25                 30
            Thr Pro Val Leu Phe Leu His Gly Asn Pro Thr Ser Ser Tyr Val Trp
                           35                 40                 45
            Arg Asn Ile Ile Pro His Val Ala Pro Thr His Arg Cys Ile Ala Pro
                50                 55                 60
            Asp Leu Ile Gly Met Gly Lys Ser Asp Lys Pro Asp Leu Gly Tyr Phe
             65                 70                 75                 80
            Phe Asp Asp His Val Arg Phe Met Asp Ala Phe Ile Glu Ala Leu Gly
                               85                 90                 95
            Leu Glu Glu Val Val Leu Val Ile His Asp Trp Gly Ser Ala Leu Gly
                           100                105                110
            Phe His Trp Ala Lys Arg Asn Pro Glu Arg Val Lys Gly Ile Ala Phe
                           115                120                125
            Met Glu Phe Ile Arg Pro Ile Pro Thr Trp Asp Glu Trp Pro Glu Phe
                           130                135                140
            Ala Arg Glu Thr Phe Gln Ala Phe Arg Thr Thr Asp Val Gly Arg Lys
            145                150                155                160
            Leu Ile Ile Asp Gln Asn Val Phe Ile Glu Gly Thr Leu Pro Met Gly
                           165                170                175
            Val Val Arg Pro Leu Thr Glu Val Glu Met Asp His Tyr Arg Glu Pro
                           180                185                190
            Phe Leu Asn Pro Val Asp Arg Glu Pro Leu Trp Arg Phe Pro Asn Glu
                           195                200                205
            Leu Pro Ile Ala Gly Glu Pro Ala Asn Ile Val Ala Leu Val Glu Glu
                           210                215                220
            Tyr Met Asp Trp Leu His Gln Ser Pro Val Pro Lys Leu Leu Phe Trp
            225                230                235                240
            Gly Thr Pro Gly Val Leu Ile Pro Pro Ala Glu Ala Ala Arg Leu Ala
                           245                250                255
            Lys Ser Leu Pro Asn Cys Lys Ala Val Asp Ile Gly Pro Gly Leu Asn
                           260                265                270
            Leu Leu Gln Glu Asp Asn Pro Asp Leu Ile Gly Ser Glu Ile Ala Arg
                           275                280                285
            Trp Leu Xaa Xaa Leu Xaa Xaa Xaa Xaa
                           290                295

<210> SEQ ID NO 71
<211> LENGTH: 297
<212> TYPE: PRT
<213> ORGANISM: Artificial Sequence
<220> FEATURE:
<223> OTHER INFORMATION: A synthetic mutant DhaA sequence
<220> FEATURE:
<221> NAME/KEY: SITE
<222> LOCATION: (1)..(1)
<223> OTHER INFORMATION: Xaa = M or G
<220> FEATURE:
<221> NAME/KEY: SITE
<222> LOCATION: (2)..(2)
<223> OTHER INFORMATION: Xaa = A or S
<220> FEATURE:
<221> NAME/KEY: SITE
<222> LOCATION: (291)..(291)
<223> OTHER INFORMATION: Xaa = S, Q or P
<220> FEATURE:
<221> NAME/KEY: SITE
<222> LOCATION: (292)..(292)
<223> OTHER INFORMATION: Xaa = T, E or A
```

```
<220> FEATURE:
<221> NAME/KEY: SITE
<222> LOCATION: (294)..(294)
<223> OTHER INFORMATION: Xaa = Q or E
<220> FEATURE:
<221> NAME/KEY: SITE
<222> LOCATION: (295)..(295)
<223> OTHER INFORMATION: Xaa = Y or I
<220> FEATURE:
<221> NAME/KEY: SITE
<222> LOCATION: (296)..(296)
<223> OTHER INFORMATION: Xaa = S or absent
<220> FEATURE:
<221> NAME/KEY: SITE
<222> LOCATION: (297)..(297)
<223> OTHER INFORMATION: Xaa = G or absent

<400> SEQUENCE: 71

Xaa Xaa Glu Ile Gly Thr Gly Phe Pro Phe Asp Pro His Tyr Val Glu
 1               5                  10                  15

Val Leu Gly Glu Arg Met His Tyr Val Asp Val Gly Pro Arg Asp Gly
             20                  25                  30

Thr Pro Val Leu Phe Leu His Gly Asn Pro Thr Ser Ser Tyr Val Trp
         35                  40                  45

Arg Asn Ile Ile Pro His Val Ala Pro Thr His Arg Cys Ile Ala Pro
     50                  55                  60

Asp Leu Ile Gly Met Gly Lys Ser Asp Lys Pro Asp Leu Gly Tyr Phe
65                  70                  75                  80

Phe Asp Asp His Val Arg Phe Met Asp Ala Phe Ile Glu Ala Leu Gly
                 85                  90                  95

Leu Glu Glu Val Val Leu Val Ile His Asp Trp Gly Ser Ala Leu Gly
            100                 105                 110

Phe His Trp Ala Lys Arg Asn Pro Glu Arg Val Lys Gly Ile Ala Phe
        115                 120                 125

Met Glu Phe Ile Arg Pro Ile Pro Thr Trp Asp Glu Trp Pro Glu Phe
    130                 135                 140

Ala Arg Glu Thr Phe Gln Ala Phe Arg Thr Thr Asp Val Gly Arg Lys
145                 150                 155                 160

Leu Ile Ile Asp Gln Asn Val Phe Ile Glu Gly Thr Leu Pro Met Gly
                165                 170                 175

Val Val Arg Pro Leu Thr Glu Val Glu Met Asp His Tyr Arg Glu Pro
            180                 185                 190

Phe Leu Asn Pro Val Asp Arg Glu Pro Leu Trp Arg Phe Pro Asn Glu
        195                 200                 205

Leu Pro Ile Ala Gly Glu Pro Ala Asn Ile Val Ala Leu Val Glu Glu
    210                 215                 220

Tyr Met Asp Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255

Lys Ser Leu Pro Asn Cys Lys Ala Val Asp Ile Gly Pro Gly Leu Asn
            260                 265                 270

Leu Leu Gln Glu Asp Asn Pro Asp Leu Ile Gly Ser Glu Ile Ala Arg
        275                 280                 285

Trp Leu Xaa Xaa Leu Xaa Xaa Xaa Xaa
    290                 295

<210> SEQ ID NO 72
<211> LENGTH: 63
```

```
<212> TYPE: PRT
<213> ORGANISM: Artificial Sequence
<220> FEATURE:
<223> OTHER INFORMATION: A synthetic mutant DhaA tail sequence

<400> SEQUENCE: 72

Glu Ile Ser Gly Gly Gly Gly Ser Gly Gly Gly Ser Gly Gly Gly
1               5                   10                  15

Gly Glu Asn Leu Tyr Phe Gln Ala Ile Glu Leu Gly Thr Arg Gly Ser
            20                  25                  30

Ser Arg Val Asp Leu Gln Ala Cys Lys Leu Ile Arg Leu Leu Thr Lys
        35                  40                  45

Pro Glu Arg Lys Leu Ser Trp Leu Leu Pro Pro Leu Ser Asn Asn
    50                  55                  60

<210> SEQ ID NO 73
<211> LENGTH: 293
<212> TYPE: PRT
<213> ORGANISM: Artificial Sequence
<220> FEATURE:
<223> OTHER INFORMATION: A synthetic mutant DhaA sequence

<400> SEQUENCE: 73

Met Ala Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
            20                  25                  30

Thr Pro Val Leu Phe Leu His Gly Asn Pro Thr Ser Ser Tyr Leu Trp
        35                  40                  45

Arg Asn Ile Ile Pro His Val Ala Pro Ser His Arg Cys Ile Ala Pro
    50                  55                  60

Asp Leu Ile Gly Met Gly Lys Ser Asp Lys Pro Asp Leu Gly Tyr Phe
65                  70                  75                  80

Phe Asp Asp His Val Arg Tyr Leu Asp Ala Phe Ile Glu Ala Leu Gly
                85                  90                  95

Leu Glu Glu Val Val Leu Val Ile His Asp Trp Gly Ser Ala Leu Gly
            100                 105                 110

Phe His Trp Ala Lys Arg Asn Pro Glu Arg Val Lys Gly Ile Ala Cys
        115                 120                 125

Met Glu Phe Ile Arg Pro Ile Pro Thr Trp Asp Glu Trp Pro Glu Phe
    130                 135                 140

Ala Arg Glu Thr Phe Gln Ala Phe Arg Thr Ala Asp Val Gly Arg Glu
145                 150                 155                 160

Leu Ile Ile Asp Gln Asn Ala Phe Ile Glu Gly Ala Leu Pro Met Gly
                165                 170                 175

Val Val Arg Pro Leu Thr Glu Val Glu Met Asp His Tyr Arg Glu Pro
            180                 185                 190

Phe Leu Lys Pro Val Asp Arg Glu Pro Leu Trp Arg Phe Pro Asn Glu
        195                 200                 205

Leu Pro Ile Ala Gly Glu Pro Ala Asn Ile Val Ala Leu Val Glu Ala
    210                 215                 220

Tyr Met Asn Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255

Glu Ser Leu Pro Asn Cys Lys Thr Val Asp Ile Gly Pro Gly Leu Asn
            260                 265                 270
```

```
Phe Leu Gln Glu Asp Asn Pro Asp Leu Ile Gly Ser Glu Ile Ala Arg
        275                 280                 285

Trp Leu Pro Ala Leu
        290
```